United States Patent
Wu et al.

(10) Patent No.: US 10,386,300 B2
(45) Date of Patent: Aug. 20, 2019

(54) SPECTRALLY AND SPATIALLY MULTIPLEXED FLUORESCENT PROBES FOR IN SITU CELL LABELING

(71) Applicant: Verily Life Sciences LLC, Mountain View, CA (US)

(72) Inventors: Cheng-Hsun Wu, Palo Alto, CA (US); Victor Marcel Acosta, San Francisco, CA (US); Ian Peikon, Mountain View, CA (US); Paul Lebel, San Mateo, CA (US); Jerrod Joseph Schwartz, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 408 days.

(21) Appl. No.: 15/384,918

(22) Filed: Dec. 20, 2016

(65) Prior Publication Data

US 2017/0176338 A1    Jun. 22, 2017

Related U.S. Application Data

(60) Provisional application No. 62/270,530, filed on Dec. 21, 2015, provisional application No. 62/342,270, (Continued)

(51) Int. Cl.
*G01N 21/64* (2006.01)
*G06T 7/90* (2017.01)
(Continued)

(52) U.S. Cl.
CPC .......... *G01N 21/6458* (2013.01); *G01J 3/021* (2013.01); *G01J 3/0208* (2013.01);
(Continued)

(58) Field of Classification Search
CPC .......... G01N 21/6408; G01N 21/6428; G01N 21/4795; G01N 21/6456;
(Continued)

(56) References Cited

U.S. PATENT DOCUMENTS

| | | | |
|---|---|---|---|
| 2,828,670 A | 4/1958 | Luboshez | |
| 5,577,137 A * | 11/1996 | Groger ............... | G01N 21/6428 250/227.11 |

(Continued)

FOREIGN PATENT DOCUMENTS

| | | |
|---|---|---|
| EP | 0916981 A1 | 5/1999 |
| EP | 2720075 A1 | 4/2014 |

(Continued)

OTHER PUBLICATIONS

Qing Ye et al., "High-efficiency electrically tunable phase diffraction grating based on a transparent lead magnesium niobate-lead titanite electro-optic ceramic", Optics Letters, Optical Society of America, vol. 36, No. 13, Jul. 1, 2011, pp. 2453-2455.
(Continued)

*Primary Examiner* — Obafemi O Sosanya
(74) *Attorney, Agent, or Firm* — McDonnell Boehnen Hulbert & Berghoff LLP

(57) ABSTRACT

Methods are provided to identify spatially and spectrally multiplexed probes in a biological environment. Such probes are identified by the ordering and color of fluorophores of the probes. The devices and methods provided facilitate determination of the locations and colors of such fluorophores, such that a probe can be identified. In some embodiments, probes are identified by applying light from a target environment to a spatial light modulator that can be used to control the direction and magnitude of chromatic dispersion of the detected light; multiple images of the target, corresponding to multiple different spatial light
(Continued)

modulator settings, can be deconvolved and used to determine the colors and locations of fluorophores. In some embodiments, light from a region of the target can be simultaneously imaged spatially and spectrally. Correlations between the spatial and spectral images over time can be used to determine the color of fluorophores in the target.

20 Claims, 39 Drawing Sheets

Related U.S. Application Data filed on May 27, 2016, provisional application No. 62/320,681, filed on Apr. 11, 2016, provisional application No. 62/342,268, filed on May 27, 2016, provisional application No. 62/342,252, filed on May 27, 2016, provisional application No. 62/342,256, filed on May 27, 2016.

(51) Int. Cl.

| | |
|---|---|
| *G02B 21/16* | (2006.01) |
| *G02B 21/36* | (2006.01) |
| *G02B 26/08* | (2006.01) |
| *G02F 1/29* | (2006.01) |
| *G01J 3/02* | (2006.01) |
| *G01J 3/08* | (2006.01) |
| *G01J 3/14* | (2006.01) |
| *G01J 3/18* | (2006.01) |
| *G01J 3/28* | (2006.01) |
| *G01J 3/32* | (2006.01) |
| *G01J 3/44* | (2006.01) |
| *G02B 5/18* | (2006.01) |
| *G01J 3/12* | (2006.01) |

(52) U.S. Cl.
CPC .......... *G01J 3/0224* (2013.01); *G01J 3/0237* (2013.01); *G01J 3/08* (2013.01); *G01J 3/14* (2013.01); *G01J 3/18* (2013.01); *G01J 3/2823* (2013.01); *G01J 3/32* (2013.01); *G01J 3/4406* (2013.01); *G01N 21/6408* (2013.01); *G01N 21/6428* (2013.01); *G02B 5/1828* (2013.01); *G02B 21/16* (2013.01); *G02B 21/361* (2013.01); *G02B 21/367* (2013.01); *G02B 26/0808* (2013.01); *G02B 26/0833* (2013.01); *G02F 1/29* (2013.01); *G06T 7/90* (2017.01); *G01J 3/0229* (2013.01); *G01J 2003/1213* (2013.01); *G01J 2003/2826* (2013.01); *G01N 2021/6421* (2013.01); *G01N 2021/6441* (2013.01); *G01N 2021/6463* (2013.01); *G01N 2201/0633* (2013.01); *G01N 2201/0675* (2013.01); *G02F 2201/34* (2013.01); *G02F 2203/12* (2013.01); *G06T 2207/10004* (2013.01); *G06T 2207/10056* (2013.01)

(58) Field of Classification Search
CPC ..... G01N 2021/7786; G01N 2201/062; G01N 2021/6415; G01N 2021/6463; G01N 21/6458; G01J 3/4406; G01J 3/0237; G01J 3/08; G01J 3/14; G01J 3/18; G01J 3/2823; G01J 3/32; G02F 1/29; G02F 2201/34; G02F 2203/12; G06T 2207/10004
See application file for complete search history.

(56) References Cited

U.S. PATENT DOCUMENTS

| | | |
|---|---|---|
| 5,587,832 A | 12/1996 | Krause |
| 5,591,981 A | 1/1997 | Heffelfinger et al. |
| 5,606,170 A * | 2/1997 | Saaski ............... G01N 21/6428 250/227.14 |
| 6,043,882 A | 3/2000 | De Wolf et al. |
| 6,399,935 B1 | 6/2002 | Jovin et al. |
| 6,483,641 B1 | 11/2002 | MacAulay |
| 6,794,658 B2 | 9/2004 | MacAulay et al. |
| 7,339,148 B2 | 3/2008 | Kawano et al. |
| 7,460,248 B2 | 12/2008 | Kurtz et al. |
| 7,532,323 B2 | 5/2009 | Tang et al. |
| 8,233,148 B2 | 7/2012 | Bodkin et al. |
| 8,629,413 B2 | 1/2014 | Betzig et al. |
| 2004/0061914 A1 | 4/2004 | Miyawaki et al. |
| 2006/0214106 A1 | 9/2006 | Wolleschensky et al. |
| 2009/0309049 A1 | 12/2009 | Van Dijk et al. |
| 2010/0314554 A1 | 12/2010 | Galimberti et al. |
| 2011/0228267 A1 | 9/2011 | Hayashi |
| 2012/0069344 A1 | 3/2012 | Liu |
| 2012/0307247 A1 | 12/2012 | Tan et al. |
| 2013/0100525 A1 | 4/2013 | Chiang et al. |
| 2013/0329270 A1 | 12/2013 | Nielsen et al. |
| 2015/0145981 A1 | 5/2015 | Anhut et al. |
| 2016/0202178 A1 | 7/2016 | Acosta |
| 2017/0089837 A1 | 3/2017 | Matsumoto et al. |
| 2017/0176338 A1 | 6/2017 | Wu et al. |

FOREIGN PATENT DOCUMENTS

| | | |
|---|---|---|
| GB | 859208 A | 1/1961 |
| JP | S52014417 A | 2/1977 |
| JP | S63101818 A | 5/1988 |
| JP | 2015219501 A | 12/2015 |
| WO | 2015157769 A1 | 10/2015 |
| WO | 2016115018 A1 | 7/2016 |

OTHER PUBLICATIONS

Yanli Zhang et al., "High-efficiency, liquid-crystal-based, controllable diffraction grating", Journal Of The Optical Society Of America, vol. 22, No. 11, Nov. 2005, p. 2510.
Sirleto L. et al., "Electro-Optical Switch And Continuously Tunable Filter Based On A Bragg Grating In A Planar Waveguide With A Liquid Crystal Overlayer", Optical Engineering, Soc. of Photo-Optical Instrumentation Engineers, vol. 41, No. 11, Nov. 2002, pp. 2890-2898.
International Search Report of International Application No. PCT/US2016/067684 dated Mar. 9, 2017.
International Search Report of International Application No. PCT/US2017/027510 dated Jul. 7, 2017.
Cha et. al., "Nontranslational three-dimensional profilometry by chromatic confocal microscopy with dynamically configurable micromirror scanning", Applied Optics, vol. 39, No. 16, Jun. 1, 2000.
Chakrova et al., "Development of a DMD-based fluorescence microscope", Proc. of SPIE, vol. 9330, 2015.
Diem et al., "Molecular pathology via IR and Raman spectral imaging", Journal of Biophotonics, 6, No. 11-12, pp. 855-886, 2013.
Akbari et al., "Hyperspectral imaging and quantitative analysis for prostate cancer detection", Journal of Biomedical Optics, vol. 17(7), Jul. 2012.
Lu et al., "Medical hyperspectral imaging: a review", Journal of Biomedical Optics, vol. 19(1), Jan. 2014.
Panasyuk et al., "Medical hyperspectral imaging to facilitate residual tumor identification during surgery", Cancer Biology & Therapy, Mar. 1, 2007.
Schultz et al., "Hyperspectral Imaging: A Novel Approach For Microscopic Analysis", Cytometry 43:239-247, 2001.
Bodkin et al., "Snapshot Hyperspectral Imaging—the Hyperpixel Array Camera", Proc. of SPIE, vol. 7334, Apr. 2009.

(56) References Cited

OTHER PUBLICATIONS

Zheng et al., "Optical Scatter Imaging with a digital micromirror device", Optics Express, vol. 17, No. 22, Oct. 26, 2009.
Stelzer et al., "Theory and Applications of Confocal Theta Microscopy", Zoological Studies, pp. 67-69, 1995.
Olsovsky et al., "Chromatic confocal microscopy for multi-depth imaging of epithelial tissue", Biomedical Optics Express, vol. 4, No. 5, May 2013.
Weinigel et al., "Exploration of Chromatic Aberration for Multiplanar Imaging: Proof of Concept with Implications for Fast, Efficient Autofocus", Cytometry, Dec. 2009, pp. 999-1006.
Wilt et al., "Advances in Light Microscopy for Neuroscience", Annu. Rev. Neurosci., 2009.
Shaked et al., "Dispersion Compensation with a Prism-pair", Physics Optics, Nov. 4, 2014.
Favreau et al., "Thin-film tunable filters for hyperspectral fluorescence microscopy", Journal of Biomedical Optics, vol. 19(1), Jan. 2014.
"Optical Spectral Filters And Gratings", Chapter 4, pp. 71-89.
Erdogan, PhD., "Optical Filters: Tunable Filters", Semrock, A Unit of IDEX Corporation, May 31, 2011.
Anderson et al., "Angle-Tuned Thin-Film Interference Filters for Spectral Imaging", OPN Optics & Photonics News, pp. 12-13, Jan. 2011.
Erodogan, Ph.D. et al., "Semrock White Paper Series: Semrock VersaChrome, The First Widely Tunable Thin-film Optical Filters", Semrock, A Unit of IDEX.
Hanley et al., "An optical sectioning programmable array microscope implemented with a digital micromirror device", Journal of Microscopy, vol. 196, Pt. 3, pp. 317-331, Dec. 1999.
Hagen et al., "Biological applications of an LCoS-Based Programmable Array Microscope (PAM)", Proc. of SPIE vol. 6441, 2007.
De Beule et al., "Generation-3 programmable array microscope (PAM) with digital micro-mirror device (DMD)", Proc. of SPIE, vol. 7932, 2011.
Hanley et al., "Highly Multiplexed Optically Sectioned Spectroscopic Imaging in a Programmable Array Microscope", Applied Spectroscopy, vol. 55, No. 9, 2001.
Matsumoto et al., "High-quality generation of a multispot pattern using a spatial light modulator with adaptive feedback", Optics Letters, vol. 37, No. 15, Aug. 1, 2012.
Stockley et al., "Liquid crystal spatial light modulator for multispot beam steering", Society of Photo Instrumentation Engineers, 2004.
Martial et al., "Programmable Illumination and High-Speed, Multi-Wavelength, Confocal Microscopy Using a Digital Micromirror", PLOS ONE, vol. 7, Issue 8, Aug. 2012.
Krizek et al., "Spatial light modulators in fluorescence microscopy", FORMATEX 2010.
Matsumoto et al., "Stable and flexible multiple spot pattern generation using LCOS spatial light modulator", Optics Express, vol. 22, No. 20, Aug. 2014.
Heintzmann, "Structured Illumination Methods", Handbook of Biological Confocal Microscopy, Third Edition, 2006.
Xun et al., "System for demonstrating arbitrary multi-spot beam steering from spatial light modulators", Optics Express, vol. 12, No. 2, Jan. 26, 2004.
International Search Report of International Application No. PCT/US2017/034875 dated Aug. 21, 2017.
International Search Report of International Application No. PCT/US2017/034877 dated Aug. 17, 2017.
De Beule et al., "A Generation-3 Programmable Array Microscope with Digital Micro-Mirror Device", vol. 98, Issue 3, Supplement 1, p. 178a, Jan. 2010.

\* cited by examiner

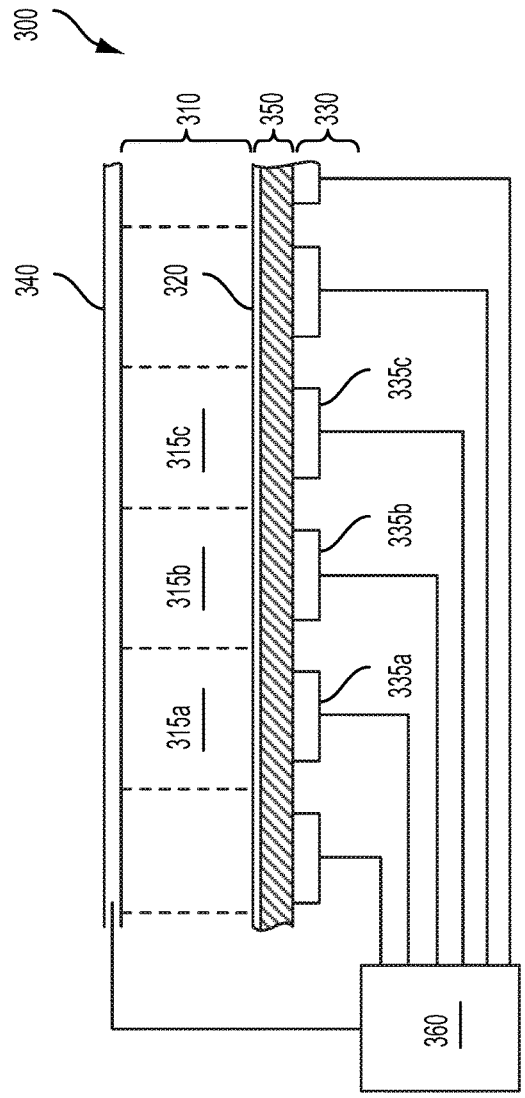
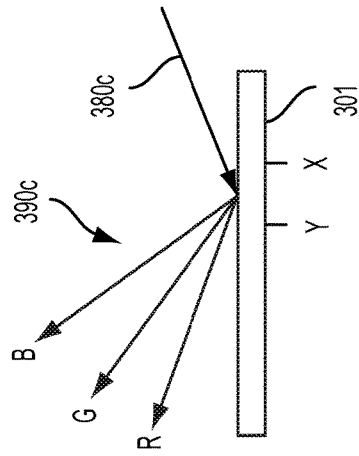
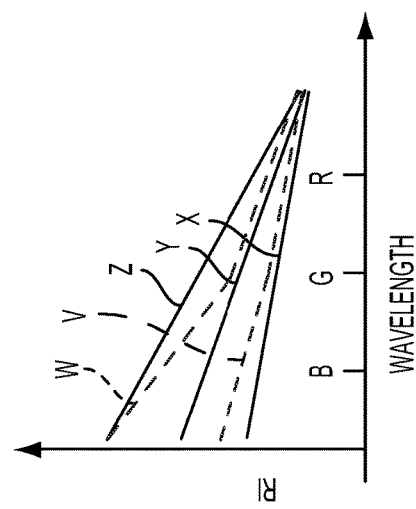
FIG. 3A
FIG. 3B
FIG. 3C

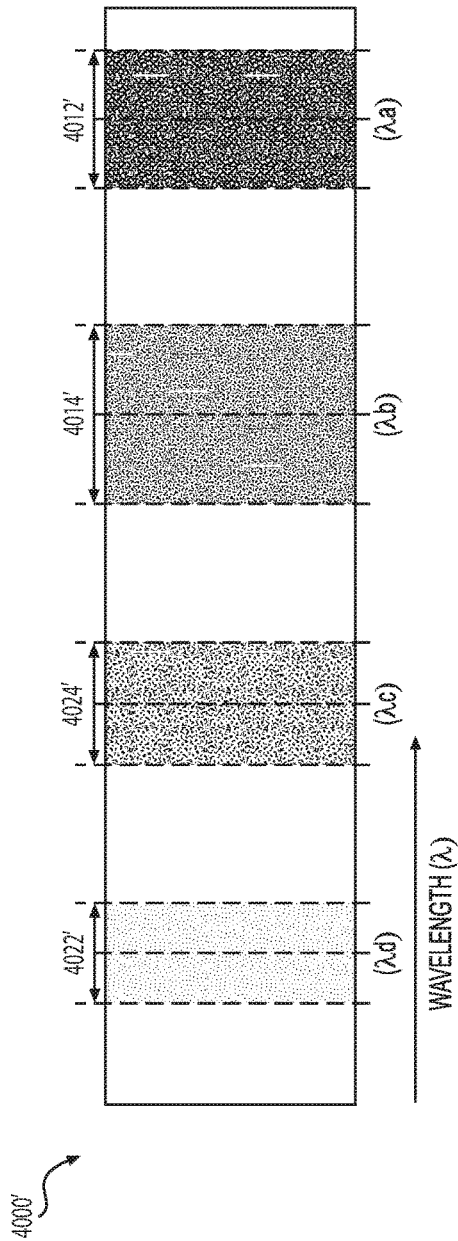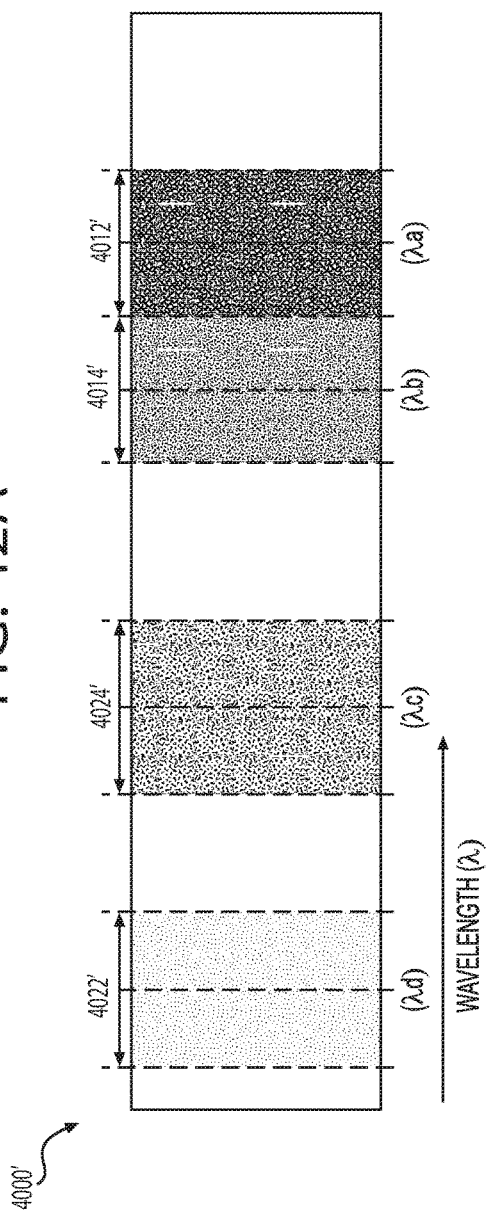

SPECTRALLY AND SPATIALLY MULTIPLEXED FLUORESCENT PROBES FOR IN SITU CELL LABELING

CROSS-REFERENCE TO RELATED APPLICATION

This application claims priority to U.S. Provisional Patent Application No. 62/270,530, filed Dec. 21, 2015; U.S. Provisional Patent Application No. 62/342,270 filed May 27, 2016; U.S. Provisional Patent Application No. 62/320,681, filed Apr. 11, 2016; U.S. Provisional Patent Application No. 62/342,268, filed May 27, 2016; U.S. Provisional Patent Application No. 62/342,252, filed May 27, 2016; and U.S. Provisional Patent Application No. 62/342,256, filed May 27, 2016, which are hereby incorporated by reference in their entirety.

BACKGROUND

Unless otherwise indicated herein, the materials described in this section are not prior art to the claims in this application and are not admitted to be prior art by inclusion in this section.

A variety of methods exist to image biological tissues or other materials at the micro-scale (i.e., at scales at or smaller than a few micrometers). Such methods can include optical microscopy according to a variety of different illumination schemes and using optical systems configured in a variety of different ways. Samples to be imaged could be broadly illuminated (e.g., in bright-field microscopy), exposed to some structured illumination (e.g., light sheet microscopy), exposed to polarized illumination (e.g., phase contrast microscopy), exposed to illumination at one or more specified points (e.g., confocal microscopy), or illuminated according to some other scheme. Conversely, light can be received and/or focused from the samples to be imaged in a variety of ways; light can be received from a wide field of the sample and focused on an imager, subjected to an aperture (e.g., an aperture corresponding to an aperture used to illuminate the sample as in, e.g., confocal microscopy) before being imaged by an imager or light sensor, or received by some other means. Further, light of different wavelengths can be used to illuminate a sample (e.g., to excite a fluorophore in the sample) and/or light of different wavelengths can be detected from the sample to determine spectrographic information (e.g., emission spectra, excitation spectra, absorbance spectra) about the sample or according to some other application.

SUMMARY

A variety of systems and methods are provided to microscopically image a sample (e.g., a sample of biological tissue) in such a way that the identity of probes present in the sample can be determined. Such probes include two or more fluorophores having respective spectral properties (e.g., colors, emission spectra, absorption spectra) and respective relative locations within the probe such that the identity of the probe can be determined based on detected spectral properties (e.g., colors) and relative locations of fluorophores in the sample. A great number of different probes could be used to tag respective different contents of a sample (e.g., to tag different proteins, different DNA or RNA sequences, to tag different protein isoforms). By creating the probes to include a number of different fluorophores and/or to include two, three, or more fluorophores arranged according to a specified shape, relative location, and/or ordering the number of uniquely identifiable probes could be very large, e.g., exponentially and/or combinatorically related to a number of different fluorophores used or a maximum number of fluorophores present in each probe.

Some embodiments of the present disclosure provide a system including: (i) a light sensor that includes a plurality of light-sensitive elements disposed on a focal surface of the light sensor; (ii) a spatial light modulator that includes a reflective layer disposed beneath a refractive layer and that is operable to have a refractive index that varies spatially across the spatial light modulator according to a controllable gradient, wherein at least the direction and magnitude of the controllable gradient are electronically controllable, and wherein the refractive layer is chromatically dispersive; (iii) an optical system; and (iv) a controller that is operably coupled to the light sensor and the spatial light modulator and that is operable to perform controller operations. The optical system (1) directs light emitted from a target toward the spatial light modulator and (2) directs light emitted from the target and reflected from the spatial light modulator to the light sensor such that the focal surface of the light sensor is conjugate to a focal surface passing through the target. The controller operations include: (i) controlling the spatial light modulator such that at least one of the direction or magnitude of the controllable gradient are different during each of a plurality of periods of time; (ii) generating, using the light sensor, a plurality of images of the target, wherein each image corresponds to a respective one of the plurality of periods of time; (iii) determining, based on the plurality of images, locations and colors of two or more fluorophores in the target; and (iv) determining, based on the determined colors and locations of the two or more fluorophores, an identity of a probe that is located in the target and that includes the two or more fluorophores.

Some embodiments of the present disclosure provide a system including: (i) a first light sensor that includes a plurality of light-sensitive elements disposed on a focal surface of the first light sensor; (ii) a second light sensor that includes a plurality of light-sensitive elements; (iii) a chromatically dispersive element; (iv) an optical system; and (v) a controller that is operably coupled to the first light sensor and the second light sensor and that is operable to perform controller operations. The optical system (1) directs light emitted from a particular region of a target to the first light sensor such that the focal surface of the first light sensor is conjugate to a focal surface passing through the particular region of the target, (2) directs light emitted from the particular region of the target toward the chromatically dispersive element, and (3) directs light emitted from the particular region of the target that has interacted with the chromatically dispersive element to the second light sensor such that light of different wavelengths that is emitted from the particular region of the target is received by corresponding different light-sensitive elements of the second light sensor. The controller operations include: (i) generating, using the plurality of light-sensitive elements of the first light sensor, a first plurality of respective time-varying waveforms of light emitted from respective different locations of the particular region of the target; (ii) generating, using the plurality of light-sensitive elements of the second light sensor, a second plurality of respective time-varying waveforms of light emitted from the particular region of the target at respective different wavelengths; (iii) determining correlations between time-varying waveforms of the first plurality of time-varying waveforms and time-varying waveforms of the second plurality of time-varying waveforms; (iv) determining, based on the determined correlations, locations and colors of two or more fluorophores in the target; and (v) determining, based on the determined colors and locations of the two or more fluorophores, an identity of a probe that is located in the target and that includes the two or more fluorophores.

Some embodiments of the present disclosure provide a method including: (i) controlling a spatial light modulator such that at least one of the direction or magnitude of a controllable gradient of a refractive index of a refractive layer of the spatial light modulator are different during each of a plurality of periods of time, wherein the spatial light modulator includes a reflective layer disposed beneath the refractive layer and is operable to have a refractive index that varies spatially across the spatial light modulator according to a controllable gradient, wherein at least the direction and magnitude of the controllable gradient are electronically controllable, and wherein the refractive layer is chromatically dispersive; (ii) generating, using a light sensor that includes a plurality of light-sensitive elements disposed on a focal surface of the light sensor, a plurality of images of a target, wherein each image corresponds to a respective one of the plurality of periods of time, wherein light that is emitted from the target is transmitted to the light sensor via an optical system, wherein the optical system (1) directs light emitted from the target toward the spatial light modulator and (2) directs light emitted from the target and reflected from the spatial light modulator to the light sensor such that the focal surface of the light sensor is conjugate to a focal surface passing through the target; (iii) determining, based on the plurality of images, locations and colors of two or more fluorophores in the target; and (iv) determining, based on the determined colors and locations of the two or more fluorophores, an identity of a probe that is located in the target and that includes the two or more fluorophores.

Some embodiments of the present disclosure provide a method including: (i) generating, using a plurality of light-sensitive elements of a first light sensor that are disposed on a focal surface of the first light sensor, a first plurality of respective time-varying waveforms of light that is emitted from respective different locations of a particular region of a target and transmitted to the light sensor via an optical system, wherein the optical system provides the emitted light from the target to the first light sensor such that the focal surface of the first light sensor is conjugate to a focal surface passing through the particular region of the target; (ii) generating, using a plurality of light-sensitive elements of a second light sensor, a second plurality of respective time-varying waveforms of light at different respective wavelengths that is emitted from the particular region of the target and transmitted to the light sensor via the optical system, wherein the optical system provides the emitted light from the target to a chromatically dispersive element, wherein the optical system provides the emitted light from the target that has interacted with the chromatically dispersive element to the second light sensor such that light of different wavelengths that is emitted from the particular region of the target is received by corresponding different light-sensitive elements of the second light sensor; (iii) determining correlations between time-varying waveforms of the first plurality of time-varying waveforms and time-varying waveforms of the second plurality of time-varying waveforms; (iv) determining, based on the determined correlations, locations and colors of two or more fluorophores in the target; and (v) determining, based on the determined colors and locations of the two or more fluorophores, an identity of a probe that is located in the target and that includes the two or more fluorophores.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3A illustrates a cross-section view of elements of an example spatial light modulator.

FIG. 3B illustrates reflection of light by the spatial light modulator of FIG. 3A.

FIG. 3C illustrates the dependence of refractive index on wavelength of light of materials that could be incorporated into the spatial light modulator of FIG. 3A.

FIG. 42A is a graphical illustration of an example spectrum of an output optical beam exiting the example system of FIG. 38.

FIG. 42B is a graphical illustration of another example spectrum of an output optical beam exiting the example system of FIG. 38.

DETAILED DESCRIPTION

Figure 1:
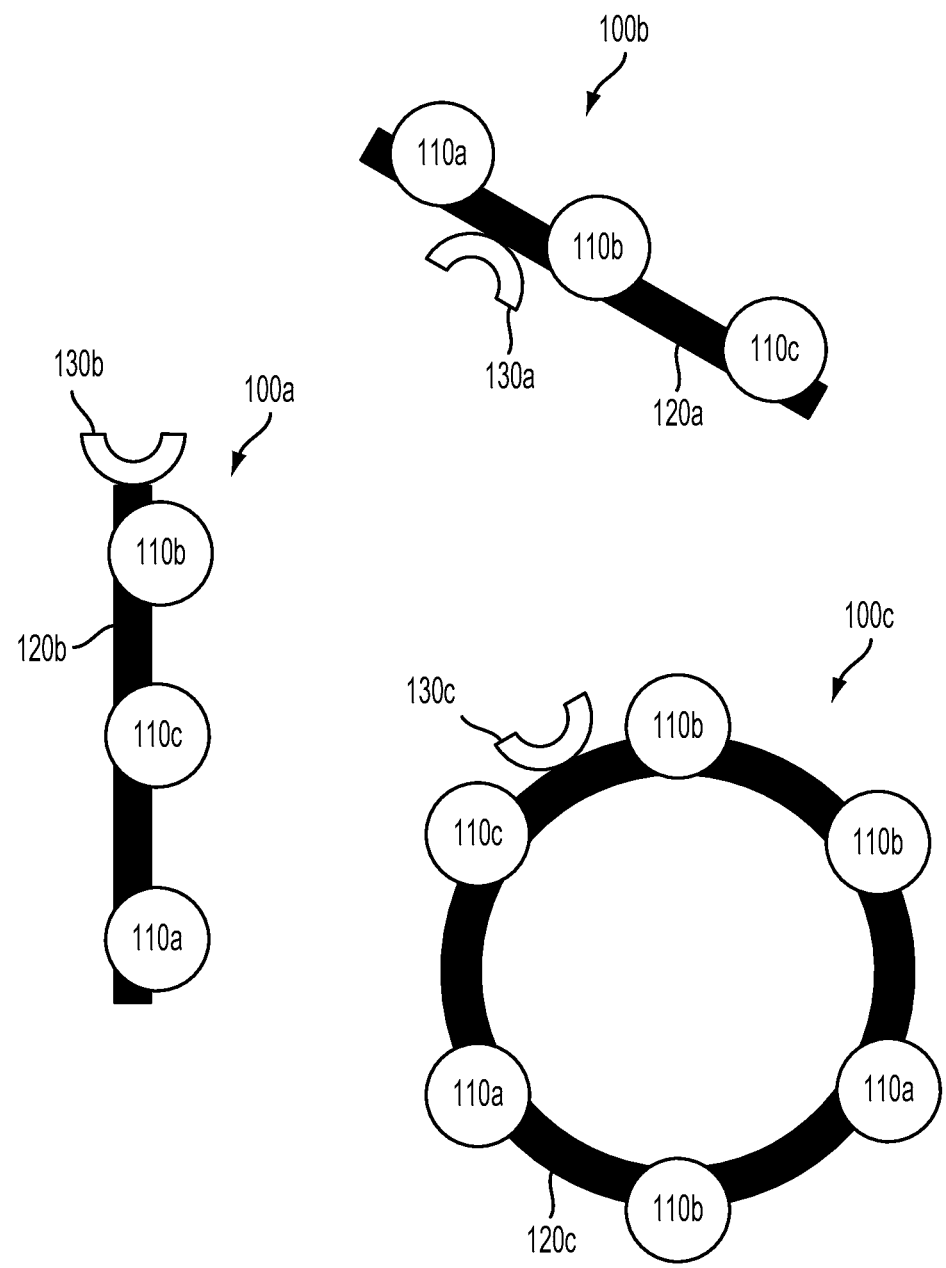
FIG. 1 illustrates an example probe.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with samples of tissue extracted from a human body, it is contemplated that the disclosed methods, systems and devices may be used in any environment where spectrographic imaging and/or optical sectioning of other tissues or other objects or elements of an environment is desired. The environment may be any living or non-living body or a portion thereof, a work piece, an implantable device, a mineral, an integrated circuit, a microelectromechanical device, etc.

I. Overview

It can be advantageous to introduce contrast agents or other probes into a target of interest (e.g., a biological sample) to facilitate imaging of specific elements of the target, e.g., to facilitate the localization and/or determine the concentration of specific chemicals, proteins, RNA or DNA segments, or other analytes in a target environment. Such probes can be optically distinct, e.g., can differ from each other with respect to an optical excitation spectrum, an optical emission spectrum, an absorption spectrum, a fluorescence lifetime or other temporal dynamics of energy absorption and re-emission/reflection, an acoustical absorption spectrum, or some other properties such that multiple different probes can be independently detected in an environment, facilitating the simultaneous detection of corresponding different analytes in the environment.

The number of distinct probes available to label and image an environment can limit the number of analytes that can be simultaneously imaged. Such a limitation could be related to a number of fluorescent labels that are available and that are compatible with an environment of interest, a spectral or temporal resolving ability and/or noise level of an imaging apparatus, a linewidth and/or tenability of an imaging light source, or some other factors related to the set of probes available to image an environment and/or an imaging apparatus provided to image the environment.

In order to increase the number of different probes that are available to facilitate imaging of respective different analytes in an environment, probes can be fabricated that each include multiple different fluorophores (e.g., multiple different quantum dots, Raman dyes, fluorescent proteins, fluorescent small molecules, or other fluorophores) arranged in a specified pattern and/or order. By increasing the number of fluorophores present on each probe and/or by increasing the number of distinguishable types of fluorophores (e.g., a number of different colors of fluorophores used), the number of distinguishably different probes can be increased. Such different probes can be functionalized to bind to or otherwise interact with respective different analytes (e.g., by including respective different antibodies, aptamers, complimentary DNA or RNA sequences, proteins, receptors, or other binding agents), facilitating simultaneous imaging of such different analytes.

Identification of such spatially and spectrally multiplexed probes can include detecting the color and relative location of fluorophores of the probes. Detecting the color of a fluorophore could include detecting a spectrum of light emitted from the fluorophore, a wavelength of light emitted from the fluorophore, an intensity of light emitted from the fluorophore within one or more ranges of wavelengths, or detecting some other characteristic of the wavelength-dependence of the light emitted from the fluorophore. Additionally or alternatively, the intensity, phase, color, spectrum, or other properties of light emitted from the fluorophore in response to illumination by light at different wavelengths could be detected and used to determine a color, an excitation spectrum, a Raman spectrum, or some other identifying spectral information about the fluorophore. This detection can include the detection of spectral information about fluorophores that are separated by very small distances (e.g., by less than approximately 50 nanometers) according to the size and configuration of the probes.

In some examples, such detection of spectral information (e.g., to determine the color of fluorophores of a probe) can include applying light received from an environment that includes the probe (e.g., light emitted from the environment responsive to illumination of the environment) to optical elements that have one or more wavelength-dependent optical properties. In some examples, this could include applying the emitted light to one or more dichroic mirrors, diffraction gratings, or other wavelength-selective reflective elements, and imaging multiple different portions of the emitted light that have been separated by such elements (e.g., generating images of light emitted from the environment within respective different ranges of wavelengths). Additionally or alternatively, the light received from the environment could be applied to a chromatically dispersive element (e.g., a prism, a diffraction grating, an Amici prism) to refract, reflect, or otherwise manipulate the light in a wavelength-selective manner, e.g., to spectrally separate the received light. Such separated light could then be imaged (e.g., by a one-dimensional or two-dimensional array of light-sensitive elements).

Such a chromatically dispersive optical element could be controllable, e.g., to control a direction and/or magnitude of the wavelength-dependent separation of different wavelengths of the received light. The chromatically dispersive element could be controlled, over time, to change the direction and/or magnitude of the wavelength-dependent separation of the received light, and multiple images of the separated light could be taken corresponding to different directions and/or magnitudes of separation. Such multiple images could then be used to determine the location and color of fluorophores in an environment (e.g., via deconvolution of the images, based on information about the directions, magnitudes, or other information about the wavelength-specific separation of the light represented in each of the images). The determined colors and locations of multiple fluorophores could be used to identify probes in the environment, to determine the location and/or orientation of the probes, to determine the location and/or concentration of analytes in the environment, or to determine some other information about the probes, analytes with which the probes are configured to interact, and/or the environment from which the light was received.

In some examples, such a chromatically dispersive element could be a spatial light modulator (SLM) that includes a refractive layer disposed on a reflective layer. The refractive layer could be controllable (e.g., electronically controllable) to have a refractive index that varies spatially across a surface of the SLM according to a controllable gradient (e.g., a substantially linear gradient). Further, the controllable refractive index of the refractive layer could be chromatically dispersive, i.e., dependent on the wavelength of light refracted by the refractive layer. A magnitude, direction, or other property of the controllable gradient in the refractive index of the SLM could be controlled according to an application, e.g., to control an angle of reflection of light incident on the SLM, to control a degree of spectral dispersion of light reflected from the SLM (e.g., to control a spectral resolution at which an imager receiving the dispersed light could determine spectrographic information for the light reflected form the SLM), or according to some other application.

In some examples, detecting the color and relative location of fluorophores of the probes can include splitting light received from a particular region of an environment (e.g., a region that is being illuminated by a confocal microscope or otherwise confocally imaged) such that the light can be spatially imaged by a first light sensor and spectrally imaged by a second light sensor. This could include applying the received light to a partially silvered mirror, a polarizing mirror, or some other optical element(s) to split the light.

Spatially imaging a portion of the received light could include detecting, using a plurality of light-sensitive elements (e.g., pixels) of the first light sensor, a respective plurality of time-varying waveforms of light (e.g., waveforms of the intensity of the light) received from respective different locations of the particular region of the environment. Such time-varying waveforms could be used to determine the locations of different fluorophores in the region of the environment, e.g., by determining correlations between different time-varying waveforms. Such locations could be determined to a resolution beyond the diffraction limit of an optical system used to image the received light. Light received from a particular fluorophore (e.g., from a particular quantum dot) can exhibit similar patterns of intensity over time, such that there can be a higher correlation between time-varying waveforms of light received from locations proximate the location of the particular fluorophore.

Spectrally imaging a portion of the received light could include detecting, using a plurality of light-sensitive elements (e.g., pixels) of the second light sensor, a respective plurality of time-varying waveforms of light received from the particular region of the environment at respective different wavelengths. This could include applying the portion of the received light to a chromatically dispersive element (e.g., a prism, a diffraction grating, an SLM as described above) such that different light-sensitive elements of the second light sensor receive light having respective different wavelengths and/or within respective different ranges of wavelengths. Such time-varying waveforms could be used to determine the colors of different fluorophores in the region of the environment, e.g., by determining correlations between time-varying waveforms produced by the first light sensor and time-varying waveforms produced by the second light sensor. Light received from a particular fluorophore (e.g., from a particular quantum dot) can exhibit similar patterns of intensity over time, such that there can be a higher correlation between time-varying waveforms of light received from locations proximate the location of the particular fluorophore and time-varying waveforms of light at wavelengths that are emitted by the particular fluorophore (e.g., at one or more emission wavelengths of the fluorophore).

Other configurations, modes and methods of operation, and other embodiments are anticipated. For example, a target environment could be imaged, according to the methods described herein, when illuminated by light at different wavelengths, e.g., wavelengths corresponding to different excitation wavelengths of respective different fluorophores of one or more probes. Systems and/or methods described herein could include additional microscopic or other imaging modalities and/or optical systems or elements to improve the identification of probes as described herein or other contents of portions of a target environment according to an application. A system as described herein could include multiple light sources, multiple spatial light modulators, multiple chromatically dispersive elements (e.g., SLMs, prisms, diffraction gratings), multiple light sensors (e.g., cameras, spectrometers), controllable apertures (e.g., according to a confocal imaging configuration), multiple micromirror devices, and/or additional components according to an application. Systems and methods described herein could be used to identify and localize spatially and spectrally multiplexed probes in a variety of different environments, e.g., in vitro environments, in vivo environment, or ex vivo environments. Further, systems and methods as described herein could be configured or operated according to and/or in combination with a variety of different microscopic or other imaging techniques, e.g., stimulated emission depletion, ground state depletion, saturated structured illumination microscopy, 4 pi imaging, photobleaching, or other methods or techniques.

It should be understood that the above embodiments, and other embodiments described herein, are provided for explanatory purposes, and are not intended to be limiting.

II. Spatially and Spectrally Multiplexed Probes

As noted above, a number of different distinguishable fluorophores can be assembled into probes such that the ordering, relative locations, colors, or other properties of the fluorophores can be detected and used to identify different probes. By using multiple fluorophores (e.g., quantum dots, fluorescent proteins, or Raman dyes, or other materials that can absorb and re-emit light) and controlling the number, ordering, and/or relative spacing of the fluorophores within each probe, the number of identifiable probes can be much greater than the number of distinguishable fluorophores used to produce the probes. The fluorophores could be distinguishable by differing with respect to an excitation spectrum, an excitation wavelength, an emission spectrum, an emission wavelength, a Raman spectrum, a fluorescence lifetime, or some other properties that may differ between different types of fluorophore.

Such probes could include fluorophores arranged in a linear arrangement, a circular or elliptical arrangement (e.g., in a ring), a triangular arrangement, or according to some other geometry. In some examples, the fluorophores could be arranged according to a three-dimensional geometry (e.g., at the vertices of a tetrahedron or other shape), and detecting the relative locations of the fluorophores in order to identify the probes could include determining the relative locations of the fluorophores in three dimensions (e.g., by three dimensional confocal imaging, by imaging probe from multiple different directions).

FIG. 1 illustrates a number of example probes 100a, 100b, 100c. The example probes include different types of fluorophores 110a, 110b, 110c that have respective different colors (e.g., respective different emission wavelengths, respective different emission spectra) and that are arranged on respective backbone structures 120a, 120b, 120c. Each probe 100a, 100b, 100c further includes a respective binding agent 130a, 130b, 130c configured to selectively interact with a respective analyte (e.g., by reversibly or irreversibly binding to the analyte and/or to an element of the analyte). The first 100a and second 100b probes include fluorophores that are arranged in a substantially linear arrangement, while the third probe 100c includes fluorophores in a substantially circular arrangement.

As shown in FIG. 1, the first 100a and second 100b probes include the same number of fluorophores and number of each type of fluorophore (specifically, each includes one of each type of fluorophore). However, the ordering of the types of fluorophores on each probe is different, such that detecting the colors (or other identifying information, e.g., excitation spectrum, blinking dynamics) and locations of the fluorophores of a probe can facilitate identification of the probe. A probe could include multiple instances of a particular type of fluorophore (e.g., two instances of a blue quantum dot and one instance of a red quantum dot), could include multiple instances of a single type of fluorophore, and/or could include no instances of one or more types of fluorophores used to create a set of different probes.

The number of identifiable probes that is able to be created using a particular number of different types of fluorophores can be related to the number of fluorophores on each type of probe, the arrangement of the fluorophores on each probe (e.g., a linear arrangement, a ring arrangement), whether different types of probe have respective different numbers of fluorophores, or other factors. Note that the number of identifiably different probes can be reduced by symmetries between probes that are different but that may appear similar when imaged. For example, the third probe 100c could be indistinguishable from another probe that includes the same fluorophores, in the same order, but oriented at a different angle on the backbone 120c relative to the binding agent 130c and/or relative to some other element(s) of the probe 100c.

The fluorophores 110a, 110b, 110c could include a variety of substances and/or structures configured to inelastically scatter, absorb and fluorescently re-emit, or otherwise absorb and re-emit light. The fluorophores could include quantum dots, fluorescent proteins, fluorescent small molecules, Raman dyes, plasmonic rods or other plasmonic structures, or other substances or elements or combinations of elements configured to absorb light and to responsively emit light (e.g., by fluorescent absorption and re-emission, by inelastic scattering, by plasmonic excitation and photonic emission) in a manner that is detectable and that is distinguishable between different types of fluorophores. Quantum dots may be preferred, due to resistance to photobleaching and broad excitation spectra, such that multiple different quantum dots (e.g., quantum dots that emit light at respective different wavelengths in response to excitation) can be excited by illumination at a single wavelength. The different types of fluorophores may differ with respect to a wavelength of light emitted by the fluorophores; for example, the different types of fluorophores could be different types of quantum dots, each configured (e.g., by having a respective diameter, layer thickness, or composition) to emit light at a respective wavelength within a range of wavelengths, e.g., to emit light at a wavelength between approximately 500 nanometers and approximately 800 nanometers. Further, different types of fluorophore could operate via different mechanisms; for example, a first fluorophore of a probe could be a quantum dot, and a second fluorophore of the probe could be a fluorescent protein.

The backbone (e.g., 120a, 120b, 120c) of probes as described herein could be composed of a variety of materials or substances. For example, such backbones could be composed of single- or double-stranded DNA. A backbone could be composed of a single length of DNA folded back on itself and/or multiple lengths of DNA connected together to increase the rigidity of the backbone, e.g., by forming a DNA origami structure. This could include connected specified portions of one or more strands of DNA together using complementary staple strands of DNA. The fluorophores could be connected to such staple strands and/or to the DNA to which the staple strands are configured to bind, e.g., via covalent bonding or some other mechanism. The sequences of the staple strands and/or of the DNA strands to which the staple strands are configured to bind could be specified to control a shape, size, rigidity, or geometry of the backbone and/or to control the location of fluorophores on such a formed backbone. Different probes (e.g., probes having different numbers, types, spacings, and/or orderings of fluorophores) could be formed by using different staple strands and/or different sequences of base DNA to which such staple strands are configured to bind.

The rigidity of the backbone, the overall size of the probes, the spacing of the fluorophores, and/or some other properties of the probes could be specified to facilitate identification of the probes, motion of the probes within an environment of interest, or to facilitate some other process related to the probes and/or to an environment of interest. For example, the probes could be formed to have a length, a diameter, or some other largest dimension that is less than approximately 1 micron, e.g., to facilitate motion of the probes within cells or other environments of interest and/or to minimize the effect of such probes on biological or chemical processes within a cell or other environment of interest. Correspondingly, the fluorophores of such probes could be separated in space (e.g., along the length of a linear backbone, or along the circumference of a ring-shaped backbone) by a distance that is sufficiently large that the colors of adjacent fluorophores can be resolved, e.g., by distances greater than approximately 20 nanometers. Further, the fluorophores could be separated in space by a sufficiently small distance such that a desired number of fluorophores can be located on the backbone, e.g., by distances less than approximately 50 nanometers. Further, the backbone could have a rigidity that is sufficiently great that the backbone is substantially rigid across distances greater than the distances between the fluorophores on the backbone, e.g., such that the order of fluorophores along the backbone of the probe can still be determined when the backbone is being deformed by thermal process or other forces expected to be present in an environment of interest.

As noted above, each type of probe (e.g., 100a, 100b, 100c) could be configured to selectively bind with or otherwise selectively interact with an analyte of interest, or to otherwise selectively interact with an environment of interest (e.g., to be selectively taken up via endocytosis by a cell type of interest) to facilitate detection of some properties of the environment of interest (e.g., to detect a location or concentration of a protein, a DNA segment, a cytoskeletal element, or some other analyte of interest). This could include the probes including respective different binding agents 130a, 130b, 130c that are configured to selectively bind to or otherwise selectively interact with an analyte of interest. Such a binding agent could include a protein, an antibody, a receptor, a recognition protein, a DNA segment, an aptamer, an RNA segment, a small molecule, or some other element configured to selectively interact with and/or to be interacted with by an analyte of interest.

III. Identifying Probes by Repeated Imaging using a Spatial Light Modulator

A variety of methods could be used in order to locate and identify, in an environment of interest, spatially and spectrally multiplexed probes as described elsewhere herein. Such methods can include detecting the locations and colors of fluorophores in the environment and using such determined information to determine the identity or other information (e.g., location, orientation) of probes in the environment by matching detected patterns of fluorophore types (e.g., orders of colors of linearly, circularly, or otherwise arranged patterns fluorophores) within the environment to known patterns of fluorophores that corresponds to the identities of potential probes in the environment. Detecting the color of a fluorophore could include determining an emission spectrum, a characteristic wavelength, or some other characteristic(s) of the spectral content of light emitted from a fluorophore.

Detection of the locations and colors of fluorophores can include applying light received from an environment of interest (e.g., light emitted from fluorophores in the environment in response to illumination) to a chromatically dispersive element (e.g., a prism, a diffraction grating, or some other element(s) configured to reflect, refract, and/or diffract light in a wavelength-specific manner) and imaging light that is spectrally dispersed due to interaction with the chromatically dispersive element. Light that is spectrally dispersed may exhibit a change in an angle of propagation of the light, a direction of polarization of light, or a change in some other properties of the light that is related to the wavelength of the light. This could include changing, in a wavelength-dependent way, an angle of propagation of light received from an environment such that redder wavelengths of such spectrally dispersed light are shifted, relative to light-sensitive elements (e.g., pixels) of a light sensor (e.g., a camera), in a first direction by a first amount while bluer wavelengths are shifter in the first direction by a lesser amount and/or are shifted opposite the first direction. An image generated from such spectrally dispersed light will be distorted, relative to a non-spectrally dispersed image of the environment, in a manner that is related to the direction, magnitude, or other property of the spectral dispersion caused by the chromatically dispersive element. By controlling such a direction, magnitude, and/or other property of the spectral dispersion of the light during different periods of time and imaging the light so dispersed during the different periods of time, the color and location of fluorophores in the environment can be determined.

In some examples, a 2-dimensional array of light sensitive elements of a light sensor (e.g., a 2-dimensional array of pixels of a camera) could be used to image such spectrally dispersed light. In such examples, wherein light is received from a plurality of regions of a target (e.g., as in bright-field microscopy), each light-sensitive element of such a 2-dimensional array could receive light of a variety of different wavelengths from a variety of respective different locations of the target. A correspondence between an individual light-sensitive element of such an array to light of a range of locations of a target at a range of corresponding wavelengths could be determined (e.g., by modeling or simulation of elements of such an imaging system, by empirical testing of such a system using one or more calibration targets having respective known patterns of spectrographic properties) and such a correspondence could be used to determine spectrographic information (e.g., a color) for one or more locations of an imaged target based on a number of images of the target taken while operating a chromatically dispersive element according to a respective number of different directions and/or magnitudes of spectral dispersion of the received light (e.g., via a process of deconvolution). Such information could be used to determine the locations and colors of fluorophores in the target.

In an example, the chromatically dispersive element could include a prism, diffraction grating, or other element(s) that is mechanically actuated, e.g., to control a direction of the spectral dispersion of light applied to the prism. In another example, the chromatically dispersive element could include a spatial light modulator (SLM) composed of a chromatically dispersive refractive layer disposed on a reflective layer. Controlling a direction and magnitude of a gradient of the refractive index of the refractive layer across the SLM could provide control of a direction, magnitude, or other properties of the spectral dispersion of the imaged light received from the target.

Figure 2B:
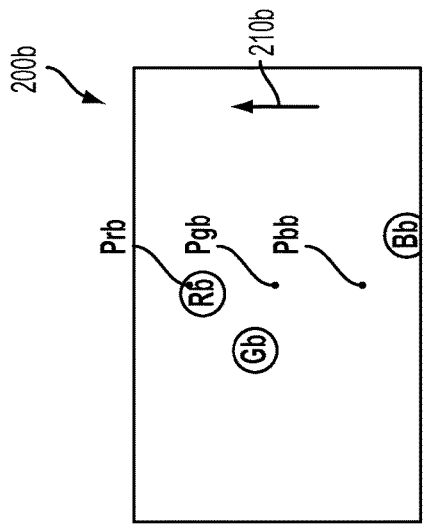
FIG. 2B illustrates an example image of the probe of FIG. 2A.
Figure 2D:
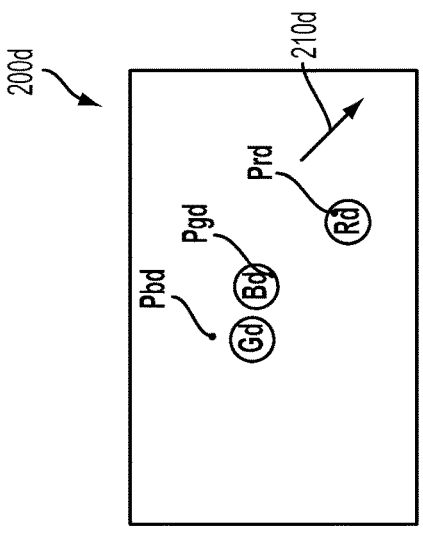
FIG. 2D illustrates an example image of the probe of FIG. 2A.
Figure 2A:
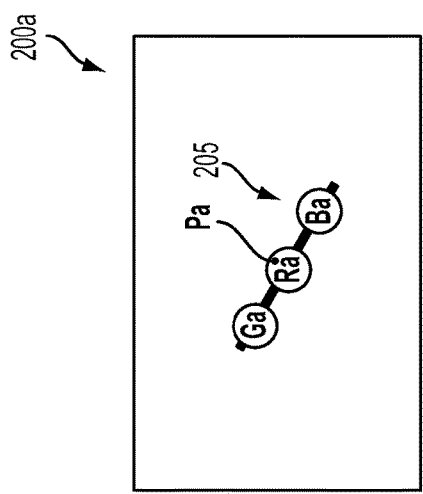
FIG. 2A illustrates an example probe that could be imaged.

FIG. 2A illustrates a target 200a. Within the target 200a is a probe 205 that includes, in order, a green fluorophore, Ga, a red fluorophore, Ra, and a blue fluorophore, Ba, disposed on a substantially linear backbone. Thus, spectrographic properties (e.g., colors) of locations of the target 200a are such that red light is emitted from the location of Ra in response to illumination, green light is emitted from the location of Ga in response to illumination, and blue light is emitted from the location of Ba in response to illumination. The target 200a could be imaged by an imaging system as described elsewhere herein.

FIG. 2B illustrates a portion of a first image 200b of the target 200a. This first image 200b is taken of light received from the target that has been spectrally dispersed by a chromatically dispersive element during a first period of time. In this example, the chromatically dispersive element includes an SLM that includes a chromatically dispersive refractive layer disposed on a reflective layer, wherein a direction and magnitude of a gradient of the refractive index of the refractive layer across the SLM is controllable. The first image 200b includes illuminated regions Rb, Gb, and Bb due to illumination of corresponding regions of a light sensor by spectrally dispersed light from the red, green, and blue fluorophores (Ra, Ga, and Ba), respectively, of the probe 205. The SLM is operated during the first period of time such that its refractive layer has a refractive index that varies spatially across the SLM according to a gradient in a first direction (indicated by the arrow 210b) such that light of different wavelengths is dispersed in the first direction 210b when imaged by a light sensor (e.g., as in the first image 200b). Such dispersion affects imaging of the dispersed light during the first period of time by shifting light at longer wavelengths farther in the direction of the arrow within the first image 200b; as a result, the first image 200b of the target 200a includes illuminated regions Rb, Gb, and Bb arranged as shown.

Figure 2C:
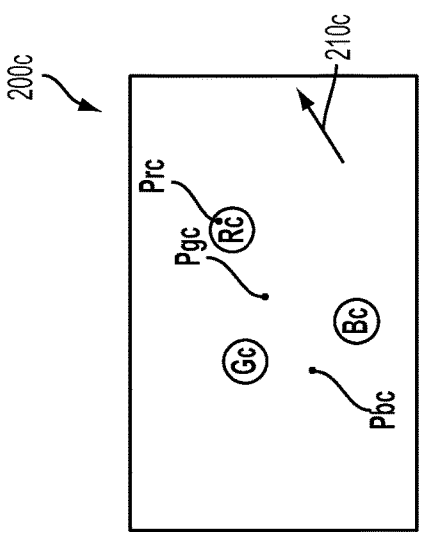
FIG. 2C illustrates an example image of the probe of FIG. 2A.

An imaging system as described elsewhere herein could be operated in this way during a plurality of further periods of time to generate a further plurality of respective images of light received from the target and dispersed by the SLM (or by some other controllable chromatically dispersive element(s)). The SLM could be operated during such further periods of time such that its refractive layer has a refractive index that varies spatially across the SLM according to respective gradients in respective further directions and/or having respective further magnitudes or according to some other set of respective patterns. FIGS. 2C and 2D illustrate portions of a second image 200c and a third image 200d, respectively, of the target 200a. The second image 200c and third image 200d are taken of light received from the target that has been spectrally dispersed by the SLM during respective second and third periods of time. The second image 200c and third image 200d include respective sets of illuminated regions Rc, Gc, and Bc and Rd, Gd, and Bd due to illumination of corresponding regions of the light sensor by dispersed light from the red, green, and blue fluorophores (Ra, Ga, and Ba), respectively, of the probe 205.

The SLM is operated during the second and third periods of time such that its refractive layer has a refractive index that varies spatially across the SLM according to a gradient in a second direction and a third direction, respectively (indicated by the arrows 210c, 210d, respectively) such that light of different wavelengths is dispersed in the second direction 210c and third direction 210d when imaged during the second and third periods of time by the light sensor (e.g., as in the second 200c and third 200d images). Such dispersion affects imaging of the dispersed light during the second and third periods of time by shifting light at longer wavelengths farther in the direction of respective arrows within the second 200c and third 200d images. As a result, the second image 200c of the target 200a includes illuminated regions Rc, Gc, and Bc and the third image 200d of the target 200a includes illuminated regions Rd, Gd, and Bd arranged as shown.

Such multiple images of the target 200a, taken from light dispersed in respective multiple ways by the SLM operated according to respective multiple configurations of refractive index (e.g., according to gradients having respective different directions and/or magnitudes) could be used to determine spectrographic information (e.g., colors) for one or more locations (e.g., particular region Pa) of the target 200a and/or to determine the location of fluorophores (g., Ra, Ga, Ba) or other light-emitting contents of the target 200a. In some examples, such information could be determined for a plurality of regions across the target 200a allowing, e.g., hyperspectral imaging of the target 200a. A plurality of such images, in combination with a model or other algorithm describing the effects of the plurality of patterns of refractive index of the SLM and/or the effects of such configurations to disperse light received from the target 200a during the periods of time corresponding to the plurality of images. Such a determination could include a process of deconvolution or some other computational process.

In an illustrative example, spectrographic information about the particular region Pa of the target 200a, corresponding to the location of the red fluorophore, Ra, could be determined based on the amplitude or other detected information about light detected at regions of the light sensor (e.g., by one or more light-sensitive elements or pixels of the light sensor) corresponding, according to the location of the particular region Pa and the dispersive effects of the SLM during the plurality of periods of time corresponding to the plurality of images.

For example, an amplitude of red light emitted from Pa, where the red fluorophore is located, in response to illumination by the imaging system could be determined based on a linear combination or other function of the light detected at points Prb, Prc, and Prd in the first 200a, second 200b, and third 200c images of the target. Similarly, an amplitude of green light emitted from Pa in response to illumination by the imaging system could be determined based on a linear combination or other function of the light detected at points Pgb, Pgc, and Pgd in the first 200a, second 200b, and third 200c images of the target and an amplitude of blue light emitted from Pa in response to illumination by the imaging system could be determined based on a linear combination or other function of the light detected at points Pbb, Pbc, and Pbd in the first 200a, second 200b, and third 200c images of the target. The amount of green and blue light emitted from Pa would be less than the amount of red light emitted from Pa because the red fluorophore emits more light, in response to being illuminated, at red wavelengths than at blue or green wavelengths. An intensity of light at a variety of different wavelength that is emitted from Pa could be determined, based on the light detected at respective different points in respective different images, and used to determine the color of a fluorophore in the environment 200a.

The location of such corresponding locations (e.g., Prb, Prc, Prd, Pgb, Pgc, Pgd, Pbb, Pbc, Pbd) could be determined based on a model of an imaging system (e.g., based on the magnitude and direction of a gradient of refractive index of the refractive layer across the SLM) and/or on an empirical measurement of the properties of the imaging system (e.g., based on a set of images of a calibration target having known spectrographic information/content or some other calibration information or procedure). Note that the colors (red, green, and blue) and operation of the SLM to disperse light in the illustrated different directions are intended as non-limiting examples; different wavelengths and/or ranges of wavelengths of spectrographic information could be determined for locations of a target, e.g., locations of fluorophores in a target. Further, an SLM could be operated to have a pattern of refractive index according to gradients having respective different directions, magnitudes, or according to some other set of patterns of refractive index.

An SLM as described herein and used to provide hyperspectral imaging and/or the determination of spectrographic data (e.g., a color) for one or more locations of a target (e.g., for locations of fluorophores of probes in a target) has one or more chromatically dispersive properties that are electronically (or otherwise) controllable and that allow the SLM to spectrally disperse light presented to the SLM. A chromatically dispersive property of an object or material is an optical property that has a dependence on the wavelength of light interacting with the object or material. For example, certain glasses have chromatically dispersive refractive indexes in that the refractive indexes of the glasses are different for different wavelengths of light. In another example, certain diffraction gratings have different effective absorbances and/or angles of reflection for different wavelengths of light. Thus, such objects or materials having chromatically dispersive properties can be used to spectrally disperse light, i.e., to interact with light applied to the object or material in a wavelength-dependent manner such that light emitted from the object or material (e.g., reflected from, absorbed by, transmitted through, optically rotated by) has one or more properties (e.g., an angle, an amplitude, an orientation of polarization) that are wavelength-dependent that were substantially not wavelength-dependent in the applied light. As an example, a prism (e.g., a triangular prism) composed of a glass having a chromatically dispersive refractive index could interact with a beam of white light (e.g., a beam containing light at a variety of amplitudes across the visible spectrum) such that light emitted from the prism at a various visible wavelengths is emitted at respective different angles (e.g., as a 'rainbow').

An example of such an electronically-controlled chromatically dispersive element is illustrated in cross-section in FIG. 3A. FIG. 3A illustrates the configuration of a spatial light modulator (SLM) 300 that includes a reflective layer 320 (composed of, e.g., aluminum, silver, or some other material that is reflective to light within a range of wavelengths of interest) disposed beneath a refractive layer 310. A substantially transparent first electrode 340 (composed, e.g., of indium-tin-oxide (ITO) or some other material that is electrically conductive and substantially transparent to light within a range of wavelengths of interest) is located on the refractive layer 310 opposite from the reflective layer 320. Light directed toward the SLM 300 could be transmitted through the first electrode 340, refracted by the refractive layer 310, reflected by the reflective layer 320, refracted again by the refractive layer 310, and transmitted away from the SLM 300 through the first electrode 340. The SLM 300 additionally includes a dielectric layer 350 and a plurality of further electrodes 330 (including second 335a, third 335b, and fourth 335c electrodes) disposed beneath the reflective layer 320. A controller 360 is configured to control voltages between the first electrode 340 and each of the further electrodes 330. Note that the reflective layer 320 and dielectric layer 350 are illustrated as distinct structures of the SLM 300, but in practice could be the same structure (e.g., the dielectric layer 350 could be composed of a reflective material such that the reflective layer 320 is simply the surface of the dielectric layer 350, the reflective layer 320 could comprise a polished or otherwise formed or treated surface of the dielectric layer 350 such that the reflective layer 320 is reflective).

The refractive layer 310 is composed of a material (e.g., a liquid crystal) that is chromatically dispersive with respect to its refractive index. That is, the refractive index of the refractive layer 310 depends on the wavelength of light refracted by the refractive layer 310. In some examples, the refractive index of the refractive layer 310 could vary substantially linearly with wavelength for wavelengths within a specified range of wavelengths (e.g., visible wavelengths, a range of wavelengths including emission wavelengths of two or more fluorophores). Further, the refractive index of the refractive layer 310 can be controlled electronically by applying a controlled electric field to the refractive layer 310, e.g., by applying a voltage between the first electrode 340 and one or more of the further electrodes 330. The refractive index of the refractive layer 310 could be related to a linear or nonlinear function of a DC voltage, an amplitude, frequency, duty cycle, pulse width, or other property of an AC voltage, or some other property of voltage applied between the first electrode 340 and one or more of the further electrodes 330. Further, the refractive index of individual regions or cells of the refractive layer 310 could be controlled independently or semi-independently by applying different voltages, voltage waveforms, or other different electronic signals between the first electrode 340 and one or more of the further electrodes 330 corresponding to the individual regions or cells of the refractive layer 310. For example, the refractive index of first 315a, second 315b, and third 315c regions of the refractive layer 310 could be controlled by controlling a voltage or voltage waveform applied between the first electrode 340 and the first 335a, second 335b, and third 335c further electrodes, respectively.

Note that the SLM 300 is illustrated in cross-section in FIG. 3A and thus shows only a single row of regions (e.g., 315a-c) and corresponding electrodes (e.g., 335a-c) of the SLM 300. The SLM 300 could include a regular, two-dimensional array of such regions. Such an array could include a rectangular, square, hexagonal, or other repeating or non-repeating array of such regions and electrodes. Alternatively, an SLM could be configured to have electrodes and corresponding cells or other regions of a refractive layer according to some other pattern or application, e.g., a repeating pattern of linear electrodes (e.g., a 1-dimensional array of regions across the surface of the SLM). The voltages, voltage waveforms, or other electronic signals applied to the electrodes could be controlled such that the refractive index of the refractive layer varies across the surface of the SLM according to a specified pattern, e.g., according to a locally or globally substantially linear or nonlinear gradient. Such a local or global gradient could have a specified magnitude, a specified direction, or some other specified properties. Further, such specified patterns (e.g., gradients) could be changed over time according to some application. For example, light could be received from a target, reflected from such an SLM, and imaged by a light sensor, camera, or other imaging element to allow image capture of light received from a target during a plurality of periods of time when operating the SLM according to respective different patterns (e.g., gradients having respective specified magnitudes and directions) to spectrally disperse the imaged light in a plurality of respective ways, allowing determination of spectrographic information for regions of the target based on the plurality of images, e.g., via a process of deconvolution.

FIG. 3B illustrates a variety of functions describing the dependence of the refractive index of regions of the refractive layer 310 (the vertical axis, 'RI') on the wavelength of refracted light (the horizontal axis, 'WAVELENGTH') when composed of different materials and/or when exposed to different electrical fields (e.g., when a specified voltage or voltage waveform is applied between the first electrode 340 and one of further electrodes 330 corresponding to a region of the SLM 300). 'B', 'G', and 'R' indicate the wavelengths of blue, green, and red light, respectively.

Functions X, Y, and Z illustrate the wavelength-dependent refractive index of a first refractive layer material composition. The first refractive layer material composition has a refractive index that varies substantially linearly across the illustrated range of wavelengths. Functions X, Y, and Z illustrate the refractive index of a region of the first refractive layer material composition as an applied electronic signal is varied (e.g., X, Y, and Z are the refractive index of the region as a voltage between electrodes opposite the cell is increased). X, Y, and Z show increasing overall refractive index as well as a decreasing slope of dependence between the refractive index and wavelength. Similarly, functions V and W illustrate the wavelength-dependent refractive index of a second refractive layer material composition; V and W illustrate the refractive index of a region of the second refractive layer material composition as an applied electronic signal is varied.

Note that the illustrated functions are intended to illustrate configurations and operations of embodiments described herein, and not to limit the embodiments described herein or to describe any particular refractive layer material composition or dependence of optical properties thereof on electronic signals. A refractive index at one or more wavelengths, a slope and/or offset of the refractive index across a range of wavelengths, a nonlinearity of the relationship between the refractive index and wavelength, or some other property of the refractive index of material included in a refractive layer of an SLM as described herein could change linearly or nonlinearly with one or more properties of an applied electrical signal (e.g., an electric field magnitude, an electric field direction, an applied current magnitude, an applied current direction, a frequency, duty cycle, pulse width, or other property of an applied electrical signal).

FIG. 3C illustrates the use of an SLM 301 configured similarly to SLM 300 and having a refractive layer composed of the first material composition. The SLM 301 is operated such that the refractive layer has a substantially linear gradient of refractive index between the locations indicated by 'X' and 'Y' and such that the locations indicated by 'X' and 'Y' have wavelength-dependent refractive indexes corresponding to the functions 'X' and 'Y', respectively (e.g., by controlling electrodes of regions proximate to 'X' and 'Y' according to corresponding voltages or voltage waveforms and controlling one or more regions located between 'X' and 'Y' according to some intermediate voltages). Incoming light 380c includes light at wavelengths corresponding to the 'R', 'G', and 'B' indications in FIG. 3B. The incoming light 380c is reflected and refracted by the SLM 301 and emitted as reflected light 390c. Due to the wavelength-dependence of the refractive index of the refractive layer of the SLM 301, reflected light 390c is spectrally dispersed (illustrated as separate 'R', 'G', and 'B' rays of light). The angle of each ray of the reflected light 390c could be related to the thickness of the refractive layer of the SLM 301 and the pattern of change of the refractive index of the refractive layer for each ray across the refractive layer. For example, the angle of the 'B' ray could be related to a magnitude and/or angle of a gradient of the refractive index of the refractive layer for light at wavelength 'B' across the SLM 301 in the area proximate the intersection of the SLM 301 and the incoming light 380c.

An amount of spectral dispersion of light reflected by an SLM could be increased by increasing a magnitude of a gradient or other rate of change in a pattern of the refractive index of the refractive layer. Such an increase in spectral dispersion could allow spectrographic information for a received light to be determined with a higher spectral resolution, e.g., by causing light of two different wavelengths to be detected by light-sensitive elements (e.g., pixels) of a light sensor that are farther apart by increasing an angle between rays of dispersed light at the two different wavelengths.

Note that the described regular array of electrodes disposed as part of an SLM to allow the electronic control of the refractive index of respective cells or other specified regions of a refractive layer (or other refractive element(s)) of the SLM is intended as one example embodiment of an SLM having a refractive layer having a refractive index that can be electronically controlled to vary across the refractive layer according to a controllable gradient having at least one of a specified direction or magnitude. Alternative embodiments could electronically control one or more lasers or other light sources to optically control the refractive index of a refractive element of an SLM. Other configurations and operations of an SLM as described herein are anticipated. Further, an SLM could be operated in a transmissive mode, i.e., could lack a reflective layer. In such examples, a beam of light (e.g., a beam of light received from an illuminated target) could be spectrally dispersed by the SLM by being transmitted through a refractive layer of the SLM that has a pattern of refractive index that can be electronically controlled. In some examples, an SLM could act to provide electronically controlled spectral dispersion of a beam of light by controlling a pattern of reflective and absorptive elements on a surface and/or within a volume of the SLM to provide a diffraction grating having one or more properties (e.g., a grating spacing, a grating width, a grating orientation) that can be electronically controlled to control one or more properties of spectrally dispersed light reflected from and/or transmitted through the SLM in response to receiving light from a target.

In order to produce images of a target, as described above, that can be used to identify probes in the target by determining the locations and colors of fluorophores of the probes in the target, an SLM (e.g., 200) or other chromatically dispersive element as described elsewhere herein could be incorporated into an imaging system that includes additional elements, e.g., sources of illumination, optical systems, apertures, light sensors, or other elements configured to illuminate a target, to apply light responsively emitted from the target (e.g., from fluorophores of probes of the target) to the SLM and then to apply such light that has interacted with (e.g., by spectrally dispersed by) the SLM to a light sensor to be imaged. Such illumination and/or reception of light can be of/from a wide area of the target (e.g., bright-field microscopy) or of/from some specified region of the target (e.g., a plurality of specified small volumes of the target, as in confocal microscopy). Spectrographic information could be detected/determined for one or more regions of the target by illuminating the target with multiple lights having multiple respective spectrographic properties (e.g., containing light at multiple respective wavelengths) and/or by detecting a wavelength-dependence of the amplitude or other properties of the received light (e.g., by detecting the amplitude of the received light within multiple ranges of wavelengths).

Figure 4:
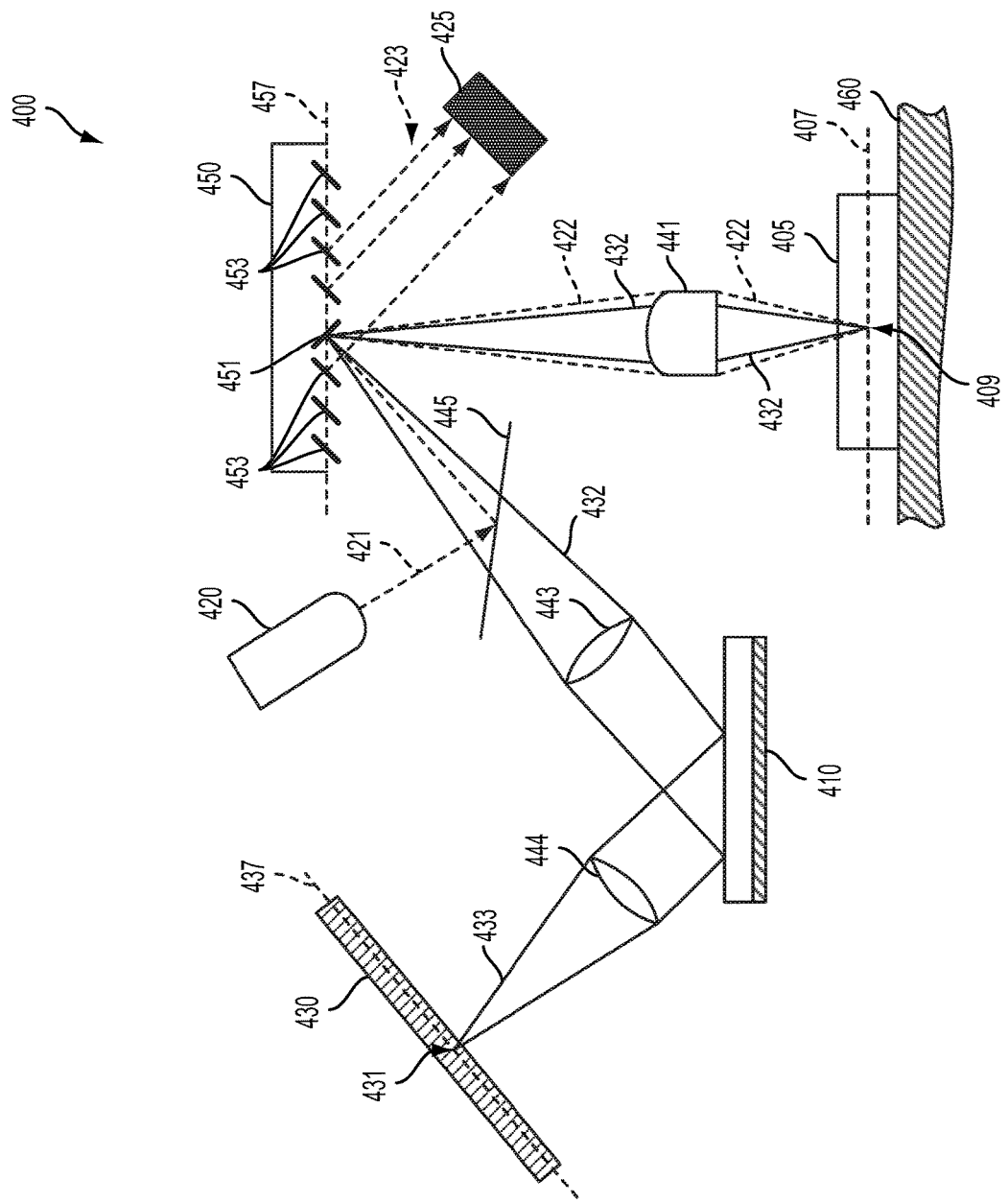
FIG. 4 illustrates an example imaging apparatus.

FIG. 4 illustrates in cross-section elements of an example imaging system 400 configured to image a target 405. The system 400 includes a light source 420 (e.g., a laser), a light sensor 430 (illustrated as a plane of light-sensitive elements located on a focal plane 437 of the light sensor 430), a micromirror device (MD) 450 (that includes a plurality of electronically actuated micromirrors located on a focal plane 457), a spatial light modulator (SLM) 410, and an optical system (including an objective 441, first 443 and second 444 relay lenses, a dichroic mirror 445, and an optical sink 425) configured to direct light to and from the target 405 and between the elements of the system 400. The system 400 additionally includes a stage 460 to which the target 405 is mounted. Note that the MD 450 and light sensor 430 comprise two-dimensional arrays of micromirrors and light-sensitive elements, respectively. Further, note that the optical system (e.g., 441, 443, 444, 445) and SLM 410 are configured to direct light between the target, 405, MD 450, and light sensor 430 such that locations on the focal surfaces 457, 437 of the MD 450 and light sensor 430 correspond to respective locations on a focal surface 407 that passes through the target 405.

The system 400 illuminates a specified region 409 on the focal surface 407 in the target 405 by emitting a first illumination 421 from the light source 420 and reflecting the first illumination 421 from the dichroic mirror 445 toward the MD 450. A selected set of at least one mirror 451 of the MD 450 (illustrated in FIG. 4 as a single mirror) that has a location on a focal surface 457 of the MD 450 corresponding to the specified region 409 is controlled to reflect the first illumination 421 toward the target 405 as in-focus illumination 422 via the objective 441. Other mirrors 453 of the MD 450 are controlled to reflect the remainder of the first illumination 421 as waste illumination 423 toward the optical sink 425 to be absorbed. As illustrated, a single mirror (451) is controlled to illuminate (and to receive light from) a corresponding region 409 of the target 405; however, additional mirrors (e.g., selected from other mirrors 453) could be operated simultaneously, sequentially, or according to some other scheme to illuminate (and to receive light from) corresponding additional regions of the target 405.

The system 400 receives light (including conjugate light 432) emitted from the specified region 409 in response to illumination via the objective 441. The conjugate light 432 arrives, in-focus, at the selected mirror 451 and is reflected (through the dichroic mirror 445) toward the SLM 410. The first relay lens 443 (and/or some other optical elements of the system 400) collimates the received light and presents the substantially collimated light to the SLM 410. The SLM 400 reflects the conjugate light 432 as spectrally dispersed light 433 toward the second relay lens 444 that is configured to present the spectrally dispersed light 433 in-focus to a specified region 431 on a focal surface 437 of the light sensor 430 corresponding to the specified region 409 (e.g., to a region of the light sensor having one or more light-sensitive elements and/or pixels of the light sensor 430). The SLM 410 is configured and/or operated such that the spectrally dispersed light 433 is spectrally dispersed relative to the conjugate light 432 in a controlled manner such that spectrographic information of the particular region 409 and/or of the conjugate light 432 (e.g., a color and/or location of one or more fluorophores of one or more probes located at the particular region 409) can be detected or determined. In some examples, the spectrally dispersed light 433 is spectrally dispersed in a manner related to an electronically controlled direction, magnitude, and/or some other property of a spatial gradient in the refractive index of a layer of the SLM 410.

Note that the system 400 and elements thereof shown in FIG. 4 are intended as a non-limiting example of systems and methods as described elsewhere herein for generating hyperspectral or otherwise spectrographic images of a target (e.g., 405) in order to, e.g., identify probes within a target by determining locations and colors of fluorophores of probes in the target. Imaging systems could include more or fewer elements, and could image a target according to similar or different methods. As shown, the system 400 can be operated to image the target 405 confocally; i.e., to illuminate a specified region of the target 409 in-focus and to receive light responsively emitted from the specified region 409 in-focus using the micromirror device 450 (e.g., to control the spatial pattern of light emitted toward and received from the target 405). Illumination could be delivered to the target 405 and light received from the target 405 in different ways and using differently configured elements (e.g., different optics). The target 405 could be illuminated along an optical path separate from the optical path used to receive light responsively emitted from the target 405. For example, illumination could be transmitted through a target before being received to image the target. Particular regions of the target 405 could be illuminated, and light received from such regions, by steering a beam of illumination using one or more controllable mirrors, lenses, diffraction gratings, or other actuated optical elements.

An SLM (e.g., 410) as described herein could be configured and operated as part of a variety of different imaging systems (e.g., bright-field microscopes, 4-pi microscopes, confocal microscopes, fluorescence microscopes, structured illumination microscopes, dark field microscopes, phase contrast microscopes) to provide controlled spectral dispersion of light for a variety of applications (e.g., to allow hyperspectral or otherwise spectrographic imaging of a target in order to identify spatially and spectrally multiplexed probes within the target). For example, an SLM as described herein could be inserted into the path of light received by some other variety of microscope or imager (e.g., a bright-field microscope). The SLM could be operated to have a plurality of different specified magnitudes and/or directions of refractive index gradient across the SLM during a respective plurality of periods of time, and such an imager could be configured to generate a plurality of images of the received light reflected from the SLM during the plurality of periods of time. In such examples, spectrographic information about a particular portion of a target (e.g., a target from which the received light is received) could be determined based on a plurality of detected amplitudes (or other properties of light) of pixels across the plurality of images according to a model (e.g., a black-box model fitted to calibration data for the imager) or other description of the relationship between the detected amplitudes and spectrographic properties (e.g., colors) of regions of the target (e.g., regions that include one or more fluorophores of one or more probes) depending on the configuration of the SLM (e.g., via a process of deconvolution performed on the plurality of images and based on a wavelength-dependent point-spread function determined for the imager). Further, an SLM as described herein could be used to control a direction and/or spectral content of a beam of illumination, e.g., to effect a tunable light source in combination with a source of broad-spectrum light and, e.g., an aperture.

The light source 420 could include a variety of light-emitting elements configured to produce illumination 421 having one or more specified properties (e.g., specified wavelength(s)). This could include lasers, light-emitting diodes (LEDs), or other substantially monochromatic light sources. Additionally or alternatively, the light source 420 could include a light emitting element that emits light across a wider range of wavelengths (e.g., an arc lamp). In some examples, this non-monochromatic light could be emitted through one or more filters (e.g., filters including one or more Bragg reflectors, prisms, diffraction gratings, slit apertures, monochromators) configured to only allow the transmission of light within a narrow range of wavelengths. In some examples, the light source 420 could be configured to emit light at a specified wavelength or having some other specified property to excite a fluorophore (e.g., to excite a fluorescent protein, to excite one or more types of quantum dots) in the target 405 or to otherwise selectively interact with (e.g., excite, quench, photobleach) one or more elements of the target 420. For example, the illumination 421 could include light at substantially one wavelength (i.e., could contain light of wavelengths within a specified narrow range of wavelengths) corresponding to an excitation wavelength of a fluorophore (e.g., a green fluorescent protein, a dsRED protein) in the target 405.

In some examples, the light source 420 could include a tunable laser or some other light-emitting element(s) controllable to emit light at any of a plurality of different wavelengths (e.g., wavelengths ranging between approximately 400 nanometers and approximately 2.5 micrometers). Such a tunable laser could include an excimer laser, a dye laser, a $CO_2$ laser, a free-electron laser, or some other laser element configured to emit light at a plurality of different, controllable wavelengths. In some examples, the wavelength of the light emitted by such a tunable laser could be controlled by controlling a geometry or size of one or more elements (e.g., a reflector, a resonating cavity) of the tunable laser. In some examples, a Bragg reflector or other element of the light source 420 (e.g., of a tunable laser) could be rotated or otherwise actuated to control the wavelength of light emitted by the light source 420. In some embodiments, the light source 420 could include a plurality of lasers or other sources of substantially monochromatic light configured to emit light at wavelengths corresponding to respective different wavelengths (e.g., excitation wavelengths of respective fluorophores in the target 405), and operation of the light source 420 to emit light of a particular wavelength could include operating the corresponding laser of the light source 420 to emit light at the controlled wavelength. Other configurations and operations of a light source 420 are anticipated.

The light sensor 430 could include a plurality of light-sensitive elements disposed on the focal surface 437. The light-sensitive elements could be configured to detect the intensity or other properties of light received by the light sensor 430 across a broad range of wavelengths (e.g., across a range of wavelengths of light that can be emitted by elements of the target 405, e.g., a range that includes emission wavelengths of one or more quantum dots, fluorescent proteins, or other fluorophores in the target 405). That is, the light sensor 430 could be configured to act as broadband monochrome light sensor, receiving light from the target 405 (via, e.g., the SLM 410, MD 450, and optical system) during a plurality of periods of time and outputting a respective plurality of images related to the absorption, fluorescent re-emission, or other interactions of the target 405 with light (e.g., light of a corresponding plurality of wavelengths) emitted by the light source 420 during a the respective plurality of periods of time. This could include the light sensor 430 containing a regular two-dimensional (or otherwise arranged) array of light sensitive elements (e.g., photodiodes, phototransistors, pixels of a charge-coupled device (CCD), active pixel sensors) disposed on the focal surface 437 configured such that the output of an individual light sensitive element is related to the intensity of the light received by the light sensor 430 from a particular direction and at a particular wavelength (corresponding to a particular portion of the target 405 and the configuration of the SLM 410 and/or MD 450).

Note that the configuration and/or operation of the system 400 to illuminate and to receive light from a specified region 409 on a focal surface 407 of the target 405 is intended as a non-limiting example. Alternatively, a larger and/or differently-shaped region of the target (e.g., a line within the target; substantially the entire target and/or the entire target within a field of view of the imaging system) could be illuminated by operating the mirrors 451, 453 of the MD 450 according to a different set of controlled angles than those illustrated. For example, a plurality of spatially separated regions proximate to the focal surface 407 of the target 405 could be illuminated and imaged simultaneously by controlling a corresponding plurality of spatially separated mirrors of the MD 450 to reflect the first illumination 421 toward the plurality of the regions of the target 405. The mirrors 451, 453 of the MD 450 could be controlled according to some other pattern, e.g., to approximate some other coded aperture on the focal surface 457 of the MD 450. Further, the light source 420 could emit illumination at a controllable wavelength (e.g., illumination that is substantially monochromatic, but having a wavelength that can be altered by operation of the light source) and spectrographic information could be determined for regions of the target 405 based on images of the target 405 generated when the target 405 is illuminated by different wavelengths of light (e.g., to generate a corresponding plurality of emission spectra for the region corresponding to the different wavelengths of illumination).

Further, note that the location of the focal surface 407 within the target 405 could be controlled (e.g., to allow imaging of elements of the target 405 at different depths within the target 405). In some examples, the stage 460 could be actuated relative to other elements of the system 400 (e.g., relative to the objective 441) such that a location of the target 405 in one or more dimensions could be controlled. For example, the stage 460 could be actuated in a direction parallel to the direction of the conjugate illumination 432 (i.e., in the vertical direction of FIG. 4) such that the location (e.g., the depth) of the focal surface 407 within the target 405 could be controlled. In such an example, a plurality of images and/or spectrographic information could be detected/determined of the target 405 when the focal surface 407 is controlled to be at variety of respective locations (e.g., depths) within the target 405, allowing a 3-dimensional image of the target 405 to be generated from the plurality of images and/or spectrographic information. In some examples, the location of the particular region 409 on the focal surface 407 within the target 405 could be controlled by actuating the stage 460 to control the location of the target 405 relative to the system. Actuation of the stage 460 could include one or more piezo elements, servo motors, linear actuators, galvanometers, or other actuators configured to control the location of the stage 460 (and a target 405 mounted on the stage 460) relative to element(s) (e.g., 441) of the system 400.

The imaging system 400 (or other example imaging and/or microscopy systems described herein) could include additional elements or components (not shown). The imaging system 400 could include one or more controllers configured to operate the SLM 410, light source 420, light sensor 430, MD 450, actuator(s) configured to control the location of the stage 460, and/or other elements of the imaging system 400. The imaging system 400 could include communications devices (wireless radios, wired interfaces) configured to transmit/receive information to/from other systems (e.g., servers, other imaging devices, experimental systems, sample perfusion pumps, optogenetic or other stimulators) to enable functions and applications of the imaging system 400. For example, the imaging system 400 could include an interface configured to present images of the target 405 generated by the imaging system 400 and/or images of the location, distribution, concentration, or other information about identified probes within the target 405. The imaging system 400 could include an interface configured to present information about the imaging system 400 to a user and/or to allow the user to operate the imaging system 400 (e.g., to set a spectrographic resolution, to set a spatial resolution, to set a temporal resolution/imaging sample rate, to set an operational mode (e.g., conjugate or non-conjugate confocal imaging, bright-field imaging, stimulated emission depletion (STED) imaging), so set a maximum emitted illumination power, to set a range of wavelengths of interest).

Additionally or alternatively, the imaging system 400 (or other example imaging systems described herein) could be configured to communicate with another system (e.g., a cellphone, a tablet, a computer, a remote server) and to present a user interface using the remote system. In some examples, the imaging system 400 could be part of another system. For example, the imaging system 400 could be implemented as part of an electrophysiological experimentation system configured to apply optical, electrical, chemical, or other stimuli to a biological sample (e.g., a sample of cultured or extracted neurons). The imaging system 400 could provide information about changes in the configuration of the biological sample in response to stimuli (e.g., by determining information about the tissue related to the presence and/or location of probes in cells of the sample) and/or could provide information to inform to delivery of stimuli. In some examples, the imaging system 400 could include multiple SLMs 410, light sources 420, light sensors 430, MDs 450, or other additional components. The imaging system 400 could include sensors and/or be in communication with sensors configured to image other properties of a target environment (e.g., 405). Other configurations, operations, and applications of imaging systems as described herein are anticipated.

Other methods of configuring and/or operating a light source, light sensor, SLM, MD, and/or other elements of an imaging system (e.g., to identify and/or locate spatially and spectrally multiplexed probes in a target) are anticipated.

IV. Identifying Probes by Correlation Between Spatial and Spectral Images

As described above, the colors and locations of fluorophores (e.g., fluorophores of spatially and spectrally multiplexed probes) within an environment of interest can be determined by determining spectrographic information (e.g., a color) for a plurality of locations within the environment. Additionally or alternatively, light emitted from a particular region (e.g., a small region, having a size corresponding to a diffraction limit of an optical system used to image the environment) of the environment of interest could be split and simultaneously used to spatially and spectrally image the particular region. The intensity of light emitted from a particular fluorophore within the particular region can vary over time due to a variety of factors, e.g., due to blinking of quantum dots or molecular fluorophores.

A pattern over time of such changes in intensity can be substantially independent between different fluorophores within the environment. As a result, time-varying waveforms of light detected from a location of a particular fluorophore in spatial images of the particular region may be correlated with time-varying waveforms of light detected from wavelengths of light that correspond to the color of the particular fluorophore in spectral images of the particular region. Correlations can be determined between such detected time-varying waveforms of light received from different locations of a particular region of an environment and such detected time-varying waveforms of light received at different wavelengths from the particular region of the environment and such correlations can be used to determined colors and/or locations of fluorophores (e.g., fluorophores of probes) within the environment.

In order to generate such time-varying waveforms of light received from different locations and at different wavelengths from a particular region of a target (e.g., a biological sample), light emitted from the particular region of the environment can be split (e.g., by a partially silvered mirror, by a polarizing filter) into two portions and each portion could be applied to a respective light sensors. The first light sensor could receive a first portion of the emitted light such that the light is imaged, in-focus, by an array of light-sensitive elements of the first light sensor. Each light-sensitive element of the first sensor could be used to generate a time-varying waveform of light emitted from a respective location of the particular region of the target.

The second light sensor could receive a second portion of the emitted light that has interacted with a chromatically dispersive element (e.g., a prism, a diffraction grating, one or more Amici prisms, a spatial light modulator (SLM) as described elsewhere herein). The light could be received by the second sensor, having been spectrally dispersed by interaction with (e.g., reflection from, refraction through) the chromatically dispersive element, such that the light is detected by an array of light-sensitive elements of the second light sensor. Such an array could be a 2-dimensional array (e.g., such that the light could be detected at different times having been spectrally dispersed in different directions and/or by different amounts by an SLM) or a 1-dimensional array (e.g., the chromatically dispersive element could be configured to spectrally disperse the second portion of light in the direction of the 1-dimensional array of elements). Each light-sensitive element of the second sensor could be used to generate a time-varying waveform of light emitted from the particular region of the target (e.g., from substantially the entire particular region) at a respective wavelength.

Figure 5A:
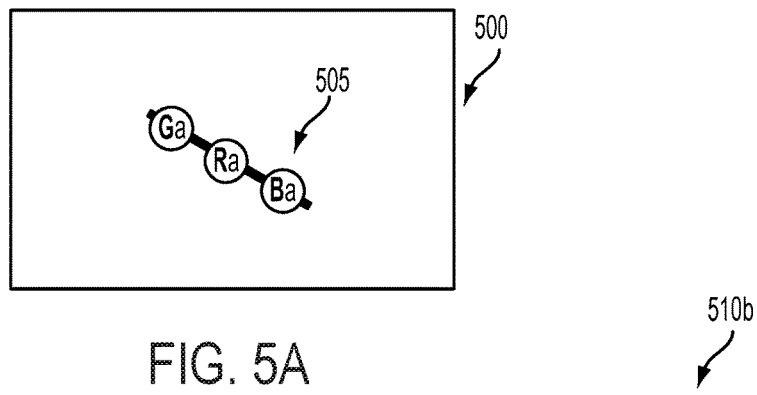
FIG. 5A illustrates an example probe that could be imaged.

FIG. 5A illustrates a particular region 500 of a target. Within the particular region 500 of the target is a probe 505 that includes, in order, a green fluorophore, Ga, a red fluorophore, Ra, and a blue fluorophore, Ba, disposed on a substantially linear backbone. Thus, spectrographic properties (e.g., colors) of locations of the particular region 500 are such that red light is emitted from the location of Ra in response to illumination, green light is emitted from the location of Ga in response to illumination, and blue light is emitted from the location of Ba in response to illumination. The particular region 500 could be imaged by an imaging system as described elsewhere herein.

Figure 5B:
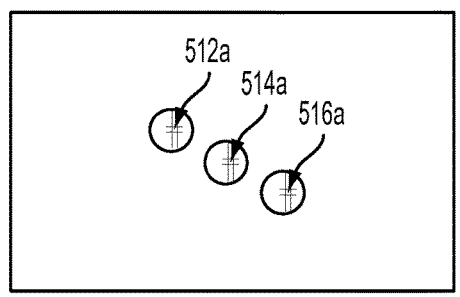
FIG. 5B illustrates an example spatial image of the probe of FIG. 5A.

FIG. 5B illustrates a portion of a first image 510a of the particular region 500. This first image 510a is taken of light received from the target that has been imaged by light-sensitive elements of a first light sensor (e.g., a camera). The light-sensitive elements of the first light sensor are arranged on a focal surface of the first light sensor and the received light is presented to the first light sensor (e.g., by optics of an imaging system) such that the focal surface of the first light sensor is conjugate to a focal surface passing through the particular region 500. Thus, first image 510a includes illuminated regions (indicated in FIG. 5B by three circles) illuminated by light emitted from the red, green, and blue fluorophores (Ra, Ga, and Ba) of the probe 505. Light-sensitive elements of the first light sensor that correspond to the illuminated regions (illustrated in FIG. 5B as example light-sensitive elements 512a, 514a, 516a) can be used to detect, over time, time-varying waveforms of light emitted from the red, green, and blue fluorophores (Ra, Ga, and Ba).

Figure 5D:
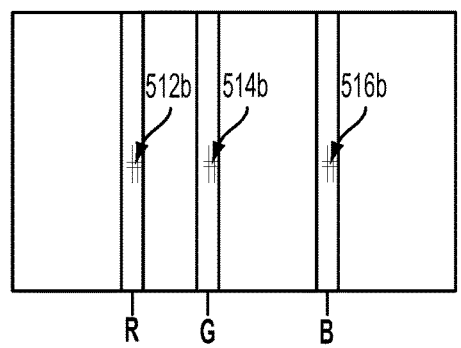
FIG. 5D illustrates an example spectral image of a particular region of a target that includes the probe of FIG. 5A.
Figure 5C:
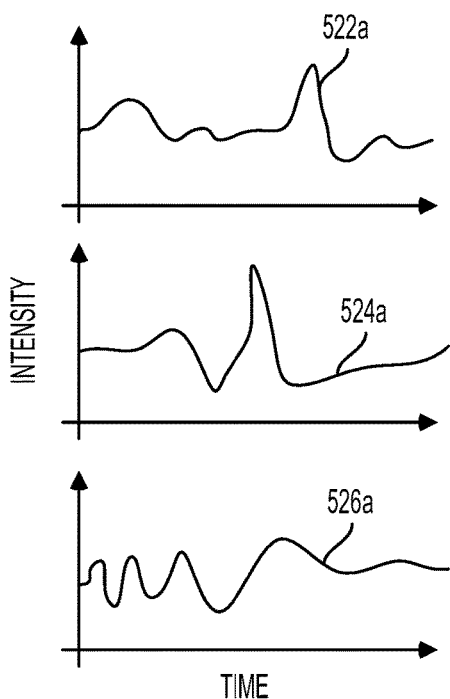
FIG. 5C illustrates example time-varying waveforms of light.

FIG. 5C illustrates example time-varying waveforms 522a, 524a, and 526a generated using the first 512a, second 514a, and third 516a example light-sensitive elements, respectively. As the example light-sensitive elements 512a, 514a, 516a receive light from respective different fluorophores, the time-varying waveforms 522a, 524a, 526a may be different and may correspond to the substantially independent changes over time of the amount of light emitted from each of the fluorophores (e.g., according to substantially random and independent blinking or other processes of the fluorophores). This is illustrated in FIG. 5C by the example time-varying waveforms 522a, 524a, 526a being different.

Note that time-varying waveforms could be generated for each of the light-sensitive elements of a light sensor. In examples wherein each of the light-sensitive elements of the light sensor receives light from a respective location of a target (e.g., as illustrated in FIGS. 5A and 5B), correlations between such time-varying waveforms could be used to determine the location of fluorophores within the target. This could include performing principal components analysis, independent components analysis, clustering, determining pairwise correlations between the time-varying waveforms and using the determined correlations to determine sets of similar time-varying waveforms, or some other method or methods to determine similarities between sets of time-varying waveforms and then using such determined similarities to determine the location of fluorophores within a target. Additionally or alternatively, pattern matching or other techniques could be used to determine the centers of illuminated regions of one or more images (e.g., 510a) of the target. Note that illuminated regions of a light sensor that correspond to respective different fluorophores of a probe in a target may significantly overlap. In such examples, the time-varying waveform of light generated using a particular light-sensitive element of a light sensor may include a combination of waveforms corresponding to the change over time of the light emitted from multiple different fluorophores.

FIG. 5D illustrates a portion of a second image 510b of the particular region 500. This second image 510b is taken of light received from the particular region 500 that has been spectrally dispersed by a chromatically dispersive element. With respect to the example second image 510b, the chromatically dispersive element is configured to spectrally disperse light received from the particular region 500 in a horizontal direction such that longer wavelengths of light are received by light-sensitive elements of the light sensor to the left in FIG. 5D and such that shorter wavelengths of light are received by light-sensitive elements of the light sensor to the right in FIG. 5D. Thus, the second image 510b includes illuminated regions (indicated in FIG. 5D by three vertical bars, whose wavelengths are indicated by R, G, and B along the horizontal axis of the image 510b) due to illumination of corresponding regions of a light sensor by spectrally dispersed light from the red, green, and blue fluorophores (Ra, Ga, and Ba), respectively, of the probe 505. Light-sensitive elements of the second light sensor that correspond to the illuminated regions (illustrated in FIG. 5D as example light-sensitive elements 512b, 514b, 516b) can be used to detect, over time, time-varying waveforms of light emitted from the red, green, and blue fluorophores (Ra, Ga, and Ba).

Figure 5E:
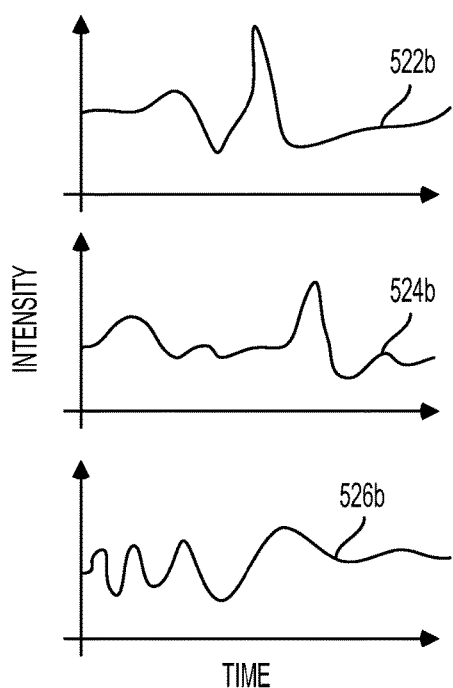
FIG. 5E illustrates example time-varying waveforms of light.

FIG. 5E illustrates example time-varying waveforms 522b, 524b, and 526b generated using the first 512b, second 514b, and third 516b example light-sensitive elements, respectively. As the example light-sensitive elements 512b, 514b, 516b receive light from respective different fluorophores, the time-varying waveforms 522b, 524b, 526b may be different and may correspond to the substantially independent changes over time of the amount of light emitted from each of the fluorophores (e.g., according to substantially random and independent blinking or other processes of the fluorophores). This is illustrated in FIG. 5C by the example time-varying waveforms 522b, 524b, 526b being different. Note that, as the time-varying waveforms 522b, 524b, 526b correspond to the changes over time in the amount of light emitted from the fluorophores of the probe 505, they may be similar to time-varying waveforms of light received, by light-sensitive elements of the first light sensor, from corresponding fluorophores of the probe 505.

This is illustrated, by way of example, in FIGS. 5C and 5E by time-varying waveforms 522a and 524b being similar. Time-varying waveform 522a corresponds to changes over time in the amount of light received, by light-sensitive element 512a of the first light sensor, from the green fluorophore, Ga, of the probe 505. The green fluorophore emits green light; thus, time-varying waveform 524b corresponds to changes over time in the amount of light received, by light-sensitive element 524b of the second light sensor, from the green fluorophore. As a result, time-varying waveforms 522a and 524b are similar and may have a high degree of correlation or some other metric of similarity. Similarly, time-varying waveforms 524a and 522b are similar (due to correspondence with changes over time in the amount of light emitted from the red fluorophore, Ra) and time-varying waveforms 526a and 526b are similar (due to correspondence with changes over time in the amount of light emitted from the blue fluorophore, Ba).

Correlations between time-varying waveforms generated using light-sensitive elements of the first light sensor and second light sensor could be determined and used to determine the color and/or location of fluorophores within the target. This could include performing principal components analysis, independent components analysis, clustering, determining pairwise correlations between the time-varying waveforms and using the determined correlations to determine sets of similar time-varying waveforms, or some other method or methods to determine similarities between sets of time-varying waveforms and then using such determined similarities to determine colors of fluorophores in the target. This could include determining that a determined correlation between a particular time-varying waveform of light generated using a light-sensitive element of the first light sensor (e.g., a time-varying waveform of light corresponding to light emitted from a particular location of a target that includes a fluorophore) and a particular time-varying waveform of light generated using a light-sensitive element of the second light sensor (e.g., a time-varying waveform of light corresponding to a wavelength of light emitted from the fluorophore in the target) is greater than a threshold. If the particular time-varying waveform generated by the first light sensor corresponds to a determined location of a fluorophore, the correlation being greater than the threshold could be used to determine that the color of the fluorophore includes a wavelength of light corresponding to the particular time-varying waveform generated by the second light sensor.

Note that different fluorophores location in a particular region of a target that is being imaged (e.g., as shown in FIG. 5A) may emit light at the same wavelength. This could be due to the different fluorophores having the same color and/or being the same type of fluorophore. Additionally or alternatively, one or more of the fluorophores could emit light at multiple different wavelengths (e.g., a first quantum dot could emit light at a red wavelength and a blue wavelength, while a second quantum dot could emit light at a red wavelength and a green wavelength). In such examples, the time-varying waveform of light generated using a particular light-sensitive element of a light sensor (e.g., the second light sensor) may include a combination of waveforms corresponding to the change over time of the light emitted from multiple different fluorophores.

Further, note that, while the second light sensor discussed in combination with FIGS. 5A-E includes a two-dimensional array of light-sensitive elements, the second light sensor could alternatively be configured to have a one-dimensional array of light-sensitive elements configured to generate respective time-varying waveforms of light received from a particular region of a target by the light-sensitive elements at respective different wavelengths. In examples wherein the second light sensor comprises a two-dimensional array of light-sensitive elements, a chromatically dispersive element that is used to spectrally disperse the light received by the second light sensor could be operated, during different period of time, to disperse the light in different directions, by different amounts, or according to some other consideration. Two-dimensional images generated by the second light sensor in such an example could be used (e.g., via a process of deconvolution) to provide spectrographic information for locations of the particular region of the target.

Time varying waveforms could be generated, using each light-sensitive element of a light sensor, in a variety of ways. In some examples, each light-sensitive element could be connected to a respective amplifier, digitizer, filter, or other component configured to generate a time-varying waveform using the light-sensitive element. Alternatively, light-sensitive elements of a light sensor could be operated to repeatedly image a target. For example, the light sensor could include a charge-coupled device (CCD), and imaging the target using the light sensor could include operating the CCD to sequentially transfer charges accumulated by the light-sensitive elements (e.g., pixels) of the CCD to one or more digitizers to be sampled. Generating a time-varying waveform for a particular light-sensitive element of the light sensor could, in such examples, include using a plurality of such images to determine the intensity of light received by the particular light-sensitive element over time, at a plurality of points in time corresponding to the timing of generation of the plurality of images. Further, the first and second light sensors could be part of the same device, e.g., the same CCD. That is, light-sensitive elements of the first and second light sensor could comprise respective first and second sets of light-sensitive elements of the same light-sensing device. In such an example, optical elements of an imaging system used to image a target using the first and second light sensors could be configured to split the light received from a target into first and second portions, spectrally disperse the second portion, and present the first and second portions to respective set of light-sensitive elements (e.g., respective different areas) of a single light-sensing device.

In order to produce time-varying waveforms of light received from different locations of a particular region of a target and to produce time-varying waveforms of light received from the particular region of the target at different wavelengths, as described above, that can be used to identify probes in the target by determining the locations and colors of fluorophores of the probes in the target, a variety of different optical elements could be incorporated into an imaging system. Such an imaging system could include various sources of illumination, optical systems, apertures, light sensors, or other elements configured to illuminate a particular region of a target, receive light responsively emitted from the particular region of the target (e.g., from fluorophores in the particular region), split the received light into first and second portions, apply a first portion to be spatially imaged by a first light sensor, and apply a second portion to be spectrally dispersed by a chromatically dispersive element (e.g., a prism, an SLM) and spectrally imaged by a second light sensor. Such an imaging system could include apertures, optics, micromirror devices, Nipkow discs, or other elements configured to selectively receive light from the particular region of the target and/or to selectively illuminate the particular region of the target. This could include using techniques and/or apparatus for confocally imaging the particular region of the target.

Figure 6:
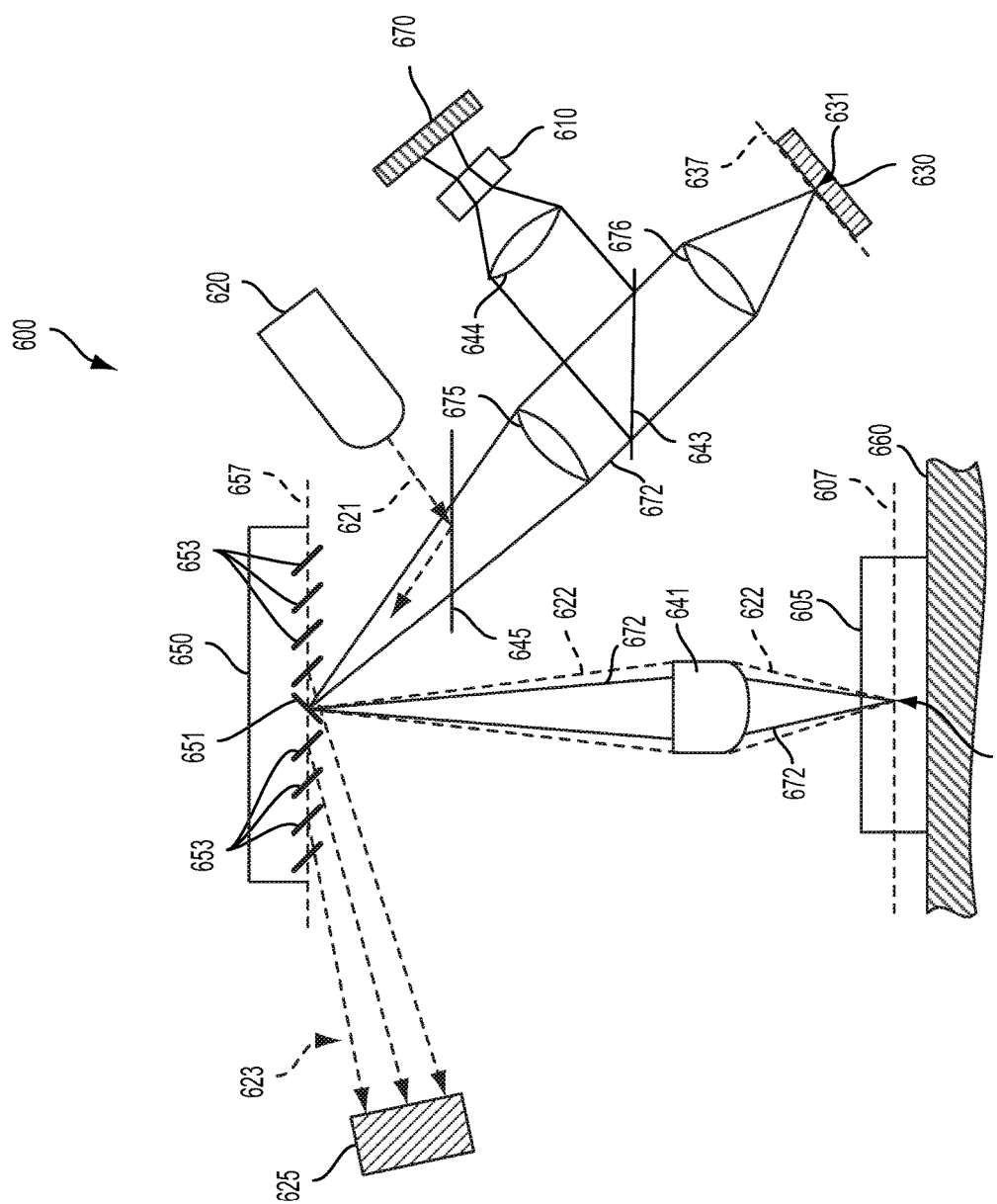
FIG. 6 illustrates an example imaging apparatus.

FIG. 6 illustrates in cross-section elements of an example imaging system 600 configured to image a target 605. The system 600 includes a light source 620 (e.g., a laser), a first light sensor 630 (illustrated as a plane of light-sensitive elements located on a focal plane 637 of the first light sensor 630), a second light sensor 670 (illustrated as a plane of light-sensitive elements), a micromirror device (MD) 650, a chromatically dispersive element 610 (e.g., a prism, one or more Amici prisms, an SLM, a diffraction grating), and an optical system (including an objective 641, first 675, second 676, and third 644 relay lenses, a dichroic mirror 645, a beam splitter 643, and an optical sink 625) configured to direct light to and from the target 605 and between the elements of the system 600. The system 600 additionally includes a stage 660 to which the target 605 is mounted. Note that the MD 650 and first light sensor 630 comprise two-dimensional arrays of micromirrors and light-sensitive elements, respectively. The second light sensor 670 may comprise a two-dimensional or one-dimensional array of light-sensitive elements. Further, note that the optical system (e.g., 641, 643, 644, 645, 675, 676) and chromatically dispersive element 610 are configured to direct light between the target 605, MD 650, and first light sensor 630 such that locations on the focal surfaces 657, 637 of the MD 650 and first light sensor 630 correspond to respective locations on the focal surface 607 passing through a particular region 609 in the target 605.

The system 600 illuminates a particular region 609 in the target 605 by emitting a first illumination 621 from the light source 620 and reflecting the first illumination 621 from the dichroic mirror 645 toward the MD 650. A selected mirror 651 of the MD 650 that has a location on a focal surface 657 of the MD 650 corresponding to the particular region 609 is controlled to have a first angle to reflect the first illumination 621 toward the target 605 as confocal illumination 622 via the objective 641. Other mirrors 653 of the MD 650 are controlled to have a second angle to reflect the remainder of the first illumination 621 as waste illumination 623 toward the optical sink 625 to be absorbed. As illustrated, a single mirror (651) is controlled to illuminate (and to receive light from) a corresponding region 609 of the target 605; however, additional mirrors (e.g., selected from other mirrors 653) could be operated simultaneously, sequentially, or according to some other scheme to illuminate (and to receive light from) corresponding additional regions of the target 605.

The system 600 receives light (including conjugate light 672) emitted from the target 605 (e.g., from the particular region 609) in response to illumination via the objective 641. The conjugate light 672 is split, by the beam splitter 643, into first and second portions of illumination. The first portion of the conjugate light is presented, in-focus, to a specified region 631 on a focal surface 637 of the first light sensor 630 corresponding to the particular region 609 (e.g., to a region of the first light sensor having one or more light-sensitive elements and/or pixels of the first light sensor 630). The second portion of the conjugate light is applied to the chromatically dispersive element 610 to spectrally disperse the second portion of light. The spectrally dispersed portion of light is then presented to the second light sensor 670. Such manipulations of the conjugate light 672 (e.g., reflections, splitting, spectral dispersions) are provided by relay optics 675, 676, 644, beam splitter 643, chromatic dispersive element 610, or by some other optical element(s).

Note that, while the chromatically dispersive element 610 is illustrated in FIG. 6 as being a transmissive element (that is, an element that spectrally disperses light that is transmitted through the chromatically dispersive element 610), an imaging system as described herein could include a reflective, a refractive, a diffractive, or some other variety of chromatically dispersive element and/or a combination of chromatically dispersive elements. In some examples, the chromatically dispersive element 610 could include an SLM as described elsewhere herein that can be operated to control a direction, a magnitude, or some other properties of the spectral dispersion applied to light that is presented to the second light sensor 670.

The location of the particular region 609 within the target 605 could be controlled (e.g., to allow imaging of elements of the target 605 at different depths within the target 605). In some examples, the stage 660 could be actuated relative to other elements of the system 600 such that a location of the target 605 in one or more dimensions could be controlled. For example, the stage 660 could be actuated in a direction parallel to the direction of the illumination (i.e., in the vertical direction of FIG. 6) such that the location (e.g., the depth) of the particular region 609 within the target 605 could be controlled. Actuation of the stage 660 could include one or more piezo elements, servos motors, linear actuators, galvanometers, or other actuators configured to control the location of the stage 660 (and a target 605 mounted on the stage 660) relative to element(s) (e.g., 641) of the system 600.

Note that the configuration and/or operation of the system 600 to illuminate and to receive conjugate light from a particular region 609 of a target 605 is intended as a non-limiting example. Alternatively, a larger and/or differently-shaped region of the target could be illuminated by operating the mirrors 651, 653 of the MD 650 according to a different set of controlled angles than those illustrated. For example, a plurality of spatially separated regions proximate of the target 605 could be illuminated and imaged simultaneously by controlling a corresponding plurality of spatially separated mirrors of the MD 650 to reflect the first illumination 621 toward the plurality of regions of the target 605. A separation distance between such spatially separated regions could be greater than a specified distance such that light from each region does not interfere with detection of spectral and/or spatial information for other regions using the first 630 and/or second 670 light sensors, respectively (e.g., such that spots of light projected onto the second light sensor 670 from each of the spatially separated regions following being spectrally dispersed by the chromatically dispersive element 610 do not overlap).

Further, the size of the illuminated regions could be sufficiently large (e.g., could be illuminated by sufficiently many mirrors of the MD 650) that sufficiently many pixels of the first 630 and/or second 670 cameras are illuminated to allow statistical analysis to be performed (e.g., to allow sufficiently many correlations to be determined to determine colors and locations of fluorophores in the target 605). The size of the illuminated regions could also be sufficiently small that spectral information for different fluorophores is smeared, across pixels of the second light sensor 670, by a sufficiently small amount by spatial distances between different fluorophores in each illuminated region that spectral information (e.g., colors) can be determined for all of the fluorophores in each illuminated region.

The mirrors 651, 653 of the MD 650 could be controlled according to some other pattern, e.g., to approximate some other coded aperture on the focal surface 657 of the MD 650. Further, the light source 620 could emit illumination at a controllable wavelength (e.g., illumination that is substantially monochromatic, but having a wavelength that can be altered by operation of the light source) and spectrographic information could be determined for regions of the target 605 based on images of the target 605 generated when the target 605 is illuminated by different wavelengths of light (e.g., to generate a corresponding plurality of emission spectra for fluorophores of probes in the target corresponding to the different wavelengths of illumination).

The system 600 could be operated in a variety of ways to provide confocal, hyperspectral, or other types of images of the target 605. For example, the system could be operated during a number of periods of time to illuminate respective particular regions of the target (e.g., by controlling respective specified sets of mirrors of the DM to have first or second angles), to image light received from the target 605 using the second 670 and first 630 light sensors, respectively, or to operate some other element(s) of the system 600 over time to identify and/or locate probes in a target or according to some other application.

Note that non-conjugate light received from a target (e.g., light from the target 605 that is reflected by the second set of mirrors 653 of the MD 650) could be used to determine spatial or spectral information about fluorophores and/or probes in the target (e.g., to generate time-varying waveforms of light received from different locations of a particular region of the target and/or to generate time-varying waveforms of light received from the particular region of the target at different wavelengths). For example, an MD could be used to partition light received from a particular region of a target such that a first portion is presented, in-focus, to a first light sensor (e.g., to spatially image the particular region) and such that a second portion is spectrally dispersed and presented to a second light sensor (e.g., to spectrally image the particular region).

Figure 7:
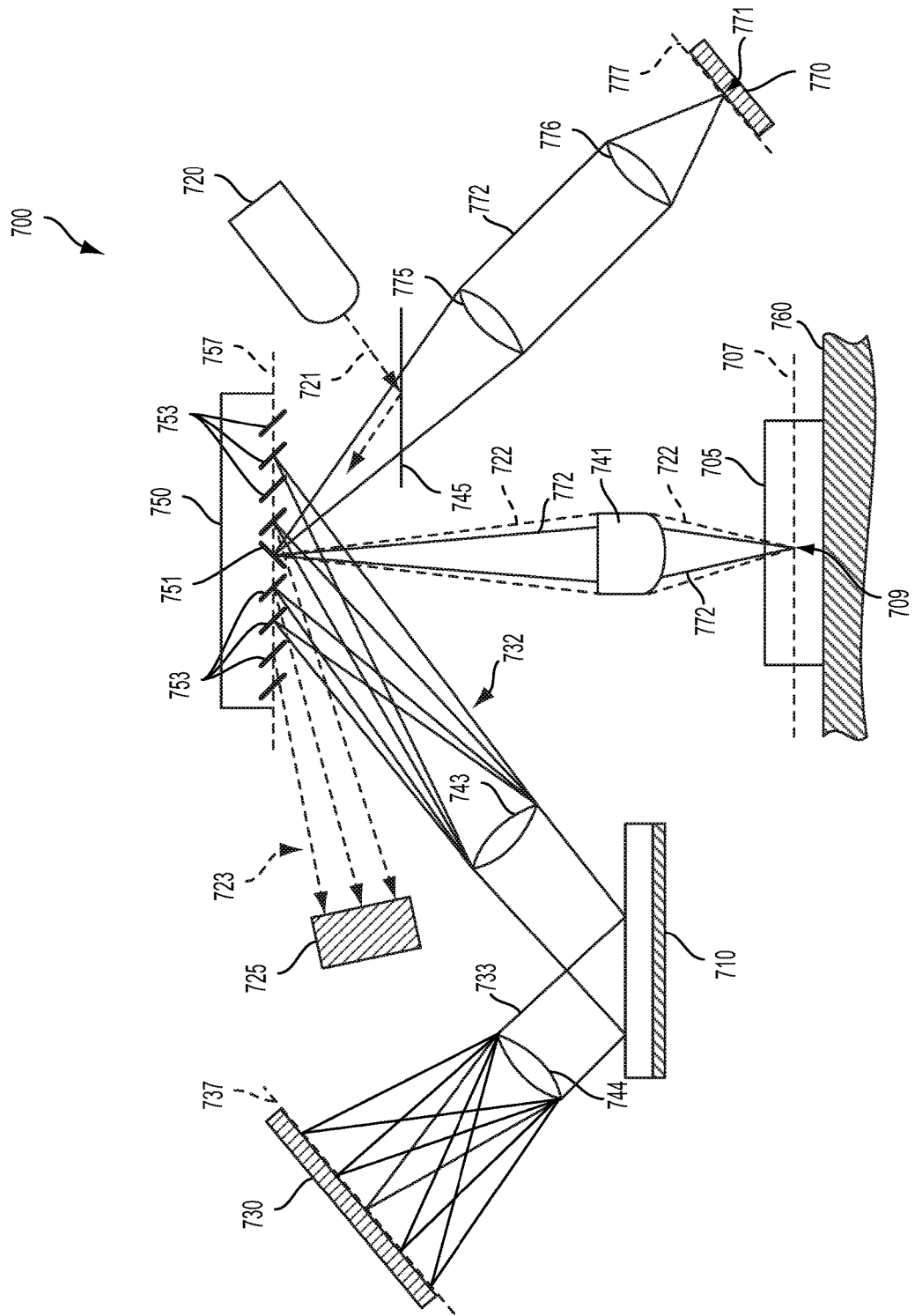
FIG. 7 illustrates an example imaging apparatus.

Such a scenario is illustrated by way of example in FIG. 7. FIG. 7 illustrates in cross-section elements of an example imaging system 700 configured to image a target 705 in order to, e.g., identify and/or locate spatially and spectrally multiplexed probes in the target 705. The system 700 includes a light source 720 (e.g., a laser), a second light sensor 730 (illustrated as a plane of light-sensitive elements located on a focal plane 737 of the second light sensor 730), a first light sensor 770 (illustrated as a plane of light-sensitive elements located on a focal plane 777 of the first light sensor 770), a micromirror device (MD) 750, a spatial light modulator (SLM) 710, and an optical system (including an objective 741, first 743, second 744, third 775, and fourth 776 relay lenses, a dichroic mirror 745, and an optical sink 725) configured to direct light to and from the target 705 and between the elements of the system 700. The system 700 additionally includes a stage 760 to which the target 705 is mounted. Note that the MD 750 and second 730 and first 770 light sensor comprise two-dimensional arrays of micromirrors and light-sensitive elements, respectively. Further, note that the optical system (e.g., 741, 743, 744, 745, 775, 776) and SLM 710 are configured to direct light between the target 705, MD 550, and second 730 and first 770 light sensors such that locations on the focal surfaces 757, 737, 777 of the MD 750 and light sensors 730, 770 correspond to respective locations on a focal surface 707 that passes through a particular region 709 in the target 705.

The system 700 illuminates a particular region 709 in the target 705 by emitting a first illumination 721 from the light source 720 and reflecting the first illumination 721 from the dichroic mirror 745 toward the MD 750. A selected mirror 751 of the MD 750 that has a location on a focal surface 757 of the MD 750 corresponding to the specified region 709 is controlled to have a first angle to reflect the first illumination 721 toward the target 705 as confocal illumination 722 via the objective 741. Other mirrors 753 of the MD 750 are controlled to have a second angle to reflect the remainder of the first illumination 721 as waste illumination 723 toward the optical sink 725 to be absorbed. As illustrated, a single mirror (751) is controlled to illuminate (and to receive light from) a corresponding particular region 709 of the target 705; however, additional mirrors (e.g., selected from other mirrors 753) could be operated simultaneously, sequentially, or according to some other scheme to illuminate (and to receive light from) corresponding additional regions of the target 705.

The system 700 receives light (including conjugate light 772) emitted from the target 705 (e.g., from the particular region 709) in response to illumination via the objective 741. The conjugate light 772 is directed, in-focus, to a specified region 771 on a focal surface 777 of the first light sensor 770 corresponding to the particular region 709 (e.g., to a region of the first light sensor having one or more light-sensitive elements and/or pixels of the first light sensor 770). Such light is directed to the first light sensor 770 from the MD 750 via relay optics 775, 776 or via some other optical element(s).

The system 700 also receives non-conjugate light 732 emitted from the target via the objective 741. The non-conjugate light 732 arrives at the MD 750 and is reflected by mirrors of the MD 750 that are controlled to have the second angle (e.g., 753) toward the SLM 710. The first relay lens 743 (and/or some other optical elements of the system 700) collimates the received light and presents the substantially collimated light to the SLM 710. The SLM 700 reflects the non-conjugate light 732 as spectrally dispersed light 733 toward the second relay lens 744 that is configured to present the spectrally dispersed light 733 to a focal surface 737 of the second light sensor 730. The SLM 710 is configured and/or operated such that the spectrally dispersed light 733 is spectrally dispersed relative to the non-conjugate light 732 in a controlled manner such that spectrographic information of one or more particular regions of the target 705 and/or of the non-conjugate light 732 can be detected or determined (e.g., based on a plurality of time-varying waveforms of light received from the particular region 709 at respective different wavelengths by respective different light-sensitive elements of the second light sensor 730). In some examples, the spectrally dispersed light 733 is spectrally dispersed in a manner related to an electronically controlled direction, magnitude, and/or some other property of a spatial gradient in the refractive index of a layer of the SLM 710.

Note that the configuration and/or operation of the system 700 to illuminate and to receive conjugate light from a particular region 709 of the target 705 is intended as a non-limiting example. Alternatively, a larger and/or differently-shaped region of the target could be illuminated by operating the mirrors 751, 753 of the MD 750 according to a different set of controlled angles than those illustrated. For example, a plurality of spatially separated regions of the target 705 could be illuminated and imaged simultaneously by controlling a corresponding plurality of spatially separated mirrors of the MD 750 to reflect the first illumination 721 toward the plurality of the regions of the target 705. The mirrors 751, 753 of the MD 750 could be controlled according to some other pattern, e.g., to approximate some other coded aperture on the focal surface 757 of the MD 750. Further, the light source 720 could emit illumination at a controllable wavelength (e.g., illumination that is substantially monochromatic, but having a wavelength that can be altered by operation of the light source) and spectrographic information could be determined for regions of the target 705 based on images of the target 705 and/or time-varying waveforms of light received from the target 705 generated when the target 705 is illuminated by different wavelengths of light (e.g., to generate a corresponding plurality of emission spectra for one or more fluorophores of a probe corresponding to the different wavelengths of illumination).

The location of the particular region 709 within the target 705 could be controlled (e.g., to allow imaging of elements of the target 705 at different depths within the target 705). In some examples, the stage 760 could be actuated relative to other elements of the system 700 such that a location of the target 705 in one or more dimensions could be controlled. For example, the stage 760 could be actuated in a direction parallel to the direction of the illumination (i.e., in the vertical direction of FIG. 7) such that the location (e.g., the depth) of the particular region 709 within the target 705 could be controlled. Actuation of the stage 760 could include one or more piezo elements, servos motors, linear actuators, galvanometers, or other actuators configured to control the location of the stage 760 (and a target 705 mounted on the stage 760) relative to element(s) (e.g., 741) of the system 700.

The system 700 could be operated in a variety of ways to provide confocal, hyperspectral, or other types of images of the target 705. For example, the system could be operated during a number of specified periods of time to illuminate different regions of the target (e.g., by controlling respective specified sets of mirrors of the DM to have first or second angles, by controlling an actuated stage 760), to electronically control a gradient of refractive index across a refractive layer of the SLM to have respective different specified magnitude(s) or direction(s) or to control the refractive index of element(s) of the SLM according to some other patterns, to image conjugate or non-conjugate light received from the target 705 using the first 770 and second 730 light sensors, respectively, or to operate some other element(s) of the system 700 over time according to an application.

Figure 8:
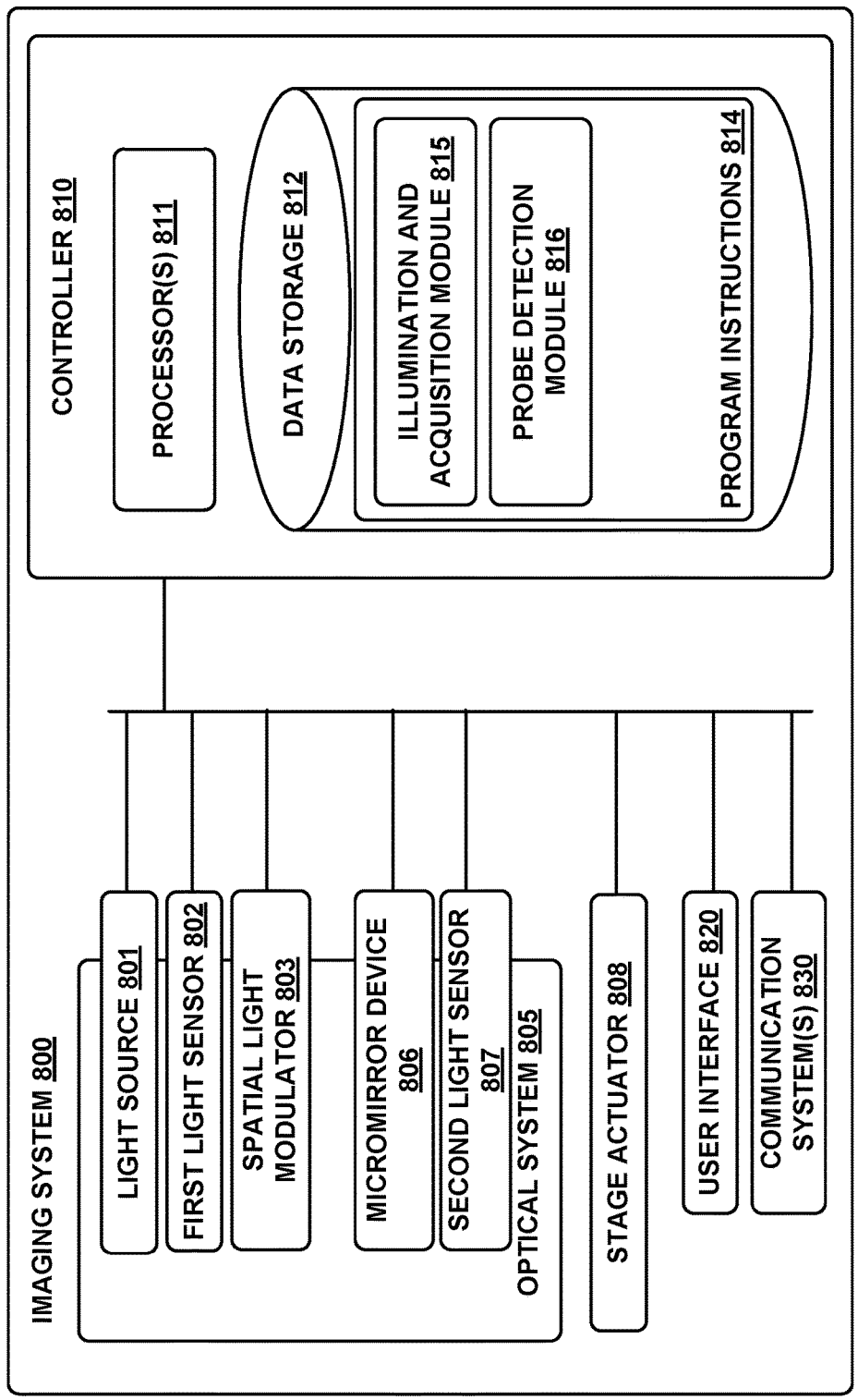
FIG. 8 is a functional block diagram of an example imaging system.

Other methods of configuring and/or operating a light source, light sensor(s), one or more apertures, SLM, MD, and/or other elements of an imaging system (e.g., to identify and/or locate spatially and spectrally multiplexed probes in a target) are anticipated V. Example Electronics of an Imaging Apparatus FIG. 8 is a simplified block diagram illustrating the components of an imaging system 800, according to an example embodiment. Imaging system 800 and/or elements thereof may take the form of or be similar to one of the example systems or elements 300, 400, 600, 700 shown in FIGS. 3, 4, 6, and 7 or of some other systems. For example, imaging system 800 and/or elements thereof may take the form of or be similar to one of the example systems or elements shown in FIGS. 13, 14, 15, 16, 17, 18, 19, 20, 21, 25, 28, 29, 30, 31, 35, 36, 38, and 39. Imaging system 800 may take a variety of forms, such as a wall, table, ceiling, or floor-mounted device. Imaging system 800 may take the form of a bench-top or table-top device (e.g., a bench-top microscope). Imaging system 800 and/or elements thereof could also take the form of a system, device, or combination of devices that is configured to be part of another device, apparatus, or system. For example, imaging system 800 or element(s) thereof (e.g., spatial light modulator 803) could take the form of a system or element configured to be mounted to or otherwise disposed as part of some other imaging system (e.g., imaging system 800 and/or the spatial light modulator 803 or other elements thereof could be configured to be part of a confocal microscope or other imaging system, e.g., to spectrally disperse one or more beams or fields of light of the imaging system in an electronically-controllable manner). Imaging system 800 could take the form of a system configured to contents of an industrial environment, medical environment, scientific environment, or some other environment. Imaging system 800 also could take other forms.

In particular, FIG. 8 shows an example of an imaging system 800 having a light source 801, a first light sensor 802, a spatial light modulator (SLM) 803, a micromirror device (MD) 806, a second light sensor 807, an optical system 805, a stage actuator 808, a user interface 820, communication system(s) 830 for transmitting data to a remote system, and controller 810. The components of the imaging system 800 may be disposed on or within a mount or housing or on some other structure for mounting the system to enable stable imaging or other functions relative to a target of interest, for example, a biological sample mounted to a stage (e.g., a stage having a location relative to other elements of the imaging system 800 that is actuated in at least one dimension by the stage actuator 808). The imaging system 800 could include additional components, for example, a perfusion pump configured to provide aerated or otherwise chemically specified perfusate to a cell culture or other biological sample comprising a target of the imaging system 800, one or more electrophysiological or optogenetic stimulators and/or sensors, an integrated circuit test rig, or some other instrument(s) or other component(s) according to an application.

The light source 801, light sensors 802, 807, optical system 805, SLM 803, MD 806, and/or stage actuator 808 could be configured and/or disposed as part of the imaging device 800 as described elsewhere herein for similar elements. The optical system 805 is configured to direct light emitted by the light source 801 to illuminate one or more regions of a target (e.g., via reflection from one or more mirrors of the MD 806). The optical system 805 is further configured to receive light responsively emitted from the target and to direct such light and/or components of such light (e.g., a conjugate component of the received light, a non-conjugate component of the received light, an otherwise partitioned portion of the received light) to one or both of the light sensors 801, 807 (e.g., via reflection from one or more mirrors of the MD 806, via reflection from, transmission through, or some other chromatically disperse interaction with the SLM 803 and/or some other chromatically dispersive element(s) of the imaging system 800). The optical system 805 is configured to direct such light between elements (e.g., 802, 806, 807) of the imaging system 800 such that focal surfaces of one or more such elements (e.g., a focal surface of the first light sensor 801 on which is disposed light-sensitive elements of the light sensor, a focal surface of the MD 806 on which is disposed mirrors of the MD 806) are optically conjugate with each other and/or with a focal surface on or within a target of the imaging system 800.

Controller 810 may be provided as a computing device that includes one or more processors 811. The one or more processors 811 can be configured to execute computer-readable program instructions 814 that are stored in a computer readable data storage 812 and that are executable to provide the functionality of an imaging system 800 as described herein.

The computer readable data storage 812 may include or take the form of one or more non-transitory, computer-readable storage media that can be read or accessed by at least one processor 811. The one or more computer-readable storage media can include volatile and/or non-volatile storage components, such as optical, magnetic, organic or other memory or disc storage, which can be integrated in whole or in part with at least one of the one or more processors 811. In some embodiments, the computer readable data storage 812 can be implemented using a single physical device (e.g., one optical, magnetic, organic or other memory or disc storage unit), while in other embodiments, the computer readable data storage 812 can be implemented using two or more physical devices.

The program instructions 814 stored on the computer readable data storage 812 may include instructions to perform any of the methods described herein. For instance, in the illustrated embodiment, program instructions 814 include an illumination and acquisition module 815 and a probe detection module 816.

The illumination and acquisition module 815 can include instructions for operating the light source 801, first light sensor 802, SLM 803, MD 806, second light sensor 807, and/or stage actuator 808 to enable any of the functions or applications of an imaging system to identify, determine an orientation of, and/or locate spatially and spectrally multiplexed probes in a target and/or to hyperspectrally image, confocally image, or otherwise image or optically interact with a target as described herein. Generally, instructions in the illumination and acquisition module 815 provide methods of operating the light source 801 and/or MD 806 to illuminate one or more regions of a target with light at one or more specified wavelengths during one or more respective periods of time. Instructions in the illumination and acquisition module 815 further provide methods of operating the SLM 803 and/or some other chromatically dispersive element(s) to spectrally disperse light directed toward the SLM 803 according to one or more specified directions, magnitudes, or other properties of dispersion of light during one or more respective periods of time (e.g., periods of time synchronous with and/or overlapping periods of time of operation of the MD 806 and/or light source 801).

Instructions in the illumination and acquisition module 815 further describe methods of operating the light sensor(s) 801, 807 to generate images, time-varying waveforms, or other information about light received from illuminated regions of a target via the optical system 805, micromirror device 806, and/or SLM 803 during one or more periods of time (e.g., periods of time of operation of the MD 806, SLM 803, light source 801, or other components of the imaging system 800). In some examples, generating an image and/or one or more time-varying waveforms of received light using the light sensor(s) 801, 807 could include reading out information (e.g., values or signals describing of related to the intensity or other property of light detected by light-sensitive elements of the light sensor(s) 801, 807. In such examples, a particular light-sensitive element or set of light-sensitive elements of the light sensor could be substantially unable to detect light when being read out. For example, one or both of the light sensor(s) could be CMOS cameras configured to have a global shutter (i.e., to read out an entire frame of image data from the light sensor at a time) and/or to have a rolling shutter (i.e., to read out a row of image data from the light sensor at a time). In such embodiments, the illumination and acquisition module 815 could describe operations of an MD 806 or other elements to not illuminate regions of a target corresponding to locations (e.g., light-sensitive elements) of the light sensor(s) that are not able to detect light from such regions (e.g., light-sensitive elements that are being read out). Other operations, functions, and applications of the light source 801, first light sensor 802, SLM 803, MD 806, second light sensor 807, stage actuator 808, and/or of other components of the imaging system 800 as described herein could be implemented as program instructions in the illumination and detection module 815.

The probe detection module 816 can include instructions for identifying, locating, determining the orientation of, or determining some other information about probes disposed within a target. This could include determining colors and locations of fluorophores of such probes and using such determined colors and locations to identify and/or locate probes within the target, e.g., by matching a pattern of fluorophore locations and/or an order of fluorophore colors to a template pattern or order that corresponds to a particular type of probe. Such determinations could be based on one or more images, time-varying waveforms of light, or other information of signals generated by the light sensor(s) 801, 807.

For example, the probe detection module 816 can include instructions for determining information about colors and locations of fluorophores in a target based on one or more images of spectrally dispersed light received from the target. Such a determination could include processes as described herein (e.g., a process of deconvolution, a process similar to the process described by example in relation to FIGS. 2A-D, some other process(es)). Such processes could be based on a description of correspondences between the location of light-sensitive elements of the light sensor(s) 801, 807 and corresponding locations on or within the target. Such correspondences could be wavelength-dependent and could be determined based on a model of the imaging system 800 (e.g., based on the magnitude and direction of a gradient of refractive index of a refractive layer across the SLM 803 during one or more periods of time corresponding to images generated by the light sensor(s) 801, 807) and/or on an empirical measurement of the properties of the system 800 (e.g., based on a set of images of a calibration target having known spectrographic information/content or some other calibration information or procedure).

In another example, the probe detection module 816 can include instructions for determining information about colors and locations of fluorophores in a target based on one or more pluralities of time-varying waveforms of light received form the target and generated using the light sensors 801, 807. In a particular example, the optical system 805 could be configured to receive light emitted from a particular region of a target (e.g., from a region that is being illuminated by via an aperture of the optical system 805 and/or via a synthetic aperture formed from one or more mirrors of the MD 806) and to present portion of such light to the first 801 and second 807 light sensors. The optical system 805 could present a first portion of the received light to the first light sensor 801 such that each light-sensitive element of the first light sensor 801 receives light from a respective location of the particular region (e.g., such that the light-sensitive elements are location on a focal surface of the first light sensor 801 that is conjugate to a focal surface passing through the particular region of the target). The optical system could present a second portion of the received light to the second light sensor 807, via a chromatically dispersive element (e.g., via reflection from the SLM 803) such that each light-sensitive element of the second light sensor 807 receives light from the particular region at a respective wavelength.

Time varying waveforms of light received by light-sensitive elements of the light sensors 801, 807 could be generated and used by the probe detection module 816 to determine colors and locations of fluorophores of probes in the target. Such a determination could include processes as described herein (e.g., a process of determining pairwise correlations between time-varying waveforms of light, by performing a principal components analysis, an independent components analysis, by performing a clustering analyses, or by performing some other process(es)).

Some of the program instructions of the illumination and acquisition module 815 and/or probe detection module 816 may, in some examples, be stored in a computer-readable medium and executed by a processor located external to the imaging system 800. For example, the imaging system 800 could be configured to illuminate and to receive light from a target (e.g., a biological sample) and then transmit related data to a remote server, which may include a mobile device, a personal computer, the cloud, or any other remote system, for further processing (e.g., for the determination of spectrographic information of one or more regions of the target, for identifying the region of the target and/or contents thereof based on the determined spectrographic content, to identify and/or determine locations of probes in the target).

User interface 820 could include indicators, displays, buttons, touchscreens, head-mounted displays, and/or other elements configured to present information about the imaging system 800 to a user and/or to allow the user to operate the imaging system 800. Additionally or alternatively, the imaging system 800 could be configured to communicate with another system (e.g., a cellphone, a tablet, a computer, a remote server) and to present elements of a user interface using the remote system. The user interface 820 could be disposed proximate to the light source 801, first light sensor 802, SLM 803, MD 806, second light sensor 807, stage actuator 808, controller 810, or other elements of the imaging system 800 or could be disposed away from other elements of the imaging system 800 and could further be in wired or wireless communication with the other elements of the imaging system 800. The user interface 820 could be configured to allow a user to specify some operation, function, or property of operation of the imaging system 800. The user interface 820 could be configured to present an image of a target (e.g., an image of the location or distribution of one or more types of probes within the target) generated by the imaging system 800 or to present some other information to a user. Other configurations and methods of operation of a user interface 820 are anticipated.

Communication system(s) 830 may also be operated by instructions within the program instructions 814, such as instructions for sending and/or receiving information via a wireless antenna, which may be disposed on or in the imaging system 800. The communication system(s) 830 can optionally include one or more oscillators, mixers, frequency injectors, etc. to modulate and/or demodulate information on a carrier frequency to be transmitted and/or received by the antenna. In some examples, the imaging system 800 is configured to indicate an output from the controller 810 (e.g., one or more images of a target) by transmitting an electromagnetic or other wireless signal according to one or more wireless communications standards (e.g., Bluetooth, WiFi, IrDA, ZigBee, WiMAX, LTE). In some examples, the communication system(s) 830 could include one or more wired communications interfaces and the imaging system 800 could be configured to indicate an output from the controller 810 by operating the one or more wired communications interfaces according to one or more wired communications standards (e.g., USB, FireWire, Ethernet, RS-232).

The computer readable data storage 812 may further contain other data or information, such as contain calibration data corresponding to a configuration of the imaging system 800, a calibration target, or some other information. Calibration, imaging, and/or other data may also be generated by a remote server and transmitted to the imaging system 800 via communication system(s) 830.

VI. Example Methods

Figure 9:
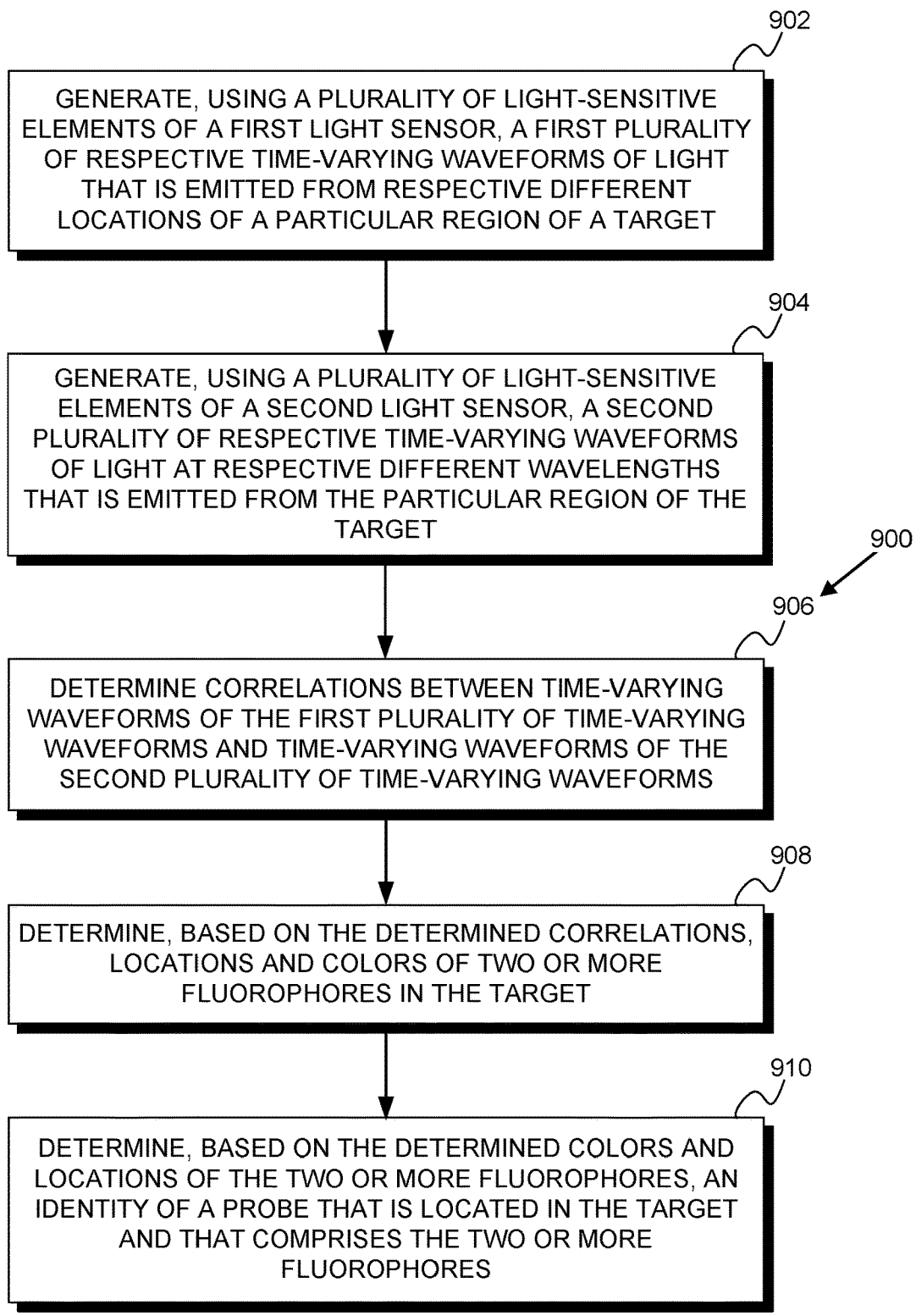
FIG. 9 is a flowchart of an example method.

FIG. 9 is a flowchart of an example method 900 for operating elements of an imaging system to identify spatially and spectrally multiplexed probes in a target environment and/or to provide some other functions and/or applications of the imaging system. The method 900 includes generating, using a plurality of light-sensitive elements of a first light sensor, a first plurality of respective time-varying waveforms of light that is emitted from respective different locations of a particular region of a target (902). This could include generating a plurality of images of the target, during a respective plurality of periods of time, and determining each of the time-varying waveforms based on the intensity of light received by a respective light-sensitive element of the first light sensor in each of the generated images. Alternatively, generating a time-varying waveform of light received by a particular light-sensitive element of the first light sensor could include operating an amplifier, one or more filters, a digitizer, or some other elements to generate a time-varying waveform using the particular light-sensitive element. The light emitted from the particular region of the target could be provided to the first light sensor via an optical system, e.g., such that a focal surface of the first light sensor is conjugate to a focal surface passing through the particular region of the target. This could include the emitted light passing through an aperture of the optical system (e.g., an aperture of a Nipkow disk) and/or being reflected by a virtual aperture formed from a set of actuated mirrors of a micromirror device.

The method 900 additionally includes generating, using a plurality of light-sensitive elements of a second light sensor, a second plurality of respective time-varying waveforms of light at respective different wavelengths that is emitted from the particular region of a target (904). This could include generating a plurality of one- or two-dimensional images of the target, during a respective plurality of periods of time, and determining each of the time-varying waveforms based on the intensity of light received by a respective light-sensitive element of the second light sensor in each of the generated images. Alternatively, generating a time-varying waveform of light received by a particular light-sensitive element of the second light sensor could include operating an amplifier, one or more filters, a digitizer, or some other elements to generate a time-varying waveform using the particular light-sensitive element. The light emitted from the particular region of the target could be provided to the second light sensor via an optical system that includes one or more chromatically dispersive elements (e.g., a prism, an SLM). Such an optical system could be configured such light of different wavelengths that is emitted from the particular region is spread, according to the wavelength of the light, across a number of the light-sensitive elements of the second light sensor.

The method 900 additionally includes determining correlations between time-varying waveforms of the first plurality of time-varying waveforms and time-varying waveforms of the second plurality of time-varying waveforms (906). This could include determining, for each combination of time-varying waveforms for the first plurality of time-varying waveforms and the second plurality of time-varying waveforms, or for a subset of such combinations, a correlation coefficient or some other metric of similarity (e.g., an inner product). This (906) could include performing a principal components analysis, an independent components analysis, a clustering analysis, or some other method to determine sets of time-varying waveforms within or between the first and second pluralities of time-varying waveforms that are similar.

The method 900 additionally includes determining, based on the determined correlations, locations and colors of two or more fluorophores in the target (908). This could include comparing a set of determined pairwise correlation coefficients, independent and/or principal component loadings, or other similarity metrics in order to determine sets of time-varying waveforms of the first plurality of time-varying waveforms that are similar and that could be associated with a single fluorophore. A location of such a single fluorophore could be determined based on the locations of the light-sensitive elements of the first light sensor that were used to generate such a determined set of time-varying waveforms (e.g., by determining a centroid of the locations of such light-sensitive elements). A color of such a single fluorophore could be determined by comparing determined correlations between time-varying waveforms of light detected from the location of the single fluorophore by a light-sensitive element of the first light sensor and time-varying waveforms of light received by light-sensitive elements of the second light sensor (e.g., by determining a color of the single fluorophore based on wavelengths of light corresponding to generated time-varying waveforms of light having correlations with the time-varying waveform(s) of light corresponding to the location of the fluorophore that are greater than a threshold). Other methods of determining locations and/or colors of fluorophores in a target based on time-varying waveforms of light as described herein are anticipated.

The method 900 additionally includes determining, based on the determined colors and locations of the two or more fluorophores, an identity of a probe that is located in the target and that comprises the two or more fluorophores (910). This could include matching detected patterns of fluorophore colors (e.g., orders of colors of linearly, circularly, or otherwise arranged patterns fluorophores) within the environment to known patterns of fluorophores that corresponds to the identities of potential probes in the environment. This (910) could include using determined colors and locations of fluorophores to identify and/or locate probes within the target, e.g., by matching a pattern of fluorophore locations and/or an order of fluorophore colors to a template pattern or order that corresponds to a particular type of probe. In some examples, identifying a probe could include determining a probability that a set of detected fluorophores (e.g., fluorophores whose locations and/or colors have been determined) correspond to a single probe and/or determining the probability that such a probe is of one or more types. This could include determining a number of possible probe identifications based on one or more missing fluorophores in a detected pattern of fluorophores in a target. Other methods for identifying a probe, based on determined locations and colors of fluorophores in a target, are anticipated.

The method 900 could include other additional steps or elements. The method could include electronically controlling a spatial light modulator (SLM) to control a direction, magnitude, or other properties of the spectral dispersion applied to the light received by the second light sensor. The method 900 could include operating a micromirror device to control the angle of actuated mirrors of the micromirror device, e.g., to direct light from the particular region of the target toward one or both of the first and second light sensors. The method 900 could include illuminating the particular region of the target, e.g., by reflecting illumination generated by a laser or other light source toward the particular region of the target by controlling one or more actuated mirrors of a micromirror device to reflect the illumination toward the particular region of the target. The method 900 could include any additional steps, or could include details of implementation of the listed steps 902, 904, 906, 908, 910 or of other additional steps, as described herein in relation to the operation of an imaging system. Additional and alternative steps of the method 900 are anticipated.

Figure 10:
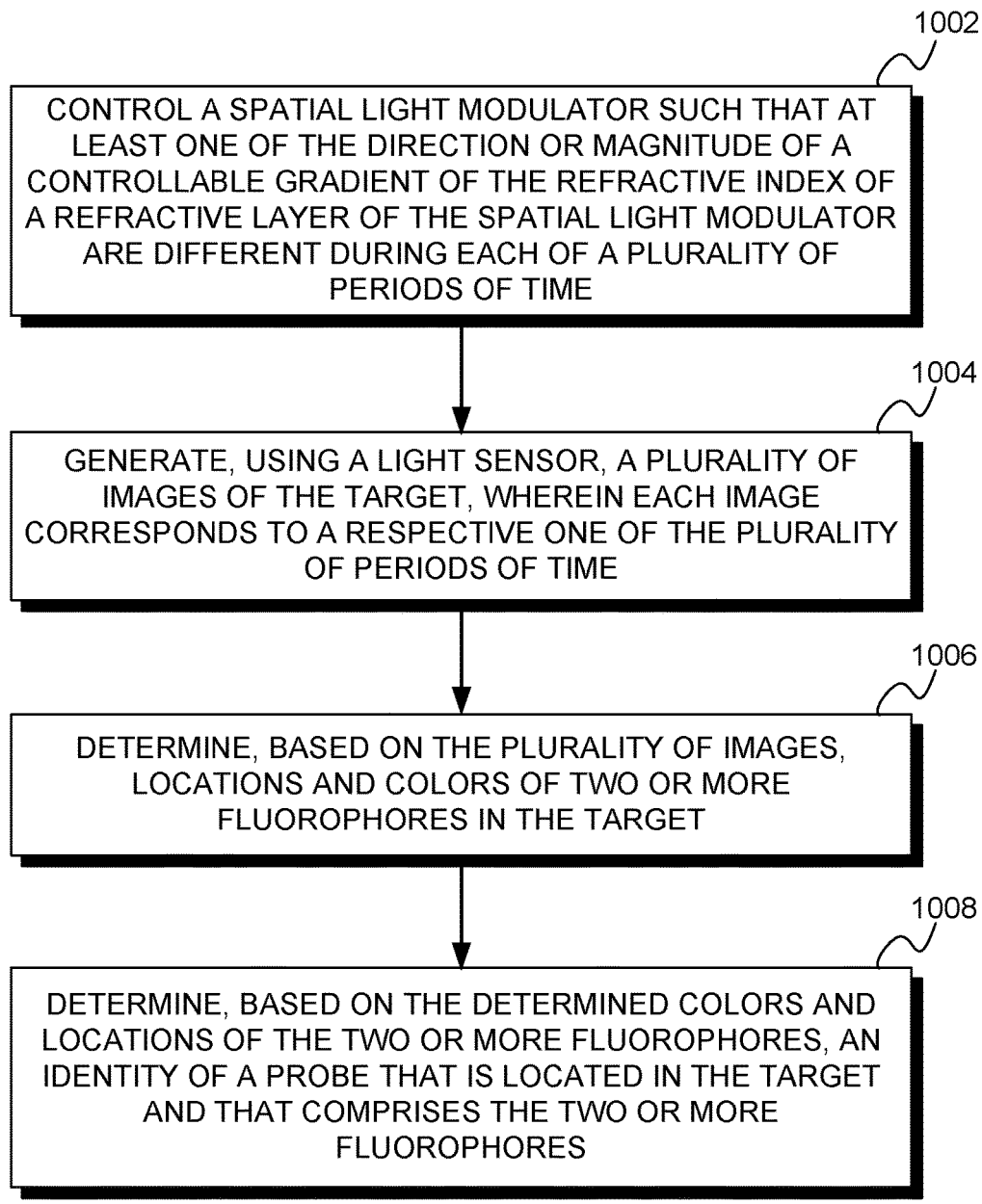
FIG. 10 is a flowchart of an example method.

FIG. 10 is a flowchart of an example method 1000 for operating elements of an imaging system to identify spatially and spectrally multiplexed probes in a target environment and/or to provide some other functions and/or applications of the imaging system. The method 1000 includes controlling a spatial light modulator (SLM) such that at least one of the gradient or magnitude of a controllable gradient of the refractive index of a refractive layer of the SLM are different during each of a plurality of period of time (1002). In some examples, the controlled refractive index could be a refractive index of a chromatically dispersive refractive layer such that light directed toward, reflected from, transmitted through, or otherwise having interacted with the SLM is spectrally dispersed. In some examples, the SLM could further include a reflective layer disposed beneath the refractive layer. In some examples, the SLM could include an array of regions having respective electronically controllable refractive indexes and electronically controlling the SLM (1002) could include electronically controlling the refractive indexes of the cells such that the refractive indexes of the cells vary in a direction corresponding to a specified direction of the controllable gradient at a spatial rate of change corresponding to a specified magnitude of the controllable gradient.

The method 1000 additionally includes generating, using a light sensor, a plurality of images of the target, wherein each image corresponds to a respective one of the plurality of periods of time (1004). This could include operating a charge-coupled device (CCD), CMOS camera, array of active pixel sensors, or other imaging apparatus to generate images during the plurality of periods of time.

The method 1000 further includes determining, based on the plurality of images, locations and colors of two or more fluorophores in the target (1006). This could include using a process of deconvolution. Such a deconvolution could be based on information about the operation of the SLM during the plurality of periods of time (e.g., information about the direction and magnitude of the controllable gradient of the refractive index of the refractive layer of the SLM during each of the periods of time) and based on information about an imaging system used to receive light from the target, apply the light to the SLM, and provide the light from the SLM to the light sensor. Other methods, such as methods described in combination with FIGS. 2A-D, could be used to determine the locations and colors of two or more fluorophores in the target.

The method 1000 additionally includes determining, based on the determined colors and locations of the two or more fluorophores, an identity of a probe that is located in the target and that comprises the two or more fluorophores (1008). This could include matching detected patterns of fluorophore colors (e.g., orders of colors of linearly, circularly, or otherwise arranged patterns fluorophores) within the environment to known patterns of fluorophores that corresponds to the identities of potential probes in the environment. This (1008) could include using determined colors and locations of fluorophores to identify and/or locate probes within the target, e.g., by matching a pattern of fluorophore locations and/or an order of fluorophore colors to a template pattern or order that corresponds to a particular type of probe. In some examples, identifying a probe could include determining a probability that a set of detected fluorophores (e.g., fluorophores whose locations and/or colors have been determined) correspond to a single probe and/or determining the probability that such a probe is of one or more types. This could include determining a number of possible probe identifications based on one or more missing fluorophores in a detected pattern of fluorophores in a target. Other methods for identifying a probe, based on determined locations and colors of fluorophores in a target, are anticipated.

The method 1000 could include other additional steps or elements. The method 1000 could include operating a micromirror device to control the angle of actuated mirrors of the micromirror device, e.g., to direct light from the target toward the SLM. The method 1000 could include illuminating the target, e.g., by reflecting illumination generated by a laser or other light source toward one or more specified regions of the target by controlling one or more actuated mirrors of a micromirror device to reflect the illumination toward the one or more regions of the target. The method 1000 could include any additional steps, or could include details of implementation of the listed steps 1002, 1004, 1006, 1008 or of other additional steps, as described herein in relation to the operation of an imaging system. Additional and alternative steps of the method 1000 are anticipated.

VII. Imaging Using a Spectrally Dispersed Illumination

The above methods and systems for imaging of a sample (e.g., a biological sample) in order to identify probes in the sample, to detect the location, color, or other properties of fluorophores in the sample (e.g., fluorophores of such a probe), or to provide some other benefit are intended as non-limiting example embodiments. In some examples, it could be advantageous to image a sample in such a way that the excitation and emission spectra of fluorophores (e.g., of probes) or other contents of the sample may be efficiently detected or determined. This could include applying illumination to the sample that is spatially encoded with respect to wavelength; that is, illuminating the sample such that different regions of the sample receive illumination of different wavelengths. Embodiments of the present disclosure may be implemented using a microscope, such as a fluorescence microscope, a confocal microscope (with confocality along at least one dimension), a transmission microscope, or a reflectance microscope, having one or more 2-D imaging devices, e.g., a CCD or CMOS sensor or camera. Alternatively, an optical system may be built according to embodiments of the present disclosure using suitable optical elements.

Rather than acquiring a hyperspectral image of the sample for each excitation wavelength of interest, embodiments of the present disclosure allow for acquiring a 2-D image of emission spectra corresponding to more than one excitation wavelengths for a subset of areas on a sample. A plurality of the 2-D images can be acquired and computationally reconstructed to obtain a 4-D hyperspectral-imaging dataset of a sample.

According to an aspect of the present disclosure, excitation light having one or more wavelengths may be used to excite fluorophores in the sample. The excitation light may be generated by a multi-color light source that emits light with one or more wavelengths. In some embodiments, the multi-color light source may have a continuous spectrum. For example, the multi-color light source may be a broadband light source, such as a supercontinuum laser, a white light source (e.g., a high-pressure mercury lamp, a xenon lamp, a halogen lamp, or a metal halide lamp), or one or more LEDs. In other embodiments, the multi-color light source may have a discrete spectrum. For example, the multi-color light source may be a combination of pulsed or continuous "single-wavelength" lasers that emit light with very narrow spectra.

According to an aspect of the present disclosure, excitation light emitted by the light source may be structured for exciting a subset of areas on the sample in an excitation pattern using a spatial light modulator (SLM). To structure the excitation light, the SLM may modulate the phase or amplitude of the excitation light by selectively actuating or switching its pixels. In some embodiments, the SLM may be selected from a group of SLMs including a digital micromirror device (DMD), a diffractive optical element, a liquid crystal device (LCD), and a liquid crystal-on-silicon (LCOS) device.

According to an aspect of the present disclosure, the structured excitation light may be spectrally dispersed in a first lateral direction (e.g., the vertical direction y or the horizontal direction x). Spectral dispersion of the excitation light may separate or split one or more wavelengths of the spectrum of the excitation light in the first lateral direction. In some embodiments, at least one dispersive element may be used to spectrally disperse the excitation light before it illuminates the sample in the excitation pattern. The at least one dispersive element may be a diffractive grating or a prism, or a combination of one or more prisms. Therefore, a spectrally dispersed excitation pattern may be generated to illuminate areas at various spatial locations on the sample.

Fluorophores or other types of optical labels in the sample may be excited by the excitation light illuminating the sample. When they relax to the ground state, the fluorophores or optical labels may emit light in a range of wavelengths known as the emission spectrum. The fluorophores or optical labels may have different emission spectra corresponding to different wavelengths of the excitation light.

As described herein, fluorophores are used in this disclosure as an exemplary optical label. Descriptions in references to fluorophores are equally applicable to other types of optical labels consistent with the embodiments of this disclosure. For example, the excitation light emitted from the light source may also excite other types of optical labels, which upon excitation, may emit light with an emission spectrum. Therefore, fluorescent light and fluorescence emission spectrum used in the descriptions in this disclosure may also be used to represent the emission light and emission spectra of other optical labels.

According to an aspect of the present disclosure, fluorescent light emitted by the fluorophores excited by the excitation light in a given area of the sample may be spectrally dispersed in a second lateral direction (e.g., the horizontal direction x or the vertical direction y). At least one dispersive element may be employed to spectrally disperse the fluorescent light into a fluorescence emission spectrum corresponding to the excitation wavelength at that given area. The fluorescence emission spectra of a subset of areas on the sample may be acquired as a 2-D image in one exposure by the 2-D imaging device.

According to an aspect of the present disclosure, fluorescence excitation and emission spectra of all the areas across the sample or across a field of view may be acquired by scanning the spectrally dispersed excitation pattern in the first and second lateral directions and acquiring a 2-D image of the fluorescence emission spectra at each spatial location of the excitation pattern.

In some embodiments, the excitation pattern is scanned across the sample or the field of view by modulating the pixels of the SLM. In other embodiments, an x-y translation stage may be used to laterally scan the excitation pattern across the sample or the field of view by moving the sample or a diffraction grating in the first and second lateral directions. The stage may be a motorized translation stage, a piezoelectric translation stage, or any suitable stage that allows for lateral linear movement.

Advantageously, the 4-D hyperspectral-imaging dataset may be computationally reconstructed from the 2-D images of the emission spectra, each 2-D image corresponding to the excitation pattern at a different spatial location on the sample.

In some aspects, systems and methods according to the present disclosure allows for confocal optical sectioning. This may allow for acquisition of a hyperspectral-imaging dataset for a plurality of focal planes along an axial direction of the sample. According to an aspect of the present disclosure, a hyperspectral-imaging dataset for a focal plane may be acquired by implementing one or more optical pinholes at a plane conjugate to the selected focal plane. The optical pinholes may be one or more spatial pinholes, or programmable artificial pinholes formed by pixels of a second SLM.

Advantageously, a degree of confocality may be adjusted as needed by changing the size and/or separation of the artificial pinholes by the SLM. Additionally, a pinhole pattern may be formed by the SLM by selectively modulating or switching its pixels to match the excitation pattern of the excitation light. The pinhole pattern may advantageously allow for confocal imaging of a plurality of areas on the sample simultaneously illuminated by the excitation pattern. This may increase the speed and/or throughput of acquiring hyperspectral-imaging datasets across the sample at the focal plane comparing to traditional confocal microscopes that use sequential point-by-point scanning.

Reference will now be made in detail to embodiments and aspects of the present disclosure, examples of which are illustrated in the accompanying drawings. Where possible, the same reference numbers will be used throughout the drawings to refer to the same or like parts.

As described herein, to illustrate different wavelengths or frequencies of light, different densities of dotted texture are used in the attached drawings. Higher densities correspond to longer wavelengths or lower frequencies of light. Additionally, vertical and horizontal directions are used as examples for illustrating first and second lateral directions. Alternatively, the horizontal direction may be the first lateral direction and the vertical direction may be the second lateral direction. As described herein, any two suitable different directions or a pair of non-parallel, e.g., orthogonal, directions may be used as first and second lateral directions.

Exemplary Schemes for Acquiring a Hyperspectral-Imaging Dataset

Figure 11:
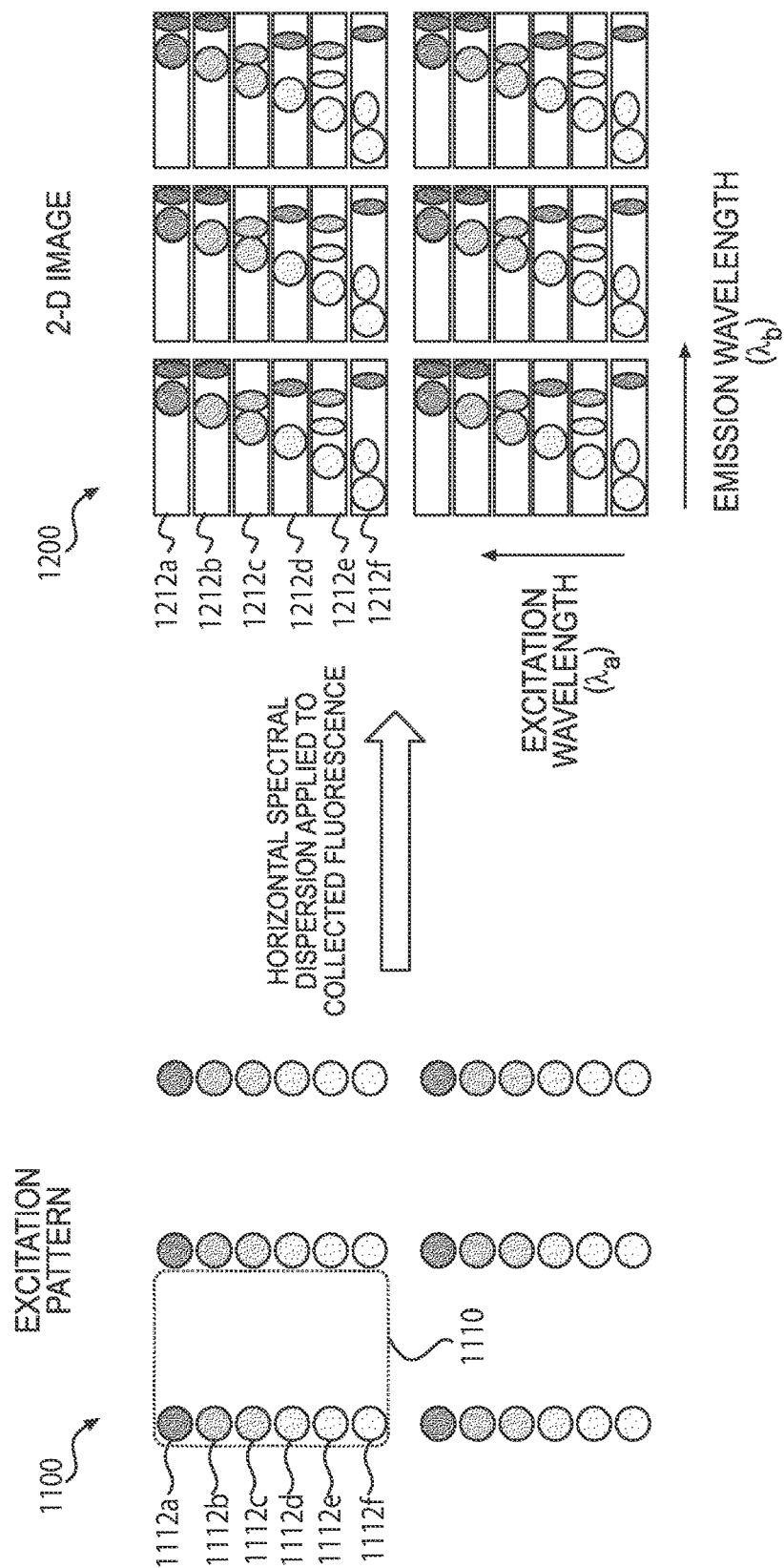
FIG. 11 is a graphical illustration of an example scheme for acquiring a hyperspectral-imaging dataset.

FIG. 11 graphically illustrates an exemplary scheme for acquiring a hyperspectral-imaging dataset used by methods and systems of the present disclosure. As shown in FIG. 11, excitation light having a discrete spectrum is illuminated onto a sample in an excitation pattern 1100. Excitation pattern 1100 may include a 2-D array of excitation spots. For example, FIG. 11 illustrates a portion of an exemplary 2-D array of circular excitation spots. Additional spots of the array may be located above, below, to the left, and/or to the right of the exemplary array (not shown). As described herein, a suitable size of the array, and a suitable shape, size, and/or separation of the spots may be predetermined according to the application.

The discrete spectrum of the excitation light includes a plurality of discrete wavelengths or a plurality of narrow spectral bands. Thus, when the excitation light is spectrally dispersed by a dispersive element along a given lateral direction, excitation pattern 1100 may be spectrally dispersed such that different wavelengths of light are directed to different locations in the given lateral direction. For example, as shown in FIG. 11, excitation pattern 1100 may include a plurality of scanning cells 1110, e.g., a 2-D array of scanning cells 1110. When the excitation light is spectrally dispersed along the vertical direction, each scanning cell 1110 may include a plurality of excitation spots 1112a, 1112b, 1112c, 1112d, 1112e, and 1112f vertically offset from one another and corresponding to different excitation wavelengths of the excitation light generated by the spectral dispersion.

The vertical separation between the excitation spots may or may not be uniform, and may be predetermined by various factors, such as the excitation wavelengths, the size of the spots, and the amount of dispersion of the excitation light. The total number of the vertically dispersed excitation spots in scanning cell 1110 may depend on the number of discrete wavelengths or narrow spectral bands of the excitation light.

To generate an excitation spectrum of a given spatial location on the sample, spectrally dispersed excitation pattern 1100 as shown in FIG. 11 may be scanned in the vertical direction such that the excitation spots corresponding to different excitation wavelengths may be shifted to this given spatial location. For example, when excitation pattern 1100 is shifted in the vertical direction, areas in each scanning cell 1110 previously illuminated by excitation spots 1112a, 1112b, 1112c, 1112d, 1112e, and 1112f can be illuminated by different ones of these excitation spots. For instance, by shifting excitation pattern 1100 over one excitation spot, the areas previously illuminated by excitation spots 1112b are illuminated by excitation spots 1112a, the areas previously illuminated by excitation spots 1112c are illuminated by excitation spots 1112b, the areas previously illuminated by excitation spots 1112d are illuminated by excitation spots 1112c, the areas previously illuminated by excitation spots 1112e are illuminated by excitation spots 1112d, the areas previously illuminated by excitation spots 1112f are illuminated by excitation spots 1112e, and the areas previously illuminated by excitation spots 1112a are illuminated by excitation spots 1112f shifted from scanning cells located above (not shown).

Areas within each scanning cell 1110 may be scanned by shifting spectrally dispersed excitation pattern 1100 in the vertical and horizontal directions. For example, by shifting excitation pattern 1100 over the length of scanning cell 1110 in the vertical direction, a given area in scanning cell 1110 can be illuminated by the different excitation spots corresponding to the different excitation wavelengths of the light source. By shifting excitation pattern 1100 vertically and/or horizontally in a continuous fashion or at predetermined separations (e.g., based on the desired vertical and/or horizontal resolution) over the lengths of scanning cell 1110, each given area in scanning cell 1110 can be illuminated by the different excitation spots.

As shown in FIG. 11, the excitation spots of excitation pattern 1100 are separated in the horizontal direction at a given period. Advantageously, the periodic separation of the excitation spots in the horizontal direction allows for measuring the fluorescence emission spectra of the excited areas on the sample. For example, the emitted fluorescent light from a given area illuminated by an excitation spot can be spectrally dispersed in the horizontal direction without overlapping with that of another area. Therefore, the fluorescence emission spectra of a plurality of areas simultaneously illuminated by the excitation spots can be generated and acquired by a 2-D imaging sensor or device.

FIG. 11 shows a 2-D image 1200 of the fluorescence emission spectra with the excitation wavelengths ($\lambda_a$) represented in the vertical direction and the emission wavelengths ($\lambda_b$) represented in the horizontal direction. FIG. 11 graphically illustrates that, in 2-D image 1200, areas excited by excitation spots 1112a, 1112b, 1112c, 1112d, 1112e, and 1112f corresponding to different excitation wavelengths may generate different fluorescence emission spectra 1212a, 1212b, 1212c, 1212d, 1212e, and 1212f extending in the horizontal direction and correspondingly offset from one another in the vertical direction. Therefore, a plurality of fluorescence emission spectra can be acquired in 2-D image 1200, with each emission spectrum corresponding to an excited spot of excitation pattern 1100 at a different spatial location on the sample.

As described above, different areas in each scanning cell 1110 may be illuminated by spatially shifting excitation pattern 1100 laterally in the vertical and horizontal directions. At each spatial position of excitation pattern 1100, fluorescence emission spectra of the illuminated areas can be acquired on 2-D image 1200. Therefore, a plurality of 2-D images 1200 of fluorescence emission spectra may be acquired corresponding to a series of excitation patterns 1100 laterally shifted from one another.

By combining datasets of the acquired 2-D images 1200, a fluorescence excitation-emission matrix (EEM) may be acquired for each pixel or spatial location in the 2-D images 1200. The fluorescence EEM may record or display fluorescence intensities as a function of a plurality of excitation wavelengths and a range of emission wavelengths. Therefore, a 4-D hyperspectral-imaging dataset of the sample having both the excitation and emission spectra may be collected and reconstructed from the acquired 2-D images 1200.

Figure 12:
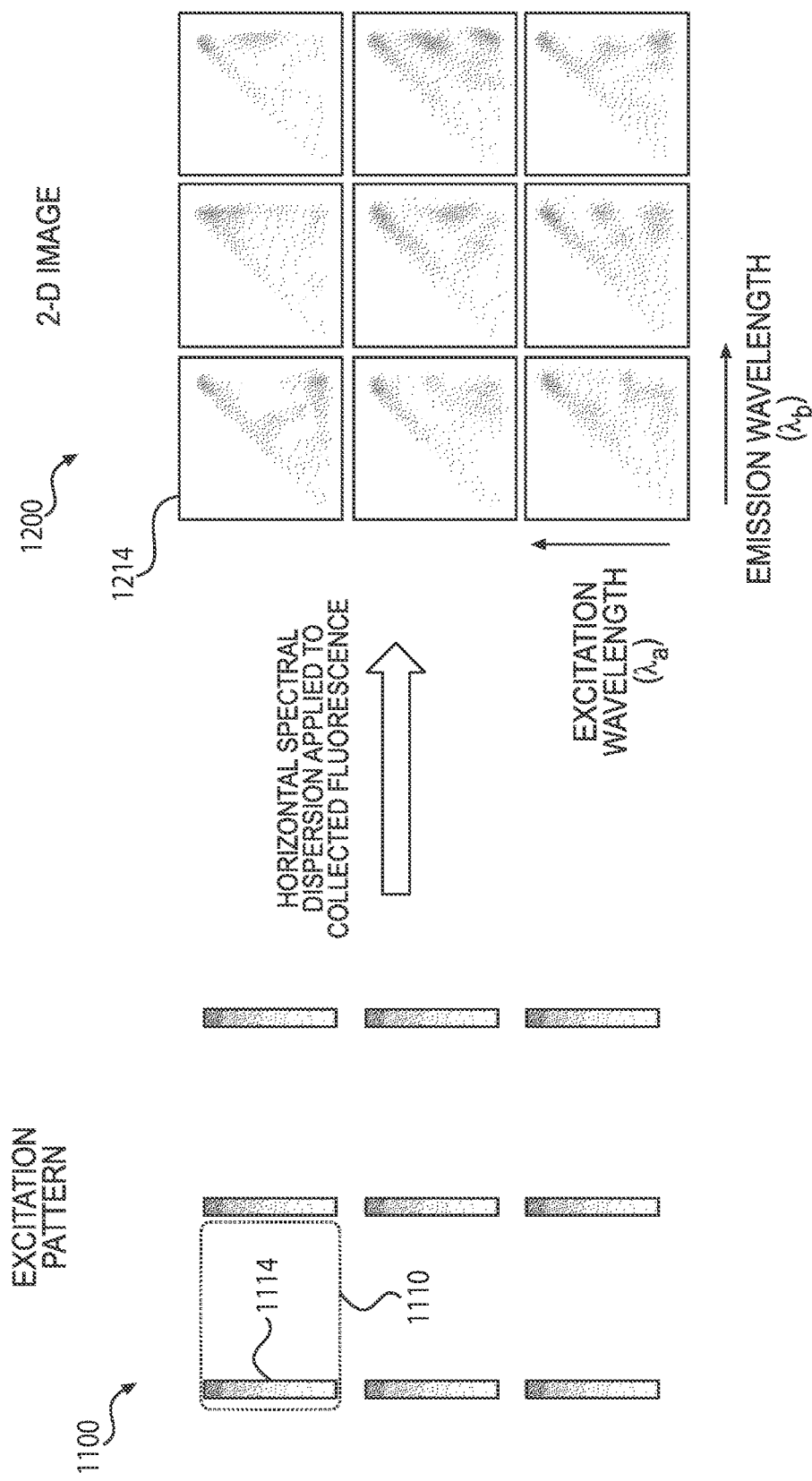
FIG. 12 is a graphical illustration of another example scheme for acquiring a hyperspectral-imaging dataset.

FIG. 12 graphically illustrates another exemplary scheme for acquiring a hyperspectral-imaging dataset by methods and systems of the present disclosure. As shown in FIG. 12, when the excitation light has a continuous spectrum and is spectrally dispersed by a dispersive element along the vertical direction, a focused spot of the excitation light may be spectrally dispersed into a continuous excitation line along the vertical direction. In such instances, as shown in FIG. 12, excitation pattern 1100 may be spectrally dispersed into a 2-D array of excitation lines 1114, each representing the range of wavelengths of the excitation light vertically offset in a continuous fashion.

FIG. 12 illustrates a portion of an exemplary 2-D array of excitation lines 1114, which shows a three-by-three 2-D array. Other excitation lines of the array may be located above, below, to the left, and/or to the right of the exemplary array (not shown). As described herein, a suitable size of the array, a suitable shape, size, and/or separation of the excitation lines may be selected according to a given application.

Areas within each scanning cell 1110 may be similarly scanned as described above by shifting spectrally dispersed excitation pattern 1100 in the vertical and horizontal directions. An array of fluorescence emission spectra 1214 corresponding to the array of excitation lines 1114 of excitation pattern 1100 may be similarly acquired on 2-D image 1200. Each fluorescence emission spectrum 1214 in 2-D image 1200 corresponds to a continuous strip on the sample illuminated by an excitation line 1114 of excitation pattern 1100.

In the scheme shown in FIG. 12, in some embodiments, when shifting spectrally dispersed excitation pattern 1100 in the vertical direction, an area excited at a first wavelength along excitation line 1114 may then be excited at a second wavelength longer or shorter than the first wavelength after the vertical shifting. Therefore, by shifting excitation pattern 1100 vertically in a continuous fashion or over predetermined separations (e.g., based on the desired vertical resolution), areas illuminated by excitation lines 1114 in each scanning cell 1110 can be illuminated in the different excitation wavelengths of the light source. Similar to the scheme shown in FIG. 11, other areas on the sample in each scanning cell 1110 may be illuminated by the different excitation lines by shifting excitation pattern 1100 in the horizontal direction.

As described herein, the areas on the sample illuminated by excitation pattern 1100 may be substantially determined by the size and shape of the excitation spots or excitation lines of excitation pattern 1100. The size and shape of the excitation spots or excitation lines may be determined by many factors of the optical system, including the size and shapes of the pixels of the SLM, the magnification of the optical system, and the degree of spectral dispersion of the excitation light.

The spatial separation, horizontal and/or vertical, between excitation spots or lines of excitation pattern 1100 may be predetermined based on various factors, such as the excitation wavelengths, the size of the sample, the field of view of the optical system, the desired measurement throughput, spatial resolution, and/or speed, and the amounts of spectral dispersion of excitation light and/or emitted fluorescent light.

For example, the spatial separation between the excitation spots or lines in the vertical direction may be predetermined based on the amount of spectral dispersion of the excitation light such that the excitation spots or lines do not overlap in the vertical direction. The spatial separation between the excitation spots or lines in the horizontal direction may be predetermined based on the range of the fluorescence emission spectra in the horizontal direction such that the fluorescence emission spectra do not overlap with each other in the horizontal direction.

In some embodiments, the horizontal and/or vertical periods of an array of excitation spots for different wavelengths may be the same. In other embodiments, the horizontal and/or vertical periods of an array of excitation spots for different wavelengths may be different. Different spatial periods may be convenient for computationally reconstructing the 4-D hyperspectral imaging dataset in some cases, for example, where the SLM is placed at a Fourier plane of the sample to generate excitation pattern 1100 as described further below.

Embodiments to be described below in reference to schematic representations of optical systems and/or components are directed to systems and methods for achieving the above-described schemes for acquiring a 4-D hyperspectral-imaging dataset. The schematic representations are to be understood as not being drawn to scale.

Exemplary Optical Systems and Components

Figure 13:
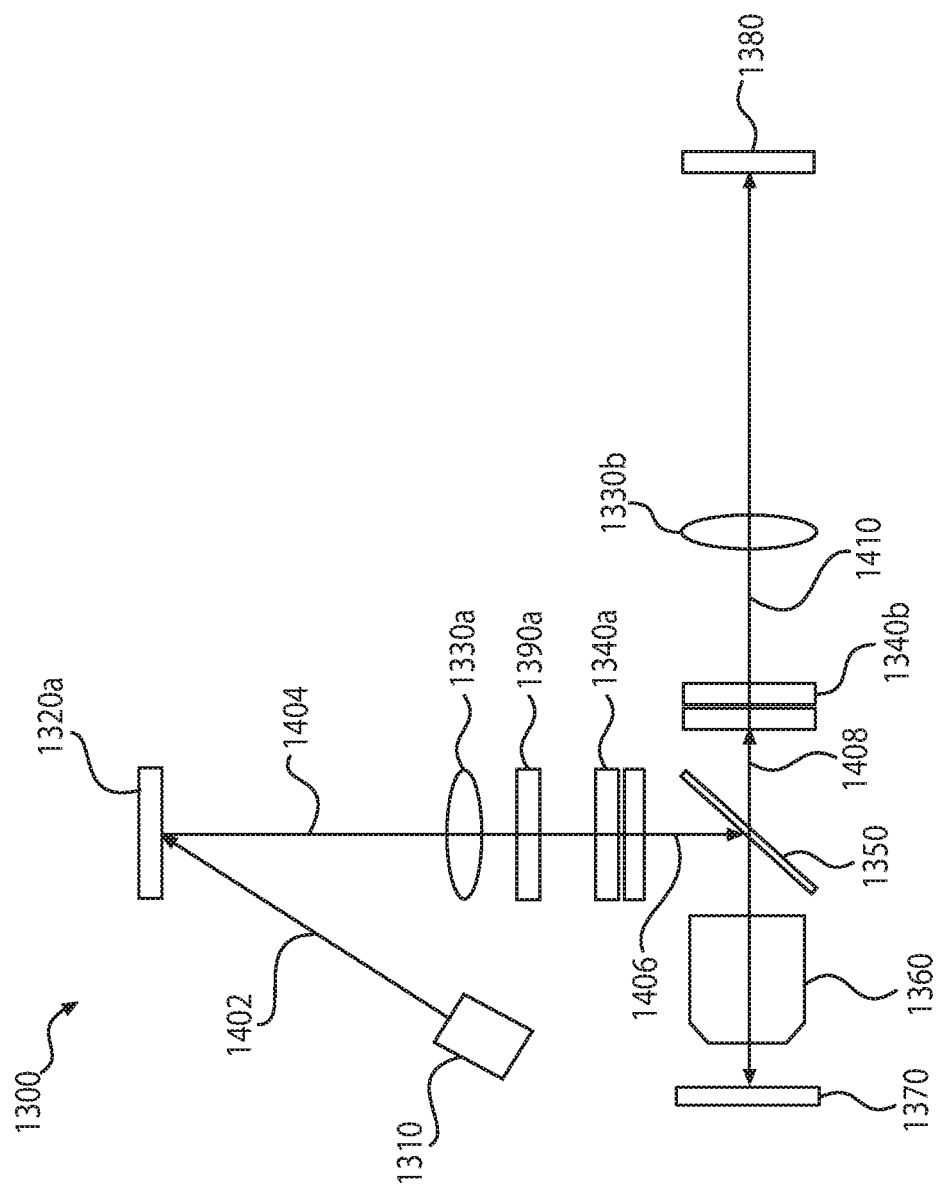
FIG. 13 is a schematic representation of an example hyperspectral imaging system.

FIG. 13 is a schematic representation of an exemplary hyperspectral imaging system 1300. In some embodiments, system 1300 may be a fluorescence microscope, a transmission microscope, or a reflectance microscope, or a confocal fluorescence microscope (with confocality along at least one dimension). Embodiments of the present disclosure are applicable to other suitable microscopy techniques for performing hyperspectral imaging.

As shown in FIG. 13, system 1300 may include an illumination system and a detection system, each having a plurality of components. The illumination system may include a light source 1310, a first SLM 1320a, at least one lens, e.g., lens 1330a, and at least one dispersive element, e.g., dispersive element 1340a. The detection system may include a 2-D imaging device 1380, at least one lens, e.g., lens 1330b, and at least one dispersive element, e.g., dispersive element 1340b. Depending on its layout, geometry, and/or application, system 1300 may further include a beamsplitter 1350, an objective 1360, a polarizer 1390a, and/or a sample holder 1370 where a sample to be imaged is placed. System 1300 may further include other optical elements, such as mirrors, beam dumps, etc.

As described herein, an optical axis of system 1300 may define a path along which the excitation light and emitted fluorescent light from the sample propagate through system 1300.

In the illumination system, as shown in FIG. 13, light source 1310 emits excitation light 1402, which is directed to SLM 1320a. Excitation light 1402 may be collimated and/or expanded using one or two lenses (not shown). SLM 1320a may structure excitation light 1402 through modulating the phase or amplitude of excitation light 1402 by selectively actuating or switching its pixels. At least a portion of the pixels of SLM 1320a reflect excitation light 1402 and direct it along the optical axis of system 1300.

As shown in FIG. 13, reflected excitation light 1404 transmits through lens 1330a and dispersive element 1340a. Lens 1330a may collimate reflected excitation light 1404 along the optical axis. Dispersive element 1340a spectrally disperses reflected excitation light 1404 along a first lateral direction. For example, dispersive element 1340a may cause small wavelength-dependent angular deflection to reflected excitation light 1404. Spectrally dispersed excitation light 1406 may be reflected by beamsplitter 1350 and directed towards objective 1360. Objective 1360 then focuses spectrally dispersed excitation light 1406 to a sample placed on sample holder 1370.

In the detection system, as shown in FIG. 13, fluorescent light emitted by excited fluorophores in the sample is collected and/or collimated by objective 1360. Fluorescent light 1408 transmits through beamsplitter 1350 and dispersive element 1340b along the optical axis of system 1300. Dispersive element 1340b spectrally disperses fluorescent light 1408 along a second lateral direction as described above. Spectrally dispersed fluorescent light 1410 transmits through lens 1330b and is acquired by 2-D imaging device 1380. Imaging device 1380 may be placed about one focal length away from lens 1330b such that lens 1330b may image and focus the spectrally dispersed fluorescent light 1410 onto a 2-D sensor of imaging device 1380.

Other configurations of system 1300 are possible using additional optical elements, such as mirrors, lenses, etc., as further described below.

Functions and the working principles of various components of system 1300 are described in detail below.

Light Source

As described above, light source 1310 may have a continuous spectrum or a discrete spectrum. Light source 1310 may be a white light source, such as a supercontinuum laser, or a combination of "single-wavelength" lasers with discrete narrow spectral bands. In some embodiments, excitation light 1402 emitted by light source 1310 may be directed straight towards SLM 1320a. In other embodiments, excitation light 1402 may be collimated and/or expanded by lenses before being incident on SLM 1320a. Additionally or alternatively, excitation light 1402 may be diffused using a diffuser or a despeckling element to reduce the speckle effect of coherent illumination.

In some embodiments, light source 1310 may be operably connected to a controller (not shown) having a processor and a computer-readable medium that stores instructions or operational steps. These instructions or steps, when executed by the processor, modulate the operational states of light source 1310. For example, the processor may activate or deactivate light source 1310, modulate the duration of a pulse when light source 1310 is a pulsed light source, and/or switch or tune the emission wavelengths of light source 1310.

Spatial Light Modulator for Modulating Excitation Light

As described above, to structure excitation light 1402 for illuminating the sample in excitation pattern 1100, SLM 1320a may modulate the amplitude or phase of excitation light 1402 by selectively modulating its pixels between operational states.

Amplitude Modulation

In some embodiments, the amplitude of excitation light 1402 may be modulated by SLM 1320a. For example, SLM 1320a may be a digital micromirror device (DMD) having an array of multiple micromirrors (not shown). These mirrors may be individually actuated to switch between two operational positions, an "on" position and an "off" position. When a micromirror is configured to be in the "on" position, excitation light 1402 is reflected to propagate along the optical axis as reflected excitation light 1404 directed to the sample. When a micromirror is configured to be in the "off" position, excitation light 1402 is reflected towards a direction deviated from the optical axis and is not directed to the sample (not shown). In some embodiments, excitation light 1402 reflected by the "off" micromirrors may be directed to other optical elements, such as a mirror or a beam dump (not shown).

In some embodiments, the micromirrors are of a square shape having a length of its sides ranging from about a few micrometers to about 10 µm. Other shapes and sizes of the micromirrors are also possible and may be suitably used. The DMD is typically capable of changing or alternating the "on" and "off" positions of the micromirrors very rapidly.

In some embodiments, a single micromirror of the DMD may be referred to as a single pixel. In other embodiments, a plurality of micromirrors may be referred to as a single pixel. For example, a group of immediately adjacent micromirrors may be referred as a single pixel and may be modulated or actuated to the same position.

An amplitude modulation pattern may be formed by the micromirrors or pixels of the DMD in the "on" position. The amplitude modulation pattern may be imaged onto the sample as excitation pattern 1100 by lens 1330a and objective 1360. For example, lens 1330a is used as a tube lens and combined with objective 1360 to form an imaging configuration. The DMD is placed at a conjugate plane to the sample or at about one focal length before lens 1330a. Depending on the focal lengths of lens 1330a and objective 1360, excitation pattern 1100 may be a magnified or de-magnified image of the amplitude modulation pattern.

In other embodiments, to modulate the amplitude of excitation light 1402, SLM 1320a may be a liquid crystal device (LCD) or a liquid crystal-on-silicon (LCOS) device. Pixels of SLM 1320a may create an amplitude modulation pattern by manipulating the polarization of light incident on the pixels. Similar to the DMD, the LCD or LCOS device may be placed at a conjugate plane to the sample. Pixels of the LCD or LCOS device may be electrically modulated between an "on" state and an "off" state in a pixel-by-pixel fashion. The "on" pixels may rotate the orientation of linearly polarized light by about 90° while the "off" pixels do not perform the rotation. In such instances, a first linear polarizer (not shown) may be used to linearly polarize excitation light 1402. A second linear polarizer or a polarizing beamsplitter (PBS) (not shown) may be used to transmit excitation light 1404 reflected by the "on" pixels and block excitation light 1402 reflected by the "off" pixels.

A disadvantage of modulating the amplitude of excitation light 1402 using SLM 1320a is the loss of light during the modulation. This is because most of the pixels of SLM 1320a are typically in the "off" state. Accordingly, most of excitation light 1402 is steered away from the optical axis and would not reach the sample, and thus is lost. Excitation light recycling systems may be used to reduce this loss by redirecting off-optical axis excitation light back to the optical axis as described further below.

Phase Modulation

Figure 14:
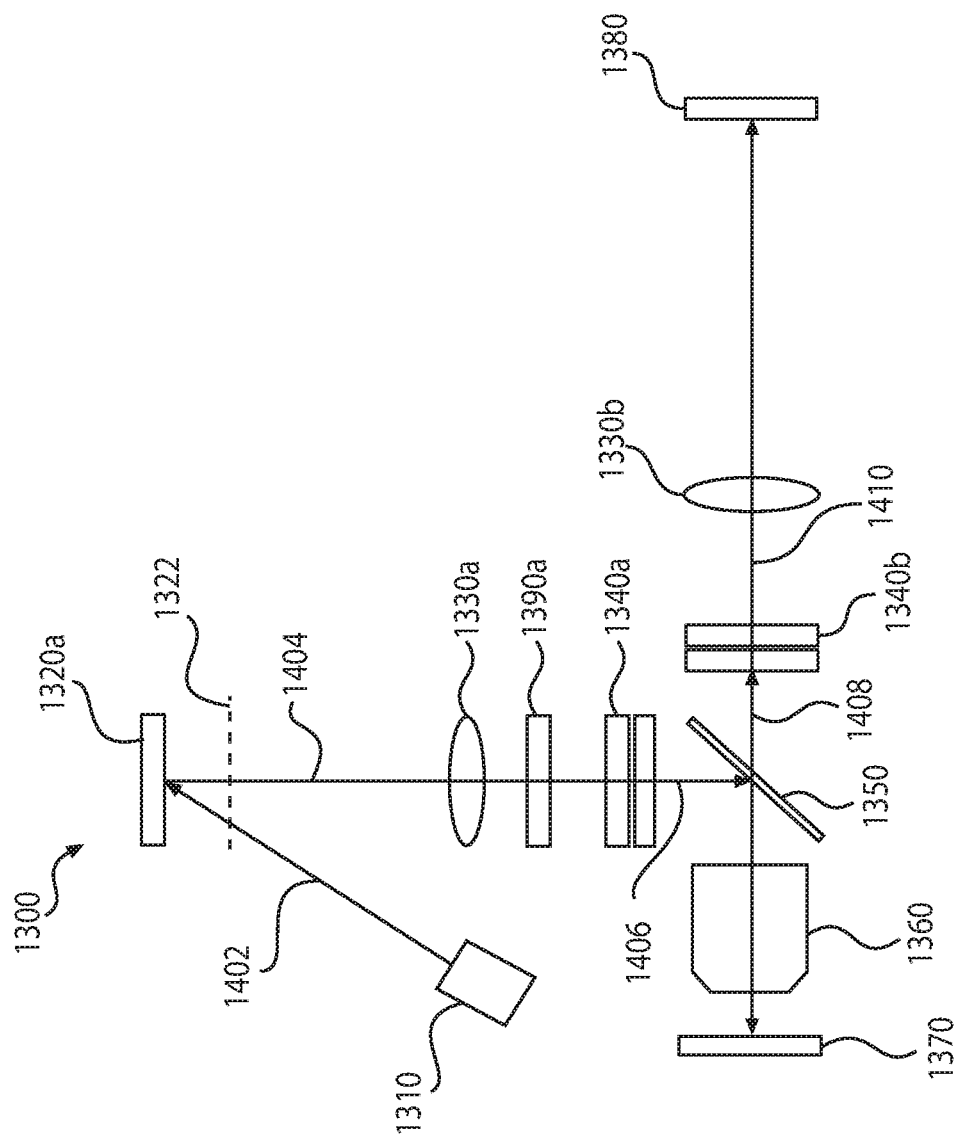
FIG. 14 is a schematic representation of another example hyperspectral imaging system.

In some embodiments, the phase of excitation light 1402 may be modulated by SLM 1320a. SLM 1320a may be a reflection type LCD or LCOS device. FIG. 14 is a schematic representation of an exemplary system 1300 using a LCD or LCOS device as SLM 1320a. As shown in FIG. 14, the LCD or LCOS device may be placed close to a conjugate plane 1322 to the sample. A custom phase modulation pattern may be formed by the pixels of the LCD or LCOS device. The phase modulation pattern may create an array of off-axis lens phase profiles. Wavefront of excitation light 1402 may then be modulated by the phase modulation pattern and form a preliminary excitation pattern (e.g., a diffraction pattern) at conjugate plane 1322. This preliminary excitation pattern may be a magnified or de-magnified image of excitation pattern 1100 and may include an array of focused spots.

Conjugate plane 1322 may be located a short distance beyond SLM 1320a. The focal plane of the focused spots of the preliminary excitation pattern may be wavelength dependent. Therefore, different wavelengths of excitation light 1402 may not all focus on conjugate plane 1322. In some embodiments, the focal plane for the center wavelength of excitation light 1402 is approximately at conjugate plane 1322. The preliminary excitation pattern formed at or close to conjugate plane 1322 is then imaged onto the sample as excitation pattern 1100 by lens 1330a and objective 1360. Although different wavelengths of excitation pattern 1100 in this configuration may have slightly different focal planes, modulating the phase of excitation light 1402 increases the efficiency of using excitation light 1402 comparing to amplitude modulation.

In other embodiments, the LCD or LCOS device may be placed at an aperture plane, which may be a conjugate plane to the back aperture of objective 1360 or a Fourier plane to the sample. For example, one exemplary configuration of system 1300 may have two tube lenses (not shown) placed between SLM 1320a and objective 1360. A first tube lens may be located about one focal length behind SLM 1320a. A second tube lens may be located about two focal lengths behind the first tube lens. Objective 1360 may be located about one focal length behind the second tube lens.

The pixels of the LCD or LCOS device may form a custom phase modulation pattern to modulate the wavefront of excitation light 1402. Upon the reflection of excitation light 1402 by the LCD or LCOS device, phases at different locations of the wavefront of the reflected excitation light 1404 may be selectively changed according to the phase modulation pattern. In some embodiments, pixels of the LCD or LCOS device may be electrically modulated between an "on" state and an "off" state in a pixel-by-pixel fashion. If pixels of the LCD or LCOS device are in the "on" state, they may change the phase of the reflected light by changing the optical path length of light traveled in the liquid crystal; and if they are in the "off" state, they may not change the phase of the reflected light. This allows the phase modulation pattern formed by the pixels to be digitally customized as needed. In other embodiments, pixels of the LCD or LCOS device may have multiple states or levels of adjustment (e.g., 256 levels) and may be individually modulated to desired states or levels. Advantageously, increasing the states or levels of adjustment of the pixels increases the continuity of the adjustment of the phase modulation pattern and thus the adjustment of the phase of excitation light 1402.

The phase modulation may render wavelets of reflected excitation light 1404 having different directions and/or phases. As reflected excitation light 1404 propagates along the optical axis, each of the tube lenses and objective 1360 may perform Fourier Transform on the wavefront of reflected excitation light 1404. A diffraction pattern may then be formed at the focal plane of objective 1360. This diffraction pattern is referred to herein as excitation pattern 1100 when illuminated on the sample.

In the above-described configuration, because the phase modulation pattern is at or approximately at a Fourier plane to the sample, the phase modulation pattern is the inverse Fourier transform of a desired excitation pattern 1100 illuminated on the sample. Because Fourier Transform includes a scaling factor proportional to the wavelength of light, the spatial periods of the array of excitation spots for different wavelengths in excitation pattern 1100 may be different. For example, longer wavelength would diffract at larger angles, which can be converted to larger spatial periods. This may cause the corresponding fluorescence emission spectra arrays acquired in 2-D image 1200 to have different spatial periods. Customized computer algorithms may be used for generating time-varying phase modulation patterns for scanning across the field of view and/or for computationally reconstructing the 4-D hyperspectral-imaging dataset from datasets of such 2-D images.

Advantageously, modulating the phase of excitation light 1402 may allow it to propagate with substantially uniform intensity in the near field of the LCD or LCOS device and thus reduce loss of light. The modulated excitation light may then form customizable or programmable excitation pattern 1100 on the sample in the far field. Therefore, comparing to modulating the amplitude of excitation light 1402 as described above, modulating the phase of excitation light 1402 to create excitation pattern 1100 may substantially increase the efficiency of illumination of system 1300 by reducing loss of excitation light 1402. Additionally, increasing the continuity of the phase modulation of excitation light 1402 may further increase the diffraction efficiency of the LCD or LCOS device and thus the efficiency of illumination of system 1300.

The LCD or LCOS device for modulating the amplitude or phase of excitation light 1402 may alternatively be a transmission type device implemented along the optical axis. The geometry of the illumination system may be suitably designed such that the amplitude or phase modulation pattern formed by the pixels of the device may modulate the amplitude or phase of excitation light 1402 similarly as described above.

Whether SLM 1320a modulates the amplitude or phase of excitation light 1402, excitation pattern 1100 can be programmed and customized as needed by modulating pixels of SLM 1320a between two or multiple operational states or levels in a pixel-by-pixel fashion. Further, excitation pattern 1100 can be translated or shifted in a given spatial direction, such as the horizontal or vertical direction, by scanning or shifting the modulation of the pixels of SLM 1320a. This advantageously allows for scanning excitation pattern 1100 across the field of view of system 1300 without moving the sample and/or sample holder 1370 using an x-y translation stage.

In some embodiments, depending on the type and modulation features of the pixels of SLM 1320a, excitation light 1402 may be directed towards SLM 1320a at a predetermined angle relative to a plane of SLM 1320a. The predetermined angle may depend on the type of SLM 1320a and/or the geometry of system 1300. In some instances, when SLM 1320a is a reflection type SLM that modulates the phase of excitation light 1402, excitation light 1402 may be directed towards SLM 1320a at an angle such that reflected excitation light 1404 propagates along the optical axis of system 1300. In other instances, when SLM 320a is a DMD, excitation light 1402 may be directed towards the DMD at an angle such that excitation light 404 reflected by the "on" micromirrors propagates along the optical axis.

In some embodiments, SLM 1320a may be operably connected to a controller (not shown) having a processor and a computer-readable medium that stores instructions or operational steps. These instructions or steps, when executed by the processor, modulate the operational states of the pixels of SLM 1320a to form a desired excitation pattern 1100 and/or to translate excitation pattern 1100 in a desired spatial direction over a predetermined distance across the field of view.

Lenses and Objective

Various lenses of system 1300, such as lenses 1330a and 1330b, may be achromatic, such as achromatic doublets or triplets, to limit or reduce the effects of chromatic and/or spherical aberration of the system. Further, objective 1360 of system 1300 may be achromatic. Alternatively or additionally, objective 1360 may be an infinity-corrected objective such that objective 1360 may form a desired focus (e.g., focused spots or focused pattern) of a collimated light beam entering from its back aperture. Using achromatic lenses and/or achromatic or infinity-corrected objective may allow excitation light 1402 of different wavelengths to have at least approximately the same focus in the sample. Further, using achromatic lenses and/or achromatic objective may allow fluorescent light of different wavelengths from a focal plane in the sample to similarly form a focused image at imaging device 1380. Therefore, using achromatic lenses and/or achromatic objective may improve the quality of 2-D images 1200 of fluorescence emission spectra, and thus the quality of the reconstructed hyperspectral-imaging dataset.

Dispersive Elements

Dispersive elements 1340a and 1340b may be diffraction gratings or prisms, such as non-deviating prisms (e.g., Amici prisms or double Amici prisms). The types of dispersive elements 1340a and 1340b may be the same or may be different. The degree of dispersion caused by dispersive elements 1340a and 1340b may be same or different, and may be predetermined based on various factors, such as the spectral ranges of excitation light and fluorescent light, the size of the sample or the field of view, the size of imaging device 1380, the desired spectral resolution, and the application of system 1300.

In some embodiments, the degree of dispersion caused by dispersive elements 1340a and 1340b may be adjustable. For example, dispersive element 1340a may be a pair of double Amici prisms placed along the optical axis of system 1300. At least one of the pair of double Amici prisms is rotatable relative to the other around the optical axis. The rotation of the double Amici prisms relative to each other may allow for continuous control of the amount and/or angular orientation of the spectral dispersion of excitation light 1402. Similarly, dispersive element 1340b may be a pair of double Amici prisms, allowing for continuous control of the amount and/or angular orientations of the spectral dispersion (e.g., dispersion angles) of fluorescent light 1408.

Excitation Light Blocking

Because the intensity of excitation light 1402 may be orders of magnitude stronger than fluorescent light 1408, excitation light 1402 reflected and/or scattered by the sample and/or sample holder 1370 may enter the detection system and affect the detection or acquisition of the fluorescence emission spectra by imaging device 1380. Therefore, embodiments of the present disclosure may reduce or block excitation light 1402 from propagating into the detection system as described below.

In some embodiments, beamsplitter 1350 may be used to reject or block excitation light 1402 from propagating into the detection system. For example, beamsplitter 1350 of system 1300 may be a dichroic beamsplitter, a polarizing beamsplitter (PBS), or other suitable type of beamsplitter.

When light source 1310 or excitation light 1402 has a discrete spectrum having one or more discrete wavelengths or narrow spectral bands, beamsplitter 1350 may be a dichroic beamsplitter that selectively reflects and transmits light depending on its wavelength. For example, beamsplitter 1350 may be a multiband dichroic that has multiple cut-off wavelengths and passbands. The multiband dichroic may be selected to substantially reflect wavelengths of excitation light 1402 and to substantially transmit wavelengths of fluorescent light 1408. In such instances, some wavelengths of fluorescent light 1408 that are the same or close to that of excitation light 1402 may be substantially blocked, and thus may have substantially reduced intensity in 2-D image 1200 acquired by imaging device 1380.

Alternatively or additionally, when light source 1310 or excitation light 1402 has a discrete spectrum, a set of corresponding notch filters or a single multi-notch filter (not shown) may be added to the detection system along the optical axis. The notch filters or multi-north filter may selectively reflect the discrete wavelengths or narrow spectral bands of excitation light 1402, thereby blocking excitation light 1402 from reaching imaging device 1380. Again, some wavelengths of fluorescent light 1408 that are the same or close to that of excitation light 1402 may be substantially blocked by the notch filters, and thus may have substantially reduced intensity in 2-D image 1200 acquired by imaging device 1380.

When light source 1310 or excitation light 1402 has a continuous spectrum, beamsplitter 1350 may be a long-pass dichroic beamsplitter that reflects at least a portion of the wavelengths of excitation light 1402 and transmits at least a portion of the wavelengths of fluorescent light 1408. The spectrum of excitation light 1402 typically ranges from the ultraviolet through the visible spectra, and the spectrum of fluorescent light 1408 typically ranges from the visible into the near infrared spectra. Therefore, the long-pass dichroic beamsplitter may block wavelengths of excitation light 1402 and transmit wavelengths of fluorescent light 1408. However, in some instances, both the spectrum of excitation light 1402 and spectrum of fluorescent light 1408 may include short to long wavelengths and they may overlap, e.g., in the visible spectrum. In such instances, the long-pass dichroic beamsplitter may block at least some fluorescent light 1408 in the visible spectrum, and may not be suitable for rejecting excitation light 1402 in applications where the blocked spectrum of fluorescence light 1408 contains desired spectral information, for example.

Regardless of the types of spectrum of light source 1310 or excitation light 1402 (whether or not discrete or continuous), in some embodiments, polarizer 1390a and beamsplitter 1350 may be used in combination to block excitation light 1402 from entering the detection system and thus from propagating towards imaging device 1380. For example, beamsplitter 350 may be a polarizing beamsplitter (PBS) that reflects light whose vibration orientation aligns with the transmission axis of polarizer 1390a.

For example, polarizer 1390a may be placed at any suitable location along the optical axis to linearly polarize excitation light 1402. The PBS may be selected to reflect light having a vibration orientation same as that of the polarized excitation light and to transmit light having a vibration orientation perpendicular to that of the polarized excitation light. Most of the excitation light collected by objective 1360 would therefore reflect from this PBS and would not reach imaging device 1380. In some instances, both the sample and objective 1360 may depolarize reflected and/or scattered excitation light to a small degree, and thus undesirably allow some excitation light to transmit through the PBS and enter the detection system.

2-D Imaging Device

Imaging device 1380 may include a suitable 2-D sensor located at an image plane conjugate to a selected focal plane in the sample. The sensor could be implemented with a CMOS sensor, a CCD sensor, a 2-D array of silicon avalanche photodiodes (APDs), an electron-multiplied CCD (EMCCD), an intensified CCD, or other suitable types of 2-D sensors.

Imaging device 1380 may be operatively connected to a controller or a computing device (not shown) that controls its operation. For example, controller (not shown) may have a processor and one or more computer-readable medium that stores instructions or operational steps. The instructions or operational steps, when executed by the processor, may operate the exposure of imaging device 1380, acquire 2-D images 1200, and/or store the datasets of 2-D image 1200 to a memory. The computer-readable medium may further store instructions or operational steps that, when executed by the processor, perform data processing of the acquired 2-D image datasets and/or reconstruct the 4-D hyperspectral-imaging dataset from the 2-D image datasets.

System 1300 may advantageously have additional technical features and capabilities to enhance its functionality and performance as described in detail below.

Time-Resolved Capability

In some embodiments, time-resolved capability may be advantageously added to system 1300 to allow for fluorescence lifetime imaging (FLIM) or time-resolved fluorescence spectroscopy. For example, a pulsed light source, such as a supercontinuum laser, may be used as light source 1310, together with a 2-D imaging device 1380 having picosecond to nanosecond time-gating capability, such as an intensified CCD camera or an optoelectronic streak camera. Alternatively, a conventional 2-D CCD or CMOS sensor may be used in combination with an electro-optic shutter. In some embodiments, a modulated, electron-multiplied fluorescence lifetime imaging microscope (MEM-FLIM) camera may be used in combination with a modulated light source 1310, e.g., a pulsed light source.

The lifetime of the fluorophores or fluorescent molecules in the sample may be calculated from the acquired time-resolved 2-D images of the fluorescence emission spectra for each spatial location in the field of view. This adds another dimension of information to the hyperspectral-imaging dataset, thereby providing additional information about the fluorophores or fluorescent molecules in the sample.

Because FLIM excites the fluorophores with short excitation pulses in the time-domain, the FLIM capability of system 1300 may substantially reject the scattered and/or reflected excitation light by discarding the signals close to zero delay. This may advantageously reduce or minimize the effect of the scattered and/or reflected excitation light in the acquired fluorescence signals, e.g., 2-D image 1200.

Fluorescence Polarization

In some embodiments, system 1300 may advantageously allow for fluorescence polarization (or anisotropy) measurement to obtain additional information about the fluorophores or fluorescent molecules in the sample. Relationships between the polarization of the excitation light and the emitted fluorescent light subsequently detected may be used to analyze and study various chemical and/or physical processes of the molecules in the sample, such as rotational diffusion, binding interactions, and orientation.

Figure 15:
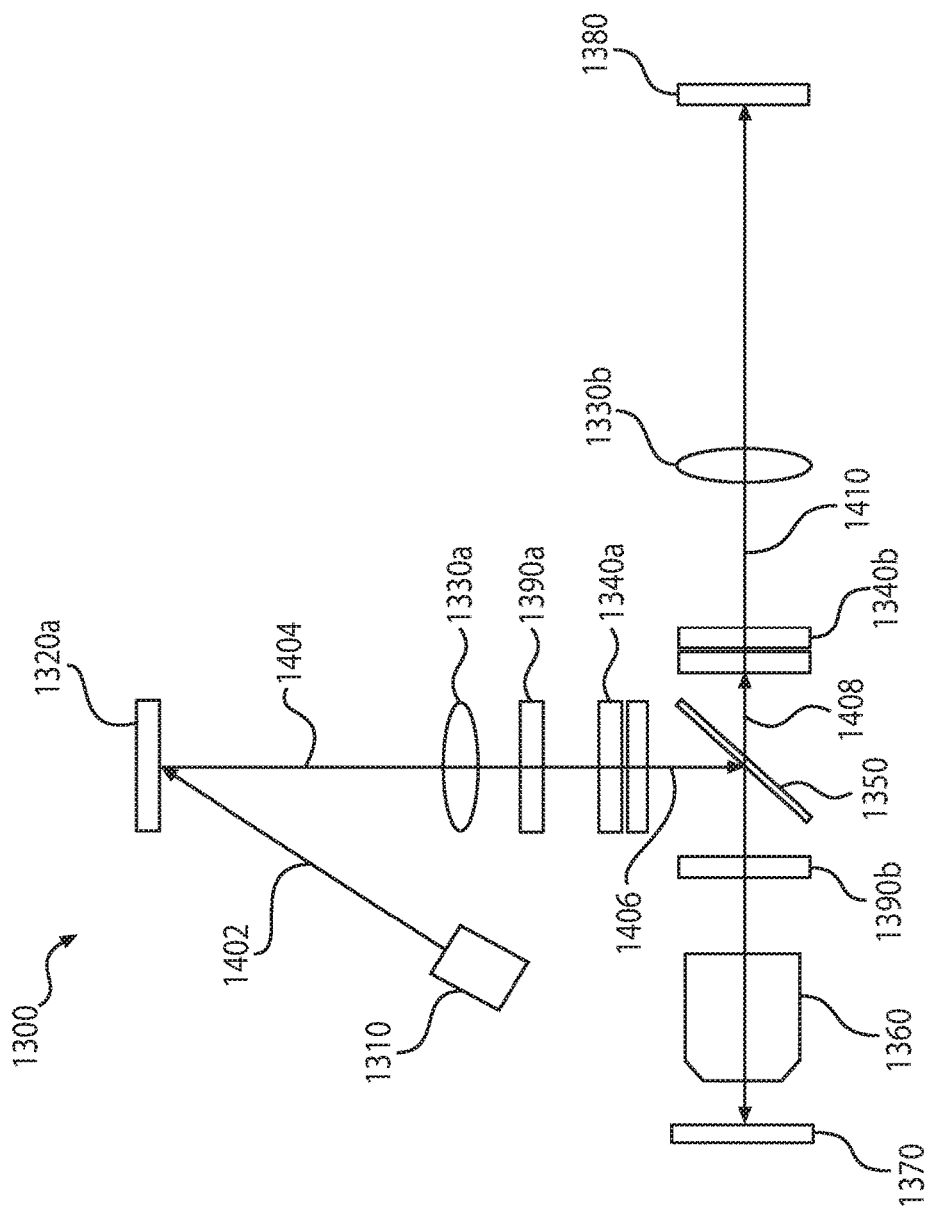
FIG. 15 is a schematic representation of another example hyperspectral imaging system.

To add the capability for measuring fluorescence polarization, as shown in FIG. 15, system 1300 may include polarizer 1390a and an optical element, such as a waveplate or a polarizer. For example, the optical element may be an achromatic half-wave plate (HWP) 1390b. Polarizer 1390a may be a linear polarizer located in the illumination system, thereby generating linearly polarized excitation light, e.g., vertically polarized light. Depending upon the orientation of their absorption dipoles, individual fluorophores in the sample are preferentially excited by the linearly polarized excitation light. The fluorescent light emitted from the sample may be partially depolarized due to random orientation, diffusion, and/or rotation of the fluorophores.

Beamsplitter 1350 may be a polarizing beamsplitter (PBS) that substantially transmits horizontally polarized light and reflects vertically polarized light. For example, as shown in FIG. 15, the excitation light vertically polarized by polarizer 1390a can be reflected by the PBS and then propagates towards HWP 1390b. HWP 1390b may be placed at a suitable location, such as before beamsplitter 1350 along the optical axis. In such instances, HWP 1390b may rotate the vibration orientations of both the linearly polarized excitation light and the collected fluorescent light from the sample by about twice the angle between a vertical axis and the fast axis of the HWP, for example. Rotating HWP 1390b around the optical axis would advantageously rotate the vibration directions of both the excitation light and fluorescent light. Beamsplitter 1350 may substantially block the polarized excitation light and transmit at least a portion of polarized fluorescent light to be acquired by imaging device 1380.

Depending on the application, such fluorescence polarization assays may be performed in steady state or with time-resolved measurements, such as utilizing the FLIM capability as described above.

Measurement of fluorescence polarization (or anisotropy) adds another dimension of information to the hyperspectral-imaging dataset acquired by system 1300. This additional dimension of information may complement the information in the other dimensions of the hyperspectral-imaging dataset about the local chemical and physical environments of fluorophore-tagged molecules in the sample, such as molecular mass and orientation of the molecules. The augmented hyperspectral-imaging dataset acquired by system 1300 may further improve the accuracy of diagnosis of physiologic or pathologic changes of the sample.

Excitation Light Recycling System

As described above, because most of excitation light 1402 is steered away from the optical axis and would not reach the sample, modulating the amplitude of excitation light 1402 using SLM 1320a, e.g., a DMD or a LCD, to generate excitation pattern 1100 results in loss of light. Therefore, in some embodiments, system 1300 may advantageously include an excitation light recycling system 1500 to increase efficiency of utilization of excitation light 1402. Recycling system 1500 may redirect the off-optical axis excitation light back to the optical axis towards the sample as described below.

Reflection-Based Scheme

Figure 16:
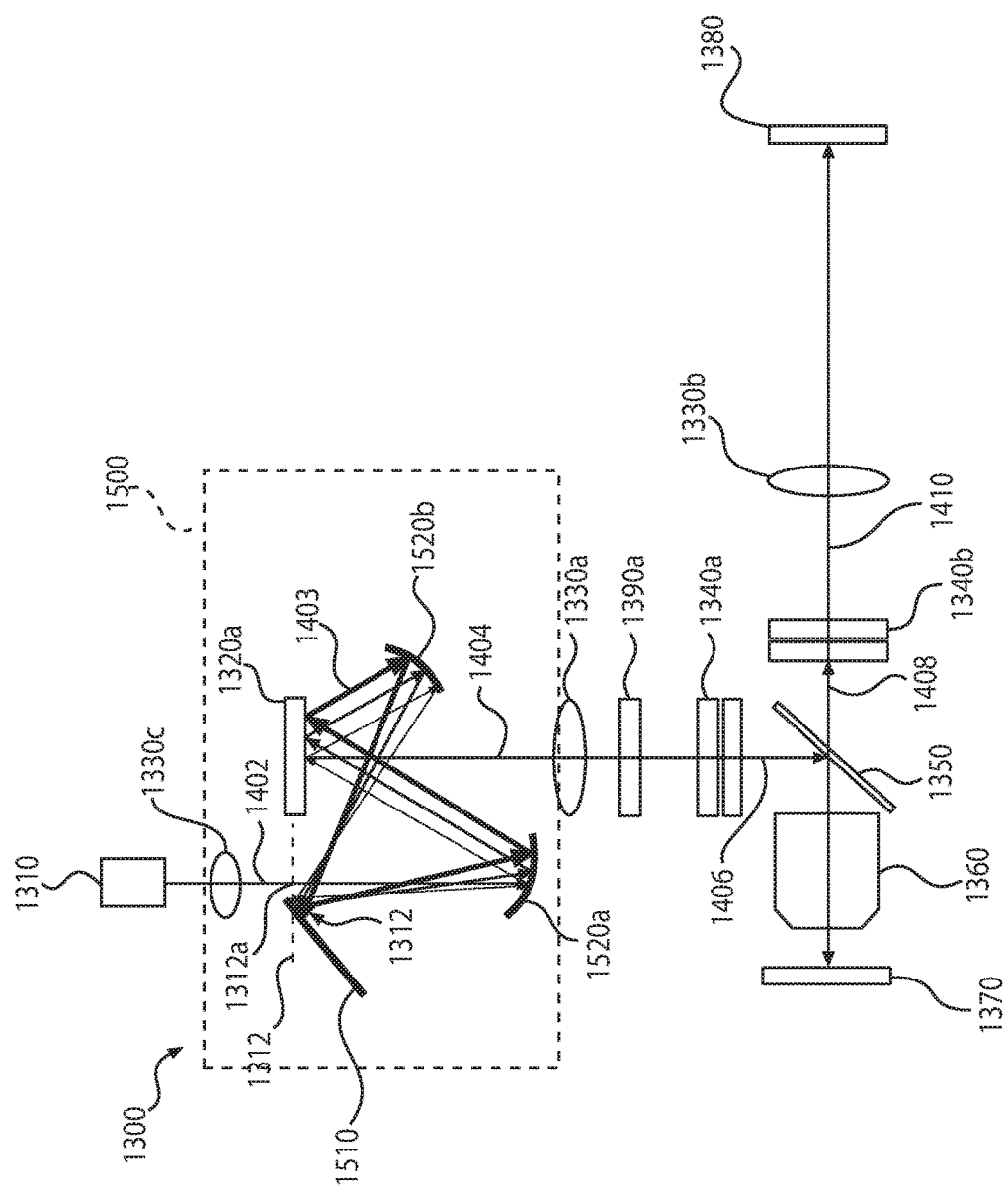
FIG. 16 is a schematic representation of another example hyperspectral imaging system.

In some embodiments, excitation light recycling system 1500 uses a reflection-based scheme as shown in FIG. 16. Recycling system 1500 may include one or more lenses and mirrors. For example, recycling system 1500 may include a lens 1330c, a flat mirror 1510, a first concave mirror 1520a, and a second concave mirror 1520b. The concave mirrors may be replaced by a combination of a flat mirror and a lens.

Excitation light 1402 may be collimated before passing lens 1330c. Lens 1330c may focus collimated excitation light 1402 to a focal point 1312a of mirror 1520a at a given plane 1312 near or aligned with the plane of SLM 1320a. Then, excitation light 1402 expands as it propagates from focal point 1312a to mirror 1520a. Mirror 1520a may re-collimate excitation light 1402 and direct it to SLM 1320a.

As described above, when SLM 1320a is a DMD, a small fraction of excitation light 1402 may be reflected by the "on" pixels towards lens 1330a along the optical axis, while the rest, e.g., off-axis excitation light 1403, is reflected by the "off" pixels at a different angle and away from the optical axis. Mirror 1520b may be configured to intercept this off-axis excitation light 1403 and reflect it back to a point 1312b very close to focal point 1312a. The separation between point 1312b and focal point 1312a may be just large enough to allow the edge of mirror 1510 to intercept the returned off-axis excitation light 1403 without substantially blocking the original excitation light 1402. Mirror 1510 then may direct off-axis excitation light 1403 back to SLM 1320a via a path that is nearly aligned with the original path. In such configuration, excitation light 1402 can be incident onto SLM 1320a many times through multiple reflections between the mirrors, thereby recycling off-axis excitation light 1403 back to the optical axis.

As described herein, the three paths for the recycling of off-axis excitation light 1403 shown in FIG. 16 are exemplary only. Multiple or infinite recycling paths may be possible.

A few design considerations of system 1300 are discussed in the following. In some instances, the recycled off-axis excitation light 1403 may be slightly divergent. For each recycling path of off-axis excitation light 1403 propagating in recycling system 1500, because off-axis excitation light 1403 is not returned to focal point 1312a, off-axis excitation light 1403 would have a slightly different angle when it reaches SLM 1320a from that of the original excitation light 1402. The angular difference (or divergent angle) may be defined as $\Delta\theta = \Delta x/f$, where "$\Delta x$" is the separation between focal point 1312a and point 1312b, and "f" is the focal length of mirror 1520a (or a lens) for re-collimating the off-axis excitation light reflected by mirror 1510. $\Delta x$ may be at least greater than any unusable rough edge of mirror 1510, and greater than the diffraction limited spot size of excitation light 1402. Depending on the values of $\Delta x$ and f, $\Delta\theta$ may be less than 1 degree. Such small degree of angular difference (or divergence angle) may not affect the formation of excitation pattern 1100.

In some instances, when SLM 1320a is a DMD, the DMD may have a diffraction effect on reflected excitation light 1404. For example, a single micromirror of the DMD may have a side length of approximately 10 μm. A typical divergence angle for reflected excitation light 1404 caused by the diffraction of the micromirror array may be about $\lambda_a/10$ μm, where $\lambda_a$ is the wavelength of excitation light 1402. Therefore, the divergence angle may be about less than one radian, e.g., 1/20 radian, or less than a few degrees, e.g., 3 degrees. Thus, most of excitation light 1404 reflected by the "on" pixels or micromirrors of the DMD from different recycling paths in recycling system 1500 may overlap and propagate along the optical axis, and thus may not affect the formation of excitation pattern 1100.

In some instances, reflected excitation light 1404 from different recycling paths in recycling system 1500 may exhibit optical interference. For a light source 1310 having discrete wavelengths or narrow spectral bands, this interference may cause reflected excitation light 1404 to have unstable intensities when focused on the sample. Additional optical components may be added to control the relative phases of excitation light 1403 propagating in different recycling paths to reduce the optical interference effect. However, this may complicate the design of system 1300. Therefore, the reflection-based scheme shown in FIG. 16 for recycling system 1500 may be more suitable for systems 1300 having a light source 1310 with a broadband spectrum, such as a white light source. For such systems 1300, the effect of the interference may impose very rapid small oscillations on the spectrum of reflected excitation light 1404. Fluorophores typically have spectrally broad absorption features, allowing these oscillations to average out during excitation. Therefore, the optical interference effect may have little effect on the acquired fluorescence emission spectra when light source 1310 has a broadband spectrum.

Polarization-Based Scheme

Figure 17:
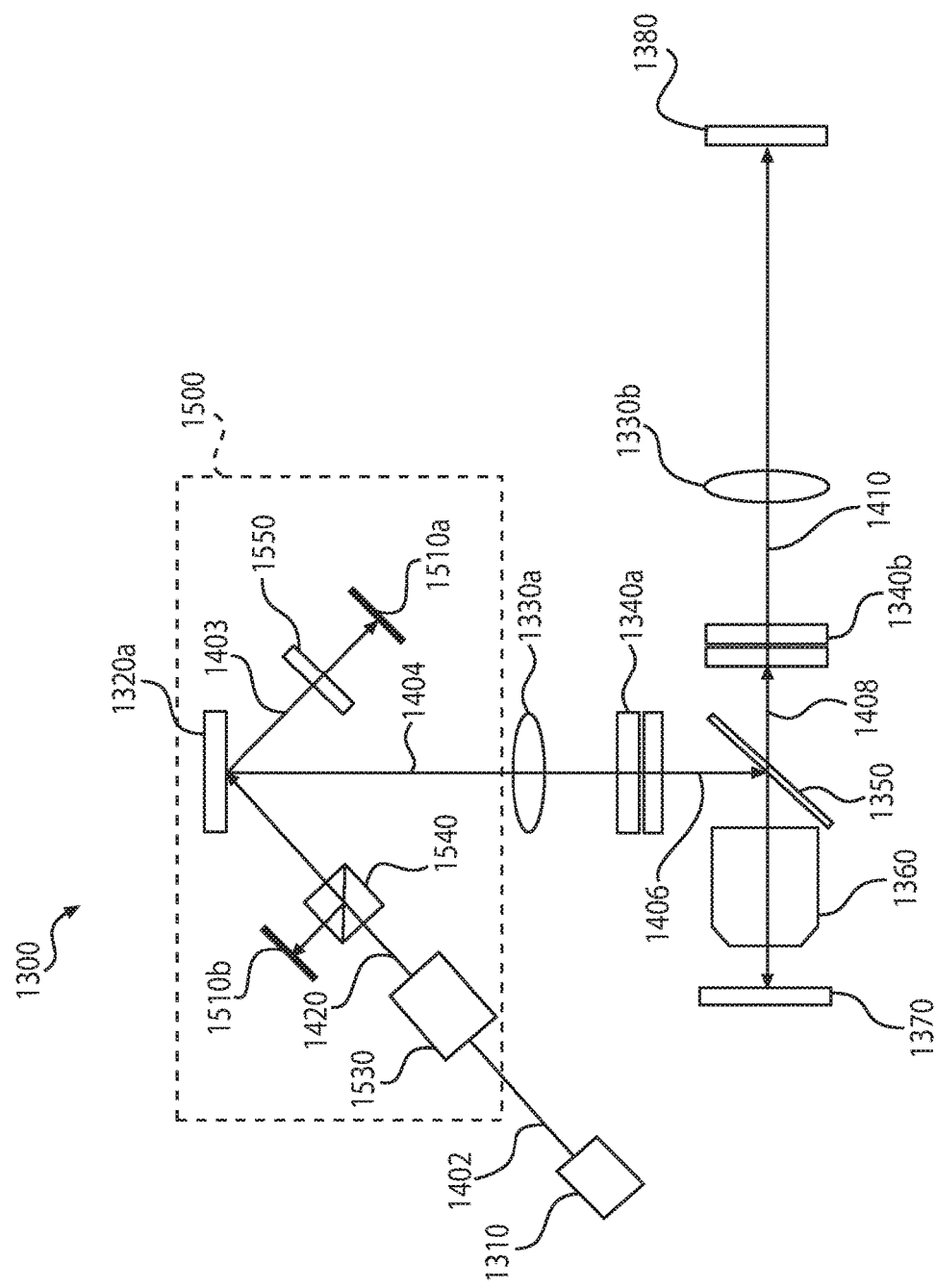
FIG. 17 is a schematic representation of another example hyperspectral imaging system.

To solve the above-described technical problem for recycling excitation light 1402 having discrete wavelengths or narrow spectra bands, in some embodiments, excitation light recycling system 1500 may use a polarization-based scheme as shown in FIG. 17.

As shown in FIG. 17, polarization-based recycling system 1500 may include one or more optical components. For example, recycling system 1500 may include an optical isolator 1530, a polarizing beamsplitter (PBS) 1540, a quarter-wave plate (QWP) 1550, and one or more mirrors, e.g., a first mirror 1510a and a second mirror 1510b. In some embodiments, optical isolator 1530 may include a linear polarizer or may be optionally replaced by a linear polarizer.

In this scheme, optical isolator 1530 allows the propagation of excitation light 402 in only one forward direction. Excitation light 1402 may be a linearly polarized light, or may become linearly polarized after passing through optical isolator 1530. The linearly polarized excitation light after passing through optical isolator 1530 is referred to as excitation light 1420. PBS 1540 may be configured to transmit light having a vibration orientation parallel with that of excitation light 1420 and reflect light having a vibration orientation orthogonal to that of excitation light 1420. For example, excitation light 1420 may be horizontally polarized or have a vibration orientation in a horizontal direction. PBS 1540 may transmit horizontally polarized light and reflect vertically polarized light. Therefore, excitation light 1420 transmits through PBS 540 and propagates towards SLM 1320*a*.

Description below of the polarization-based scheme of recycling system 1500 uses excitation light 1420 that is horizontally polarized as an example. Embodiments of the polarization-based scheme of recycling system 1500 is equally applicable for linearly polarized excitation light 1420 having any vibration orientation.

As described above, when SLM 1320*a* is a DMD, a small fraction of excitation light 1420 may be reflected by the "on" micromirrors of the DMD towards lens 1330*a* along the optical axis, while the off-axis excitation light 1403 reflected by the "off" pixels are steered away from the optical axis. Mirror 1510*a* may be configured to intercept the off-axis excitation light 1403 and reflect it back to the "off" pixels on the DMD. Off-axis excitation light 1403 may pass through QWP 550 a first time when it propagates towards mirror 1510*a* and a second time when it is directed back to the DMD by mirror 1510*a*, which rotate the vibration orientation of off-axis excitation light 1403 by 90°. For example, horizontally polarized excitation light 1403 may be changed to be vertically polarized after passing through QWP 1550 twice. The vertically polarized excitation light is then reflected by the "off" micromirrors of the DMD towards PBS 1540.

Because the vertically polarized excitation light reflected to PBS 1540 has a vibration orientation orthogonal to that of horizontally polarized excitation light 1420, it is reflected by PBS 1540 and directed to mirror 1510*b*. Without changing its vibration orientation, mirror 1510*b* and PBS 1540 then reflect the vertically polarized excitation light back to the DMD, where the "on" micromirrors then reflect the vertically polarized excitation light towards lens 1330*a* along the optical axis. The "off" micromirrors reflect the vertically polarized excitation light, which again transmits through QWP 1550 and mirror 1510*a* twice and becomes horizontally polarized. This horizontally polarized excitation light would pass through PBS 1540, but would not propagate back to light source 1310 because of optical isolator 1530.

In the above-described polarization-based scheme of recycling system 1500, because QWP 1550 rotates the vibration orientation of off-axis excitation light 1403 by 90°, excitation light 1404 reflected towards the optical axis, which includes the portion of the off-axis excitation light 1403 that is recycled, would have orthogonal polarizations. In such instances, rather than a polarizing beamsplitter, beamsplitter 1350 may suitably be a multiband dichroic that has multiple cut-off wavelengths and passbands. As described above, the multiband dichroic may be selected such that wavelengths of excitation light 1402 having a discrete spectrum are substantially reflected and wavelengths of emitted fluorescent light 1408 are substantially transmitted. Therefore, this polarization-based scheme may work better in systems 1300 using a light source 1310 having discrete wavelengths or narrow spectra bands, such as a combination of a set of lasers operating at discrete wavelengths.

Confocal Optical Sectioning Capability

As described above, system 1300 may allow for confocal optical sectioning, which allows for selecting the depth of a focal plane in the sample. The depth of the focal plane may be selected by introducing one or more optical pinholes at a plane conjugate to the selected focal plane.

Figure 18:
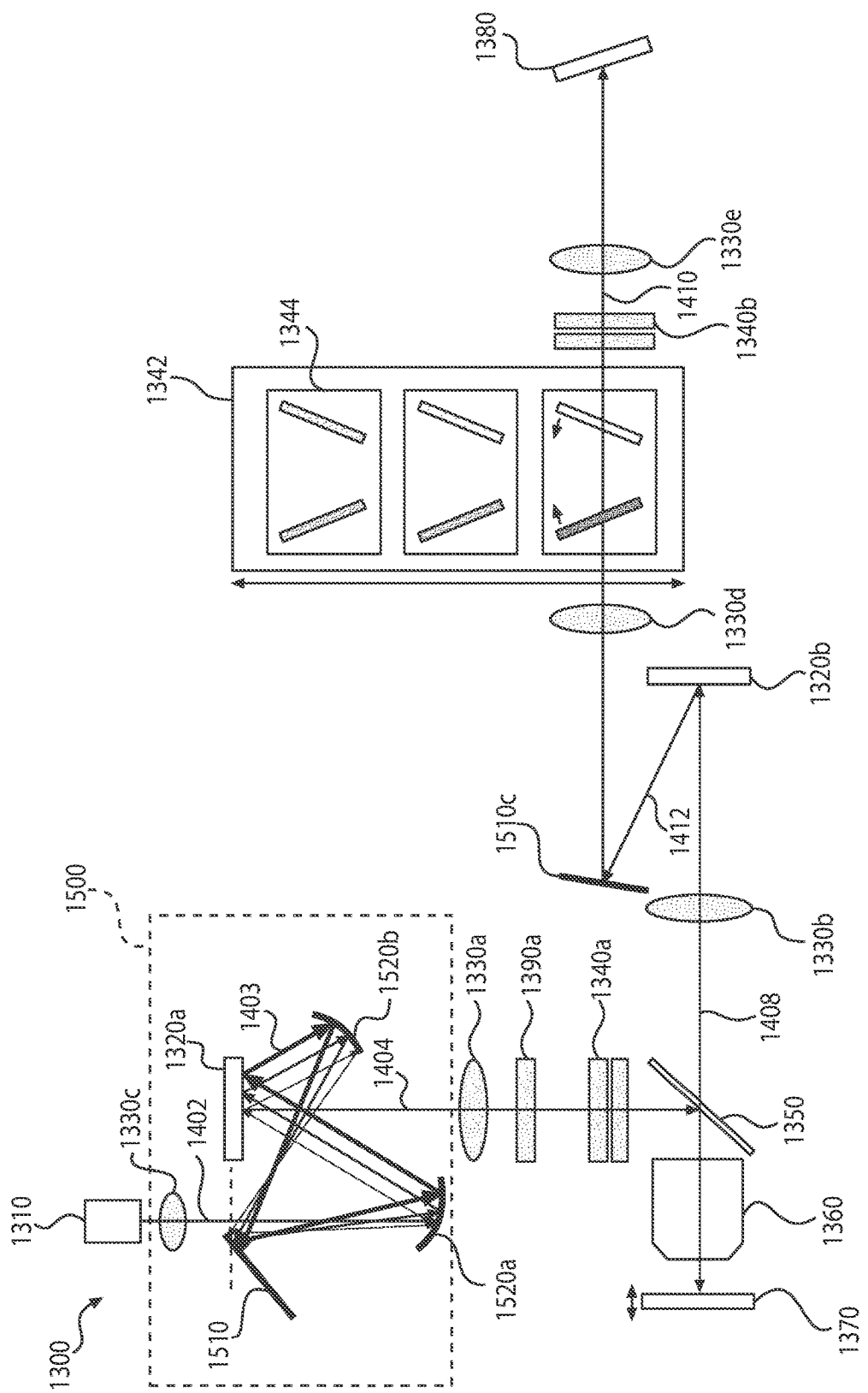
FIG. 18 is a schematic representation of another example hyperspectral imaging system.

FIG. 18 is a schematic representation of an exemplary system 1300 that allows for confocal optical sectioning. As shown in FIG. 18, system 1300 may include the first SLM 1320*a* for generating excitation pattern 1100 as described above, a second SLM 1320*b* for confocal optical sectioning, at least one additional mirror 1510*c*, one or more tube lenses, e.g., 1330*d* and 1330*e*, and a z-axis translation stage or a tunable liquid lens (not shown). SLM 1320*b* may have similar types and features as described above for SLM 1320*a*. For example, pixels of SLM 1320*b* may be individually modulated in the same manners as those described for SLM 1320*a*.

SLM 1320*b* may be placed at about a plane conjugate to a focal plane located at a desired depth in the sample along the optical axis. For example, lens 1330*b* and objective 1360 may form an imaging configuration. As shown in FIG. 18, lens 1330*b* may be located behind objective 1360 and SLM 1320*b* may be located about one focal length behind lens 1330*b*. The space between the back aperture of objective 1360 and lens 1330*b* is a collimated space, which may be adjusted as need based on various factors, such as the geometry of system 1300 and a desired location of a minimum beam aperture. In some embodiments, lens 1330*b* is placed about one focal length behind objective 1360.

Pixels of SLM 1320*b* may be selectively actuated or switched to "on" or "off" states to form a pinhole pattern matching or conjugating excitation pattern 1100 on the sample. The pinhole pattern may include a plurality of artificial optical pinholes at the conjugate plane and reject out-of-focus fluorescent light from the sample. Therefore, out-of-focus fluorescent light would not pass through the detection system and are substantially removed or eliminated from the acquired 2-D image 1200.

The size and separations of the artificial pinholes in the pinhole pattern are programmable, and may be customized based on the magnification of the imaging configuration formed by objective 1360 and lens 1330*b*. In some instances, the pinhole pattern may include a plurality of "on" pixels in elongated shapes to allow fluorescent light emitted from multiple locations on the sample (e.g., areas excited by excitation spots 1112*a*-1112*f*) to be acquired simultaneously. In other instances, the pinhole pattern may include an array of "on" pixels that match the size of the excitation lines or excitation spots in excitation pattern 1100.

The fluorescent light 1412 reflected by the "on" pixels of SLM 1320*b* is then imaged to imaging device 1380 by tube lenses 1330*d* and 1330*e*. For example, mirror 1510*c* may be placed at a suitable position along the optical axis and for directing fluorescent light 1412 reflected by the "on" pixels to the tube lenses. Tube lens 1330*d* may be located about one focal length beyond the image produced by lens 1330*b* (e.g., about one focal length behind SLM 1320*b*) such that it re-collimates the fluorescent light from the sample. Imaging device 1380 may be located about one focal length behind tube lens 1330*e* or at a conjugate plane of SLM 1320*b*. Because the fluorescent light is collimated in the space between tube lenses 1330*d* and 1330*e*, the distance between tube lenses 1330*d* and 1330*e* may be adjusted as desired. In some embodiments, tube lens 1330*e* may be about two focal lengths behind tube lens 1330*d* such that a plane midway between tube lens 1330*d* and 1330*e* is conjugate to an exit pupil of system 1300.

By digitally changing and/or laterally shifting excitation pattern 1100 and the matching pinhole pattern on SLM 1320*b* correspondingly, the whole field of view may be scanned for acquiring a confocal-imaging dataset. By further scanning the field of view across the sample, the whole sample can be scanned to obtain a complete confocal-imaging dataset of the sample.

In some embodiments, imaging device 1380 may be suitably tilted to reduce aberrations and thus improve the quality of the acquired 2-D image dataset. This is at least because the "on" pixels of SLM 1320b direct fluorescent light 1412 at an angle that is not perpendicular to the surface plane of SLM 1320b such that an image plane formed by tube lenses 1330d and 1330e may be tilted. Aberrations caused by this tilting effect may be compensated by properly tilting imaging device 1380. Aberrations may be further reduced if a dispersion angle of dispersive element 1340b is adjusted to be parallel to a rotation axis of the tilted imaging device 1380.

To change or select a depth of the focal plane, in some embodiments, sample holder 1370 may be installed on the z-axis translation stage. The desired depth of the focal plane may be selected by moving sample holder 1370 along the optical axis using the z-axis translation stage. Alternatively, objective 1360 may be installed on the z-axis translation stage and the desired depth of the focal plane may be selected by moving objective 1360 along the optical axis. As describe herein, the z-axis translation stage may also include x-y translation capability to move the field of view of system 1300 across the sample in lateral directions. In other embodiments, the desired depth of the focal plane may be selected by tuning the focus of a tunable liquid lens (not shown) placed behind objective 1360. Additionally, the z-translation stage or the tunable liquid lens may be controlled by a computer program to achieve autofocusing.

Advantageously, a degree of confocality may be adjusted as needed by changing the size and/or separation of the artificial pinholes formed by SLM 1320b. For example, increasing the sizes of the pinholes by increasing the number of pixels in the pinholes and/or reducing the pinhole spacing may reduce the degree of confocality and thus the degree of depth selectivity of the desired focal plane. On the other hand, decreasing the size of the pinholes by reducing the number of pixels in the pinholes and/or increasing the pinhole spacing may increase the degree of confocality and thus the degree of depth selectivity of the desired focal plane. In some embodiments, the depth selectivity may be proportional to the ratio of the number of "off" and "on" pixels of SLM 1320b. Therefore, SLM 1320b may advantageously allow for switching between wide-field and confocal imaging as desired by conveniently adjusting the pinhole size and/or separation.

Additionally, the pinhole pattern formed by pixels of SLM 1320b advantageously allows for confocal imaging of a plurality of areas on the sample simultaneously illuminated by excitation pattern 1100. This may increase the speed and/or throughput of acquiring hyperspectral-imaging datasets across the sample at the desired focal plane comparing to traditional confocal microscopes that use sequential point-by-point scanning.

As shown in FIG. 18, in embodiments of system 1300 using SLM 1320b, dispersive element 1340b may be located in the collimated space between tube lenses 1330d and 330e. Because the pinhole pattern on SLM 1320b matches excitation pattern 1100 on the sample, fluorescent light 1412 reflected by the artificial pinholes of SLM 1320b can be dispersed by dispersive element 1340b as described above such that the fluorescence emission spectra corresponding to the excitation spots of excitation pattern 1100 can be acquired by the 2-D sensor of imaging device 1380.

Selective Filtering of Fluorescence Emission Spectrum

In some applications, different fluorophores having fluorescence emission spectra that are spaced apart, such as green and red fluorophores, may be used or exist in the sample. This may result in lateral gaps in a fluorescence emission spectrum acquired in 2-D image 1200 along the emission wavelength axis, resulting in inefficient use of the space on the 2-D sensor of imaging device 1380.

In other applications, the combination of different fluorophores may result in an overall broad fluorescence emission spectrum to be acquired by imaging device 1380. In some instances, multiple spectral regions within the broad emission fluorescence spectrum may be more useful than other regions. Acquiring the complete broad fluorescence emission spectrum may result in inefficient use of the space on the 2-D sensor of imaging device 1380 and further reduce the throughput of acquiring the hyperspectral-imaging dataset.

To increase the efficiency of using the sensor space of imaging device 1380 and increase the throughput of system 1300, a spectral slicing system 1342 may be included at a collimated space along the optical axis in the detection system. For example, as shown in FIG. 18, spectral slicing system 1342 may be located between tube lenses 1330d and 1330e, and may be placed before dispersive element 1340b in the detection system. Spectral slicing system 1342 may selectively pass one or more spectral bands with tunable bandwidths and/or center wavelengths, thereby allowing for acquiring a hyperspectral-imaging dataset with desired spectral bands and/or desired spectral resolutions.

As shown in FIG. 18, spectral slicing system 1342 may include a plurality of spectral slicing modules 1344. Fluorescent light 1408 emitted by the sample may enter spectral slicing system 1342 after being collimated or re-collimated. Using one or more beamsplitters and/or motorized flip mirrors, spectral slicing system 1342 may split an input collimated fluorescent light beam into one or more beams, each having a different spectral band, and direct them through spectral slicing modules 1344 respectively. Each spectral slicing module 1344 may filter one of the beams to have a desired bandwidth and a center wavelength. After the filtering, spectral slicing system 1342 may combine the filtered beams into an output beam using one or more beamsplitters and/or motorized flip mirrors.

Spectral slicing modules 1344 may each operate as a tunable bandpass filter with a tunable passband width and/or a tunable center wavelength. For example, spectral slicing module 1344 may include a long-pass filter and a short-pass filter along its optical axis. At least one of the long-pass filter and short-pass filter is rotatable relative to the optical axis. Rotating the filters may adjust the angle of incidence of the beam on the filters and thus shift the wavelengths of their absorption or reflection edges. Thus, rotating the long-pass filter and/or short-pass may tune the bandwidth and/or center wavelength of the spectral passband formed by the long-pass and shot-pass filters. Alternatively, spectral slicing modules 1344 may each include a tunable bandpass filter whose passband may be tuned by rotating the filter and thus tuning the angle of incidence of the beam on the filter.

Spectral slicing system 1342 allows the measured fluorescence emission spectra to be adjustably filtered to desired spectral ranges useful for a particular application. By selecting the desired spectral ranges, the space on the 2-D sensor of imaging device 1380 can be used more efficiently. For example, as described above, the degree of dispersion caused by dispersive element 1340b can be adjustable. The spectral resolution of the selected spectral ranges of the fluorescence emission spectra may be increased by increasing the degree of spectral dispersion using dispersive element 1340b, thereby providing more information of the fluorophores or fluorescent molecules in the sample.

Additionally, selecting the desired spectral ranges may allow for reducing the lateral spacing between the fluorescence emission spectra in 2-D image 1200 along the emission wavelength axis, thereby improving the throughput of dataset acquisition. For example, by reducing the period of excitation pattern 1100 in the horizontal direction, and decreasing the degree of spectral dispersion using dispersive element 1340*b*, the period of the array of fluorescence emission spectra in the horizontal direction in 2-D image 1200 may be reduced. This may in turn increase the number of fluorescence emission spectra that can be acquired in one exposure, thereby increasing the efficiency of using the senor space of imaging device 1380.

Alternative Configurations

In some applications, more compact configurations of system 1300 may be desirable. In such instances, system 1300 may use diffractive elements in place of SLM 1320*a* and/or SLM 1320*b*. Embodiments of such configurations of system 1300 are described below in reference to FIGS. 19-23.

Figure 19:
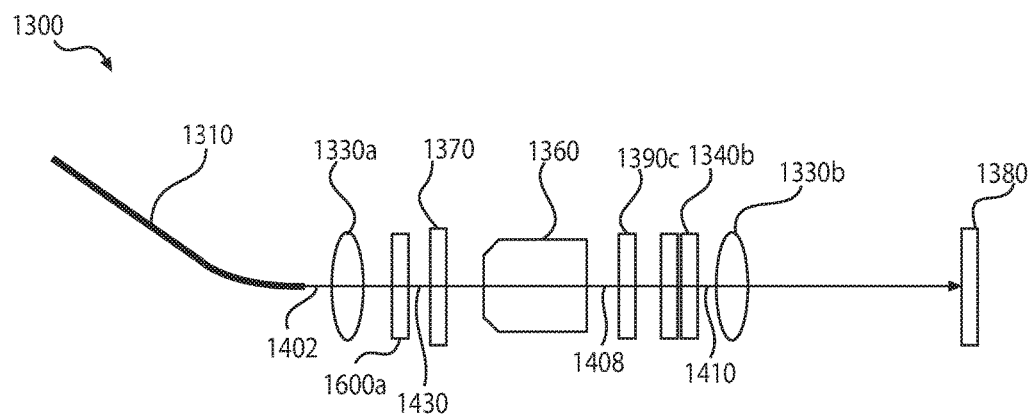
FIG. 19 is a schematic representation of another example hyperspectral imaging system.

FIG. 19 is a schematic representation of an exemplary compact embodiment of system 1300. As shown in FIG. 19, system 1300 may advantageously use a transmission-type illumination to simplify its geometry. However, reflection-type illumination configurations as shown in FIGS. 13-18 may also be used depending on the application. In the illumination system, excitation light 1402 from light source 1310, such as a supercontinuum laser source provided through an optic fiber, is collimated by lens 1330*a*, transmits through a first diffractive element 1600*a*, and then illuminates a sample placed on sample holder 1370. Diffractive element 1600*a* modulates the phase of excitation light 1402 transmitting through it and structures excitation light 1402 for generating excitation pattern 1100. The phase modulation may render a plurality of wavelets of the transmitted excitation light 1430 with different directions and/or phases, generating a diffraction pattern in the far field. The diffraction pattern focused on the sample is referred to as excitation pattern 1100.

Figure 22:
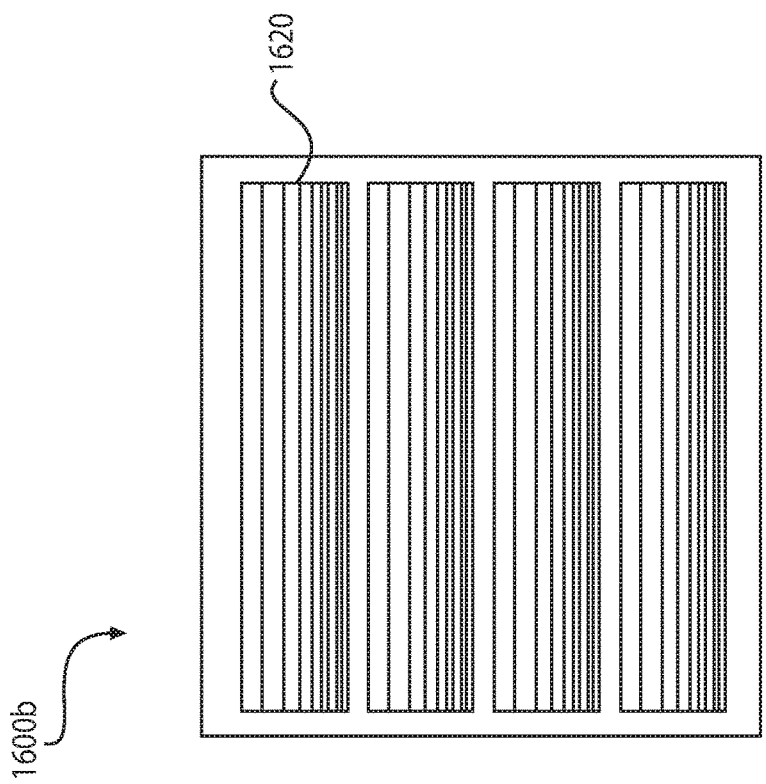
FIG. 22 is a schematic representation of an example diffractive element.

FIG. 22 is a schematic representation of an exemplary diffractive element 1600*a*. As shown in FIG. 22, in some embodiments, diffractive element 1600*a* may be a 2-D array of diffractive lenses 1610. For excitation light 1402 having a single wavelength, diffractive element 1600*a* generates a 2-D array of excitation spots, one by each diffractive lens 1610. For excitation light 1402 having multiple discrete wavelengths or a range of wavelengths, different wavelengths of excitation light 1402 are diffracted by each diffractive lens 1610 into several beams travelling in different angular directions. Therefore, when focused on the sample, the different wavelengths of excitation light 1402 may have focuses spatially shifted from one another in a first lateral direction (e.g., vertical direction), thereby generating excitation pattern 1100 as shown in FIG. 11 or FIG. 12.

In some embodiments, diffractive lenses 1610 of diffractive element 1600*a* may be zone plates that have transparent and nontransparent bands, conventional gratings made by, e.g., binary lithography, grayscale lithography, or molding processes, or subwavelength gratings made by binary lithography. In other embodiments, diffractive element 600*a* may be replaced with a 2-D lenslet array and a transmissive diffraction grating that have the phase modulation capability for generating excitation pattern 1100 as described above.

In the detection system, fluorescent light 1408 emitted by the sample is collected and collimated by objective 1360, transmits through dispersive element 1340*b*, and is then focused onto imaging device 1380 by lens 1330*b*. Dispersive element 1340*b* may spectrally disperse fluorescence light 1408 in a second lateral direction (e.g., horizontal direction) as described above. Dispersive element 1340*b* may have the same features and functions as described above.

In some embodiments, system 1300 may include a second linear polarizer 1390*c*. Fluorescent light 1408 may pass through polarizer 1390*c*. When excitation light 1402 is linearly polarized, polarizer 1390*c* may be used to substantially reflect the polarized excitation light and thus block it from reaching imaging device 1380. In other embodiments, a set of notch filters or a single multi-notch filter (not shown) may be added to the detection system along the optical axis.

Because diffractive element 1600*a* does not have the digital programmability as that of an SLM, either diffractive element 1600*a* or sample holder 1370 may be translated in spatial dimensions to scan excitation pattern 1100 across the field of view or the sample to obtain a complete 4-D hyperspectral-imaging dataset. The scanning scheme may be the same as described above in reference to FIGS. 11 and 12. Different areas in each scanning cell 1110 may be illuminated by spatially shifting excitation pattern 1100 in the vertical and horizontal directions. At each spatial position of excitation pattern 1100, at least one 2-D image 1200 of fluorescence emission spectra of the illuminated areas can be acquired. Then, a plurality of 2-D images 1200 of fluorescence emission spectra can be acquired corresponding to a series of excitation patterns 1100 laterally shifted from one another and used for reconstructing the 4-D hyperspectral-imaging dataset.

Figure 20:
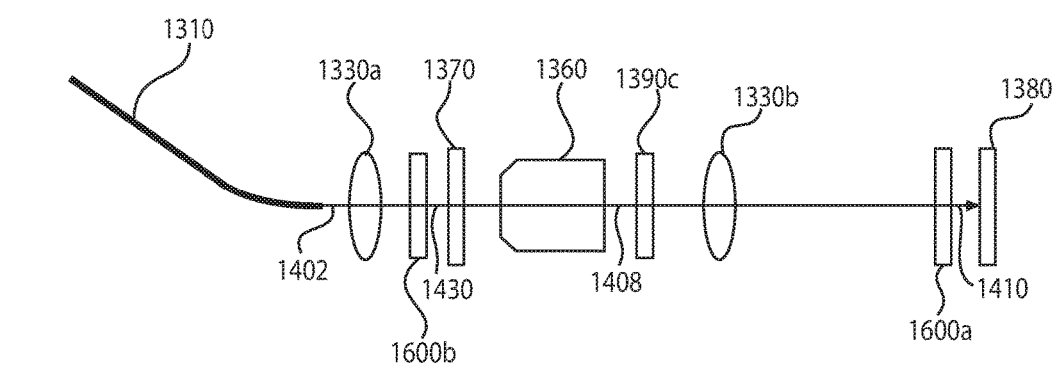
FIG. 20 is a schematic representation of another example hyperspectral imaging system.

FIG. 20 is a schematic representation of another exemplary compact embodiment of system 1300. System 1300 as shown in FIG. 20 may allow for acquiring a 4-D hyperspectral-imaging dataset by performing scanning in one lateral direction. For example, system 1300 may include diffractive element 1600*a* in the detection system and another diffractive element 1600*b* in the illumination system. As shown in FIG. 20, in the illumination system, excitation light 1402 from light source 1310 is collimated by lens 1330*a*, transmits through diffractive element 600*b*, and then illuminates a sample placed on sample holder 1370.

Figure 23:
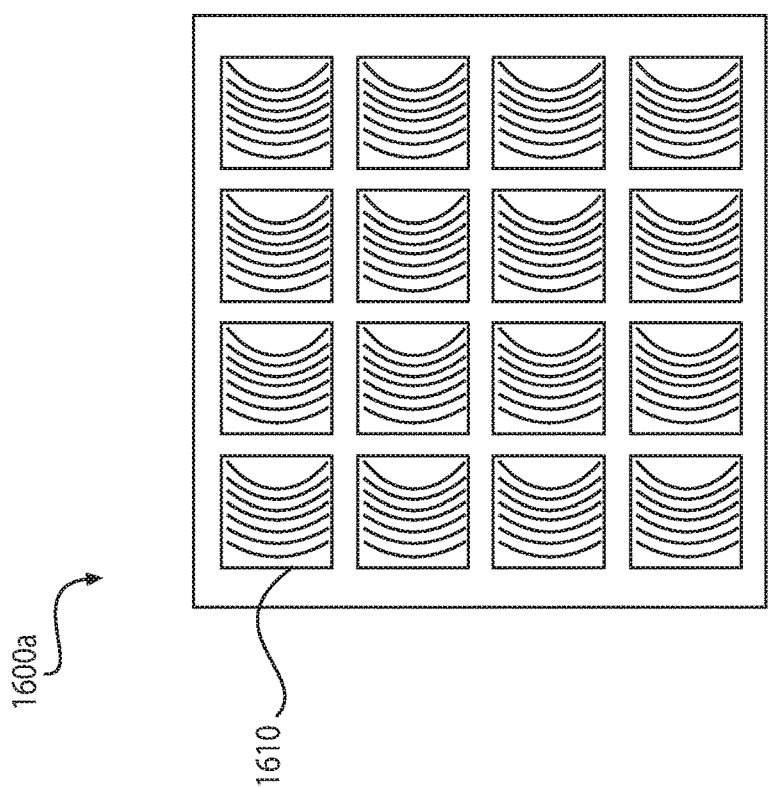
FIG. 23 is a schematic representation of another example diffractive element.

FIG. 23 is a schematic representation of an exemplary diffractive element 1600*b*. Diffractive element 1600*b* may modulate the phase of excitation light 1402 transmitting through it and render wavelets of transmitted excitation light 1430 having different directions and/or phases. In some embodiments, diffractive element 1600*b* may include a linear array of diffractive cylindrical lenslets 1620. For excitation light 1402 of a single wavelength, diffractive element 1600*b* generates a repeating pattern of single-colored stripes, one by each cylindrical lenslet 1620. For excitation light 1402 having multiple discrete wavelengths or a range of wavelengths, different wavelengths of excitation light 1402 are diffracted by each cylindrical lenslet 1620 into several beams travelling in different angular directions. Therefore, when focused on the sample, different wavelengths of excitation light 1402 may have focuses spatially shifted from one another in a first lateral direction (e.g., vertical direction), generating a repeating pattern of a series of shifted different-colored stripes. Depending on the spectrum of light source 1310, the different-colored stripes may be connected or separated in the first lateral direction. The repeating pattern of shifted different-colored stripes are then illuminated on the sample.

In the detection system, rather than using dispersive element 1340*b*, diffractive element 1600*a* may be added and placed in front of imaging device 1380. Fluorescent light 1408 emitted by the sample is collected and collimated by objective 1360, transmits through polarizer 1390c, and is then imaged onto diffractive element 600a by lens 1330b. Diffractive lenses 1610 of diffractive element 1600a may then spectrally disperse the fluorescent light in a second lateral direction (e.g., horizontal direction) and image the spectrally dispersed fluorescent light 1410 to the 2-D sensor of imaging device 1380.

In some embodiments, the focal length of lens 1330b is selected such that a diffraction-limited spot size of lens 1330b at its focal plane may cover a plurality of pixels of the 2-D sensor of imaging device 1380. This may affect the numerical aperture (NA), the focal ratio (f-ratio), and/or the magnification of lens 1330b. For example, to increase the diffraction-limited spot size of lens 1330b, lens 1330b may have a longer focal length, a smaller NA or a larger f-ratio, and/or a greater magnification.

Diffractive element 1600a may be designed or selected such that the diameters of its diffractive lenses 1610 are about the size of a diffraction-limited spot of lens 1330b. Different wavelengths of the fluorescent light 1410 deflected and focused by each diffractive lens 1610 may have focuses spatially shifted from one another in the second lateral direction, generating an array of fluorescence emission spectra as shown in FIG. 11 or FIG. 12.

Embodiments of system 1300 as shown in FIG. 20 allows for acquiring fluorescence emission spectra in a 2-D image 1200 as shown in FIG. 11 or FIG. 12 for areas or locations on the sample illuminated by the repeating pattern of a series of laterally shifted different-colored stripes. To acquire the excitation spectra, the repeating pattern may be scanned along the first lateral direction such that the areas or locations on the sample previously illuminated by a colored stripe of the repeating pattern are illuminated by a different-colored stripe. The shifting of the repeating pattern in the first lateral direction and subsequent acquisition of a corresponding 2-D image 1200 may be performed for a plurality times. In such instances, fluorescence emission spectra corresponding to the excitation wavelengths for each area or location on the sample can be acquired and used for reconstructing the 4-D hyperspectral-imaging dataset.

In the embodiments of system 1300 as shown in FIG. 20, because the repeating pattern of a series of laterally shifted different-colored stripes is continuous in the second lateral direction, the repeating pattern may only need to be scanned along the first lateral direction to obtain the excitation spectra for all areas or locations within the field of view. This may further improve the throughput and efficiency of system 1300 for acquiring the 4-D hyperspectral-imaging dataset.

Along the second lateral direction, each area illuminated by the continuous colored stripes can be imaged to a diffractive lens 1610, which then disperses the fluorescent light and focuses it to imaging device 1380. In such instances, the spatial resolution along the second lateral direction may depend on the size and focal length of diffractive lenses 1610, the focal lengths of lens 1330b and objective 1360, and/or the size of the 2-D sensor of imaging device 1380. In some embodiments, increasing the focal length of lens 1330b may allow for using larger diffractive lenses 1610. The spectral resolution along the second lateral direction may depend on the width and/or focal length of diffractive lenses 1610, and the off-axis focal shifts generated by diffractive lenses 1610 in the second lateral direction. For example, increasing groove density of diffractive lenses 1610 would increase the diffraction angles of the fluorescent light and thus the off-axis focal shifts, thereby increasing the spectral resolution in the second lateral direction.

Figure 21:
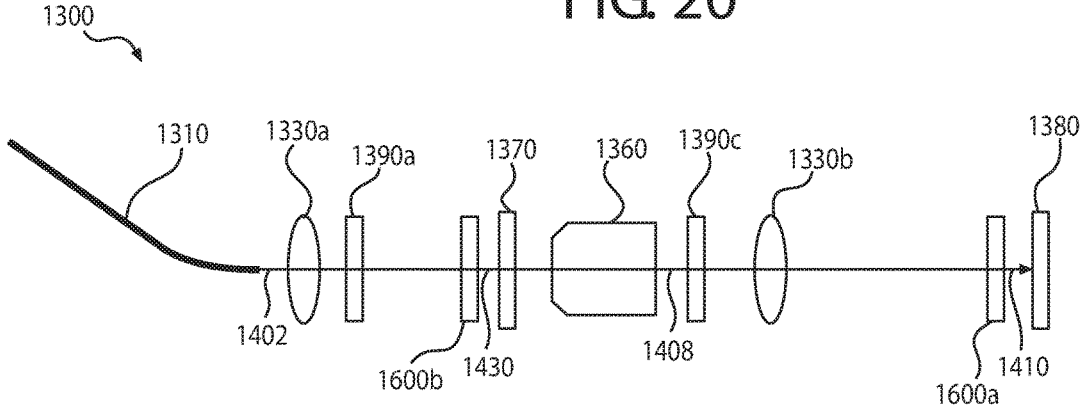
FIG. 21 is a schematic representation of another example hyperspectral imaging system.

FIG. 21 is a schematic representation of another exemplary compact embodiment of system 1300 that provides the capability for measuring fluorescence polarization. As shown in FIG. 21, system 1300 may include two polarizers 1390a and 1390c. Polarizer 1390a may be at a suitable place along the optical axis in the illumination system, thereby generating linearly polarized excitation light. Polarizer 1390c may be at a suitable place along the optical axis in the detection system, thereby transmitting emitted fluorescent light 1408 having a given vibration orientation. To perform fluorescence polarization assays, the transmission axis of polarizer 1390c may be rotated between orientations parallel and orthogonal to the vibration orientation of the linearly polarized excitation light. 2-D images 1200 of the fluorescence emission spectra of fluorescent light 1408 having vibration orientations parallel to and orthogonal to that of the polarized excitation light may be respectively acquired by imaging device 1380. The acquired 2-D images 1200 may then be used for fluorescence polarization (or anisotropy) assay.

Figure 24:
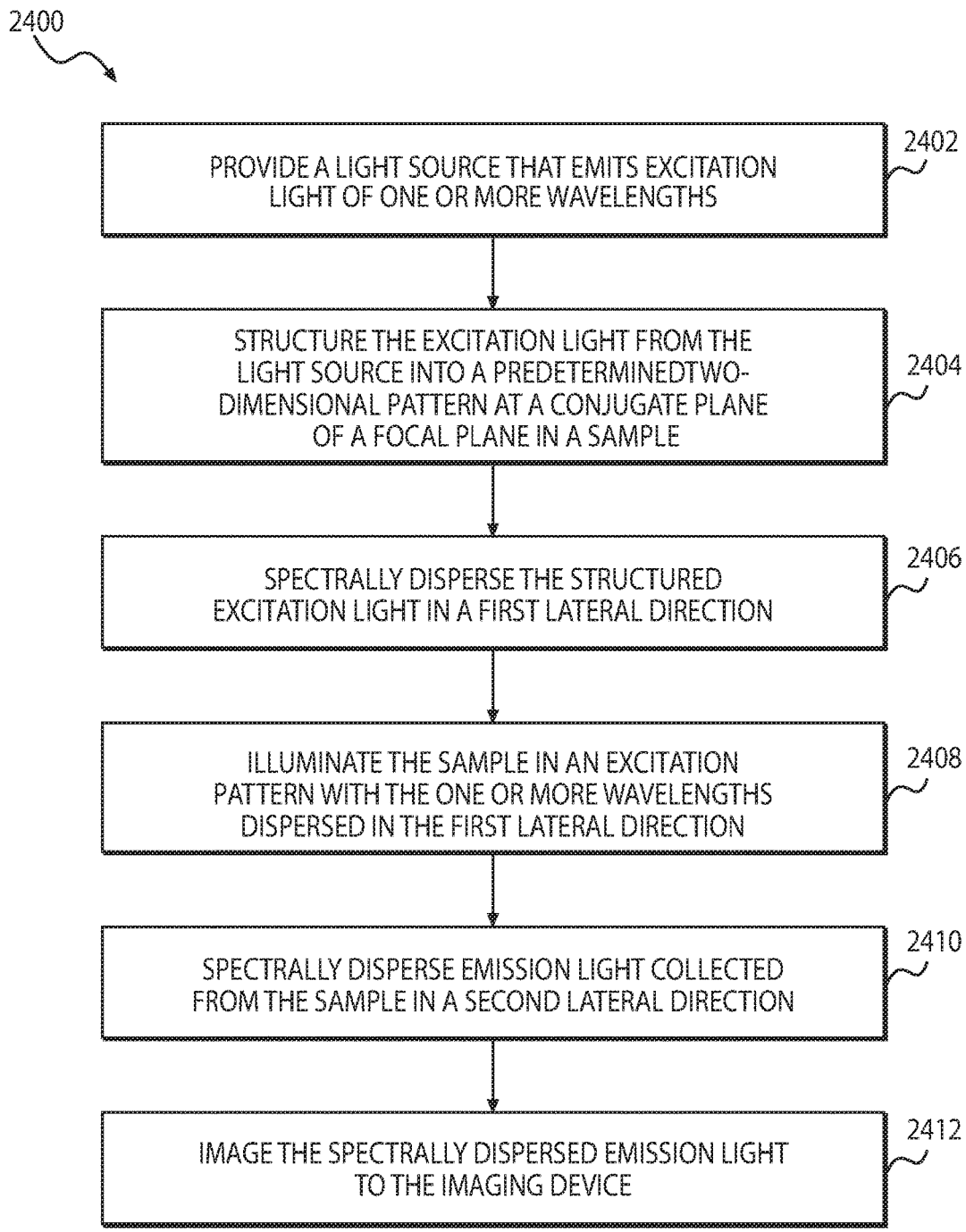
FIG. 24 is a flowchart of an example method for hyperspectral imaging.

System 1300 as described herein may be utilized in a variety of methods for hyperspectral imaging. FIG. 24 is a flowchart of an exemplary method 2400 for performing hyperspectral imaging or for acquiring a hyperspectral-imaging dataset of a sample. Method 2400 uses system 1300 and features of the embodiments of system 1300 described above in reference to FIGS. 13-23.

At step 2402, light source 1310 having a discrete spectrum or a continuous spectrum is provided and configured to emit excitation light 1402 having one or more wavelengths. At step 2404, excitation light 1402 is structured by SLM 1320a to into a predetermined two-dimensional pattern at a conjugate plane of a focal plane in the sample. At step 2406, the structured excitation light, e.g., excitation light 1404 reflected by SLM 1320a, is spectrally dispersed by dispersive element 1340a in a first lateral direction. At step 2408, spectrally dispersed excitation light 1406 is directed towards and focused on the sample, illuminating the sample in excitation pattern 1100 with the one or more wavelengths dispersed in the first lateral direction. At step 2410, fluorescent light 1408 collected from the sample is spectrally dispersed by dispersive element 1340b in a second lateral direction. At step 2412, spectrally dispersed fluorescent light 1410 is imaged to a 2-D sensor of imaging device 1380.

Method 2400 may further include additional steps. For example, method 2400 may include calibrating system 1300 before acquiring 2-D image 1200. Various optical components in system 1300 may be suitably calibrated and aligned such that focused 2-D images 1200 with reduced or minimum distortion can be acquired.

Method 2400 may further include polarizing excitation light 1402 to be directed to the sample using a first polarizer, and substantially reflecting light collected from the sample having the same polarization as that of the polarized excitation light using a second polarizer or a polarizing beamsplitter (PBS).

Method 2400 may further include illuminating the sample sequentially in a series of excitation patterns 1100 laterally shifted from one another, and obtaining a plurality of 2-D images 1200 of the spectrally dispersed emission light corresponding to the series of excitation patterns 1100, and reconstructing the plurality of 2-D images 1200 to provide a 4-D hyperspectral-imaging dataset. As described above, each 2-D image 1200 records an array of fluorescence emission spectra corresponding to each laterally shifted excitation pattern 1100.

Method 2400 may further include providing programmable artificial optical pinholes at a plane conjugate to the focal plane by SLM 1320b, forming a series of pinhole patterns by pixels of SLM 1320b, and matching the series of pinhole patterns to the series of excitation patterns 1100. As described above, light collected from SLM 1320b is imaged to imaging device 1380 using one or more lenses. A 2-D image 1200 of the spectrally dispersed emission light may be acquired after each lateral shift of excitation pattern 1100 and the formation of its matching pinhole pattern. Method 2400 may further include reconstructing the 2-D images 1200 corresponding to the series of excitation patterns 1100 to provide a 4-D hyperspectral-imaging dataset of the selected focal plane of the sample.

VIII. Imaging Using Spatially Phase-Specified Illumination

It could be beneficial to control the spatial distribution of the phase, intensity, wavefront geometry, polarization, or other properties of illumination applied to a sample in order to image the sample. Such imaging of a sample (e.g., a biological sample) could be effected in order to identify probes in the sample, to detect the location, color, or other properties of fluorophores in the sample (e.g., fluorophores of such a probe), or to provide some other benefit. Controlling the spatial properties of the applied illumination could include operating a spatial light modulator to control the relative phase of the illumination across the sample. Such a method for controlling the phase of illumination applied to a sample could be employed in addition to, or alternatively to, other methods or apparatus for illumination of a sample described elsewhere herein. Embodiments to produce such illumination may be implemented using a microscope, such as a fluorescence microscope, a confocal microscope, a transmission microscope, or a reflectance microscope, having one or more 2-D imaging devices, e.g., a CCD or CMOS sensor or camera. Alternatively, an optical imaging system may be built according to embodiments of the present disclosure using suitable optical elements.

Embodiments of the present disclosure allow for acquiring a 2-D image of a focal plane in a sample using programmable artificial pinholes with adjustable size and spacing. A plurality of 2-D images can be acquired at a plurality of focal planes and computationally reconstructed to obtain a 3-D or virtual volumetric image of a sample. Additionally, embodiments of the present disclosure allows for acquiring a hyperspectral confocal image dataset of a focal plane in the sample.

According to an aspect of the present disclosure, excitation light having one or more wavelengths may be used to excite fluorophores in the sample. The excitation light may be emitted by a single-color light source or a multi-color light source. In some embodiments, the single-color light source may be a pulsed or a continuous "single-wavelength" laser that emits light with a very narrow spectrum. In other embodiments, the single-color light source may be the output of a monochromator.

In some embodiments, the multi-color light source may have a continuous spectrum. For example, the multi-color light source may be a broadband light source, such as certain supercontinuum lasers, a white light source (e.g., a high-pressure mercury lamp, a xenon lamp, a halogen lamp, or a metal halide lamp), or one or more LEDs. In other embodiments, the multi-color light source may have a discrete spectrum. For example, the multi-color light source may be a combination of pulsed or continuous "single-wavelength" lasers that emit light with very narrow spectra.

According to an aspect of the present disclosure, excitation light emitted by the light source may be structured for illuminating a subset of areas on the sample in an excitation pattern using a first spatial light modulator (SLM). To structure the excitation light, the first SLM may modulate the phase or amplitude of the excitation light by selectively modulating, e.g., actuating or switching, its pixels. The pixels could either be digital or analog in modulation. The first SLM may be selected from a group of SLMs including a digital micromirror device (DMD), deformable mirrors (DM), a diffractive optical element, a liquid crystal device (LCD), and a liquid crystal-on-silicon (LCOS) device.

As described herein, an excitation pattern illuminated on a sample may include a plurality of focused spots of excitation light (excitation spots). The excitation pattern may be an arbitrary pattern or a predetermined pattern, such as a 2-D array of excitation spots simultaneously incident on the sample. Fluorophores or fluorescent molecules in the sample illuminated by the excitation pattern may be excited and subsequently emit fluorescent light.

In some embodiments, the excitation pattern may be scanned across the sample or the field of view by modulating the pixels of the first SLM. In other embodiments, an x-y translation stage may be used to scan the excitation pattern across the sample or the field of view by moving the sample or an objective in lateral directions. The stage may be a motorized translation stage, a piezoelectric translation stage, or any suitable stage that allows for lateral linear movement.

According to an aspect of the present disclosure, systems and methods according to the present disclosure allow for confocal optical sectioning. This allows for acquisition of images for a plurality of focal planes along an axial direction of the sample. In some embodiments, an image of a desired focal plane may be acquired by implementing one or more optical pinholes at a plane conjugate to the focal plane. The optical pinholes may be programmable artificial pinholes formed by pixels of a second SLM. The second SLM may be selected from a group of SLMs including a digital micromirror device (DMD), a liquid crystal device (LCD), and a liquid crystal-on-silicon (LCOS) device.

In some embodiments, a pinhole pattern may be formed by the pixels of the second SLM by selectively modulating or switching its pixels to match the excitation pattern of the excitation light. Advantageously, the pinhole pattern may allow for confocal imaging of a plurality of areas on the sample simultaneously illuminated by the excitation pattern. This may increase the speed and/or throughput of acquiring confocal images across the sample at the focal plane comparing to traditional confocal microscopes that use sequential point-by-point scanning. Additionally, a degree of optical sectioning or confocality may be advantageously adjustable as needed by changing the size and/or separation of the artificial pinholes formed by the second SLM, allowing for adjusting the degree of depth selectivity of the desired focal plane.

As described herein, fluorophores are used in this disclosure as an exemplary optical label in a sample. Descriptions in references to fluorophores are equally applicable to other types of optical labels consistent with the embodiments of this disclosure. For example, the excitation light emitted from the light source may also excite other types of optical labels, which upon excitation, may emit light with an emission spectrum. Therefore, fluorescent light and fluorescence emission spectrum used in the descriptions in this disclosure may also be used to represent the emission light and emission spectra of other optical labels.

According to an aspect of the present disclosure, systems and methods according to the present disclosure allows for hyperspectral imaging. Fluorescent light emitted by the fluorophores excited by the excitation light in a given area of the sample may be spectrally dispersed in a given lateral direction (e.g., the horizontal direction or the vertical direction). At least one dispersive element may be employed to spectrally disperse the fluorescent light into a fluorescence emission spectrum corresponding to that given area. The fluorescence emission spectra of a subset of areas on the sample may be acquired as a 2-D image in one exposure by the 2-D imaging device.

In some embodiments, fluorescence emission spectra of all the areas across the sample or across a field of view may be acquired by scanning the excitation pattern across the sample or the field of view. At each spatial location of the excitation pattern, a 2-D image of the fluorescence emission spectra corresponding to the excitation pattern may be acquired (e.g., each fluorescence emission spectrum corresponding to an excitation spot of the excitation pattern). Advantageously, a hyperspectral image dataset of the sample may be computationally reconstructed from a plurality of such 2-D images of the fluorescence emission spectra. Additionally, by forming a pinhole pattern that matches the excitation pattern using the second SLM during the scanning, a hyperspectral confocal image dataset of the sample can be obtained.

Reference will now be made in detail to embodiments and aspects of the present disclosure, examples of which are illustrated in the accompanying drawings. Where possible, the same reference numbers will be used throughout the drawings to refer to the same or like parts.

As described herein, to illustrate different wavelengths or frequencies of light, different densities of dotted texture are used in the attached drawings. Higher densities correspond to longer wavelengths or lower frequencies of light. Additionally, vertical and/or horizontal directions are used as examples for illustrating lateral or transversal directions.

Figure 25:
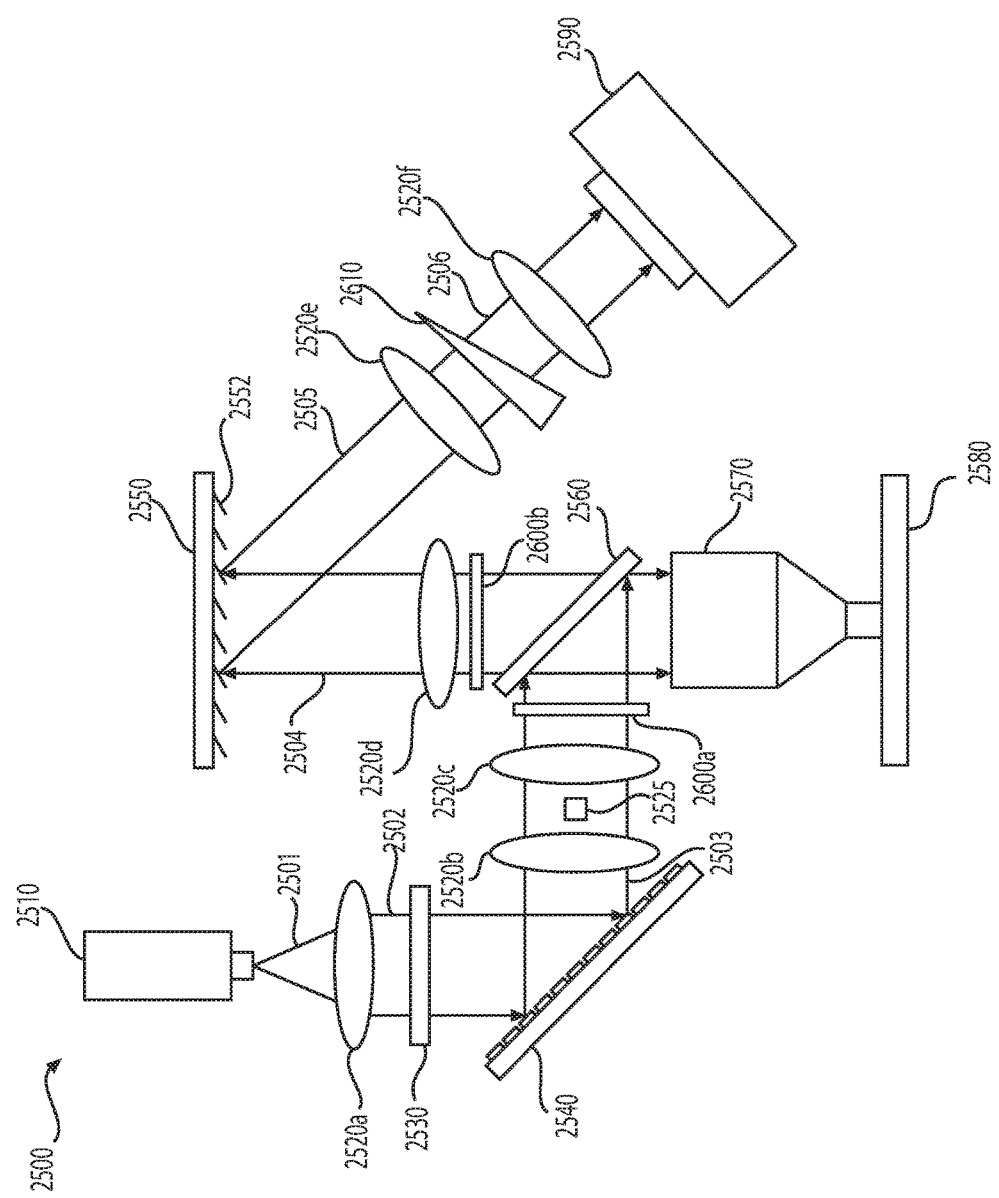
FIG. 25 is a schematic representation of an example confocal imaging system.

FIG. 25 is a schematic representation of an exemplary confocal imaging system 2500. In some embodiments, system 2500 may be a fluorescence microscope, a transmission microscope, a reflectance microscope, or a confocal fluorescence microscope. Embodiments of the present disclosure are applicable to other suitable microscopy techniques for performing confocal imaging and/or hyperspectral imaging.

As shown in FIG. 25, system 2500 may include an illumination system and a detection system. The illumination system may include a light source 2510, a first SLM 2540, and one or more lenses, e.g., lenses 2520*a*, 2520*b*, and 2520*c*. The illumination system may further include a half-wave plate 2530, an optical beam dump 2525, and/or an optical filter 2600*a*. The detection system may include a second SLM 2550, a 2-D imaging device 2590, and one or more lenses, e.g., lens 2520*d*, 2520*e*, and 2520*f*. The detection system may further include a dispersive element 2610 and/or an optical filter 2600*b*. Depending on its layout, geometry, and/or application, system 2500 may further include a beamsplitter 2560, an objective 2570, and a sample holder 2580 where a sample to be imaged is placed. System 2500 may include other optical elements, such as mirrors, beam dumps, an x-y translation stage, a z-axis translation stage or a tunable liquid lens (not shown), etc.

As described herein, an optical axis of system 2500 may define a path along which the excitation light and emitted fluorescent light from the sample propagate through system 2500.

In the illumination system, as shown in FIG. 25, light source 2510 emits excitation light 2501, which is directed to SLM 2540. Excitation light 2501 may be collimated and/or expanded using one or two lenses, e.g., lens 2520*a* or a pair of lenses 2520*a*. SLM 2540 may structure collimated excitation light 2502 through modulating the phase or amplitude of excitation light 2502 by selectively actuating or switching its pixels. SLM 2540 may be a transmission type or a reflection type SLM. While a reflection type SLM 2540 is used in the exemplary embodiment shown in FIG. 25, a transmission type SLM 2540 may alternatively be used consistent with the present disclosure. The geometry of the illumination system may be suitably designed based on the type of SLM 2540.

As shown in FIG. 25, when SLM 2540 is a reflection type SLM, at least a portion of the pixels of SLM 2540 reflect excitation light 2502 and direct the reflected excitation light 2503 along the optical axis of system 2500. In some embodiments, excitation light 2503 may be directed by SLM 2540 straight towards beamsplitter 2560 and/or objective 2570. In other embodiments, as shown in FIG. 25, reflected excitation light 2503 may pass through one or more relay lenses, e.g., lenses 2520*b* and 2520*c*, before reaching beamsplitter 2560 and/or objective 2570. Objective 2570 then focuses the excitation light to a sample placed on sample holder 2580.

In the detection system, as shown in FIG. 25, fluorescent light 2504 emitted by excited fluorophores in the sample is collected and/or collimated by objective 2570. Fluorescent light 2504 may pass through beamsplitter 2560 and lens 2520*d* along the optical axis of system 2500. SLM 2550 may be placed at about a plane conjugate to a focal plane located at a desired depth in the sample along the optical axis. For example, objective 2570 and lens 2520*d* may form an imaging configuration. When SLM 2550 is a reflection type SLM, SLM 2550 may reflect at least a portion of fluorescent light 2504 and direct the reflected fluorescent light 2505 along the optical axis of system 2500 towards imaging device 2590. Reflected fluorescent light 2505 may pass a pair of tube lenses, e.g., lenses 2520*e* and 2520*f*, before reaching a 2-D sensor of imaging device 2590.

As described herein, while a reflection type SLM 2550 is used in the exemplary embodiment shown in FIG. 25, a transmission type SLMs 2550 may alternatively be used consistent with the present disclosure. The geometry of the detection system may be suitably designed based on the type of SLM 2550.

Functions and the working principles of various components of system 2500 are described in detail below.

Light Source

As described above, light source 2510 may be a single-color light source or multi-color light source. In some embodiments, excitation light 2501 emitted by light source 2510 may be linearly polarized. Additionally or alternatively, excitation light 2501 may be collimated by lens 2520*a* and become collimated excitation light 2502 before being incident on SLM 2540.

In some embodiments, collimated excitation light 2502 may pass through half-wave plate 2530. Half-wave plate 2530 may change the polarization direction of a linearly polarized excitation light. For example, when SLM 2540 is a LCD or LCOS device, half-wave plate 2530 may rotate the polarization direction of the linearly polarized excitation light to be aligned in parallel with the orientation of the liquid crystal molecules in SLM 2540. This may increase the efficiency of reflection and/or modulation of the excitation light by the pixels of SLM 2540.

In some embodiments, light source 2510 may be operably connected to a controller (not shown) having a processor and a computer-readable medium that stores instructions or operational steps. These instructions or steps, when executed by the processor, may modulate the operational states of light source 2510. For example, the processor may activate or deactivate light source 2510, modulate the duration of a pulse of a pulsed light source 2510, and/or switch or tune the emission wavelengths of light source 2510.

Spatial Light Modulator for Structuring Excitation Light

As described above, to structure excitation light 2502 for illuminating the sample in an excitation pattern, SLM 2540 may modulate the amplitude or phase of excitation light 2502 by selectively modulating its pixels between operational states.

Amplitude Modulation

In some embodiments, the amplitude of excitation light 2502 may be modulated by SLM 2540. For example, SLM 2540 may be a reflection type LCD or LCOS device. The LCD or LCOS device may be placed at a conjugate plane to the sample. In such instances, only one of lenses 2520*b* and 2520*c* may be placed between SLM 2540 and objective 2570. For example, lens 2520*b* may be used as a tube lens and combined with objective 2570 to form an imaging configuration. SLM 2540 may be placed at about one focal length before lens 2520*b*.

Pixels of SLM 2540 may create an amplitude modulation pattern by manipulating the polarization of excitation light incident on the pixels. The amplitude modulation pattern may be imaged onto the sample as an excitation pattern by lens 2520*b* and objective 2570, for example. Depending on the focal lengths of lens 2520*b* and objective 2570, the excitation pattern may be a magnified or de-magnified image of the amplitude modulation pattern.

To create the amplitude modulation pattern, pixels of SLM 2540 may be electrically modulated between an "on" state and an "off" state in a pixel-by-pixel fashion. The "on" pixels may rotate the polarization direction of linearly polarized light by about 90° while the "off" pixels do not perform the rotation. In such instances, a first linear polarizer (not shown) may be used to linearly polarize excitation light 2502. A second linear polarizer or a polarizing beamsplitter (PBS) (not shown) may be used to pass excitation light 2503 reflected by the "on" pixels and block excitation light 2502 reflected by the "off" pixels.

A disadvantage of modulating the amplitude of excitation light 2502 using SLM 2540 is the loss of light during the modulation. This is because most of the pixels of SLM 2540 are typically in the "off" state. Accordingly, most of excitation light 2502 is steered away from the optical axis and would not reach the sample, and thus is lost.

Phase Modulation

To increase the efficiency of utilizing excitation light 2502, SLM 2540 may modulate the phase of excitation light 2502 to generate the excitation pattern. In such instances, both lenses 2520*b* and 2520*c* may be placed between SLM 2540 and objective 2570. SLM 2540 may be a reflection type LCD or LCOS device, for example. The LCD or LCOS device may be placed at an aperture plane, which may be a conjugate plane to the back aperture of objective 2570 or a Fourier plane to the sample. For example, lenses 2520*b* and 2520*c* may form an imaging configuration. Lens 2520*b* may be located about one focal length behind SLM 2540. Lens 2520*c* may be located about two focal lengths behind lens 2520*b*. Objective 2570 may be located about one focal length behind lens 2520*c*.

The pixels of SLM 2540 may form a custom phase modulation pattern to modulate the wavefront of excitation light 2502. Upon the reflection of excitation light 2502 by SLM 2540, phases at different locations of the wavefront of the reflected excitation light 2503 may be selectively changed according to the phase modulation pattern. In some embodiments, pixels of SLM 2540 may be electrically modulated between an "on" state and an "off" state in a pixel-by-pixel fashion. If pixels of SLM 2540 are in the "on" state, they may change the phase of the reflected light by changing the optical path length of light traveled in the liquid crystal; and if they are in the "off" state, they may not change the phase of the reflected light. This allows the phase modulation pattern formed by the pixels of SLM 2540 to be digitally customized as needed. In other embodiments, pixels of SLM 2540 may have multiple states or levels of phase adjustment (e.g., 256 levels between 0 and $2\pi$) and may be individually modulated to desired states or levels. Advantageously, increasing the states or levels of adjustment of the pixels increases the continuity of the adjustment of the phase modulation pattern and thus the adjustment of the phase of excitation light 2503, and may further reduce undesirable diffraction orders in the excitation pattern.

The phase modulation may render wavelets of reflected excitation light 2503 having different directions and/or phases. As reflected excitation light 2503 propagates along the optical axis, each of the lenses 2520*b* and 2520*c* and objective 2570 may perform Fourier Transform on the wavefront of reflected excitation light 2503. A diffraction pattern may then be formed at the focal plane of objective 2570. This diffraction pattern is referred to herein as the excitation pattern when illuminated on the sample.

In some embodiments, optical beam dump 2525 may be placed along the optical axis between lenses 2520*b* and 2520*c*, e.g., about a focal length behind lens 2520*b* or at a conjugate plane of the sample. This may allow the lower-order diffraction spots, e.g., zero-order and/or first-order diffraction spots, of a diffraction pattern formed by reflected excitation light 2503 at the location of optical beam dump 2525 to be substantially absorbed and blocked from reaching the sample. Because the excitation pattern is an image of the diffraction pattern formed at the location of optical beam dump 2525, the intensity of lower-order diffraction spots of the excitation pattern illuminated on the sample would be substantially reduced. Since the lower-order diffraction spots, e.g., zero-order and/or first-order diffraction spots, are typically brighter than other orders of diffraction spots, the use of optical beam dump 2525 may advantageously improve the uniformity of the intensity of the excitation pattern across the field of view.

As described above, the phase modulation pattern is at or approximately at a Fourier plane to the sample. In such instances, the electrical field of reflected excitation light 2503, whose phase has been modulated by the phase modulation pattern of SLM 2540, is further subject to Fourier Transforms by the lenses 2520*b* and 2520*c* and objective 2570 before it illuminates the sample in a desired excitation pattern. In some embodiments, the excitation pattern may be an intensity profile of the wavefront of the transformed excitation light with a desired phase profile. The desired phase profile may be predetermined to increase the diffraction efficiency of the excitation light.

In some embodiments, computer algorithms, e.g., the Gerchberg-Saxton (GS) algorithm, may be used to generate the phase modulation pattern that would result in a desired excitation pattern. Further, customized computer algorithms may be used to generate time-varying phase modulation patterns for scanning or translating the desired excitation pattern across the field of view.

Advantageously, modulating the phase of excitation light 2502 would allow it to propagate with substantially uniform intensity in the near field of SLM 2540 and thus reduce loss of excitation light 2502. The modulated excitation light may then form a customizable or programmable excitation pattern when illuminated on the sample in the far field. Therefore, comparing to modulating the amplitude of excitation light 2502 as described above, modulating the phase of excitation light 2502 to create a desired excitation pattern may substantially increase the efficiency of illumination of system 2500 by reducing loss of excitation light 2502.

SLM 2540 may alternatively be a transmission type device implemented along the optical axis. The geometry of the illumination system may be suitably designed such that the amplitude or phase modulation pattern formed by the pixels of the device may modulate the amplitude or phase of excitation light 2502 similarly as described above.

Whether SLM 2540 modulate the amplitude or phase of excitation light 2502, the excitation pattern illuminated on the sample can be programmed and customized as needed by modulating pixels of SLM 2540 between two operational states in a pixel-by-pixel fashion. Further, the excitation pattern may be translated or shifted across the sample or a field of view in a given spatial direction, such as the horizontal or vertical direction, by scanning or changing the modulation of the pixels of SLM 2540. For example, when SLM 2540 is located at a Fourier plane of the sample for modulating the phase of excitation light 2502, the excitation pattern may be scanned by changing the slope of a linear phase ramp along a spatial direction. This advantageously allows for scanning the excitation pattern across the field of view of system 2500 without moving the sample and/or sample holder 2580 using an x-y translation stage.

In some embodiments, depending on the type and modulation features of the pixels of SLM 2540, excitation light 2502 may be directed towards SLM 2540 at a predetermined angle relative to a plane of SLM 2540. The predetermined angle may depend on the type of SLM 2540 and/or the geometry of system 2500. For example, when SLM 2540 is a reflection type SLM, excitation light 2502 may be directed towards SLM 2540 at an angle such that reflected excitation light 2503 propagates along the optical axis of system 2500.

In some embodiments, SLM 2540 may be operably connected to a controller (not shown) having a processor and a computer-readable medium that stores instructions or operational steps. These instructions or steps, when executed by the processor, may modulate the operational states of the pixels of SLM 2540 to form a desired excitation pattern and/or to translate the excitation pattern in a desired spatial direction over a predetermined distance across the field of view.

Confocal Optical Sectioning

As described above, system 2500 allows for confocal optical sectioning, which allows for selecting the depth of a focal plane in the sample. The depth of the focal plane may be selected by introducing one or more optical pinholes at a plane conjugate to the selected focal plane.

SLM 2550 is used for achieving confocal optical sectioning. As described above, SLM 2550 may be placed at about a plane conjugate to a focal plane located at a desired depth in the sample along the optical axis. Lens 2520d may be used as a tube lens and together with objective 2570 may form an imaging configuration. For example, as shown in FIG. 25, lens 2520d may be located behind objective 2570 and SLM 2550 may be located about one focal length behind lens 2520d. The space between the back aperture of objective 2570 and lens 2520d is a collimated space, which may be adjusted as need based on various factors, such as the geometry of system 2500 and a desired location of a minimum beam aperture. In some embodiments, lens 2520d is placed about one focal length behind objective 2570.

In some embodiments, SLM 2550 may be a digital micromirror device (DMD) having an array of multiple micromirrors 2552. These micromirrors may be individually actuated to switch between two operational positions, an "on" position and an "off" position. When a micromirror is configured to be in the "on" position, fluorescent light 2504 from the focal plane in the sample is reflected to propagate along the optical axis as reflected fluorescent light 2505, which is directed to imaging device 2590. When a micromirror is configured to be in the "off" position, fluorescent light 2504 is reflected towards a direction deviated from the optical axis and is not directed to imaging device 2590. In some embodiments, fluorescent light 2504 reflected by the "off" micromirrors may be directed to other optical elements, such as a mirror or a beam dump (not shown).

In some embodiments, the micromirrors are of a square shape having a length of its sides ranging from about a few micrometers to about 10 μm. Other shapes and sizes of the micromirrors are also possible and may be suitably used. The DMD is typically capable of changing or alternating the "on" and "off" positions of the micromirrors very rapidly.

In some embodiments, a single micromirror of the DMD may be referred to as a single pixel. In other embodiments, a plurality of micromirrors may be referred to as a single pixel. For example, a group of immediately adjacent micromirrors may be referred as a single pixel and may be modulated or actuated in unison.

Pixels of SLM 2550 may be selectively actuated or switched to "on" or "off" positions to form a pinhole pattern matching (conjugating) the excitation pattern illuminated on the sample. The pinhole pattern may include a plurality of artificial optical pinholes at the conjugate plane and reject out-of-focus fluorescent light from the sample. Therefore, out-of-focus fluorescent light would not pass through the detection system and are substantially removed or eliminated from the acquired image by imaging device 2590.

The size and separations of the artificial pinholes in the pinhole pattern are programmable, and may be customized based on the excitation pattern and the magnification of the imaging configuration formed by objective 2570 and lens 2520d. For example, an artificial pinhole in the pinhole pattern may be formed by an array of "on" pixels to match the size of an excitation spot in the excitation pattern.

The fluorescent light 2505 reflected by the "on" pixels of SLM 2550 may then be imaged to imaging device 2590 by lenses 2520e and 2520f. For example, lens 2520e may be located about one focal length beyond the image produced by lens 2520d (e.g., about one focal length behind SLM 2550) such that it re-collimates reflected fluorescent light 2505. Imaging device 2590 may be located about one focal length behind lens 2520f or at a conjugate plane of SLM 2550. Because the fluorescent light is collimated in the space between lenses 2520e and 2520f, the distance between lenses 2520e and 2520f may be adjusted as desired. In some embodiments, lens 2520f may be about two focal lengths behind lens 2520e such that a plane midway between lenses 2520e and 2520f is conjugate to an exit pupil of system 2500.

By digitally changing and/or laterally shifting the excitation pattern using SLM 2540 and the matching pinhole pattern correspondingly using SLM 2550, the whole field of view may be scanned for acquiring a confocal image. By further scanning the field of view across the sample, the whole sample can be scanned to obtain a complete confocal image dataset of the sample.

In some embodiments, imaging device 2590 may be suitably tilted to reduce aberrations and thus improve the quality of the acquired images. This is at least because the "on" pixels of SLM 2550 may direct reflected fluorescent light 2505 at an angle that is not perpendicular to the surface plane of SLM 2550 such that an image plane formed by lenses 2520e and 2520f may be tilted. Aberrations caused by this tilting effect may be compensated by properly tilting imaging device 2590.

To change or select a depth of the focal plane, in some embodiments, sample holder 2580 may be installed on the z-axis translation stage. The desired depth of the focal plane may be selected by moving sample holder 2580 along the optical axis using the z-axis translation stage. Alternatively, objective 2570 may be installed on the z-axis translation stage and the desired depth of the focal plane may be selected by moving objective 2570 along the optical axis. As describe herein, the z-axis translation stage may also include x-y translation capability to move the field of view of system 2500 across the sample in lateral directions.

In some embodiments, when SLM 2540 is at a Fourier plane for modulating the phase of excitation light 2502, the focal depth may be adjusted by changing the phase modulation pattern formed by the pixels of SLM 2540. In such instances, excitation light 2503 modulated by the pixels of SLM 2540 may, upon reflection, include a superposition of slightly diverging or converging beams determined by the phase modulation pattern. Depending on their degree of divergence or convergence, these beams would focus at increased or reduced depth after passing through the microscope objective.

In other embodiments, the desired depth of the focal plane may be selected by tuning the focus of a tunable liquid lens (not shown) placed behind objective 2570. As described herein, the z-translation stage, the tunable liquid lens, and/or the phase modulation pattern of SLM 2540 may be controlled by a computer program to achieve autofocusing.

Advantageously, a degree of confocality may be adjusted as needed by changing the size and/or separation of the artificial pinholes formed by SLM 2550. For example, increasing the sizes of the pinholes by increasing the number of pixels in the pinholes and/or reducing the pinhole spacing may reduce the degree of confocality and thus the degree of depth selectivity of the desired focal plane. On the other hand, decreasing the size of the pinholes by reducing the number of pixels in the pinholes and/or increasing the pinhole spacing may increase the degree of confocality and thus the degree of depth selectivity of the desired focal plane. In some embodiments, the depth selectivity may be proportional to the ratio of the number of "off" and "on" pixels of SLM 2550. Therefore, SLM 2550 may advantageously allow for switching between wide-field imaging and confocal imaging as desired by conveniently adjusting the pinhole size and/or separation.

Additionally, the pinhole pattern formed by pixels of SLM 2550 advantageously allows for confocal imaging of a plurality of areas on the sample simultaneously illuminated by the excitation pattern generated by SLM 2540. This may increase the speed and/or throughput of acquiring a confocal image dataset across the sample at the desired focal plane comparing to traditional confocal microscopes that use sequential point-by-point scanning.

Hyperspectral Imaging Capability

In some embodiments, hyperspectral imaging capability may be advantageously added to system 2500 to allow for acquiring a hyperspectral-imaging dataset at a selected focal plane in the sample. A hyperspectral-imaging dataset may be represented in three-dimensions (3-D): two spatial directions (horizontal direction and vertical direction) and one spectral dimension ($\lambda$). Information in the spectral dimension of a hyperspectral-imaging dataset may reflect fluorescence intensities as a function of a range of emission wavelengths of the fluorophores in the sample.

Hyperspectral imaging capability may be achieved by using dispersive element 2610 in system 2500. For example, dispersive element 2610 may be located in the collimated space between lenses 2520e and 2520f. Dispersive element 2610 may be a diffraction grating or a prism, such as a non-deviating prism (e.g., Amici prisms or double Amici prisms). Dispersive element 2610 may spectrally disperse fluorescent light 2505 reflected from SLM 2550 along a given lateral direction. Spectrally dispersed fluorescent light 2506 then passes through lens 2520f and is acquired by imaging device 2590.

Figure 26:
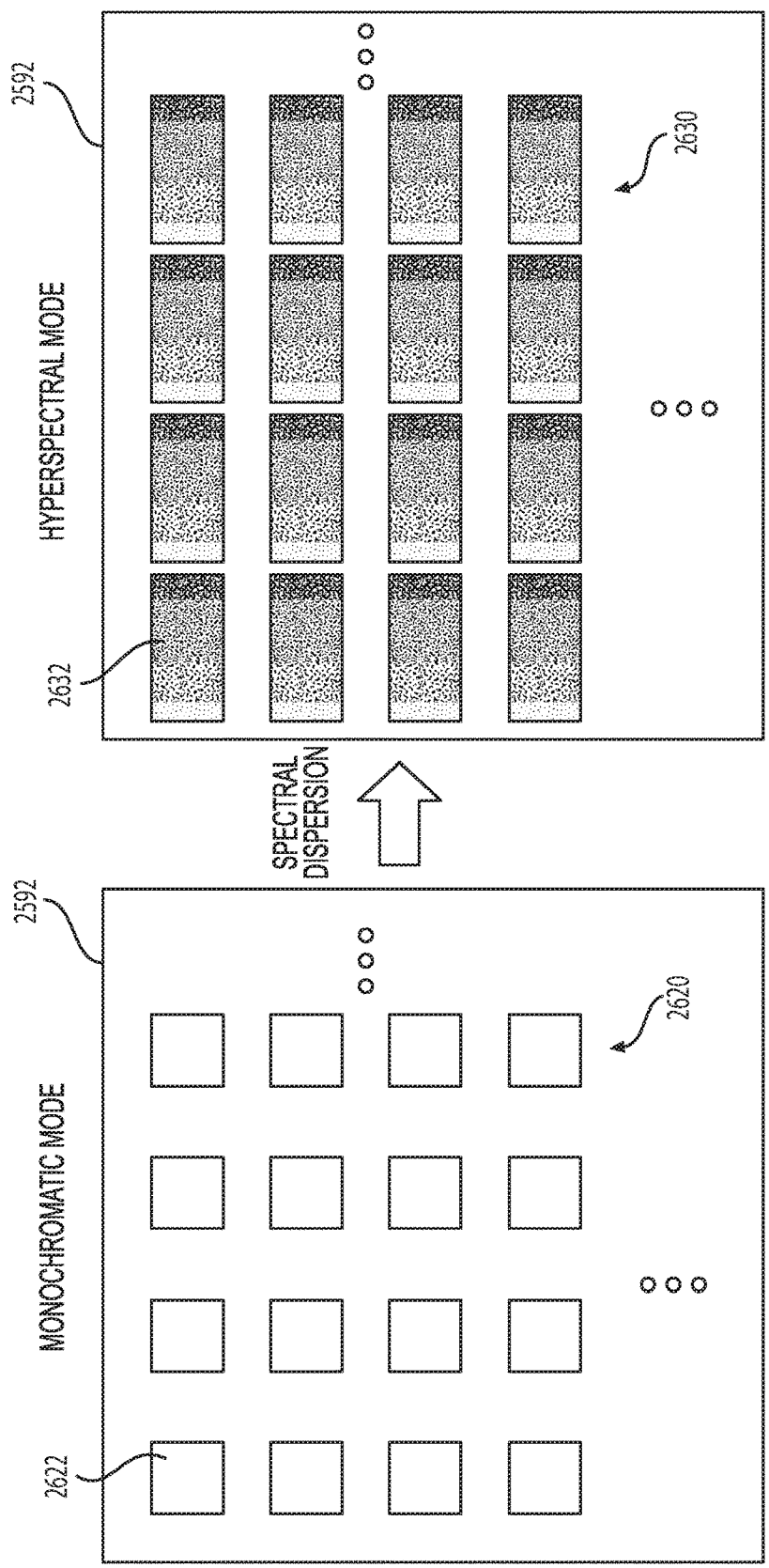
FIG. 26 is a graphical illustration for an example scheme for performing hyperspectral confocal imaging.

FIG. 26 is a graphical illustration for an exemplary scheme for performing hyperspectral confocal imaging, according to embodiments of the present disclosure. In some embodiments, when system 2500 is in a monochromatic imaging mode, imaging device 2590 may acquire an image of fluorescent light 2505 reflected by a pinhole pattern formed on SLM 2550. The pinhole pattern conjugates an excitation pattern illuminated on the sample. For example, a 2-D image 2592 acquired by imaging device 2590 may show a 2-D array 2620 of fluorescent spots 2622 corresponding to a 2-D array of excitation spots in the excitation pattern.

In other embodiments, when system 2500 is in a hyperspectral imaging mode, fluorescent light 2505 reflected by SLM 2550 is spectrally dispersed by dispersive element 2610 in a given direction, e.g., the horizontal direction. In such instances, 2-D image 2592 acquired by imaging device 2590 may show a 2-D array 2630 of fluorescence emission spectra 2632. Each fluorescence emission spectrum 2632 may be dispersed in the horizontal direction and correspond to an excitation spot of the excitation pattern at a different spatial location on the sample.

As described above, the excitation pattern may be laterally shifted, e.g., in the vertical and horizontal directions to scan across the field of view or the sample. At each spatial position of the excitation pattern, array 2630 of fluorescence emission spectra 2632 corresponding to the areas on the sample illuminated by the excitation pattern can be acquired in a 2-D image 2592. A plurality of 2-D images 2592 of fluorescence emission spectra may be acquired corresponding to a series of excitation patterns laterally shifted from one another and then computationally reconstructed to obtain a hyperspectral-imaging dataset.

Therefore, by digitally changing and/or laterally shifting the excitation pattern and the matching pinhole pattern on SLM 2550 correspondingly, the whole field of view may be scanned for acquiring a hyperspectral-imaging dataset of a sample at a focal plane. By further scanning the field of view across the sample, the whole sample can be scanned to obtain a complete hyperspectral-imaging dataset of the sample at the focal plane.

The spatial separation, horizontal and/or vertical, between excitation spots of an excitation pattern may be predetermined based on various factors, such as the excitation wavelengths, the size of the sample, the field of view of system 2500, the desired measurement throughput, spatial resolution, and/or speed, and the amounts of spectral dispersion of fluorescent light 2506. For example, the spatial separation between the excitation spots in the horizontal direction may be predetermined based on the range of fluorescence emission spectra 2632 in the horizontal direction such that the fluorescence emission spectra 2632 do not overlap with each other in the horizontal direction in 2-D image 2592.

The degree of spectral dispersion caused by dispersive element 2610 may be predetermined based on various factors, such as the spectral range of fluorescent light 2505, the size of the sample or the field of view, the size of imaging device 2590, the desired spectral resolution, and the application of system 2500.

In some embodiments, the degree of spectral dispersion caused by dispersive element 2610 may be advantageously adjustable. For example, dispersive element 2610 may be a pair of double Amici prisms placed along the optical axis of system 2500. At least one of the pair of double Amici prisms is rotatable relative to the other around the optical axis. The rotation of the double Amici prisms relative to each other may allow for continuous control of the amount and/or angular orientation (e.g., dispersion angles) of the spectral dispersion of fluorescent light 2506.

Lenses and Objective

Various lenses of system 2500, such as lenses 2520a-2520f, may be achromatic, such as achromatic doublets or triplets, to limit or reduce the effects of chromatic and/or spherical aberration of the system. Further, objective 2570 of system 2500 may be achromatic. Alternatively or additionally, objective 2570 may be an infinity-corrected objective such that objective 2570 may form a desired focus (e.g., focused spots or focused pattern) of a collimated light beam entering from its back aperture. Using achromatic lenses and/or achromatic or infinity-corrected objective may allow fluorescent light of different wavelengths from a focal plane in the sample to similarly form a focused image at imaging device 2590. Therefore, using achromatic lenses and/or achromatic objective may improve the quality of confocal images acquired by system 2500.

Optical Filters and Beamsplitter

In some embodiments, optical filter 2600a may be added in the illumination system along the optical axis. Optical filter 2600a may be a clean-up filter that substantially transmits desired wavelengths of excitation light 2502 and blocks unwanted wavelengths. For example, optical filter 2600a may have a narrow passband ranging for about a few nanometers to block noisy spontaneous emission from light source 2510 or to substantially reduce background noise.

Because the intensity of excitation light 2502 may be orders of magnitude stronger than fluorescent light 2504, excitation light 2502 reflected and/or scattered by the sample and/or sample holder 2580 may enter the detection system and affect the detection or acquisition of the fluorescent light by imaging device 2590. Therefore, embodiments of the present disclosure may reduce or block excitation light 2502 from propagating into the detection system as described below.

In some embodiments, beamsplitter 2560 may be used to block excitation light 2502 from propagating towards imaging device 2590. Beamsplitter 2560 may be a long-pass dichroic beamsplitter that substantially reflects the wavelengths of excitation light 2502 and transmits at least a portion of the wavelengths of fluorescent light 2504. The spectrum of excitation light 2502 typically ranges from the ultraviolet through the visible spectra, and the spectrum of fluorescent light 2504 typically ranges from the visible into the near infrared spectra. Therefore, the long-pass dichroic beamsplitter may block wavelengths of excitation light 2502 and transmit a range of wavelengths of fluorescent light 2504.

Alternatively or additionally, optical filter 2600b may be added in the detection system along the optical axis. Optical filter 2600b may be a notch filter that may substantially reflect the wavelengths or a narrow spectral band of excitation light 2502, thereby blocking excitation light 2502 from reaching imaging device 2590.

In other embodiments, when excitation light 2502 is linearly polarized, beamsplitter 2560 may be a polarizing beamsplitter (PBS). The PBS may be selected such that it reflects light having a polarization direction same as that of the linearly polarized excitation light and to transmit light having a polarization direction perpendicular to that of the polarized excitation light. Most of the excitation light collected by objective 2570 would therefore reflect from this PBS and would not reach imaging device 2590. In some instances, both the sample and objective 2570 may depolarize reflected or scattered excitation light to a small degree, and thus undesirably allow some excitation light to transmit through the PBS and enter the detection system.

Imaging Device

Imaging device 2590 may include a suitable 2-D sensor located at an image plane conjugate to a selected focal plane in the sample. The sensor could be implemented with a CMOS sensor, a CCD sensor, a 2-D array of silicon avalanche photodiodes (APDs), or other suitable types of 2-D sensors.

Imaging device 2590 may be operatively connected to a controller or a computing device (not shown) that controls its operation. For example, the controller (not shown) may have a processor and one or more computer-readable media that stores instructions or operational steps. The instructions or operational steps, when executed by the processor, may operate the exposure of imaging device 2590, acquire 2-D images 2592, and/or store the datasets of 2-D image 2592 to a memory. The computer-readable medium may further store instructions or operational steps that, when executed by the processor, may perform data processing of the acquired 2-D image datasets and/or reconstruct a confocal image and/or a hyperspectral-imaging dataset from the 2-D image datasets.

Figure 27:
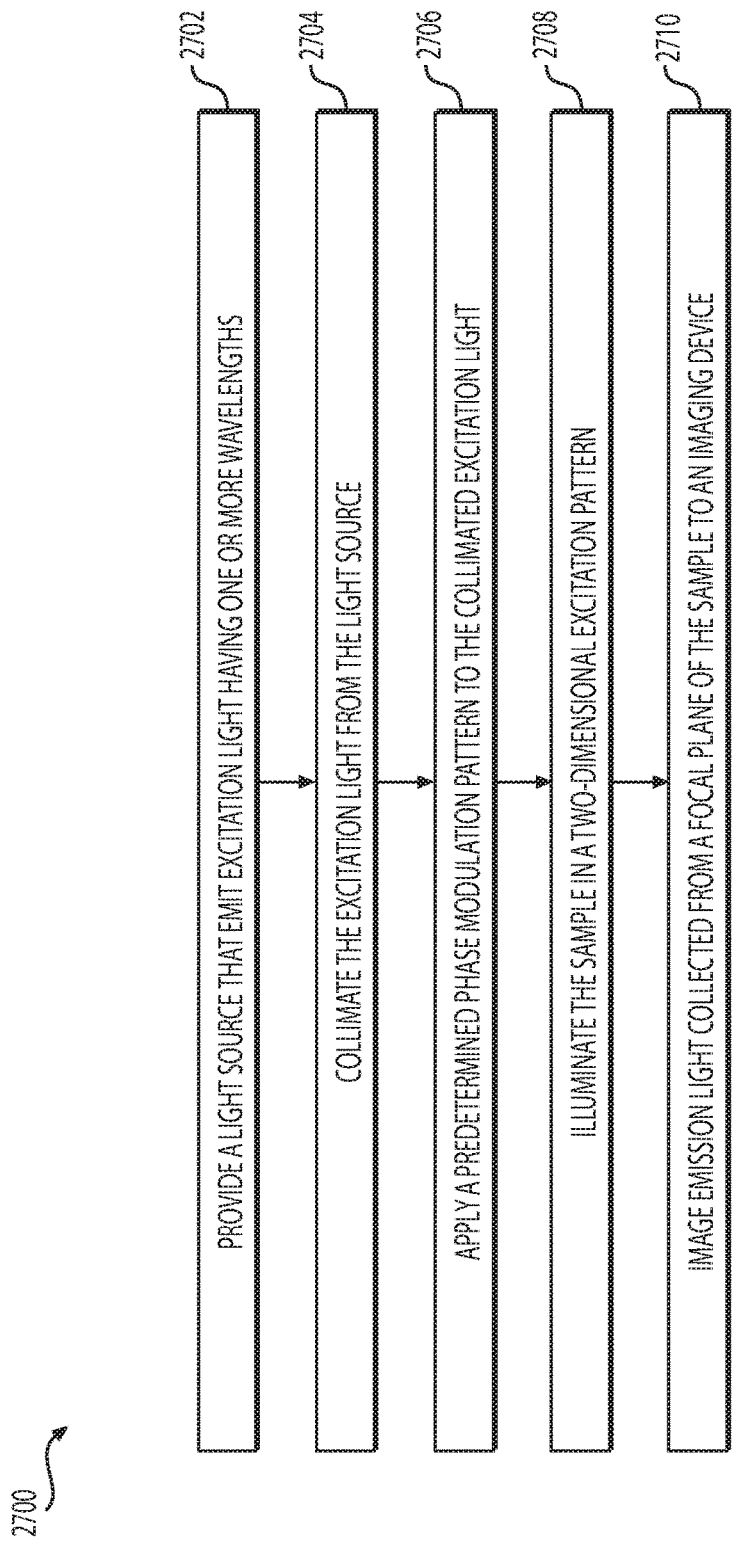
FIG. 27 is a flowchart of an example method for obtaining a confocal image.

System 2500 as described herein may be utilized in a variety of methods for confocal and/or hyperspectral imaging. FIG. 27 is a flowchart of an exemplary method 2700 for performing confocal imaging or for acquiring a confocal image of a sample. Method 2700 uses system 2500 and features of the embodiments of system 2500 described above in reference to FIGS. 25 and 26.

At step 2702, light source 2510 is provided and configured to emit excitation light 2501 having one or more wavelengths. At step 2704, excitation light 2501 is collimated by lens 2520a and become collimated excitation light 2502. At step 2706, collimated excitation light 2502 is structured or modulated by being applied with a predetermined phase modulation pattern formed by pixels of SLM 2540. At step 2708, the structured excitation light is directed towards the sample and illuminates the sample in a two-dimensional excitation pattern. The excitation pattern is located at a Fourier plane of the phase modulation pattern. At step 2710, emission light collected from a focal plane in the sample is imaged to imaging device 2590. The focal plane can be conjugate to or at a conjugate plane of a pinhole pattern formed by the pixels of SLM 2550.

Method 2700 may further include additional steps. For example, method 2700 may include calibrating system 2500 before acquiring 2-D image 2592. Various optical components in system 2500 may be suitably calibrated and aligned such that focused 2-D images 2592 with reduced or minimum aberration and/or distortion can be acquired.

Method 2700 may further include spectrally dispersing fluorescent light 2504 collected from the sample in a lateral direction using dispersive element 2610. Spectrally dispersed fluorescent light 2506 may be acquired in a 2-D image 2592 by imaging device 2590.

Method 2700 may further include illuminating the sample sequentially in a series of excitation patterns laterally shifted from one another and forming a series of pinhole patterns matching the series of excitation patterns.

In some embodiments, method 2700 may further include obtaining a plurality of 2-D images 2592 of the emission light 2505 corresponding to the series of excitation patterns, and reconstructing the plurality of 2-D images 2592 to provide a confocal image. As described above, a 2-D image 2592 may be acquired after each lateral shift of excitation pattern and the formation of its matching pinhole pattern. Each 2-D image 2592 may record an array 2620 of fluorescent spots 2622 corresponding to each laterally shifted excitation pattern.

In other embodiments, method 2700 may further include obtaining a plurality of 2-D images 2592 of the spectrally dispersed emission light 2506 corresponding to the series of excitation patterns, and reconstructing the plurality of 2-D images 2592 to provide a hyperspectral confocal image dataset. As described above, a 2-D image 2592 of the spectrally dispersed emission light may be acquired after each lateral shift of excitation pattern and the formation of its matching pinhole pattern. Each 2-D image 2592 may record an array 2630 of fluorescent emission spectra 2632 corresponding to each laterally shifted excitation pattern.

IX. Example Controllable Optically Dispersive Element

Various embodiments herein describe the use of chromatically dispersive elements or systems (e.g., prisms, diffraction gratings, SLMs) to disperse light (e.g., illumination light used to illuminate a sample, image light received from a sample) according to wavelength. This dispersion can be employed to facilitate imaging of a sample (e.g., a biological sample) in order to identify probes in the sample, to detect the location, color, or other properties of fluorophores in the sample (e.g., fluorophores of such a probe), or to provide some other benefit. In some examples (e.g., in the systems described above), it could be advantageous to apply such dispersion using "direct vision" or "non-deviating" dispersive elements to achieve flexible adjustment of the magnitude and/or orientation of the applied dispersion. Embodiments of the present disclosure may be implemented in a spectrometer, e.g., an imaging spectrometer, a monochromator, a spectral analyzer, a microscope, e.g., a fluorescence microscope, a confocal microscope, a transmission microscope, a reflectance microscope, etc., or a spectral imaging system, e.g., a hyperspectral imaging system. Alternatively, embodiments of the present disclosure may be implemented in a customized optical system built using suitable optical elements.

According to an aspect of the present disclosure, an optical system is provided for dispersing an optical beam having one or more wavelengths. The optical system may include a pair of non-deviating dispersive elements aligned along an optical axis. In some embodiments, the optical system may collimate the input optical beam before the dispersion.

In some embodiments, the optical beam may be an excitation light beam for illuminating a sample or an emission light beam collected from a sample. Additionally or alternatively, the optical beam may be filtered to have a desired spectrum before entering the optical system.

According to an aspect of the present disclosure, the pair of non-deviating dispersive elements is two double Amici prisms aligned along the optical axis. The dispersion of the two double Amici prisms may add up to the total dispersion of the optical beam by the optical system.

In some embodiments, at least one of the double Amici prisms is rotatable relative to each other around the optical axis. In other embodiments, both double Amici prisms may be independently rotatable around the optical axis. A rotational angle between the two double Amici prisms relative to each other around the optical axis may be continuously adjusted from about 0° to about 180°.

Advantageously, adjusting the rotational angle between the first and second double Amici prisms vary the total dispersion of the optical beam by the optical system. This eliminates the need to change the footprint of an optical setup in which the optical system is implemented and further allows for a compact design of the optical setup. Additionally, rotational stages for adjusting the rotational angle between the two double Amici prisms may operate at a speed faster than that of translational stages for adjusting the optical path length between two prisms or gratings. This further improves the speed for adjusting dispersion of the optical beam.

In some embodiments, adjustment of the rotational angle between the two double Amici prisms allows for adjustment of the magnitude of the dispersion of the optical beam. For example, when the rotational angle between the two double Amici prisms is about 0°, the dispersion of the two prisms add up to a maximum magnitude of dispersion, e.g., doubling the magnitude of dispersion of one prism. When the rotational angle between the two double Amici prisms is about 180°, the dispersion of the two prisms may cancel each other, leading to a minimum magnitude of dispersion, e.g., about zero dispersion. When the rotational angle between the two double Amici prisms is an intermediate angle between 0° and 180°, the magnitude of dispersion is between the two extremes. When the two double Amici prisms are identical, the maximum magnitude of the dispersion may double the magnitude of dispersion that can be generated by one of the double Amici prisms.

In some embodiments, when the rotational angle between the two double Amici prisms is continuously adjusted from about 0° to about 180°, the magnitude of the dispersion generated by the optical system may be continuously adjusted from the maximum magnitude to the minimum magnitude.

According to an aspect of the present disclosure, a predetermined wavelength, e.g., a center wavelength, of the optical beam would not change its propagation direction after passing through the optical system. For example, a predetermined wavelength of the input optical beam may enter the first double Amici prism along an input optical axis, and then exit the second double Amici prism along an output optical axis. The input optical axis and the output optical axis of the predetermined wavelength may remain collinear. The other wavelengths of the optical beam may transmit the optical system with suitable deviation angles that are determined by the design of the prisms.

In some embodiments, the orientation of the dispersion of the optical beam caused by the optical system may be adjusted by rotating both of the double Amici prisms. As described herein, the orientation of the dispersion may refer to an orientation of a dispersion line formed or focused on a plane orthogonal to the optical axis after the optical beam passes through the optical system. The dispersion line may have the spectrum of the optical beam spread out along a linear direction. Rotating both prisms may change the angle of incidence of the optical beam on the first prism, and thus change the deviation angles for the wavelengths of the optical beam exiting the second prism except for the predetermined wavelength. The changes of the deviation angles may then lead to a change of the orientation of the dispersion line.

As described herein, the optical beam entering the optical system to be dispersed may be referred to as an input optical beam, and the dispersed optical beam exiting the optical system may be referred to as an output optical beam. In some embodiments, the output optical beam may be further modulated, filtered, processed, and/or detected by a one-dimensional or two-dimensional array of photodetector or sensor of an imaging device.

Reference will now be made in detail to embodiments and aspects of the present disclosure, examples of which are illustrated in the accompanying drawings.

Figure 28:
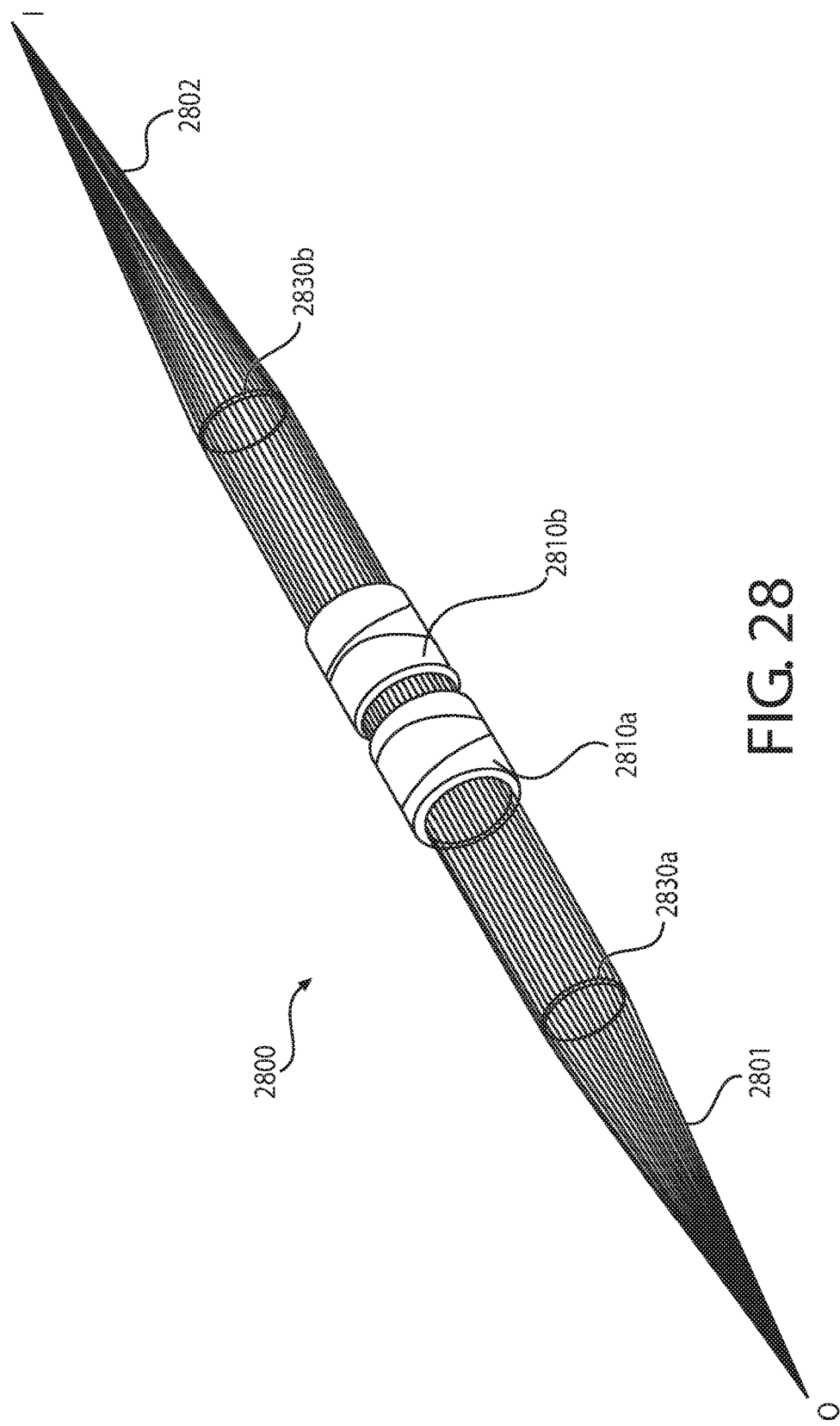
FIG. 28 is a schematic perspective representation of an example optical system.

FIG. 28 is a schematic perspective representation of an exemplary optical system 2800 for dispersing an optical beam. For example, system 2800 may be implemented in an optical setup for generating an output optical beam 2802 with a desired dispersion from an input optical beam 2801. As described herein, input optical beam 2801 refers to the optical beam entering and/or passing through system 2800 and output optical beam 2802 refers to the optical beam exiting system 2800. Input optical beam 2801 and output optical beam 2802 are referenced separately for the describing the transmission and dispersion of the optical beam by system 2800. In some embodiments, output optical beam 2802 may be further filtered, modulated, and/or acquired to obtain an optical signal with a desired spectrum and/or spectral resolution.

As shown in FIG. 28, system 2800 may include at least two double Amici prisms, e.g., prisms 2810a and 2810b. Depending on the application of system, system 2800 may further include at least two lenses 2830a and 2830b. For example, when system 2800 is implemented in a hyperspectral imaging system where emission spectra of a plurality of locations on a sample are simultaneously measured, lenses 2830a and 2830b may be in an imaging configuration. Lenses 2830a and 2830b may create a collimated space between them for input optical beam 2801 to propagate through prisms 2810a and 2810b. System 2800 may further include other optical elements, such as mirrors, beam dumps, spatial filters etc.

As described herein, an optical axis of system 2800 may define a path along which a predetermined wavelength (e.g., a center wavelength) of input optical beam 2801 and output optical beam 2802 propagates through system 2800.

As shown in FIG. 28, prisms 2810a and 2810b and lenses 2830a and 2830b are aligned along the optical axis of system 2800. Input optical beam 2801 may be collected from a focus spot ("O") in an optical system and collimated by lens 130a. For example, spot "O" may be at about one focal length before lens 2830a. Collimated input optical beam 2801 may then propagate through prisms 2810a and 2810b.

Prisms 2810a and 2810b may disperse the input optical beam 2801 to a desired magnitude, generating a spectrally dispersed output optical beam 2802 exiting prism 2810b. Additionally or alternatively, prisms 2810a and 2810b may change the orientation of the dispersion of output optical beam 2802. Output optical beam 2802 may be collected and focused by lens 2830b to a focused spot ("I"). Spot "I" may be at about one focal length after lens 2830b. Spot "I" may be in the form of a discrete or continuous spectrum with a desired spread and/or resolution. In some embodiments, spot "I" may be acquired by a sensor array.

Other configurations of system 2800 are possible using additional optical elements, such as mirrors, lenses, filters, etc. Although double Amici prisms 2810a and 2810b are used as examples for the non-deviating dispersive elements of system 2800, other suitable non-deviating dispersive elements, such as non-deviating compound prisms may be used consistent with the embodiments of the present disclosure.

Functions and the working principles of the components of system 2800 are described in detail below.

Figure 29:
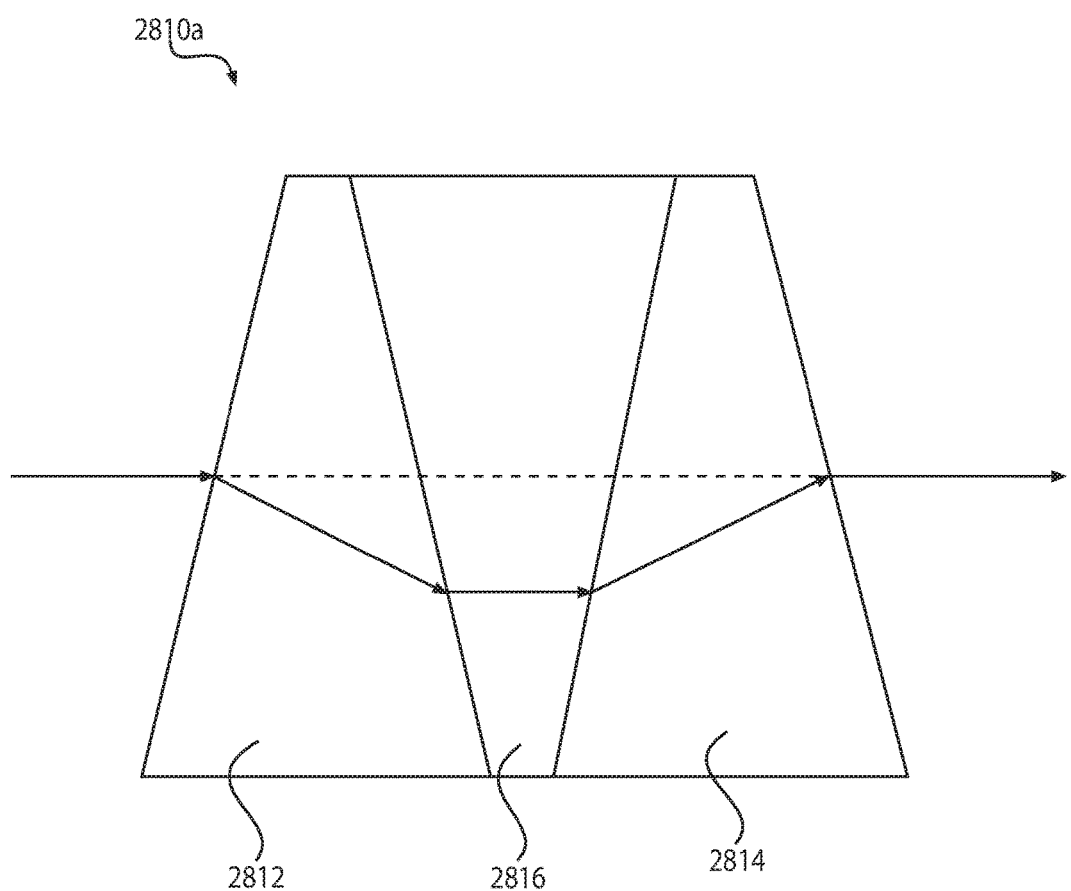
FIG. 29 is a schematic cross-sectional representation of an example non-deviating dispersive element.

FIG. 29 is a schematic cross-sectional representation of an exemplary double Amici prism 2810a. As described herein, descriptions of the features below in references to prism 2810a are equally applicable to prism 2810b.

As shown in FIG. 29, prism 2810a includes a set of prism elements placed in series, such as first element 2812, second element 2814, and third element 2816. These elements may be cemented together to form a solid assembly. First and second elements 2812 and 2814 may be made of the same glass and have the same apex angles. The design layout of prism 2810a is thus symmetric about the plane passing through the center of third element 2816.

First and second elements 2812 and 2814 are typically made of a glass having lower index of refraction relative to third element 2816. For example, first and second elements 2812 and 2814 may be made of crown glass and third element may be made of flint glass. As described herein, the materials of the prism elements may be suitably selected to achieve a desired dispersion of input optical beam 2801. In some embodiments, the selection of the materials of the prism elements of prisms 2810a and 2810b may be the same such that the dispersion that can be generated by prisms 2810a and 2810b may be the same. In other embodiments, the selection of the materials of the prism elements of prisms 2810a and 2810b may be different such that the dispersion that can be generated by prisms 2810a and 2810b may be different. Additionally, the materials of the prism elements may be designed to achieve greater linearity of total dispersion and/or to achieve higher-order dispersion effects of system 2800.

As shown in FIG. 29, prism 2810a may have two sloping faces on its two sides. A predetermined wavelength of input optical beam 2801 may pass through the first sloping face of prism 2810a and exit from the other sloping face with substantially zero deviation from the optical axis. The predetermined wavelength may depend on the design of prism 2810a, such as the composition of the materials and geometry of the prism elements 2812, 2814, and 2816. Other wavelengths of input optical beam 2801 would pass through prism 2810a with a wavelength-dependent deviation angle from the optical axis. Such deviation angles may also depend on the geometry of prism 2810a.

Advantageously, as described above, system 2800 may achieve a desired dispersion without causing deviation of the predetermined wavelength, e.g., a center wavelength of input optical beam 2801. In other words, the input optical axis of the predetermined wavelength of input optical beam 2801 remains substantially collinear with its output optical axis.

Figure 30:
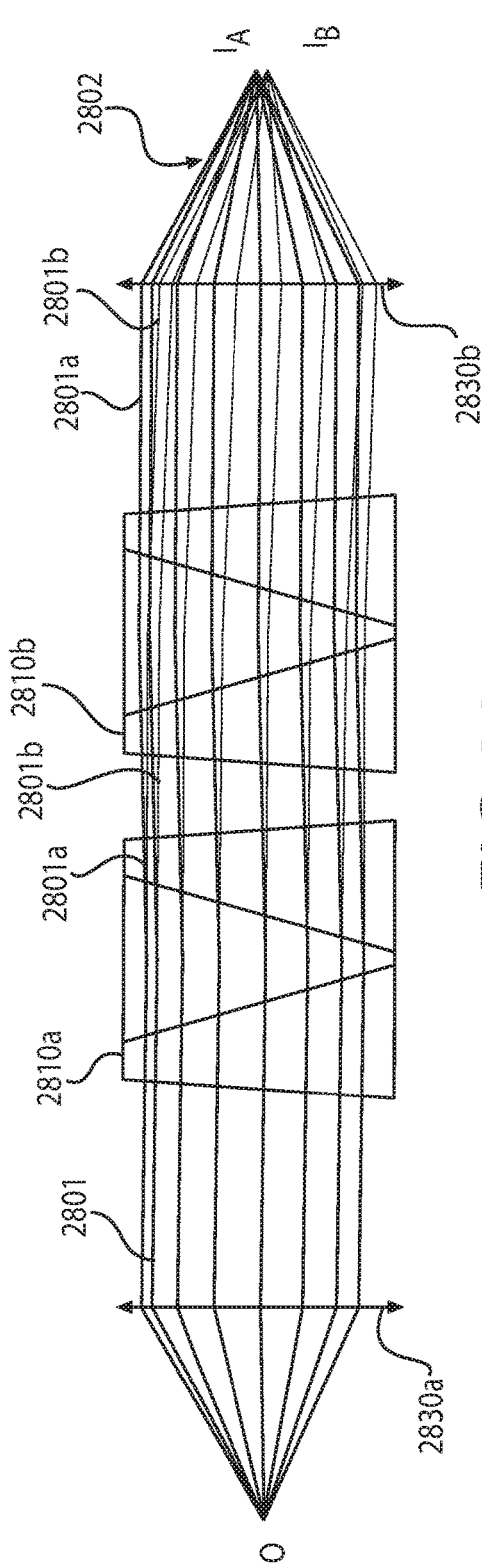
FIG. 30 is a graphical cross-sectional illustration of an example optical beam passing through the example optical system of FIG. 28.
Figure 31:
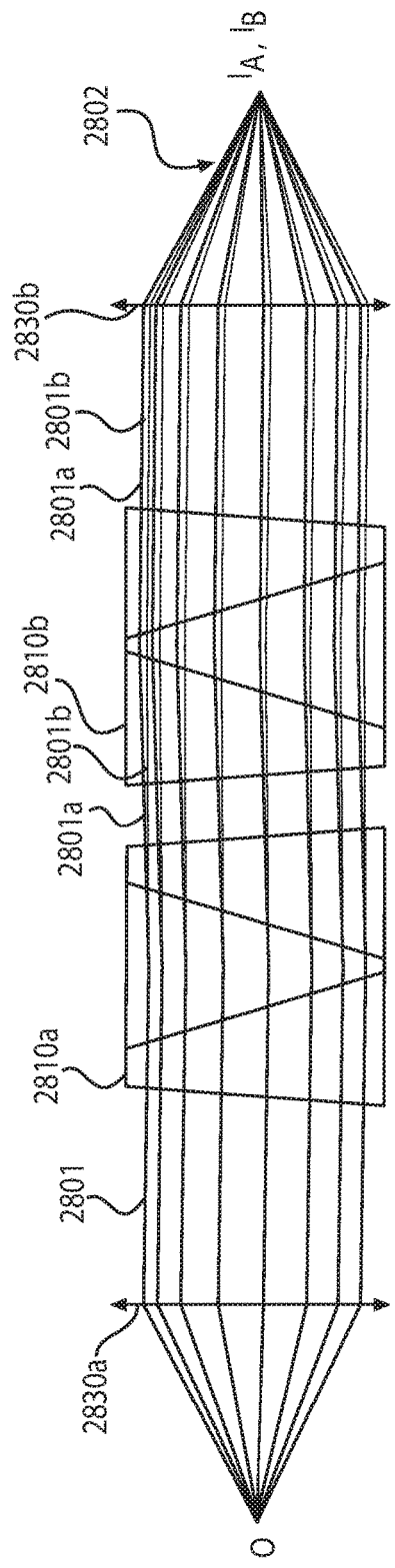
FIG. 31 is a graphical cross-sectional illustration of another example optical beam passing through the example optical system of FIG. 28.

When two prisms 2810*a* and 2810*b* are used together in system 2800, the dispersion of input optical beam 2801 may be augmented or reduced. FIGS. 30 and 31 are graphical cross-sectional illustrations of two examples of input optical beam 2801 passing through system 2800. FIG. 30 shows that prisms 2810*a* and 2810*b* are aligned around the optical axis and together double the magnitude of the total dispersion. In contrast, FIG. 31 shows that prisms 2810*a* and 2810*b* are counter-aligned around the optical axis and the dispersion generated by prism 2810*a* is reduced to a minimum or cancelled by prism 2810*b*.

As shown in FIG. 30, prisms 2810*a* and 2810*b* are aligned with a rotational angle of about 0° relative to each other. Two exemplary wavelengths 2801*a* and 2801*b* of input optical beam 2801 are deflected at different angles after passing through prism 2810*a*. While propagating in the distance from prism 2810*a* to prism 2810*b*, input optical beam 2801 is dispersed and filled with spectral information. The two wavelengths 2801*a* and 2801*b* of input optical beam 2801 are further deflected and deviated from each other after passing through prism 2810*b*. Lens 2830*b* may then focus the two wavelengths 2801*a* and 2801*b* in the output optical beam 2802 to two different spots shifted from each other, e.g., "$I_A$" and "$I_B$". If output optical beam 2802 is acquired by a sensor, the focus spots of the two different wavelengths 2801*a* and 2801*b* would end up at two different locations laterally shifted from each other on the sensor.

In contrast to the example shown in FIG. 30, FIG. 31 shows that prisms 2810*a* and 2810*b* are counter-aligned with a rotational angle of about 180° relative to each other. Two exemplary wavelengths 2801*a* and 2801*b* of input optical beam 2801 are similarly deflected at different angles after passing through prism 2810*a* as describe above. Input optical beam 2801 is thus dispersed in the space between prism 2810*a* to prism 2810*b*. Then, the two wavelengths 2801*a* and 2801*b* of input optical beam 2801 are deflected by prism 2810*b* to an opposite direction, thereby reducing or cancelling the dispersion of output optical beam 2802.

As shown in FIG. 31, in some embodiments, when prisms 2810*a* and 2810*b* are identical, the dispersion generated by prism 2810*a* of the two wavelengths 2801*a* and 2801*b* may be cancelled to zero after passing through prism 2810*b*. For example, the two wavelengths 2801*a* and 2801*b* of input optical beam 2801 may be deflected back by prism 2810*b* to be aligned with the optical axis. Lens 2830*b* may then focus the two wavelengths 2801*a* and 2801*b* to spots "$I_A$" and "$I_B$" that overlap with each other. If output optical beam 2802 is acquired by a sensor, the focus spots of the two different wavelengths 2801*a* and 2801*b* would be acquired at the same location, thereby cancelling the dispersion.

As described above, when prisms 2810*a* and 2810*b* are aligned with each other around the optical axis, the dispersion generated by system 2800 may be maximized, e.g., double of the amount of dispersion that can be generated by prism 2810*a*. When prisms 2810*a* and 2810*b* are counter-aligned with each other around the optical axis, the dispersion generated by system 2800 may be minimized, e.g., cancelled to zero when prism 2810*b* is identical to prism 2810*a*. By adjusting the rotational angle between prisms 2810*a* and 2810*b* around the optical axis from about 0° to about 180°, the dispersion of output optical beam 2802 may be varied to a desired intermediate magnitude between the maximum and minimum.

The rotation of the two prisms 2810*a* and 2810*b* around the optical axis may be achieved using any suitable rotating device, such as a stepper motor rotary stage or a thermal motor rotary stage. In some embodiments, only one of the prisms 2810*a* and 2810*b* may be rotated to adjust the dispersion of output optical beam 2802. In other embodiments, both prisms 2810*a* and 2810*b* may be rotated to adjust the dispersion of output optical beam 2802.

As described herein, the two wavelengths 2801*a* and 2801*b* of input optical beam 2801 shown in FIG. 30 are exemplary only. Multiple or infinite wavelengths of input optical beam 2801 may pass through system 2800.

As described above, output optical beam 2802 may be acquired or detected by a sensor array. For example, a light emitting spot emitting input optical beam 2801 may become multiple spots of output optical beam 2802 after passing through system 2800. The multiple spots of output optical beam 2802 acquired on the sensor may be laterally shifted from each other along a virtual dispersion line. In some situations, if input optical beam 2801 has a continuous spectrum, a light emitting spot would be acquired as a spectrally dispersed line on the sensor. The light intensity of a given spot or at a given location along the dispersed line would correspond to the intensity provided by the corresponding wavelength. Hence, the intensity versus distance along the dispersion line can be transformed to a relationship between the intensity and the wavelength.

Figure 32:
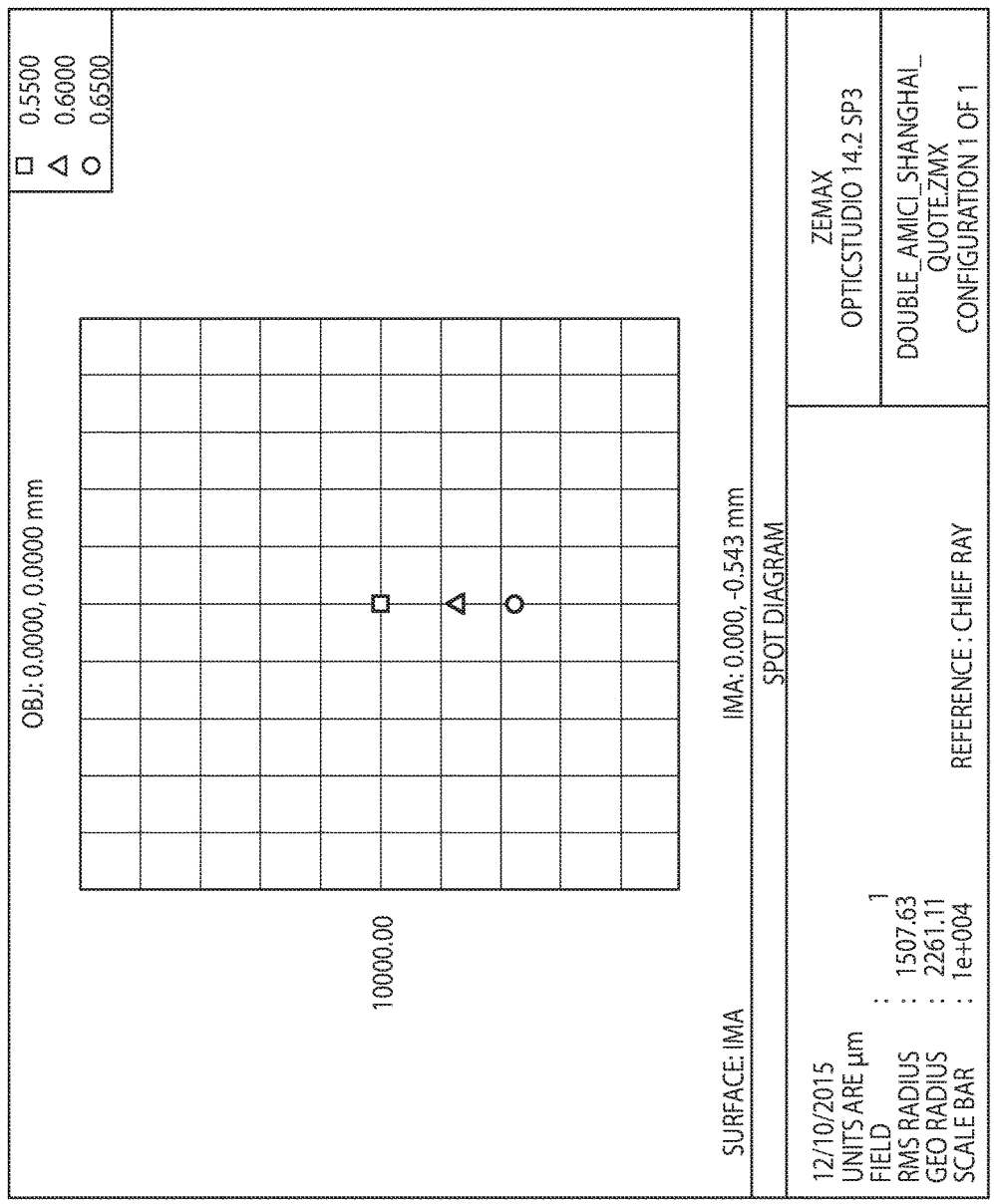
FIG. 32 is a diagram of an optical simulation result of dispersion generated by the example optical system of FIG. 28.
Figure 33:
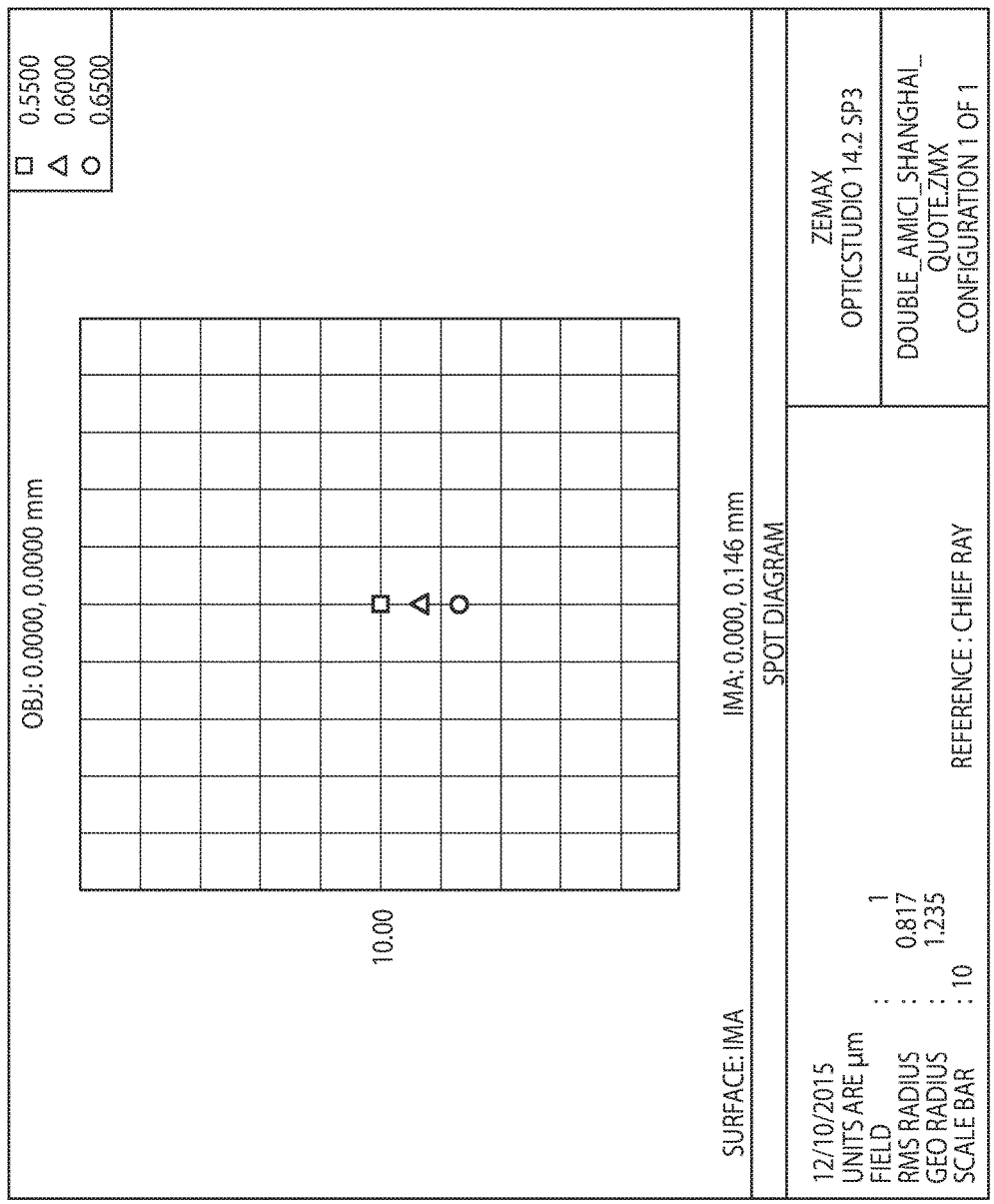
FIG. 33 is a diagram of another optical simulation result of dispersion generated by the example optical system of FIG. 28.

FIGS. 32 and 33 are diagrams of optical simulation results of dispersing an optical beam with three wavelengths (e.g., 500 nm, 600 nm, and 650 nm) by system 2800. As shown in FIGS. 32 and 33, focus spots of the three wavelengths are vertically shifted from each other along a virtual dispersion line. The spot of wavelength 550 nm is at located at the center of the diagram, the spot of wavelength 600 nm is located below that of wavelength 550 nm, and the spot of wavelength 650 nm is located below that of wavelength 600 nm.

In some embodiments, the spacing between the spots may depend on the magnitude of dispersion of system 2800. For example, a dispersion magnitude of system 2800 for generating the simulation result shown in FIG. 32 is adjusted to be greater than that for generating the simulation result shown in FIG. 33. Accordingly, the spacing between the spots of the three wavelengths is greater in FIG. 32 than that in FIG. 33.

Advantageously, the adjustment of the dispersion magnitude may allow any bandwidth of input optical beam 2801 to suitably fill a desired space of a sensor. This may improve the efficiency of using the space on the sensor and may further improve the measurement throughput of an optical measurement system.

For example, in fluorescence spectroscopy or microscopy, system 2800 may be used to increase the magnitude of dispersion of a desired range of fluorescence emission spectrum of fluorophores. This can increase the spectral resolution of the desired range, thereby providing more information of the fluorophores or fluorescent molecules in a sample. In other instances, such as in multi-spot hyperspectral imaging systems, system 2800 may be used to reduce the dispersion magnitude of sparse fluorescence emission spectra. This allows for more fluorescence emission spectra to be measured simultaneously, thereby increasing the efficiency of using the sensor space and the measurement throughput of the hyperspectral imaging system.

In some embodiments, prisms 2810*a* and 2810*b* may be designed to achieve linear dispersion of output optical beam 2802. In such instances, the distance between the focus spots of a given wavelength and a center wavelength along the dispersion line is linearly proportional to the difference between the given wavelength and the center wavelength. In other embodiments, prisms 2810*a* and 2810*b* may be designed to achieve nonlinear dispersion of output optical beam 2802. In such instances, the deviation angle of a given wavelength from the optical axis of the center wavelength may be proportional to the difference between the given wavelength and the center wavelength.

As described above, in some embodiments, prisms 2810*a* and 2810*b* may be adjusted to change the orientation of dispersion of output optical beam 2802. For example, the orientation of dispersion or the dispersion line along which the focus spots are aligned as shown in FIGS. 32 and 33 are along the vertical direction. When both prisms 2810*a* and 2810*b* are rotated together to a given angle around the optical axis, the orientation of dispersion or the dispersion line may be adjusted to a different direction. For example, if both prisms 2810*a* and 2810*b* are together further rotated by about 90°, the orientation of dispersion or the dispersion line along which the focus spots are aligned as shown in FIGS. 32 and 33 may be along a horizontal direction.

Figure 34:
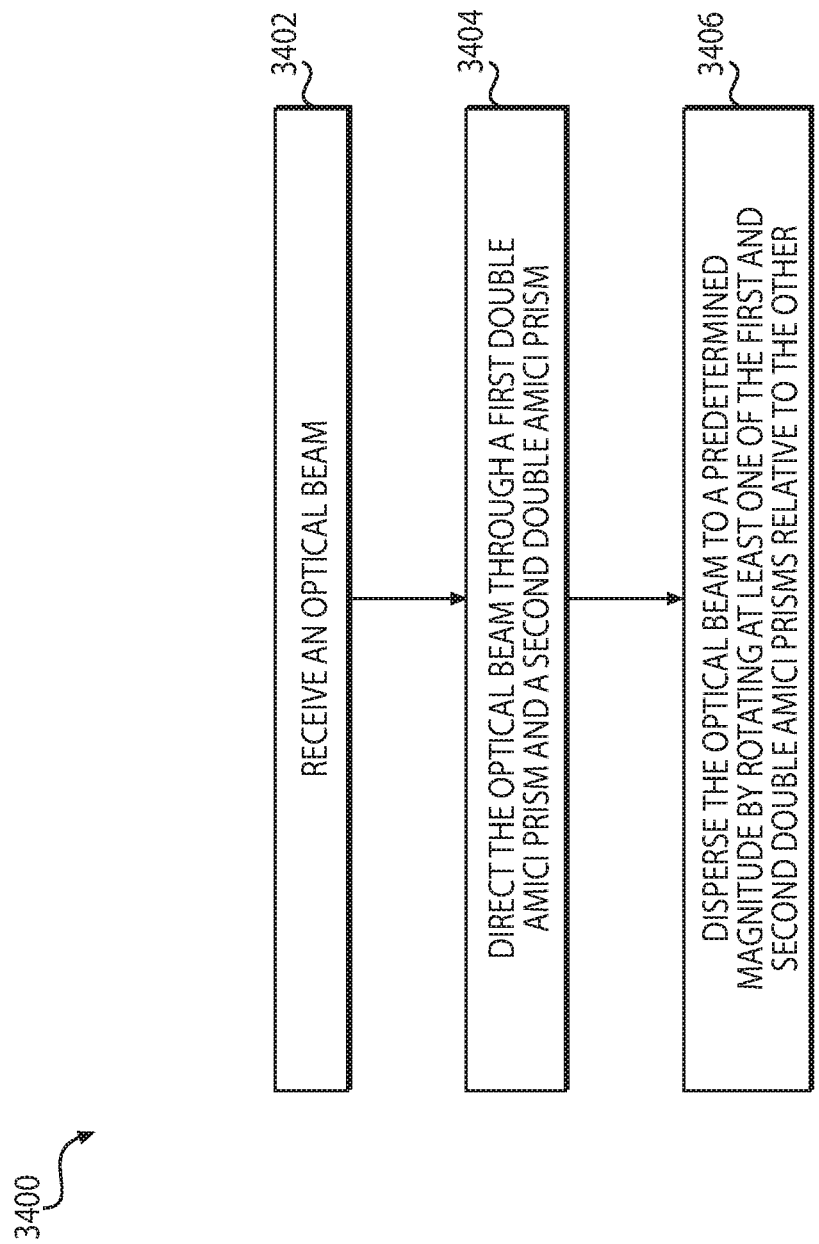
FIG. 34 is a flowchart of an example method for dispersing an optical beam.

System 2800 as described herein may be utilized in a variety of methods and devices for dispersing an optical beam. FIG. 34 is a flowchart of an exemplary method 3400 for dispersing of an optical beam. Method 3400 uses system 2800 and features of the embodiments of system 2800 described above in reference to FIGS. 28-31.

At step 3402, an optical beam may be received by system 2800. Depending on the application of system 2800 and/or the collimation status of the optical beam, the optical beam may be collected and collimated by lens 2830*a* before dispersion and focused by lens 2830*b* after dispersion. At step 3404, the optical beam may be transmitted through a pair of double Amici prisms 2810*a* and 2810*b* aligned along the optical axis. At step 3406, the optical beam may be dispersed to a predetermined magnitude by rotating at least one of prisms 2810*a* and 2810*b* relative to the other around the optical axis.

Method 3400 may further include additional steps. For example, method 3400 may include calibrating system 2800 before rotating the prisms. Other optical components in system 2800, such as lenses 2830*a* and 2830*b*, may be suitably calibrated and aligned such that the input optical axis and the output optical axis of a predetermined wavelength of the optical beam remain collinear.

In some embodiments, method 3400 may further include varying the magnitude of dispersion by adjusting a rotational angle between the first and second prisms 2810*a* and 2810*b* around the optical axis. Additionally or alternatively, method 3400 may further include adjusting the dispersion of the optical beam to a predetermined orientation by rotating both prisms 2810*a* and 2810*b* around the optical axis.

X. Example Imaging by Convolving Distance and Emitted Light Wavelength

It can be advantageous to increase the rate at which a sample (e.g., a biological sample) is imaged in order to identify probes in the sample, to detect the location, color, or other properties of fluorophores in the sample (e.g., fluorophores of such a probe), or to provide some other benefit. Fluorophores of a sample (e.g., of probes in a sample) can be excited over a range of wavelengths known as the excitation band. When they relax to the ground state, the fluorophores can emit light in a wide range of wavelengths known as the emission band. This disclosure includes embodiments that leverage the wide emission band of a fluorophore for simultaneous acquisition of multiple planes in the sample using a modified form of confocal microscopy. These embodiments may be combined with other embodiments described herein to increase the rate at which a sample may be imaged.

According to an aspect of the present disclosure, an excitation spot is sent towards a sample. The excitation spot, according to the present disclosure, may be selected such that it excites the sample over all planes of interest in the axial direction. The excitation optics should be chosen such that the variation of the excitation spot size over the planes of interest is minimized.

According to an aspect of the present disclosure, the collection optics of a microscope system intentionally have a large degree of axial chromatic aberration such that different colors (i.e., different wavelengths) conjugate with an emission or confocal pinhole at different planes. Once the light has passed through the pinhole, it can be dispersed with one or more prisms, gratings or other dispersive elements, so that the spot becomes, on a two-dimensional sensor at the image plane, a streak or band as different wavelengths are dispersed from the prism at different angles, so that the vertical spatial axis of the streak contains axial image information. A given pixel location on the sensor for a given acquisition frame corresponds to a single emission wavelength, which in turn encodes the fluorescence information from a single volumetric point in the sample.

Advantageously, for each lateral position on a sample, the axial position of the image information may be encoded by color (i.e., wavelength).

In some aspects, systems according to the present disclosure maximize the axial chromatic aberrations in the optics, contrary to the standard practice of minimizing them. By introducing large focal shift as a function of wavelength, the chromatic aberrations may be used to encode axial information in the emissions. In this way, the information density on the image sensor can be greatly increased, and fast volumetric imaging may be advantageously realized.

Embodiments of the present disclosure may be also implemented using a confocal microscope having one or more two-dimensional image sensors. In contrast to using a conventional achromatic objective, microscope systems consistent with the disclosed embodiments may include an objective that is specifically engineered for chromatic aberration as discussed herein. Advantageously, these objectives may be considerably cheaper to fabricate than objectives that are designed for minimal chromatic aberration as a result of the larger optical design space.

In certain aspects, dispersion elements may be added in the collection path in microscope systems where hyperspectral capabilities are not required.

In certain aspects, chromatic aberrations may be introduced in the optical path outside of the objective. For example, a dispersive tube lens may be used as the axial chromatic element. The chromatic aberration could also be divided among several optical elements (e.g., both the objective and the tube lens). This may allow flexible selection of the objective and/or the tube lens, modification of the degrees of chromatic aberration in the microscopy system, and/or may further simplify the system or reduce the cost of the system.

Consistent with embodiments of the present disclosure, the excitation light may be made to use the chromatic aberrations to generate a very thin excitation beam. As with some embodiments of light sheet imaging, the excitation light could be made to use a Bessel beam or multiple small Bessel beams such that, instead of point excitation at the sample, line excitation is used and dispersive elements are used to convert the line(s) to a rectangle(s) on the two-dimensional sensor.

In further exemplary embodiments, digital micromirror devices or spatial light modulators (SLMs) could be used as artificial pinholes.

Reference will now be made in detail to embodiments and aspects of the present disclosure, examples of which are illustrated in the accompanying drawings. Where possible, the same reference numbers will be used throughout the drawings to refer to the same or like parts.

Figure 35:
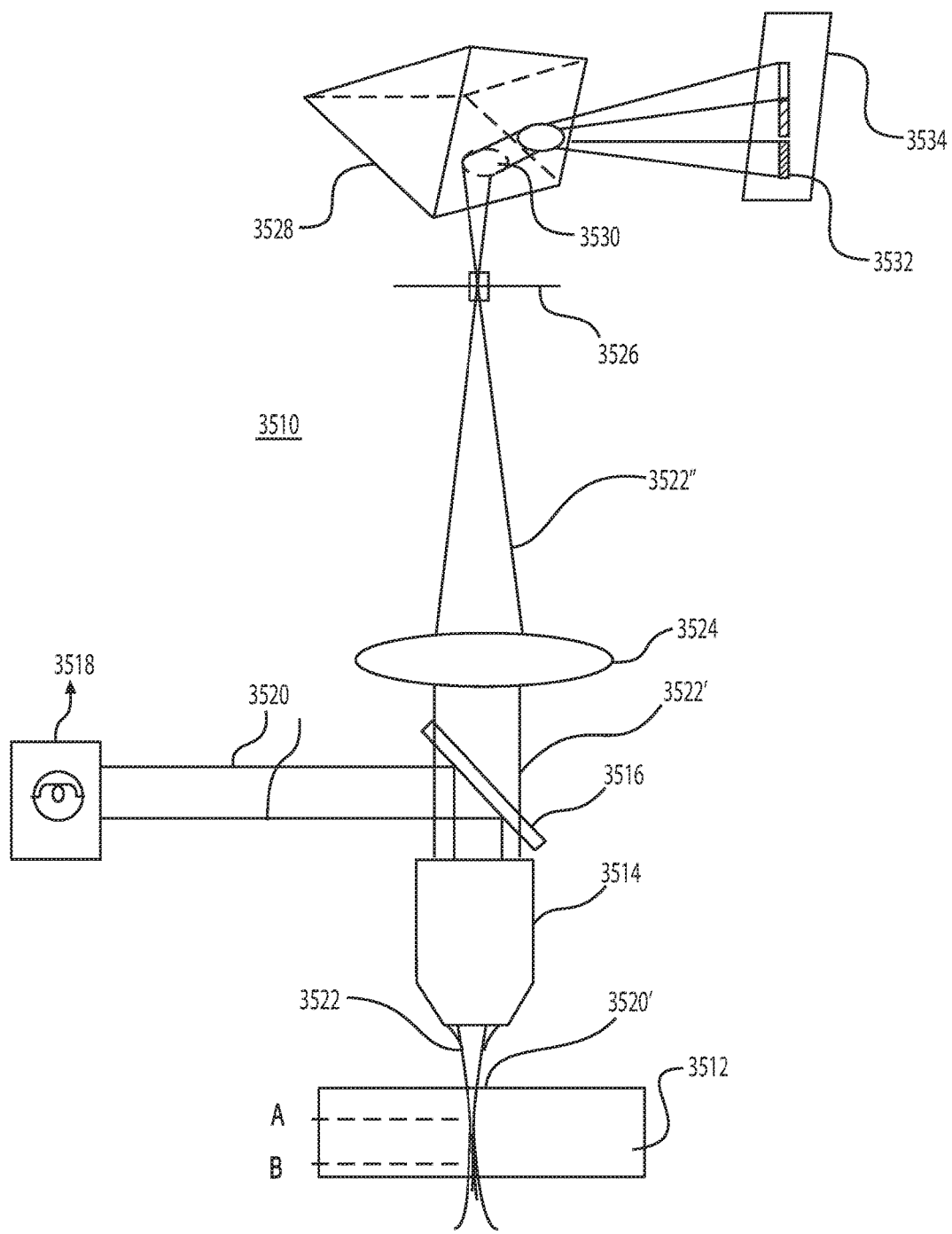
FIG. 35 is a schematic representation of an example microscope system.

FIG. 35 illustrates an exemplary embodiment in schematic form of a microscope system 3510. This schematic of FIG. 35 is to be understood as not being drawn to scale. In some embodiments, the microscope 3510 is a fluorescence microscope, and more specifically a modified form of confocal fluorescence microscope. Embodiments of the present disclosure are applicable to other microscopy techniques, such as stimulated emission depletion (STED) microscopy for example.

As shown in FIG. 35, system 3510 creates a magnified image of a sample 3512 using fluorescence and/or phosphorescence through principles of optical sectioning, which are discussed further below. In an illustrative embodiment, the sample 3512 is stained or dyed with a fluorophore compound, which absorbs light energy of a specific wavelength (i.e., excitation band) and re-emits light at a different wavelength (i.e., emission band). The difference between the excitation peak wavelength and the emission peak wavelength corresponds to the Stokes shift.

Various fluorophores may be used, including those known in the art. As will be appreciated, fluorophores have varying properties rendering them more or less useful for a given microscopic application. Excitation bands range from the ultraviolet through the visible spectra, and emission bands typically range from visible light into the near infrared region. New fluorophores may also offer various combinations of properties, both optical and chemical. In some embodiments, fluorophores may be linked, where a first fluorophore's emission is quenched by a companion fluorophore in a process known as fluorescence resonance energy transfer (FRET), allowing a different emission wavelength to be achieved.

Referring again to FIG. 35, sample 3512 is depicted having two illustrative focal planes. In an illustrative embodiment, the first focal plane A and the second focal plane B are generally parallel to one another and perpendicular to the major optical axis of the microscope system 3510. Other geometries are possible using optical elements such as lenses, mirrors, etc. Objective 3514 is an optical element that gathers light (visible or otherwise) from the sample. In exemplary embodiments, the objective 3514 is also used to project excitation radiation upon the sample 3512. In an exemplary embodiment, objective 3514 includes a chromatic lens as discussed below with reference to FIG. 36.

Dichroic filter 3516 is an optical splitter element employed to permit excitation radiation 3520 from an illumination source 3518 to pass into the objective 3514 for projection onto the sample 3512 (shown at 3520' in FIG. 35). The projected excitation radiation 3520' can take the form of a spot, which can be of varying form, e.g., circular or elliptical. The sample 3512 is penetrated by excitation radiation 3520' through multiple optical planes, for illustration planes A and B, and the fluorophores are concomitantly excited. The excited fluorophores of sample 3512 will subsequently emit radiation in an emission band, which in an illustrative embodiment can be across a range of wavelengths or have a plurality of wavelengths. The dichroic filter 3516 permits fluorophore emissions 3522 to pass through at 3522' while rejecting other wavelengths, such as the excitation radiation. In an illustrative embodiment, the fluorophore emissions 3522 pass through the objective 3514, but other optical paths are possible.

Fluorophore emissions 3522', rendered substantially parallel by the objective 3514, pass into a tube lens 3524, in an exemplary embodiment. The tube lens 3524 brings the parallel wave trains 3522' from the objective 3514 originating at the focal planes of interest, e.g., focal planes A and B, into convergence at a confocal pinhole 3526. Out-of-focus emissions do not pass through the confocal pinhole 3526 and are eliminated from the image. The focused fluorophore emission wave trains 3522" from the tube lens 3524 converge at the confocal pinhole 3526, and contain image information from a plurality of focal planes, e.g., focal planes A and B, and the confocal pinhole 3526 can be translated axially to accommodate the parameters of investigation. In an illustrative embodiment, the objective 3512 is heavily chromatic, as described below with reference to FIG. 36. In addition, a plurality of pinholes can be employed to increase throughput by obtaining an image from a different lateral position on the sample 3512.

The excitation spot 3520' can be laterally translated across the sample 3512, and can advantageously simultaneously collect images from multiple axial planes simultaneously based on the chromatic aberrations of the lens. By employing a fluorophore having a wide emission spectrum, image wave trains at different axial depths in the sample can be encoded by wavelength, as will be discussed in greater detail below.

In an illustrative embodiment, after passing through the confocal pinhole 3526, fluorophore emission wave trains 3522" can be projected onto a photomultiplier detector, e.g., a CCD sensor, or an ocular lens to obtain an image. In another illustrative embodiment, once the light has passed through the pinhole 3526 it can be dispersed with one or more prisms or gratings (e.g., prism 3528 in FIG. 35) so that the spot 3530 becomes a streak 3532 on a two-dimensional sensor (not shown) at the image plane 3534. The sensor could be implemented with an sCMOS sensor, although two-dimension silicon APDs arrays and other sensitive sensors could also be used. For each lateral position on the sample, the axial position can be encoded by color, which can subsequently be advantageously encoded onto the pixel number of the sensor. A three dimensional image can be formed by arranging the streaks obtained from various spots at lateral positions on the sample.

Figure 36:
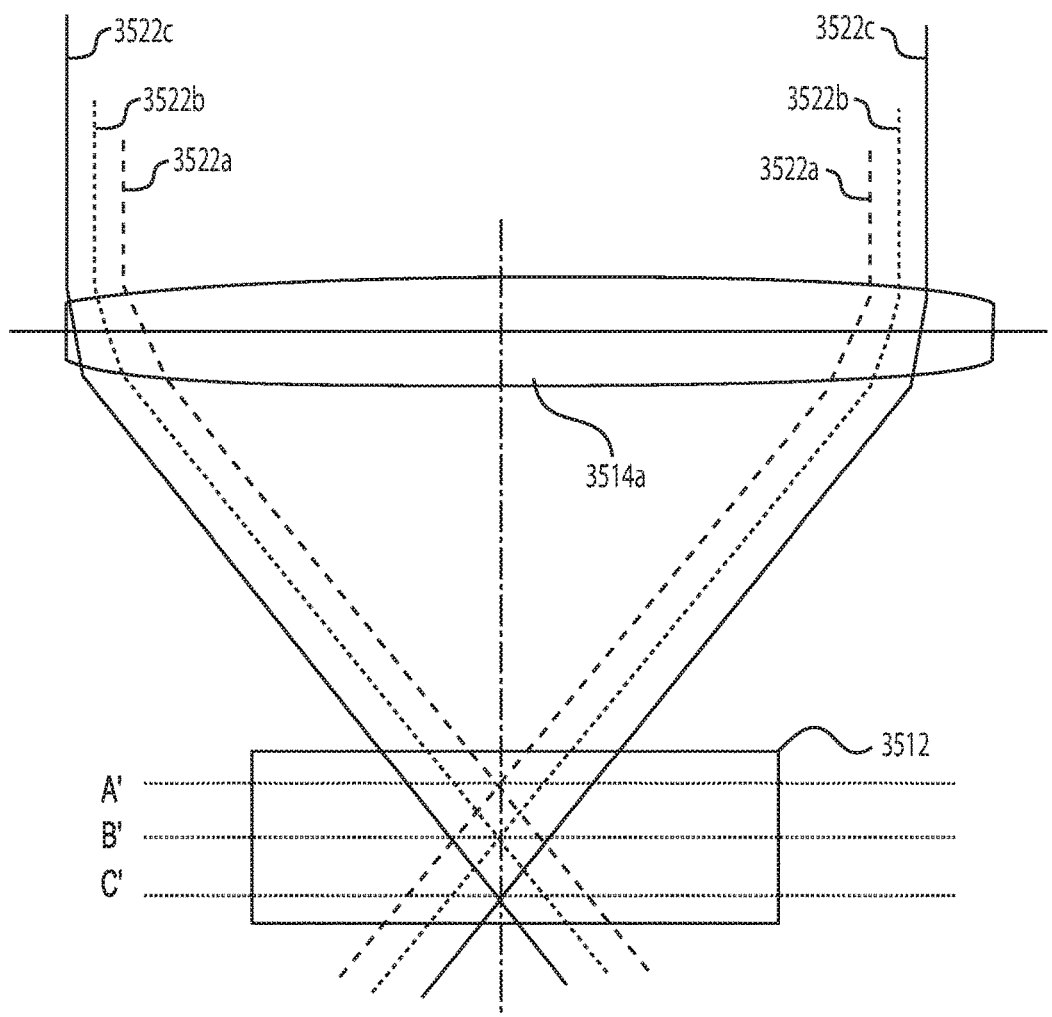
FIG. 36 is a schematic representation of an example chromatic objective lens.

Turning to FIG. 36, a schematic representation of an exemplary chromatic lens 3514a is depicted. Chromatic lens 3514a is a component lens of objective 3514 in illustrative embodiments. A chromatic lens achieves a separation of various frequencies on the image plane because of differences in the refractive index of the lens at different wavelengths of incident light. As depicted in FIG. 36, sample 3512 has three illustrative focal planes indicated at A', B' and C'. Fluorophores present in sample 3512 may have a relatively broad emission band, such that chromatic lens 3514a can, by virtue of its axial chromatic optical aberration, focus light from different planes at different wavelengths, as shown in the illustrative embodiment as emission component beams 3522a, 3522b, and 3522c. As shown, although these component beams originate at different focal planes A', B' and C', the difference in refraction of the component beams by the chromatic lens 3514a, by virtue of their different wavelengths, allows the component beams to conjugate for transmission ultimately toward the image plane.

In accordance with another aspect of the present disclosure, principles of polarization can be applied to result in polarized component beams, which can be further processed for additional optical information density.

Figure 37:
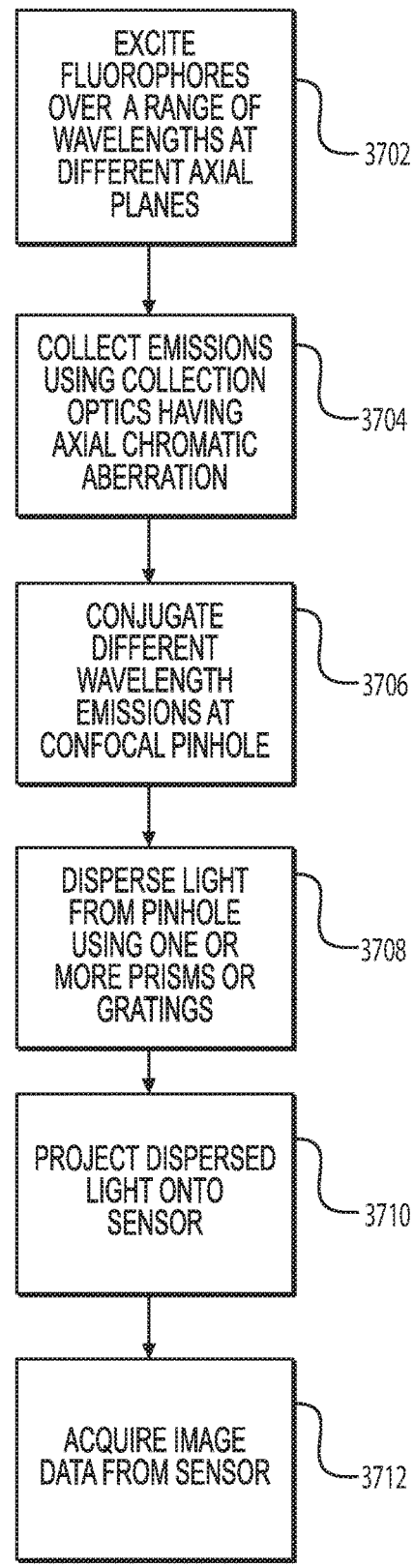
FIG. 37 is a flowchart of an example method for simultaneously obtaining an image in multiple planes with an axially chromatic lens.

FIG. 37 is a flowchart of an exemplary method 3700 for simultaneously obtaining an image in multiple planes with a microscope system with an axially chromatic lens. The illustrative method 3700 using the optical system 3512 and features of the embodiments of FIGS. 35 and 36, discuss above.

At step 3702, fluorophores of a sample are excited over a range of wavelengths over multiple planes of interest throughout the axial depth of the sample. When the fluorophores relax to the ground state, they can emit light in a wide range of wavelengths, which are collected at step 3704 using collection optics of the microscope system intentionally having a large degree of axial chromatic aberration. As a result, different colors are conjugated with an emission or confocal pinhole at different planes at step 3706. At step 3708, the light is dispersed with one or more prisms or gratings and the spot becomes a streak on a two-dimensional sensor at an image plane at step 3710. Image data is collected from the sensor at step 3712. As discussed above, for each lateral position on the sample, the axial position will be encoded by color, which may be subsequently encoded onto the pixel number of the sensor.

XI. Example Controllable Optical Filter

In some applications, it can be advantageous to apply one or more controllable bandpasses, highpasses, lowpasses, or other types of optical filtering to illumination applied to a sample and/or to image light received from such a sample. Such filtering could facilitate imaging of the sample (e.g., of a biological sample) in order to identify probes in the sample, to detect the location, color, or other properties of fluorophores in the sample (e.g., fluorophores of such a probe), or to provide some other benefit. Example systems provided herein may selectively transmit one or more spectral bands with tunable bandwidths and/or center wavelengths, allowing the generation of optical beam(s) with desired spectral bands and/or spectral resolutions. Embodiments of the present disclosure may be implemented in a spectrometer, e.g., an imaging spectrometer, a microscope, e.g., a fluorescence microscope, a confocal microscope, a transmission microscope, a reflectance microscope, etc., or a spectral imaging system, e.g., a hyperspectral imaging system. Alternatively, embodiments of the present disclosure may be implemented in a customized imaging system built using suitable optical elements.

According to an aspect of the present disclosure, an optical system is provided for filtering an input optical beam. The input optical beam may have a discrete spectrum or a continuous spectrum with a plurality of wavelengths. The input optical beam may be an excitation light beam for illuminating a sample or an emission light beam collected from a sample. The input optical beam may be filtered by the optical system to generate an output optical beam having selected spectral bands with desired bandwidths and/or center wavelengths.

According to an aspect of the present disclosure, the optical system may include one or more spectral slicing modules. Each spectral slicing module may have a passband that can be flexibly tuned to have a desired bandwidth and/or a desired center wavelength. In some embodiments, the optical system may be placed within a collimated beam in an optical setup. In other embodiments, the optical system may collimate an input optical beam before filtering the input beam and/or may focus an output optical beam after such filtering.

According to an aspect of the present disclosure, the optical system may split an input optical beam into at least two partial optical beams. For example, one or more beamsplitters may be used to split the input optical beam into a desired number of partial optical beams. At least one of the partial optical beams may be directed to transmit through a spectral slicing module. The spectral slicing module may filter the partial optical beam by transmitting wavelengths within its passband and reflecting wavelengths outside its passband. The optical system may then combine the partial optical beams, whether filtered or not, into an output optical beam using one or more beamsplitters and/or mirrors, for example.

In some embodiments, the partial optical beams having different spectral bands may be directed through a corresponding number of spectral slicing modules respectively. Each spectral slicing module may filter the partial optical beam transmitting through it to a desired spectral band. The optical system may then combine the filtered partial optical beams into an output optical beam using one or more beamsplitters and/or mirrors.

According to an aspect of the present disclosure, a beamsplitter for splitting the input optical beam may be a dichroic beamsplitter that selectively transmits and reflects light on the basis of wavelength. For example, an input optical beam incident on the dichroic beamsplitter may be spectrally split into two partial optical beams having two different spectral bands divided around a cut-off wavelength. One partial optical beam may transmit through the dichroic beamsplitter and the other may reflect off from the dichroic beamsplitter.

In some embodiments, the dichroic beamsplitter may have a passband (spectral region of high transmission/low reflectivity), a stopband (spectral region of low transmission/high reflectivity), and a transition region (the spectral region between the passband and stopband). The transition region may be defined as the region between two wavelengths, e.g., a first wavelength at about 90% and a second wavelength at about 10% peak transmission respectively. A cut-off wavelength at about 50% peak transmission may be at the center of the transition region.

According to an aspect of the present disclosure, a beamsplitter for combining two partial optical beams may allow the two partial optical beams to propagate along a common optical path after the combination. For example, a beamsplitter for combining the partial optical beams may be a dichroic beamsplitter that selectively transmits and reflects light on the basis of wavelength. One partial optical beam may transmit through the dichroic beamsplitter along its optical path and the other may reflect off from the dichroic beamsplitter to propagate along the same optical path.

In certain aspects, the beamsplitter for combining two partial optical beams into an output optical beam may have the same spectral characteristics as those of the beamsplitter for splitting the input optical beam into the two partial optical beams. For example, the two beamsplitters may be identical dichroic beamsplitters that reflect and transmit light based on the same cut-off wavelength. Advantageously, using identical dichroic beamsplitters for the splitting and combining allows for high transmission and high reflection of the two spectral bands of the two partial optical beams. This further allows for efficient direction and/or collection of the different partial optical beams split from the input optical beam to the combined output optical beam, thereby reducing loss of light.

According to an aspect of the present disclosure, the spectral slicing modules may each operate as a bandpass filter with a tunable passband. The bandwidth and/or center wavelength of the passband of each spectral slicing module may be independently adjustable to desired values. In some embodiments, each spectral slicing module may include a longpass filter and a shortpass filter aligned along its optical axis. The longpass filter and shortpass filter are independently rotatable relative to the optical axis. Rotating either of the filters may change the angle of incidence (AOI) of the partial optical beam upon the filter and thus shift the absorption or reflection edge, e.g., cut-off wavelength. For example, increasing the AOI from normal incidence to higher angles may shift the spectral transmission of the longpass filter and/or shortpass filter towards shorter wavelengths. Thus, the passband of each spectral slicing module (e.g., the bandwidth and/or center wavelength) may be tuned by rotating at least one of its longpass and/or shortpass filters relative to the optical axis.

Advantageously, the passband of each spectral slicing module varies as a function of the AOI upon the longpass and/or shortpass filters without exhibiting substantial change in the shape of the spectrum, the percentage transmission, and/or the out-of-band rejection. Additionally, the bandwidth and/or center wavelength of the passband of each spectral slicing module may be continuously tuned over an entire possible passband by changing the AOI of the partial optical beam upon the filters. Further, by using a series of spectral slicing modules with different passbands, the spectrum of the input optical beam may be selectively filtered to have spectral bands with desired bandwidths and center wavelengths.

In certain aspects, the spectral slicing modules may have a series of passbands spectrally shifted from one another with overlapping regions between two adjacent passbands. For example, two different spectral slicing modules may have two different passbands for filtering two partial optical beams. The two passbands may have an overlapping region, and a first passband may span across wavelengths generally longer than the second passband. In such instances, the transition region of the dichroic beamsplitter for splitting an input optical beam into the two partial optical beams may fall within this overlapping region. Advantageously, such characteristics of the dichroic beamsplitter and the spectral slicing modules reduce potential artifacts that may result from the spectral splitting of the input optical beam and separate filtering of the partial optical beams.

In certain aspects, at least one of the spectral slicing modules may further include a blocking filter that additionally blocks wavelengths outside of the passband of the spectral slicing module. For example, the blocking filter may be a bandpass filter that substantially blocks or rejects wavelengths beyond the passband formed by the longpass and shortpass filters, thereby reducing or eliminating spectral irregularities beyond the passband.

In certain aspects, the optical system may further include one or more mirrors configured to direct the propagation of the input optical beam, the partial optical beams split from the input optical beam, and/or the output optical beam. In some embodiments, a pair of mirrors may be configured to align a partial optical beam along the optical axis of a spectral slicing module. For example, a first mirror may receive the partial optical beam and direct it through the components of the spectral slicing module, e.g., longpass and shortpass filters. A second mirror may receive the filtered partial optical beam, and may further direct it towards a beamsplitter to be combined with another partial optical beam. The two mirrors may be independently and suitably adjusted to align the propagation of the partial optical beam along the optical axis of the spectral slicing module. Advantageously, aligning the different partial optical beams along the optical axes of the spectral slicing modules respectively may eventually allow the partial optical beams to propagate along the same direction or the same optical path after they are combined.

In certain aspects, a spectral slicing module may further include a compensation filter that realigns the partial optical beam when it is laterally deviated from the optical axis after transmitting through the longpass and/or shortpass filters. For example, a partial optical beam transmitting through the longpass and/or shortpass filters at a non-normal AOI may have a lateral displacement from the optical axis of the spectral slicing module. The compensation filter may correct the lateral displacement and realign the input optical axis and the output optical axis of the spectral slicing module.

In some embodiments, the output optical beam may propagate along the same direction as the input optical beam does. For example, the input optical beam and the output optical beam of the system may remain collinear, thereby advantageously maintaining the direction of the overall optical axis of the optical system.

In certain aspects, a spectral slicing module may further include an optical spatial compensator that adds optical path length to the partial optical beam transmitting through it. For example, a first spectral slicing module may have an optical path length (OPL) longer than a second spectral slicing module. Therefore, an optical path difference (OPD) may exist between a first partial optical beam traveling through the first spectral slicing module and a second partial optical beam traveling through the second spectral slicing module. In such instances, the second spectral slicing module may include an optical spatial compensator, e.g., a glass plate, that adds OPL traveled by the second partial optical beam. Advantageously, the addition of the optical spatial compensator reduces the OPD between the two partial optical beams when they are combined in the output optical beam. This may further reduce or eliminate undesirable optical effects, e.g., interference, that may result from a OPD between the two partial optical beams.

As described herein, the optical beam entering the optical system to be filtered may be referred to as an input optical beam, and the filtered optical beam exiting the optical system may be referred to as an output optical beam. In some embodiments, the output optical beam may be further dispersed, modulated, filtered, processed, and/or detected by a one-dimensional or two-dimensional array of photodetector or sensor of an imaging device.

Reference will now be made in detail to embodiments and aspects of the present disclosure, examples of which are illustrated in the accompanying drawings.

Figure 38:
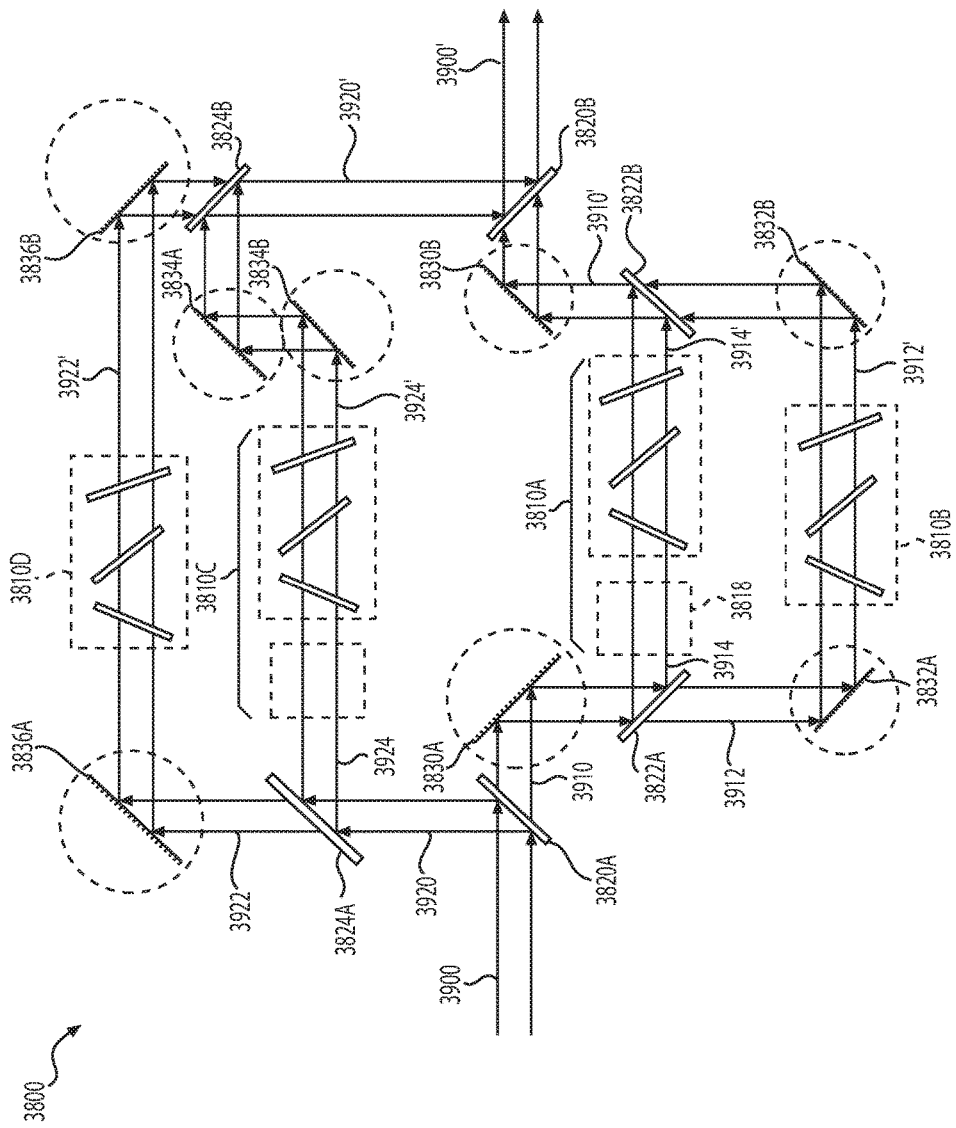
FIG. 38 is a schematic representation of an example system for filtering an optical beam.

FIG. 38 is a schematic representation of an exemplary system 3800 for filtering an optical beam. For example, system 3800 may be implemented in an optical setup for generating an output optical beam 3900' with a desired spectrum from an input optical beam 3900. As described herein, input optical beam 3900 refers to the optical beam entering and/or transmitting through system 3800 and output optical beam 3900' refers to the filtered optical beam exiting system 3800. Input optical beam 3900 and output optical beam 3900' are referenced separately for describing the transmission and filtering of the optical beam by system

3800. In some embodiments, output optical beam 3900' may be further dispersed, filtered, modulated, and/or acquired to obtain an optical signal with a desired spectrum and/or spectral resolution.

As shown in FIG. 38, system 3800 may include one or more spectral slicing modules, e.g., spectral slicing modules 3810A, 3810B, 3810C, and 3810D; a first set of beamsplitters, e.g., beamsplitters 3820A, 3822A, and 3824A; and a second set of beamsplitters, e.g., beamsplitters 3820B, 3822B, and 3824B. The first set of beamsplitters may be used to split an optical beam into separate partial optical beams with different spectral bands. For example, beamsplitter 3820A may be a dichroic beamsplitter that splits input optical beam 3900 at a first cut-off wavelength, generating two partial optical beams 3910 and 3920 with two different spectral bands. Similarly, beamsplitter 3822A further splits optical beam 3910 into two partial optical beams 3912 and 3914 at a second cut-off wavelength, and beamsplitter 3824A further splits optical beam 3920 into two partial optical beams 3922 and 3924 at a third cut-off wavelength. Therefore, the partial optical beams 3912, 3914, 3922, or 3924 split from input optical beam 3900 may each have a different spectral band.

As described herein, splitting input optical beam 3900 into four partial optical beams 3912, 3914, 3922, and 3924 as shown in FIG. 38 is used only by way of example. It is also possible to split input optical beam 3900 into a smaller or greater number of partial optical beams as desired. In that case, it would merely be necessary to provide a corresponding quantity of beamsplitters. For example, beamsplitter 3824A may be replaced by a mirror such that optical beam 3920 is not further split into additional partial optical beams. Alternatively, additional beamsplitters may be added to further split optical beams 3912 and/or 3922. It is also possible to block one or more partial optical beams so that the spectral bands corresponding to those partial optical beams are substantially removed from the spectrum of output optical beam 3900'.

As described above, when a beamsplitter is a dichroic beamsplitter, two partial optical beams split by the beampslitter from an input optical beam would have different spectral bands. In other embodiments, a beamsplitter other than a dichroic beamsplitter may be used in system 3800. In such instances, two partial optical beams split by the beamsplitter may have the same spectrum, and may be further separately filtered by transmitting through different spectral slicing modules.

In some embodiments, at least one of the partial optical beams 3912, 3914, 3922, or 3924 may be directed through a spectral slicing module. The spectral slicing module then filters the partial optical beam transmitting through it to a desired spectral band having a desired bandwidth and/or center wavelength.

For example, as shown in FIG. 38, partial optical beams 3912, 3914, 3922, or 3924 may be respectively directed through a different spectral slicing module. The spectral slicing modules 3810A, 3810B, 3810C, and 3810D, may each operate as a tunable bandpass filter with an adjustable bandwidth and an adjustable center wavelength. Therefore, the spectral slicing modules may each filter the partial optical beam transmitting through it and generate corresponding filtered partial optical beams 3912', 3914', 3922', or 3924', with desired spectral bands.

As described herein, the four exemplary spectral slicing modules 3810A, 3810B, 3810C, and 3810D, for respectively filtering the four partial optical beams are described only by way of example. It is also possible to use a smaller or greater number of spectral slicing modules, and a selected number of partial optical beams may be selected and directed through the spectral slicing modules. In such instances, a corresponding number of beamsplitters and/or mirrors may be used in system 3800.

The second set of beamsplitters may be used to combine the filtered partial optical beams 3912', 3914', 3922', or 3924' into the output optical beam 3900'. For example, beamsplitter 3822B may be a dichroic beamsplitter that transmits optical beam 3912' and reflects optical beam 3914', thereby generating a combined optical beam 3910' with a spectrum combining the spectral bands of optical beams 3912' and 3914'. Similarly, beamsplitter 3824B may be a dichroic beamsplitter that transmits optical beam 3922' and reflects optical beam 3924', thereby generating a combined optical beam 3920' with a spectrum combining the spectral bands of optical beams 3922' and 3924'. Beamsplitter 3820B may also be a dichroic beamsplitter that further transmits the combined optical beam 3910' and reflects the combined optical beam 3920', thereby generating output optical beam 3900'. Therefore, output optical beam 3900' of system 3800 would have a spectrum combining the spectral bands of optical beams 3912', 3914', 3922', and 3924'.

In some embodiments, the second set of beamsplitters may have spectral characteristics matching those of the first set of beamsplitters to reduce the loss of light. For example, beamsplitters 3822A and 3822B may be similar or identical dichroic beamplitters having the same cut-off wavelength. Similarly, beamsplitters 3824A and 3824B may be similar or identical dichroic beamplitters having the same cut-off wavelength, and beamsplitters 3820A and 3820B may be similar or identical dichroic beamplitters having the same cut-off wavelength. This matching configuration of the first and second sets of beamsplitters may allow for highly efficient transmission and reflection of the partial optical beams by reducing the mismatching of the cut-off wavelengths of these beamsplitters. Advantageously, this may further increase the efficiency of directing the partial optical beams split from input optical beam 3900 to the combined output optical beam 3900', thereby reducing loss of light In some embodiments, system 3800 may further include one or more mirrors for independently aligning the partial optical beams transmitting through the corresponding spectral slicing modules. The mirrors may be used in pairs for performing the alignment. For example, as shown in FIG. 38, a first pair of mirrors 3830A and 3830B may be adjusted to align the direction of optical beam 3914 along the optical axis of spectral slicing module 3810A. Similarly, a second pair of mirrors 3832A and 3832B may be adjusted to align the direction of optical beam 3912 along the optical axis of spectral slicing module 3810B; a third pair of mirrors 3834A and 3834B may be adjusted to align the direction of optical beam 3924 along the optical axis of the spectral slicing module 3810C; and a fourth pair of mirrors 3836A and 3836B may be adjusted to align the direction of optical beam 3922 along the optical axis of the spectral slicing module 3810D.

In some cases, a pair of mirrors for aligning a partial optical beam, e.g., mirrors 3832A and 3832B, may be separately placed at two ends of the corresponding spectral slicing module along its optical axis. In other cases, a pair of mirrors for aligning a partial optical beam, e.g., mirrors 3834A and 3834B, may be placed at the same end of the corresponding spectral slicing module along its optical axis. The mirrors of system 3800 may be independently tilted and/or rotated manually or using motorized devices. For example, the mirrors may be adjusted using stepper, servo, or DC motorized rotational stages. Alternatively, pairs of mirrors may be replaced with pairs of galvanometer scanners or galvo mirrors.

Advantageously, independent alignment of the partial optical beams along the optical axes of the spectral slicing modules allows the filtered partial optical beams to propagate along the same direction or the same optical path after they are combined. For example, as shown in FIG. 38, optical beams 3912' and 3914' would propagate along the same direction after being combined into optical beam 3910' by beamsplitter 3822B. Similarly, optical beams 3922' and 3924' would propagate along the same direction after being combined into optical beam 3920' by beamsplitter 3824B, and optical beams 3910' and 3920' would then propagate along the same direction after being further combined into output optical beam 3900' by beamsplitter 3820B.

Functions and the working principles of the spectral slicing modules of system 3800 are described in detail below.

Figure 39:
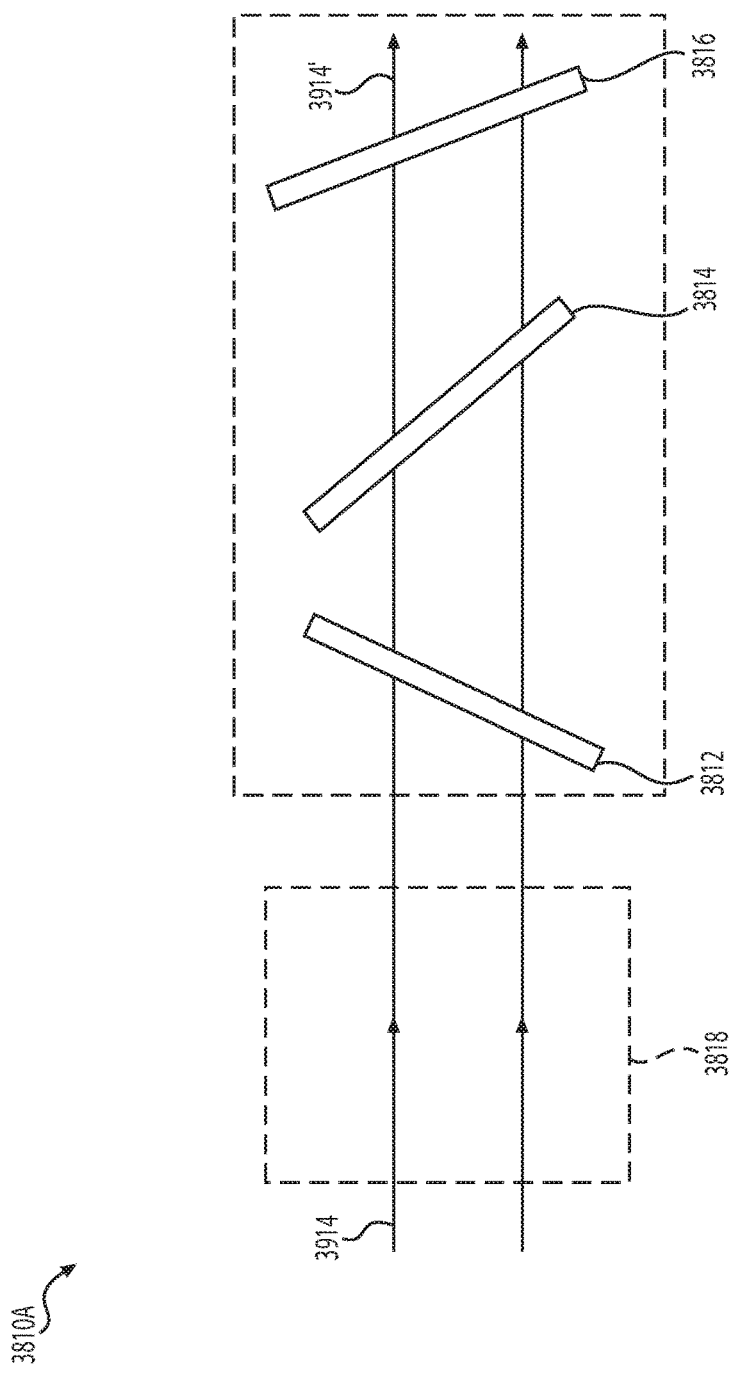
FIG. 39 is a schematic representation of an example spectral slicing module for filtering an optical beam.

FIG. 39 is a schematic representation of an exemplary spectral slicing module for filtering an optical beam. As described herein, descriptions of the features below in references to spectral slicing module 3810A are equally applicable to other spectral slicing modules of system 3800, e.g., spectral slicing modules 3810B, 3810C, and 3810D.

As shown in FIG. 39, spectral slicing module 3810A may include a longpass filter 3812 and a shortpass filter 3814 aligned along its optical axis. Longpass filter 3812 and shortpass filter 3814 may in combination form a bandpass filter with a passband delineated by their edge wavelengths or cut-off wavelengths (the cut-off wavelength of longpass filter 3812 is smaller than that of shortpass filter 3814). At least one of the longpass filter 3812 and shortpass filter 3814 is rotatable relative to the optical axis. For example, longpass filter 3812 and shortpass filter 3814 may be independently rotatable to be at an angle relative to the optical axis.

In some embodiments, longpass filter 3812 and shortpass filter 3814 may be thin-film angle-tuning filters. Rotating longpass filter 3812 may adjust the angle of incidence (AOI) of optical beam 3914 upon its surface. The cut-off wavelength of longpass filter 3812 may vary as a function of the AOI. Similarly, rotating shortpass filter 3814 may adjust the AOI of optical beam 3914 upon its surface and the cut-off wavelength of shortpass filter 3814 may vary as a function of the AOI.

For example, rotating longpass filter 3812 to change the AOI of optical beam 3914 upon its surface from normal incidence to higher angles may shift the cut-off wavelength of longpass filter 3812 towards shorter wavelengths. Alternatively, rotating longpass filter 3812 to change the AOI from higher angles to normal incidence may shift the cut-off wavelength of longpass filter 3812 towards longer wavelengths. Similarly, rotating shortpass filter 3814 to change the AOI of optical beam 3914 upon its surface from normal incidence to higher angles may shift the cut-off wavelength of shortpass filter 3814 towards shorter wavelengths. Rotating shortpass filter 3814 to change the AOI from higher angles to normal incidence may shift the cut-off wavelength of shortpass filter 3814 towards longer wavelengths.

Accordingly, tuning the AOI of optical beam 3914 upon longpass filter 3812 and/or upon shortpass filter 3814 varies the cut-off wavelengths of the passband of spectral slicing module 3810A, thereby allowing for adjustment of the bandwidth and/or center wavelength of the passband. The AOI of optical beam 3914 upon longpass filter 3812 and/or shortpass filter 3814 may be independently and continuously tuned across a given range of adjustment, e.g., from about −10° to about 60°. This may advantageously allow the passband of spectral slicing module 3810A to be continuously tuned to have any desired bandwidth and/or center wavelength across a given spectral range that could be provided by the filters.

As described herein, the order of optical beam 3914 transmitting through longpass filter 3812 and shortpass filter 3814 would not affect the tunable bandpass filtering of optical beam 3914 by spectral slicing module 3810A. This also applies to the other spectral slicing modules for filtering other partial optical beams in system 3800.

Comparing to a single tunable bandpass filter whose predetermined passband may be shifted by tuning the AOI of the optical beam on the filter, spectral slicing module 3810A advantageously allows for flexible adjustment of the bandwidth and/or the center wavelength of its passband by independently tuning the two cut-off wavelengths of the passband. Additionally, comparing to other tunable optical filters, such as liquid crystal tunable filters (LCTF), acousto-optic tunable filters (AOTF), or linear variable tunable filters (LVTF), spectral slicing module 3810A allow for high transmission, sharp cut-off edges, and polarization insensitivity provided by the longpass and shortpass filters.

In some situations, when optical beam 3914 transmits through longpass filter 3812 and/or shortpass filter 3814 at non-normal angles, filtered optical beam 3914' may laterally deviate from the optical axis of spectral slicing module 3810A. In such situations, as shown in FIG. 39, spectral slicing module 3810A may further include a compensation filter 3816 aligned along its optical axis after longpass filter 3812 and shortpass filter 3814. Compensation filter 3816 may be rotated to be at a suitable angle relative to the optical axis to generate an opposite lateral deviation to correct the lateral displacement of optical beam 3914'. In some embodiments, compensation filter 3816 may be adjusted to be at an angle relative to the optical axis ranging from about 0° to about 30°.

In some embodiments, compensation filter 3816 may be adjusted together with mirrors to align the filtered optical beam 3914' along the optical axis of spectral slicing module 3810A. For example, mirrors 3830A and 3830B and compensation filter 3816 may be independently adjusted to allow optical beam 3914' to propagate along the optical axis of spectral slicing module 3810A. Similar alignment may be performed for other optical beams, e.g. optical beams 3912', 3922', and 3924'. Additionally, as shown in FIG. 38, such independent alignment of the filtered partial optical beams may further allow them to propagate along the same optical path after they are combined into one optical beam (e.g., optical beams 3910', 3920', and 3900').

In some embodiments, longpass filter 3812, shortpass filter 3814, and/or compensation filter 3816 may be independently rotated using motorized rotational devices. For example, these filters may be adjusted using stepper, servo, or DC motorized rotational stages. Alternatively, these filters may be rotated using galvanometer scanners.

In some situations, separate optical beams, e.g., optical beams 3912 and 3914, may propagate through different optical path lengths (OPL). For example, as shown in FIG. 38, due to the geometry of system 3800, optical beam 3912' may propagate through an OPL longer than that of optical beam 3914' when they are combined at beamsplitter 3822B. The optical path length difference (OPD) between optical beams 3912' and 3914' may result in a phase shift between them when they are combined. In some instances, this phase shift may generate undesirable optical effects, e.g., interference. Therefore, in some embodiments, spectral slicing module 3810A may further include an optical spatial compensator 3818.

Optical spatial compensator 3818 may add OPL to the optical beam transmitting through it. Optical spatial compensator 3818 may be a glass plate with a selected thickness and refractive index. For example, as shown in FIG. 38, optical spatial compensator 3818 may add to the OPL traveled by optical beam 3914' to be the same as that traveled by optical beam 3912'. Advantageously, the addition of optical spatial compensator 3818 may allow two partial optical beams transmitting along two different paths in system 3800 to propagate through the same amount of OPL upon being combined into one optical beam, thereby reducing or eliminating undesirable optical effects.

In some embodiments, spectral slicing module 3810A may further include a blocking filter (not shown) that further blocks or rejects wavelengths outside of a desired passband of the spectral slicing module 3810A. For example, the blocking filter may be a bandpass filter that substantially blocks or rejects wavelengths beyond the passband formed by longpass filter 3812 and shortpass filter 3814. This advantageously allows for reducing or eliminating potential non-ideal spectral irregularities beyond the passband. Additionally or alternatively, spectral slicing module 3810A may further include another compensation filter (not shown) that compensates for astigmatism to improve the sharpness of the filtered optical beam 3914'. This may further improve the sharpness of output optical beam 3900'.

Figure 40A:
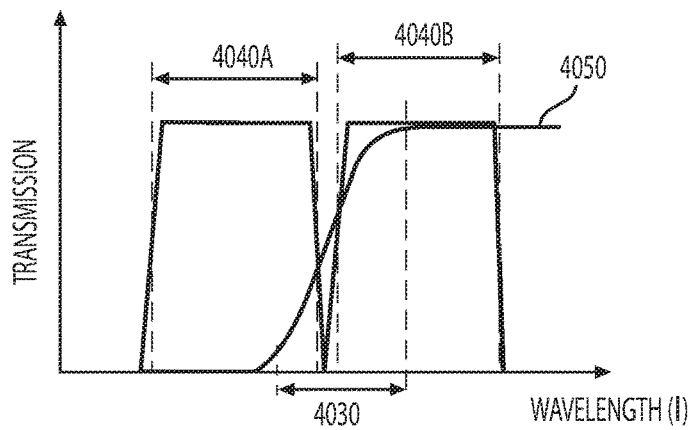
FIG. 40A is a graphical illustration of two example passbands of two example spectral slicing modules.
Figure 40B:
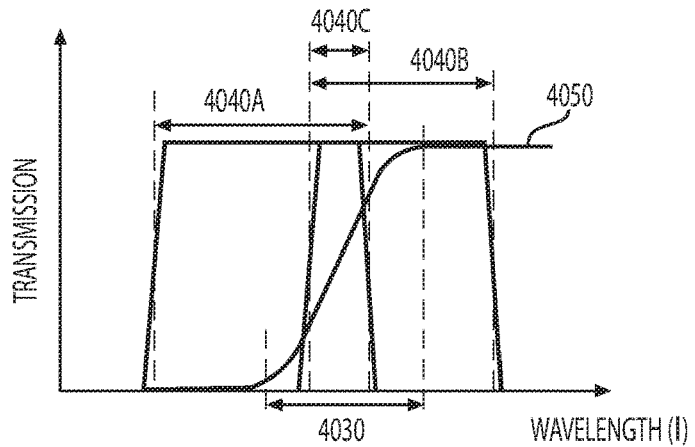
FIG. 40B is a graphical illustration of another two example passbands of two example spectral slicing modules.
Figure 40C:
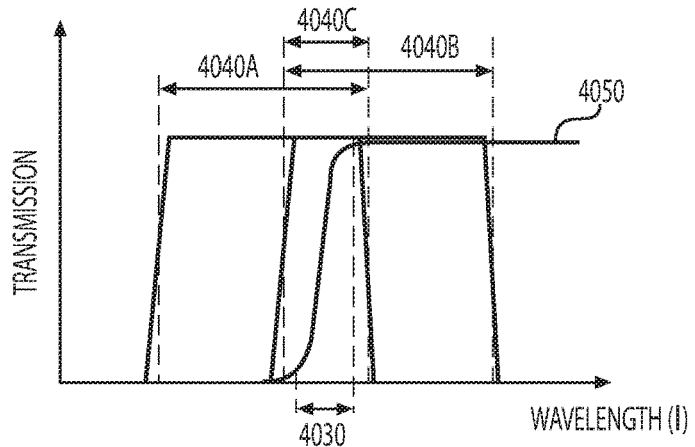
FIG. 40C is a graphical illustration of yet another two example passbands of two example spectral slicing modules.

As described above, the spectral slicing modules may have a series of passbands spectrally shifted from one another with overlapping regions between two adjacent passbands. In such instances, the transition region of the dichroic beamsplitter for splitting an input optical beam into the two partial optical beams is selected to be within the overlapping region to reduce potential artifacts from the splitting and separate filtering of the partial optical beams. FIGS. 40A-40C graphically illustrate the advantage of such characteristics of the dichroic beamsplitter and the spectral slicing modules for reducing loss of light. FIGS. 40A-40C show two exemplary passbands 4040A and 4040B of spectral slicing modules 3810A and 3810B with amount of transmission (e.g., percentage transmission) along the vertical axis and wavelength along the horizontal axis. Additionally, FIGS. 40A-40C show an exemplary transmission spectrum 4050 of beamsplitter 3822A having a transition region 4030.

As shown in FIG. 38 and FIG. 40A, passbands 4040A and 4040B do not overlap. In such instances, wavelengths of optical beam 3910 at the center of transition region 4030 partially transmit through and reflect from beamsplitter 3822A. However, because passbands 4040A and 4040B do not overlap, and may have gap regions due to the slopes of their edges, at least a portion of optical beam 3910 at these wavelengths at the center of transition region 4030 cannot pass through either passband 4040A or 4040B. This results in losing a portion of optical beam 3910 at these wavelengths. Further, wavelengths of optical beam 3910 at the two edges of transition region 4030 may be subjected to additional loss. For example, some wavelengths of optical beam 3910 in transition region 4030 may substantially transmit through beamsplitter 3822A and then through passband 4040B of spectral slicing module 3810B. But these wavelengths of optical beam 3910 are also partially reflected from beamsplitter 3822A and directed towards spectral slicing module 3810A. However, these wavelengths do not fall in passband 4040A of spectral slicing module 3810A, thereby resulting in losing a portion of optical beam 3910 at these wavelengths.

As shown in FIG. 38 and FIG. 40B, passbands 4040A and 4040B have an overlapping region 4040C narrower than transition region 4030 of beamsplitter 3822A. In such instances, the wavelengths of optical beam 3910 at the center of transition region 4030 would transmit through passbands 4040A and 4040B, thereby reducing loss of optical beam 3910. However, wavelengths of optical beam 3910 at the two edges of transition region 4030 that are outside of overlapping region 4040C may still be subjected to additional loss. For example, some wavelengths of optical beam 3910 outside overlapping region 4040 but inside transition region 4030 may substantially transmit through beamsplitter 3822A and then through passband 4040B of spectral slicing module 3810B. But these wavelengths of optical beam 3910 are also partially reflected from beamsplitter 3822A and directed towards spectral slicing module 3810A. However, these wavelengths do not fall in passband 4040A of spectral slicing module 3810A. This again results in losing a portion of optical beam 3910 at these wavelengths.

As shown in FIG. 38 and FIG. 40C, according to embodiments of the present disclosure, passbands 4040A and 4040B have an overlapping region 4040C equal to or wider than transition region 4030 of beamsplitter 3822A. In such instances, wavelengths of optical beam 3910 in transition region 4030 would fall in both passbands 4040A and 4040B. This allows for portions of optical beam 3910, whether reflecting from or transmitting through beamsplitter 3822A, to transmit through passband 4040A of spectral slicing module 3810A and/or passband 4040B of spectral slicing module 3810B, thereby advantageously reducing or eliminating of the loss of optical beam 3910.

As described herein, the adjustment of the mirrors and angle-tuning of the filters of system 3800 may be controlled by a controller (not shown). The controller may have a processor, a non-transitory memory, and a computer-readable medium that stores instructions or operational steps. The memory may store a plurality of coefficients of the filters, such as AOI and cut-off wavelengths, and parameters of the mirrors, e.g., angles relative to the optical axis along one or two spatial dimensions. The instructions or steps, when executed by the processor, may adjust the AOI of the optical beams upon the filters to suitable angles based on the desired passbands of the spectral slicing modules. Additionally, the instructions or steps, when executed by the processor, may further operate motorized rotational stages or galvanometer scanners to adjust the mirrors and/or compensation filters to align the output partial optical beams along the spectral slicing modules such that they would propagate along the same optical path after being combined.

Examples for filtering input optical beam 3900 by system 3800 to generate output optical beam 3900' with desired spectral bands are further described below in reference to their spectra. As described above, an input optical beam 3900 may be split into a plurality of partial optical beams having different spectral bands. The spectral bands of the partial optical beams may be selectively and independently filtered to desired spectral ranges by the corresponding spectral slicing modules. When the partial optical beams are combined into output optical beam 3900', the spectral bands of the partial optical beams are then combined as the spectrum of output optical beam 3900'.

Figure 41:
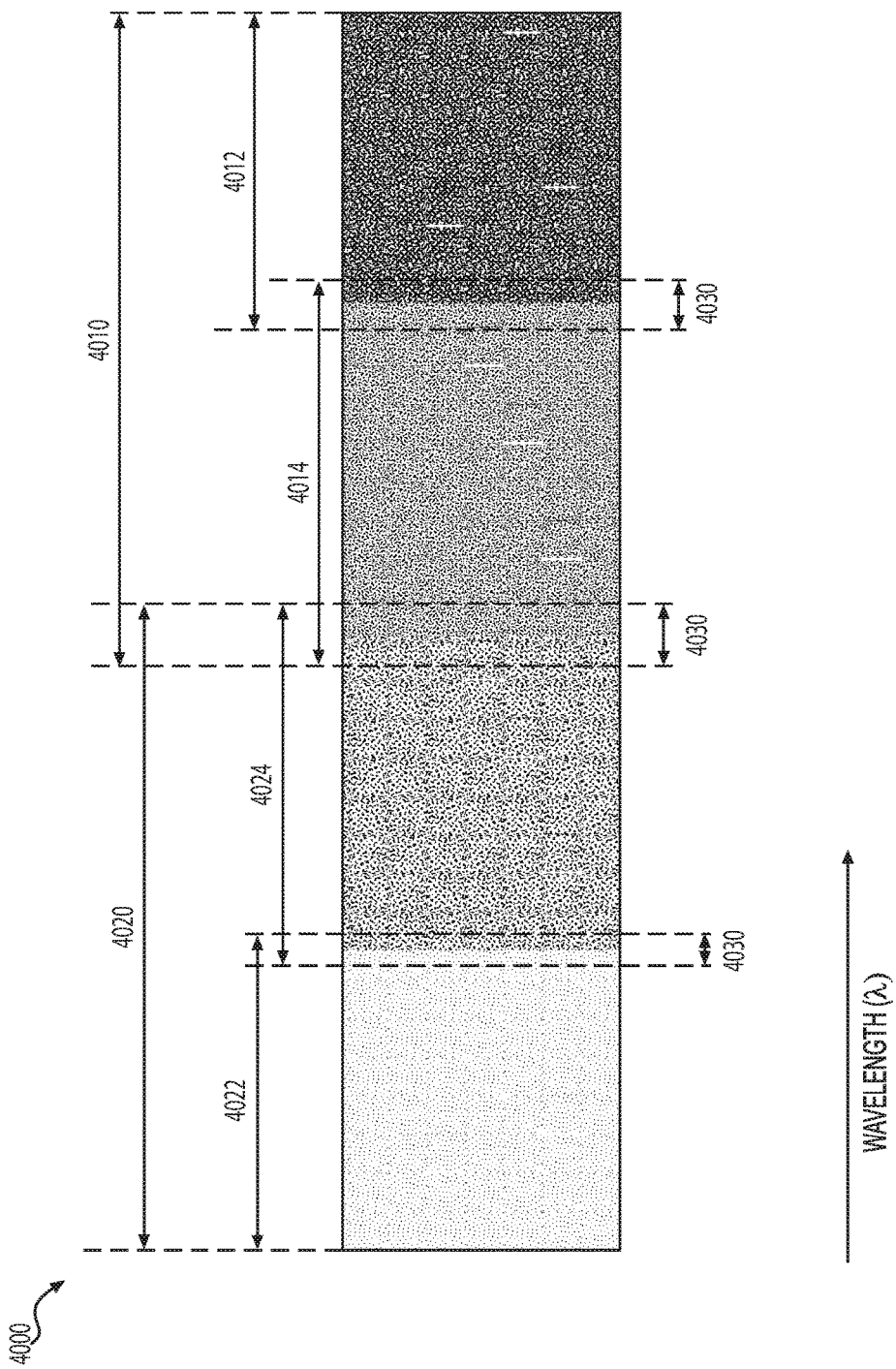
FIG. 41 is a graphical illustration of an example spectrum of an input optical beam entering the example system of FIG. 38.

FIG. 41 is a graphical illustration for an exemplary spectrum 4000 of input optical beam 3900. FIGS. 42A and 42B are graphical illustrations for examples of the spectrum 4000' of output optical beam 3900'.

As shown in FIG. 41, spectrum 4000 of input optical beam 3900 may be split into four spectral bands 4012, 4014, 4022, and 4024, corresponding to the four partial optical beams 3912, 3914, 3922, and 3924. For example, spectrum 4000 of input optical beam 3900 may first be split into spectra 4010 and 4020, corresponding to optical beams 3910 and 3920. Spectrum 4010 of optical beam 3910 may then be further split into spectral bands 4012 and 4014, corresponding to optical beams 3912 and 3914. Similarly, spectrum 4020 of optical beam 3920 may then be further split into spectral bands 4022 and 4024, corresponding to optical beams 3922 and 3924. In some embodiments, as shown in FIG. 41, adjacent spectral bands may have overlapping bands due to the transition regions 4030 of the beamsplitters.

As shown in FIGS. 42A and 42B, spectral bands 4012, 4014, 4022, and 4024 may be filtered by the corresponding spectral slicing modules to desired spectral bands 4012', 4014', 4022', and 4024', corresponding to the filtered optical beams 3912', 3914', 3922', and 3924'. Spectrum 4000' of output optical beam 3900' is the combination of the filtered spectral bands.

In one example, as shown in FIG. 42A, spectral band 4012 of optical beam 3912 may be filtered to a narrower spectrum 4012' with a center wavelength $\lambda_a$. Additionally or alternatively, as shown in FIG. 42B, spectral slicing module 3810A may be adjusted to tune the center wavelength $\lambda_a$ of spectral band 4012' towards shorter wavelengths as desired. Spectral slicing module 3810A may also be adjusted to tune the center wavelength $\lambda_a$ of spectral band 4012' towards longer wavelengths as needed (not shown).

In another example, as shown in FIG. 42A, spectral band 4014 of optical beam 3914 may be filtered to a desired spectral band 4014' with a center wavelength $\lambda_b$. Additionally or alternatively, as shown in FIG. 42B, spectral slicing module 3810B may be adjusted to reduce the bandwidth of spectral band 4014' and to shift the center wavelength $\lambda_b$ of spectral band 4014' towards longer wavelengths as desired.

As shown in FIG. 42B, spectral band 4012' of filtered optical beams 3912' and spectral band 4014' of filtered optical beams 3914' can be substantially continuous, maintaining the continuity of spectra bands 4012 and 4014 of input optical beam 3900 without substantial loss or no loss of light. This may be advantageously achieved by selectively using beamsplitter 3822A with a transition region 4030 equal to or narrower than that of overlapping region 4040C of the passbands of spectral slicing modules 3810A and 3810B as described above.

In another example, as shown in FIG. 42A, spectral band 4024 of optical beam 3924 may be filtered to a desired spectral band 4024' with a center wavelength $\lambda_c$. Additionally or alternatively, as shown in FIG. 42B, spectral slicing module 3810C may be adjusted to increase the bandwidth of spectral band 4024'. Spectral slicing module 3810C may also be adjusted to shift the center wavelength $\lambda_c$ of spectral band 4024' towards longer or shorter values (not shown).

In yet another example, as shown in FIG. 42A, spectral band 4022 of optical beam 3922 may be filtered to a desired spectral band 4022' with a center wavelength $\lambda_d$. Additionally or alternatively, as shown in FIG. 42B, spectral slicing module 3810D may be adjusted to increase the bandwidth of spectral band 4022' and tune the center wavelength $\lambda_d$ towards shorter wavelengths as needed. Alternatively, spectral slicing module 3810D may be adjusted to reduce the bandwidth of spectral band 4022', and/or tune the center wavelength $\lambda_d$ towards shorter or longer wavelengths as needed (not shown).

As described herein, FIGS. 42A and 42B only provide exemplary tuning of the spectral filtering that can be provided by the spectral slicing modules of system 3800. As described above, any of the spectral slicing modules may be adjusted to filter a partial optical beam to have any desired spectral band and center wavelength in a given spectral range. As describe herein, this given spectral range may be determined by the tunable ranges of cut-off wavelengths of the longpass and shortpass filters of each spectral slicing module.

Figure 43:
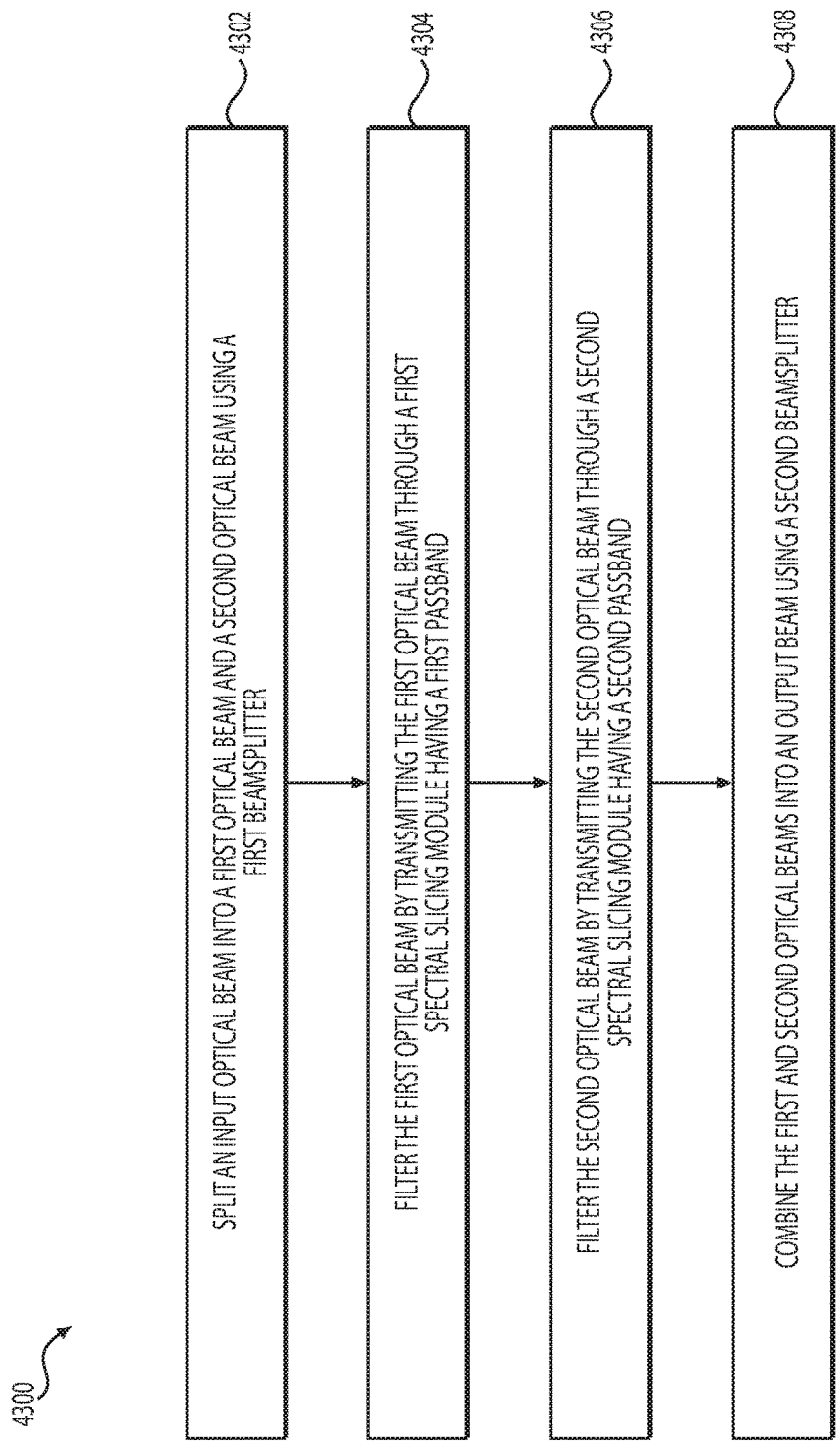
FIG. 43 is a flowchart of an example method for filtering an optical beam.

System 3800 as described herein may be utilized in a variety of methods and devices for filtering an optical beam. FIG. 43 is a flowchart of an exemplary method 4300 for filtering of an optical beam. Method 4300 uses system 3800 and features of the embodiments of system 3800 described above in reference to FIG. 38-42.

At step 4302, an input optical beam (e.g., optical beam 3910) is split into a first optical beam (e.g., optical beam 3914) and a second optical beam (e.g., optical beam 3912) using a first beamsplitter (e.g., beamsplitter 3822A). At step 4304, the first optical beam is filtered by transmitting the first optical beam through a first spectral slicing module (e.g., spectral slicing module 3810A) having a first passband (e.g., passband 4040A). At step 4306, the second optical beam (e.g., optical beam 3914) is filtered by transmitting the second optical beam through a second spectral slicing module (e.g., spectral slicing module 3820A) having a second passband (e.g., passband 4040B). At step 4308, the first optical beam may be combined with the second optical beam into an output optical beam (e.g., optical beam 3910') using a second beamsplitter (e.g., beamsplitter 3822B).

As described herein, an input optical beam may be split into a desired number of partial optical beams with different spectral bands using a suitable quantity of beamsplitters. The above-described steps may be performed for a plurality of times based on the number of spectral bands desired to be split and filtered of an input optical beam.

Various embodiments of method 4300 may include one or more of the following features or steps. For example, method 4300 may further include tuning a bandwidth and/or a center wavelength of the passband of at least one of the spectral splicing modules by varying the AOI of the partial optical beam upon its longpass filter 3812 and/or the shortpass filter 3814. In some embodiments, method 4300 may further include directing the propagation of the first and/or second optical beams using one or more mirrors, e.g., pairs of mirrors. Method 4300 may further include realigning the first and/or second optical beams laterally deviated from the optical axis after transmitting through the longpass and/or shortpass filters using one or more rotatable mirrors and/or compensation filters.

In some embodiments, method 4300 may further include directing the first and second optical beams to propagate along the same direction or optical path after they are combined. Additionally, method 4300 may further include directing the combined output optical beam to be collinear with the input optical beam.

In some embodiments, method 4300 may further include additionally blocking the wavelengths outside of the passband of at least one of the spectral splicing modules using a blocking filter. Method 4300 may further include adding optical path length to the first and/or second optical beams using at least one optical spatial compensator.

XII. Conclusion

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to image biological environments (e.g., tissues extracted from a human body) and to determine the identity of probes within such environments, it is noted that the disclosed devices, systems, and methods can be applied in other contexts as well. For example, imaging systems configured as disclosed herein may be included as part of other scientific and/or industrial imaging apparatus. Embodiments of the present disclosure may be implemented in a spectrometer, e.g., an imaging spectrometer, a microscope, e.g., a fluorescence microscope, a confocal microscope, a transmission microscope, a reflectance microscope, etc., or a spectral imaging system, e.g., a hyperspectral imaging system, or in some other imaging system Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
a light sensor that comprises a plurality of light-sensitive elements disposed on a focal surface of the light sensor;
a spatial light modulator that comprises a reflective layer disposed beneath a refractive layer and that is operable to have a refractive index that varies spatially across the spatial light modulator according to a controllable gradient, wherein at least the direction and magnitude of the controllable gradient are electronically controllable, and wherein the refractive layer is chromatically dispersive;
an optical system that (i) directs light emitted from a target toward the spatial light modulator and (ii) directs light emitted from the target and reflected from the spatial light modulator to the light sensor such that the focal surface of the light sensor is conjugate to a focal surface passing through the target; and
a controller that is operably coupled to the light sensor and the spatial light modulator and that is operable to perform controller operations comprising:
controlling the spatial light modulator such that at least one of the direction or magnitude of the controllable gradient are different during each of a plurality of periods of time;
generating, using the light sensor, a plurality of images of the target, wherein each image corresponds to a respective one of the plurality of periods of time;
determining, based on the plurality of images, locations and colors of two or more fluorophores in the target; and
determining, based on the determined colors and locations of the two or more fluorophores, an identity of a probe that is located in the target and that comprises the two or more fluorophores.

2. The system of claim 1, wherein the optical system collimates the light emitted from the target that is directed toward the spatial light modulator.

3. The system of claim 1, further comprising:
a light source; and
a micromirror device, wherein the micromirror device comprises a substantially planar array of actuatable mirrors disposed on a surface, wherein respective angles of the actuatable mirrors relative to the surface are electronically controllable,
wherein the optical system directs the light from the light source to the target via reflection from a first set of one or more of the actuatable mirrors, and wherein the optical system directs the light emitted from the target in response to the illumination toward the spatial light modulator via reflection from the first set of one or more actuatable mirrors such that the surface of the micromirror device is conjugate to the focal surface passing through the target.

4. The system of claim 1, wherein the spatial light modulator comprises an array of regions having respective electronically controllable refractive indexes.

5. A system comprising:
a first light sensor that comprises a plurality of light-sensitive elements disposed on a focal surface of the first light sensor;
a second light sensor that comprises a plurality of light-sensitive elements;
a chromatically dispersive element;
an optical system that (i) directs light emitted from a particular region of a target to the first light sensor such that the focal surface of the first light sensor is conjugate to a focal surface passing through the particular region of the target, (ii) directs light emitted from the particular region of the target toward the chromatically dispersive element, and (iii) directs light emitted from the particular region of the target that has interacted with the chromatically dispersive element to the second light sensor such that light of different wavelengths that is emitted from the particular region of the target is received by corresponding different light-sensitive elements of the second light sensor; and
a controller that is operably coupled to the first light sensor and the second light sensor and that is operable to perform controller operations comprising:
generating, using the plurality of light-sensitive elements of the first light sensor, a first plurality of respective time-varying waveforms of light emitted from respective different locations of the particular region of the target;
generating, using the plurality of light-sensitive elements of the second light sensor, a second plurality of respective time-varying waveforms of light emitted from the particular region of the target at respective different wavelengths;
determining correlations between time-varying waveforms of the first plurality of time-varying waveforms and time-varying waveforms of the second plurality of time-varying waveforms;

determining, based on the determined correlations, locations and colors of two or more fluorophores in the target; and determining, based on the determined colors and locations of the two or more fluorophores, an identity of a probe that is located in the target and that comprises the two or more fluorophores.

6. The system of claim 5, wherein the chromatically dispersive element comprises a spatial light modulator, wherein the spatial light modulator comprises a reflective layer disposed beneath a refractive layer, wherein the refractive layer is configured to have a refractive index that varies spatially across the spatial light modulator according to a controllable gradient, wherein at least the direction and magnitude of the controllable gradient are electronically controllable, and wherein the refractive layer is chromatically dispersive.

7. The system of claim 6, wherein the optical system collimates the light emitted from the target that is directed toward the spatial light modulator.

8. The system of claim 6, wherein the spatial light modulator comprises an array of cells having respective electronically controllable refractive indexes.

9. The system of claim 5, further comprising:
a light source; and
a micromirror device, wherein the micromirror device comprises a substantially planar array of actuatable mirrors disposed on a surface, wherein respective angles of the actuatable mirrors relative to the surface are electronically controllable,
wherein the optical system directs the light from the light source to the particular region of the target via reflection from a first set of one or more of the actuatable mirrors, wherein the optical system directs the light emitted from the target in response toward the first light sensor via reflection from the first set of one or more actuatable mirrors such that the surface of the micromirror device is conjugate to the focal surface passing through the particular region of the target and such that the focal surface of the first light sensor is conjugate to the focal surface passing through the particular region of the target, and wherein the optical system directs the light emitted from the target in response to the illumination toward the chromatically dispersive element via reflection from a second set of one or more of the actuatable mirrors, and
wherein the one or more actuatable mirrors in the first set have a first angle relative to the surface of the micromirror device.

10. The system of claim 5, further comprising:
a light source; and
a micromirror device, wherein the micromirror device comprises a substantially planar array of actuatable mirrors disposed on a surface, wherein respective angles of the actuatable mirrors relative to the surface are electronically controllable,
wherein the optical system directs the light from the light source to the particular region of the target via reflection from a first set of one or more of the actuatable mirrors, wherein the optical system directs the light emitted from the target in response toward the first light sensor and the chromatically dispersive element via reflection from the first set of one or more actuatable mirrors such that the surface of the micromirror device is conjugate to the focal surface passing through the particular region of the target and such that the focal surface of the first light sensor is conjugate to the focal surface passing through the particular region of the target.

11. The system of claim 5, further comprising an actuated stage, wherein the actuated stage is operable to control the location of the target relative to the optical system.

12. The system of claim 5, wherein a dimension of the particular region of the target is approximately equal to a diffraction limit of the optical system.

13. A method comprising:
generating, using a plurality of light-sensitive elements of a first light sensor that are disposed on a focal surface of the first light sensor, a first plurality of respective time-varying waveforms of light that is emitted from respective different locations of a particular region of a target and transmitted to the light sensor via an optical system, wherein the optical system provides the emitted light from the target to the first light sensor such that the focal surface of the first light sensor is conjugate to a focal surface passing through the particular region of the target;

generating, using a plurality of light-sensitive elements of a second light sensor, a second plurality of respective time-varying waveforms of light at different respective wavelengths that is emitted from the particular region of the target and transmitted to the light sensor via the optical system, wherein the optical system provides the emitted light from the target to a chromatically dispersive element, wherein the optical system provides the emitted light from the target that has interacted with the chromatically dispersive element to the second light sensor such that light of different wavelengths that is emitted from the particular region of the target is received by corresponding different light-sensitive elements of the second light sensor;

determining correlations between time-varying waveforms of the first plurality of time-varying waveforms and time-varying waveforms of the second plurality of time-varying waveforms;

determining, based on the determined correlations, locations and colors of two or more fluorophores in the target; and determining, based on the determined colors and locations of the two or more fluorophores, an identity of a probe that is located in the target and that comprises the two or more fluorophores.

14. The method of claim 13, wherein a distance between the two or more fluorophores of the probe is less than approximately 50 nanometers.

15. The method of claim 13, further comprising:
determining correlations between different time-varying waveforms of the first plurality of time-varying waveforms, wherein determining locations of two or more fluorophores in the target comprises determining the location of a fluorophore in the target based at least in part on the determined correlations between different time-varying waveforms of the first plurality of time-varying waveforms.

16. The method of claim 13, wherein determining a color of a fluorophore in the target comprises:
determining that a determined correlation between a particular generated time-varying waveform of light of the first plurality of time-varying waveforms of light and a particular generated time-varying waveform of light of the second plurality of time-varying waveforms of light is greater than a threshold, wherein the particular generated time-varying waveform of light of the first plurality of time-varying waveforms of light corresponds to light received from the location of the fluorophore in the target; and determining that the color of the fluorophore includes a wavelength of light corresponding to the particular time-varying waveform of light of the second plurality of time-varying waveforms of light.

17. The method of claim 13, further comprising:

generating illumination using a light source; and operating a micromirror device to electronically control respective angles of actuatable mirrors of the micromirror device relative to a surface of the micromirror device, wherein the actuatable mirrors comprise a substantially planar array and are disposed on the surface of the micromirror device, and wherein operating the micromirror device to electronically control respective angles of actuatable mirrors of the micromirror device comprises controlling a first set of one or more of the actuatable mirrors to have a first angle relative to the surface of the micromirror device, and wherein the optical system directs the illumination from the light source to the particular region of the target via reflection from the first set of one or more actuatable mirrors, and wherein the optical system directs the light emitted from the target in response to the illumination toward the first light sensor via reflection from the first set of one or more actuatable mirrors such that the surface of the micromirror device is conjugate to the focal surface passing through the particular region of the target.

18. The method of claim 13, wherein the chromatically dispersive element comprises a spatial light modulator, the method further comprising:

electronically controlling the spatial light modulator such that a refractive layer of the spatial light modulator has a refractive index that varies spatially across the spatial light modulator according to a controllable gradient, wherein the controllable gradient has at least a first specified direction and a first specified magnitude, wherein the spatial light modulator further comprises a reflective layer disposed beneath the refractive layer, and wherein the refractive layer is chromatically dispersive.

19. The method of claim 18, wherein the spatial light modulator comprises an array of cells having respective electronically controllable refractive indexes, and wherein electronically controlling a spatial light modulator during a first period of time such that a refractive layer of the spatial light modulator has a refractive index that varies spatially across the spatial light modulator according to a controllable gradient comprises electronically controlling the refractive indexes of the cells such that refractive indexes of the cells vary in a direction corresponding to the first specified direction and at a spatial rate of change corresponding to the first specified magnitude.

20. The method of claim 13, further comprising:

controlling, using an actuated stage, the location of the particular region of the target relative to the optical system.

* * * * *